US010556890B2

(12) United States Patent
Campbell et al.

(10) Patent No.: US 10,556,890 B2
(45) Date of Patent: Feb. 11, 2020

(54) HETEROARYL COMPOUNDS AND METHODS OF USE THEREOF

(71) Applicant: Sunovion Pharmaceuticals Inc., Marlborough, MA (US)

(72) Inventors: John Emmerson Campbell, Cambridge, MA (US); Una Campbell, Marlborough, MA (US); Taleen G. Hanania, Valhalla, NY (US); Liming Shao, Lincoln, MA (US)

(73) Assignees: Sunovion Pharmaceuticals Inc., Marlborough, MA (US); PGI DRUG DISCOVERY LLC, Paramus, NJ (US)

( * ) Notice: Subject to any disclaimer, the term of this patent is extended or adjusted under 35 U.S.C. 154(b) by 0 days.

(21) Appl. No.: 15/851,836

(22) Filed: Dec. 22, 2017

(65) Prior Publication Data
US 2018/0118727 A1 May 3, 2018

Related U.S. Application Data

(62) Division of application No. 14/377,673, filed as application No. PCT/US2013/025260 on Feb. 8, 2013, now Pat. No. 10,189,825.

(60) Provisional application No. 61/596,422, filed on Feb. 8, 2012.

(51) Int. Cl.
*C07D 409/04* (2006.01)
*C07D 409/14* (2006.01)
*C07D 491/048* (2006.01)
*C07D 495/04* (2006.01)
*C07D 405/04* (2006.01)

(52) U.S. Cl.
CPC ......... *C07D 409/04* (2013.01); *C07D 405/04* (2013.01); *C07D 409/14* (2013.01); *C07D 491/048* (2013.01); *C07D 495/04* (2013.01)

(58) Field of Classification Search
CPC .................................................. C07D 409/04
See application file for complete search history.

(56) References Cited

U.S. PATENT DOCUMENTS

| 3,470,179 | A | 9/1969 | Ott |
| 3,536,809 | A | 10/1970 | Applezweig |
| 3,549,624 | A | 12/1970 | Conover |
| 3,551,427 | A | 12/1970 | Ott |
| 3,598,123 | A | 8/1971 | Zaffaroni |
| 3,845,770 | A | 11/1974 | Theeuwes et al. |
| 3,916,899 | A | 11/1975 | Theeuwes et al. |
| 4,008,719 | A | 2/1977 | Theeuwes et al. |
| 5,059,595 | A | 10/1991 | Le Grazie |
| 5,073,543 | A | 12/1991 | Marshall et al. |
| 5,120,548 | A | 6/1992 | McClelland et al. |
| 5,134,127 | A | 7/1992 | Stella et al. |
| 5,354,556 | A | 10/1994 | Sparks et al. |
| 5,591,767 | A | 1/1997 | Mohr et al. |
| 5,639,476 | A | 6/1997 | Oshlack et al. |
| 5,674,533 | A | 10/1997 | Santus et al. |
| 5,733,566 | A | 3/1998 | Lewis |
| 6,436,943 | B1 | 8/2002 | Stoltefuss et al. |
| 6,503,913 | B1 | 1/2003 | Goldmann et al. |
| 2003/0073687 | A1 | 4/2003 | Bebbington et al. |
| 2003/0149057 | A1* | 8/2003 | Wang ................... C07D 409/04 514/256 |
| 2007/0032481 | A1 | 2/2007 | Dvorak et al. |
| 2008/0306082 | A1 | 12/2008 | Dahnke et al. |
| 2009/0069305 | A1 | 3/2009 | Gaul et al. |
| 2010/0178299 | A1 | 7/2010 | Sitkovsky et al. |
| 2015/0031709 | A1* | 1/2015 | Campbell ............ C07D 409/04 514/260.1 |

FOREIGN PATENT DOCUMENTS

| CA | 2407013 A1 | 10/2002 | |
| CN | 101468986 A | 7/2009 | |
| CN | 101468987 A | 7/2009 | |
| EP | 0431421 A2 * | 6/1991 | ............. A01N 43/54 |
| GB | 984365 | 2/1965 | |
| JP | 2002512233 A | 4/2002 | |
| JP | 2002512244 A | 4/2002 | |
| JP | 2008540369 A | 11/2008 | |
| JP | 2015510513 A | 4/2015 | |
| WO | 9901437 A1 | 1/1999 | |
| WO | 0162233 A2 | 8/2001 | |
| WO | 0172745 A1 | 10/2001 | |
| WO | 02066443 A2 | 8/2002 | |
| WO | 02083667 A2 | 10/2002 | |
| WO | 2004089913 A1 | 10/2004 | |
| WO | 2004112719 A2 | 12/2004 | |

(Continued)

OTHER PUBLICATIONS

NIH Medline Plus. "Symptoms, Diagnosis and Treatment: Alzheimer's disease." (Fall 2010), vol. 5, No. 3. (Year: 2010).*
Michael J Fox Foundation for Parkinson's Research. "Parkinson's Disease." (May 2007). Accessed Dec. 28, 2018. Available from: < https://www.michaeljfox.org/understanding-parkinsons/living-with-pd/topic.php?causes >. (Year: 2007).*
"Alzheimer's Disease Treatment, Symptoms, Stages & Life Expectancy." (Jul. 2007). Accessed Dec. 28, 2018. Available from: < https://www.medicinenet.conn/alzheimers_disease_causes_stages_and_symptoms/article.htm#alzheimers_disease_medications >. (Year: 2007).*

(Continued)

*Primary Examiner* — Andrew D Kosar
*Assistant Examiner* — John S Kenyon
(74) *Attorney, Agent, or Firm* — Heslin Rothenberg Farley & Mesiti P.C.

(57) ABSTRACT

Provided herein are thiophene compounds, methods of their synthesis, pharmaceutical compositions comprising the compounds, and methods of their use. The compounds provided herein are useful for the treatment, prevention, and/or management of various neurological disorders, including but not limited to, psychosis and schizophrenia.

14 Claims, No Drawings

(56) References Cited

FOREIGN PATENT DOCUMENTS

| WO | 2005035518 | A1 | | 4/2005 | |
|---|---|---|---|---|---|
| WO | 2005079800 | A1 | | 9/2005 | |
| WO | 2006066172 | A1 | | 6/2006 | |
| WO | 2006066950 | A2 | | 6/2006 | |
| WO | 2008011560 | A2 | | 1/2008 | |
| WO | WO-2008112913 | A1 | * | 9/2008 | ........... C07D 239/42 |
| WO | 2008119689 | A1 | | 10/2008 | |
| WO | 2010090716 | A1 | | 8/2010 | |
| WO | 2011017389 | A1 | | 2/2011 | |
| WO | 2011069063 | A2 | | 6/2011 | |
| WO | 2013119895 | A1 | | 8/2013 | |

OTHER PUBLICATIONS

"Treatment for Tourette Syndrome: Johns Hopkins Pediatric Neurology." (Apr. 2006). Accessed Dec. 28, 2018. Available from: < https://www.hopkinsmedicine.org/neurology_neurosurgery/centers_clinics/pediatric-neurology/conditions/tourettes_syndrome/treatment.html >. (Year: 2006).*

"Parkinson's disease—Symptoms, Diagnosis and Treatment." (Jan. 22, 2006). Accessed Dec. 28, 2018. Available from: < https://www.google.com/search?q=Parkinson+disease+treatment&source=Int&tbs=cdr%3A1%2Ccd_min%3A%2Ccd_max%3A2%2F8%2F2012&tbm= > . (Year: 2006).*

"Treatment: Anxiety and Depression Association of America." (Jan. 29, 2006). Accessed Dec. 28, 2018. Available from: < https://adaa.org/understanding-anxiety/depression/treatment > . (Year: 2006).*

Mayo Clinic. "Fibromyalgia treatment: Is Neurontin effective?" (Jul. 2009). Accessed Dec. 28, 2018. Available from: < https://www.mayoclinic.org/diseases-conditions/fibromyalgia/expert-answers/fibromyalgia-treatment/faq-20058273 > . (Year: 2009).*

Strekowski et al. "Synthesis of 2-Chloro-4,6-di(heteroaryl)pyrimidines" J. Heterocyclic Chem., Jul. 27-Aug. 1990.

Communication Pursuant to Article 94(3) EPC in European Application No. 13747266.8 dated Dec. 21, 2017.

Database Registry [Online] Chemical Abstract Service. Database Accession Nos. 131022-75-8, 1310059-007-4, 1310059-06-3, 1310059-08-5 and 1310059-09-6 as cited in the Mar. 14, 2017 Office Action in Japanese Application No. 2014-556702.

Database Registry [Online] Chemical Abstracts Service, Columbus, Ohio, Jun. 1, 2008, Database Accession No. 1024262-27-8.

Database Registry [Online] Chemical Abstracts Service, Columbus, Ohio, May 29, 2008, Database Accession No. 1023480-64-9.

Database Registry [Online] Chemical Abstracts Service, Columbus, Ohio, May 27, 2008, Database Accession No. 1022813-67-7.

Database Registry [Online] Chemical Abstracts Service, Columbus, Ohio, May 25, 2008, Database Accession No. 1022468-83-2.

Database Registry [Online] Chemical Abstracts Service, Columbus, Ohio, May 25, 2008, Database Accession No. 1022339-80-5.

Database Registry [Online] Chemical Abstracts Services, Columbus, Ohio, May 23, 2008, Database Accession No. 1022058-43-0.

Database Registry [Online] Chemical Abstracts Services, Columbus, Ohio, Sep. 28, 2001, Database Accession No. 359452-84-9.

Database Registry [Online] Chemical Abstracts Services, Columbus, Ohio, Sep. 28, 2001, Database Accession No. 359452-83-8.

Database Registry [Online] Chemical Abstracts Services, Columbus, Ohio, Sep. 28, 2001, Database Accession No. 359452-60-1.

Database Registry [Online] Chemical Abstracts Services, Columbus, Ohio, Jun. 14, 2001, Database Accession No. 340968-07-2.

Communication Pursuant to Article 94(3) EPC in European Application No. 13747266.8 dated Nov. 18, 2016.

Notice of Reasons for Rejection in Japanese Application No. 2014-556702 dated Jul. 19, 2016 (with translation).

Examination Report No. 2 in Australian Application No. 2013216935 dated Aug. 1, 2017.

Girke, W.P.K. "Electrophillic Aromatic Substitution Reactions with Protonated 1, 3-Diazinen, II. Preparation and Properties of 4-aryl-substituted 3, 4-Dihydroquinazoline Derivatives." Chem. Ber., (1979), vol. 112(4), pp. 1348-1358.

CAS Registry No. 790156-85-3; STN entry date: Nov. 28, 2004; Chemical Name. Quinazoline, 4-benzo[b]thien-3-yl-1, 4-dihydro—(cited Aug. 1, 2017, obtained from https://scifinder.cas.org on Aug. 10, 2017).

CAS Registry No. 775528-08-0; STN entry date: Nov. 7, 2004; Chemical Name. Quinazoline, 4-benzo[b]thien-3-yl-1, 4-dihydro-2-methyl (cited Aug. 1, 2017, obtained from https://scifinder.cas.org on Aug. 10, 2017).

CAS Registry No. 742648-33-5; STN entry date: Sep. 10, 2004; Chemical Name. Quinazoline, 4-benzo[b]thien-2-yl-1,4-dihydro—(cited Aug. 1, 2017, obtained from https://scifinder.cas.org on Aug. 10, 2017).

CAS Registry No. 736880-30-1; STN entry date: Sep. 1, 2004; Chemical Name. Quinazoline, 4-benzo[b]thien-2-yl-1,4dihydro-2-methyl—(cited Aug. 1, 2017, obtained from https://scifinder.cas.org on Aug. 10, 2017).

Notice of Reasons for Rejection in Japanese Application No. 2014-556702 dated Mar. 14, 2017 (with translation).

American Chemical Society. STN Database. RN 63463-05-8. Nov. 16, 1984.

Gould, P.L. "Salt Selection for Basic Drugs." International Journal of Pharmaceuticals. (1986), vol. 33, pp. 201-217.

Disabled World, "Neurological Disorders: Types, Research & Treatment." 2017. Available from: https://www.disabled-world.com/health/neurology.

Sakai, N., et al. "Facile and Efficient Synthesis of Polyfunctionalized Benzofurans: three-component coupling reactions from an alkynylsilane, an o-hydroxybenzaldehyde derivative, and a secondary amine by a Cu(I)—Cu(II) Cooperative Catalytic System." Tetrahedron Letters. vol. 49 (2008) pp. 3437-3440.

Lima, L.M., et al. "Bioisosterism: A Useful Strategy for Molecular Modification and Drug Design." Current Medicinal Chemistry. (2005), vol. 12, pp. 23-49.

Ellis, M. "Affective Disorders (Mood Disorders)." May 2013. Available from http://www.healthline.com/healthline.com/health/affective-disorders.

Mayo Clinic. "Seasonal Affective Disorder (SAD)." 2015. Available from http://www.mayoclinic.org/diseases-conditions/seasonal-affective-disorder/basics/definition.

Nakashima, T. et al. Regulation of Folding and Photochromic Reactivity of Terarylenes Through a Host-Guest Interaction.: Chem. Eur. J. (2011), vol. 17, pp. 10951-10957.

Emedicinehealth. "Brain Cancer: Get Facts on Treatment, Causes, and Symptoms." 2015. Available From: http://www.emedicinehealth.com/script/main/art.asp?articlekey=58940&pf=2.

Partial Supplementary European Search Report, dated Aug. 14, 2015 in European Application No. 13747266.8, 11 pages.

Gronowitz et al., "The Reaction of 5-Bromo- and 2-Bromopyrimidine with Organolithium Compounds," Acta Chemica Scandinavica 19, 1965, No. 7, 8 pages.

Van Der Stoel et al., "Di-π-methane Rearrangement of 4-Heteroaryl-1,4(or 3,4)-dihydropyrimidines," Journal of the Chemical Society, Perkin Transaction 1, Nov. 2, 1978, 4 pages.

Weis et al., "The Crystal and Molecular Structures of 4,6,6-trimethyl-2-phenyl-1,6-dihydropyrimidine," Heterocycles, vol. 19, No. 3, Jan. 1, 1982, 6 pages.

Mokrosz et al., "Structure-activity relationship studies of CNS agents. Part 14:3 Structural Requirements for the 5-HT1A and 5-HT2A receptor selectivity of simple 1-(2-pyrimidinyl)piperazine derivatives," Pharmazie 49 (1994), H. 11, 6 pages.

Database Registry [Online], Chemical Abstracts Service, Columbus, Ohio, Aug. 24, 2002, XP-02742896, 1 page.

Database Registry [Online], Chemical Abstracts Service, Columbus, Ohio, Aug. 24, 2002, XP002742897, 1 page.

Database Registry [Online], Chemical Abstracts Service, Columbus, Ohio, Aug. 24, 2002, XP002742898, 1 page.

Database Registry [Online], Chemical Abstracts Service, Columbus, Ohio, Nov. 16, 1984, XP002742899, 1 page.

Database Registry [Online], Chemical Abstracts Service, Columbus, Ohio, Sep. 3, 2004, XP002742900, 1 page.

Berge et al., "Pharmaceutical Salts," Journal of Pharmaceutical Sciences, vol. 66, No. 1, pp. 1-19, Jan. 1977.

(56) References Cited

OTHER PUBLICATIONS

Boger et al., "Thermal Cycloaddition of 1,3,5-trizine with enamines. regiospecific pyrimidine annulation," J. Org. Chem., vol. 47, No. 13, pp. 2673-2675 (1982).
Grillot et al., "Guanidinium Carboxylates: Preparation of 3-Carboxyoctahydro-9aH-pyrimidin-9a-ylium Chloride," Heterocycles, vol. 39, No. 2, pp. 435-438 (1994).
Hayakawa et al., "Addition reactions of (phenylsulfonyl)propadiene with 1-pyrrolidinyl enamines of cyclic ketones: syntheses and reactions of 1,3-dienes possessing an allyl sulfone moiety," J. Org. Chem., vol. 51, No. 26, pp. 5100-5105 (1986).
Ingebrigtsen et al., "Palladium-catalysed Synthesis of Pyrimidines," Heterocycles, vol. 65, Issue 11, pp. 2593-2603 (2005).
International Preliminary Report on Patentability issued by the International Searching Authority for International Application No. PCT/US2013-025260 dated Aug. 21, 2014, 10 pages.
International Search Report and Written Opinion issued by the International Searching Authority for International Application No. PCT/US2013/025260 dated Apr. 17, 2013, 10 pages.
Jaskowska et al., "N-Alkylation of imides using phase transfer catalysts under solvent-free conditions," J. Heterocyclic Chem., vol. 45, pp. 1371-1375, Sep.-Oct. 2008.
Movassaghi et al., "Single-Step Synthesis of Pyrimidine Derivatives," J. Am. Chem. Soc., vol. 128, No. 44, pp. 14254-14255, Sep. 4, 2006.
Quiroz et al., "A practical method for the synthesis of pyrrolizidine, indolizidine and pyrroloazepinolizidine nucleus," Tetrahedron Letters, vol. 48, Issue 8, pp. 1571-1575, Feb. 26, 2007.
Ross et al., Potential Anticancer Agents. 1 XVIII. Synthesis of Substituted 4,5-Trimethylenepyrimidines, J. Am. Chem. Soc., vol. 81, No. 12, pp. 3108-3114, Jun. 20, 1959.
Steliou et al., "Group 14 metal assisted carbon-sulfur bond formation," J. Org. Chem., vol. 50, No. 24, pp. 4969-4971 (1985).
Williams et al., "Emerging Molecular Approaches to Pain Therapy," Journal Medicinal Chemistry, vol. 42, No. 9, pp. 1481-1500, May 6, 1999.
Xi et al., "Preparation of Partially Substituted 1-Halo- and 1,4-Dihalo-1,3-dienes via Reagent-Controlled Desilylation of Halogenated 1,3-Dienes," J. Org. Chem., vol. 71, No. 8, pp. 3154-3158, Jan. 1, 2006.
Zhong et al., "Thiation Reactions of Some Active Carbonyl Compounds with Sulfur Transfer Reagents," J. Org. Chem., vol. 52, No. 2, pp. 169-172, Jan. 23, 1987.
Office Action in Canadian Application No. 2,864,085. dated Jan. 18, 2019.
Davis et al., "Benzothiophene Containing Rho Kinase Inhibitors: Efficacy in an Animal Model of Glaucoma", Bioorganic & Medicinal Chemistry Letters, vol. 20, Issue 11, pp. 3361-3366 Jun. 1, 2010.
Sridhar et al., "Synthesis and Anticancer Activity of Some Novel Pyrimidine Derivatives", International Journal of Pharmaceutical Sciences and Research, vol. 2(10), pp. 2562-2565. Sep. 29, 2011.
Shklyaeva et al., "2-Amino-6-(3,4-ethylenedioxythiophen-2-yl)-4-(2-thienyl)-pyrimidine: Synthesis and Properties", Russian Journal of Organic Chemistry, vol. 46, No. 6, pp. 938-940. 2010.
Examination Report No. 2 in Australian Application No. 2017254871. dated Aug. 30, 2019.
Notification of Reasons for Refusal in Japanese Application No. 2017-225124 (with translation). dated Sep. 3, 2019.
File Registry on STN, RN 444793-01-5. Aug. 24, 2002.
File Registry on STN, RN 444793-00-4. Aug. 24, 2002.
File Registry on STN, RN 444792-99-8. Aug. 24, 2002.
File Registry on STN, RN 40196-92-7. Nov. 16, 1984.
File Registry on STN, RN 1071058-54-2. Nov. 6, 2008.
File Registry on STN, RN 1027834-86-1. Jun. 13, 2008.
File Registry on STN, RN 40196-93-8. Nov. 16, 1984.

\* cited by examiner

HETEROARYL COMPOUNDS AND METHODS OF USE THEREOF

CROSS REFERENCE TO RELATED APPLICATIONS

This application is a divisional application of U.S. patent application Ser. No. 14/377,673, filed Aug. 8, 2014, now allowed. U.S. patent application Ser. No. 14/377,673 is a national phase filing under 35 U.S.C. § 371 of PCT International Application PCT/US2013/25260, filed Feb. 8, 2013, and published under PCT Article 21(2) as WO 2013/119895 A1 on Aug. 8, 2013. This application claims priority from U.S. provisional application 61/596,422, filed Feb. 8, 2012. The entire disclosures of all of these applications are hereby incorporated herein by reference.

I. FIELD

Provided herein are thiophene compounds useful for treating various neurological disorders, including but not limited to, psychosis and schizophrenia, compositions comprising the compounds, and methods of use thereof.

II. BACKGROUND

Central nervous system disorders affect a wide range of the population with differing severity. Generally, the major feature of this class of disorders includes the significant impairment of cognition or memory that represents a marked deterioration from a previous level of functioning.

Schizophrenia is a psychopathic disorder of unknown origin, which usually appears for the first time in early adulthood and is marked by characteristics such as, psychotic symptoms, phasic progression and development, and/or deterioration in social behavior and professional capability. Characteristic psychotic symptoms are disorders of thought content (e.g., multiple, fragmentary, incoherent, implausible or simply delusional contents, or ideas of persecution) and of mentality (e.g., loss of association, flight of imagination, incoherence up to incomprehensibility), as well as disorders of perceptibility (e.g., hallucinations), emotions (e.g., superficial or inadequate emotions), self-perceptions, intentions, impulses, and/or inter-human relationships, and psychomotoric disorders (e.g., catatonia). Other symptoms are also associated with this disorder. See, e.g., *Diagnostic and Statistical Manual of Mental Disorders*, 4$^{th}$ Ed., American Psychiatric Association (1997) (DSM-IV™).

Schizophrenia is classified into subgroups. The paranoid type is characterized by delusions and hallucinations and absence of thought disorder, disorganized behavior, and affective flattening. The disorganized type, which is also named "hebephrenic schizophrenia," in which thought disorder and flat affect are present together. The cataconic type, in which prominent psychomotor disturbances are evident, and symptoms may include catatonic stupor and waxy flexibility. The undifferentiated type in which psychotic symptoms are present but the criteria for paranoid, disorganized, or catatonic types have not been met. The symptoms of schizophrenia normally manifest themselves in three broad categories, i.e., positive, negative and cognitive symptoms. Positive symptoms are those, which represent an "excess" of normal experiences, such as hallucinations and delusions. Negative symptoms are those where the patient suffers from a lack of normal experiences, such as anhedonia and lack of social interaction. The cognitive symptoms relate to cognitive impairment in schizophrenics, such as lack of sustained attention and deficits in decision making. The current antipsychotics may be successful in treating the positive symptoms but fare less well for the negative and cognitive symptoms.

Cognitive impairment includes a decline in cognitive functions or cognitive domains, e.g., working memory, attention and vigilance, verbal learning and memory, visual learning and memory, reasoning and problem solving (e.g., executive function, speed of processing and/or social cognition). In particular, cognitive impairment may indicate deficits in attention, disorganized thinking, slow thinking, difficulty in understanding, poor concentration, impairment of problem solving, poor memory, difficulties in expressing thoughts, and/or difficulties in integrating thoughts, feelings and behavior, or difficulties in extinction of irrelevant thoughts.

Agitation is a well-recognized behavioral disorder with a range of symptoms, including hostility, extreme excitement, poor impulse control, tension and/or uncooperativeness. Agitation is common in the elderly and often associated with dementia such as those caused by Alzheimer's disease, Parkinson's disease, and Huntington's disease, and by diseases that affect blood vessels, such as stroke or multi-infarct dementia, which is caused by multiple strokes in the brain. An estimated five percent of people aged 65 and older and up to 20 percent of those aged 80 and older are affected by dementia; of these sufferers, nearly half exhibit behavioral disturbances, such as agitation, wandering, and violent outbursts. Agitated behaviors can also be manifested in cognitively intact elderly people and by those with psychiatric disorders other than dementia.

Dementia is characterized by several cognitive impairments including significant memory deficit and can stand alone, or be an underlying characteristic feature of a variety of diseases, including but not limited to, Alzheimer's disease, Parkinson's disease, Huntington's disease, and multiple sclerosis.

Therefore, there is a great need for effective treatments of various neurological disorders, including but not limited to, psychosis and schizophrenia.

III. SUMMARY

Provided herein are compounds of formula (I), or pharmaceutically acceptable salts or stereoisomers thereof:

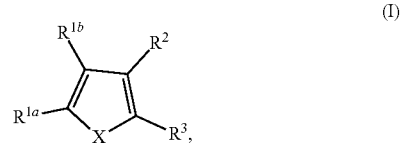

wherein $R^{1a}$, $R^{1b}$, $R^2$, and $R^3$ are defined herein elsewhere. The compounds are useful for treating various disorders, such as neurological disorders including, but not limited to, psychosis and schizophrenia.

Also provided herein are compositions and dosage forms, comprising a compound provided herein, and one or more pharmaceutically acceptable excipients. Compositions and dosage forms provided herein may further comprise one or more additional active ingredients.

Also provided herein are methods for the treatment, prevention, and/or management of various neurological disorders, including those of the central nervous system (CNS) using the compounds and compositions provided herein. In one embodiment, provided herein is a method of treating or managing one or more symptoms of a neurological disorder provided herein. Such neurological disorders include, but are not limited to, schizophrenia, schizophrenia spectrum disorder, acute schizophrenia, chronic schizophrenia, NOS schizophrenia, schizoid personality disorder, schizotypal personality disorder, delusional disorder, psychosis, psychotic disorder, brief psychotic disorder, shared psychotic disorder, psychotic disorder due to a general medical condition, drug-induced psychosis (e.g., cocaine, alcohol, amphetamine), psychoaffective disorder, aggression, delirium, Parkinson's psychosis, excitative psychosis, Tourette's syndrome, organic or NOS psychosis, seizure, agitation, post-traumatic stress disorder, behavior disorder, neurodegenerative disease, Alzheimer's disease, Parkinson's disease, dyskinesias, Huntington's disease, dementia, mood disorder, anxiety, affective disorders (e.g., depression, e.g., major depressive disorder and dysthymia; bipolar disorder, e.g., bipolar depressive disorder; manic disorder; seasonal affective disorder; and attention deficit disorder (ADD) and attention deficit hyperactivity disorder (ADHD)), obsessive-compulsive disorder, vertigo, epilepsy, pain (e.g., neuropathic pain, sensitization accompanying neuropathic pain, and inflammatory pain), fibromyalgia, migraine, cognitive impairment, cognitive impairment associated with schizophrenia (CIAS), movement disorder, restless leg syndrome (RLS), multiple sclerosis, sleep disorder, sleep apnea, narcolepsy, excessive daytime sleepiness, jet lag, drowsy side effect of medications, insomnia, substance abuse or dependency (e.g., nicotine, cocaine), addiction, eating disorder, sexual dysfunction, hypertension, emesis, Lesche-Nyhane disease, Wilson's disease, autism, Huntington's chorea, and premenstrual dysphoria.

In one embodiment, provided herein is a method of treating, preventing, and/or managing psychosis or schizophrenia. In one embodiment, provided herein is a method of treating or managing one or more symptoms of psychosis or schizophrenia. In one embodiment, provided herein is a method of treating, preventing, and/or managing psychosis or schizophrenia in a subject, such as a mammal, such as, e.g., human, rodent (such as, e.g., mice and rats), cat, dog, non-human primate, among others. In one embodiment, the method comprises contacting a compound provided herein with one or more receptors of the central nervous system. In one embodiment, the method comprises contacting a cell with a compound provided herein. In an exemplary embodiment, the cell is a brain cell, such as, e.g., a neuronal cell or a glial cell.

IV. DETAILED DESCRIPTION

Unless defined otherwise, all technical and scientific terms used herein have the same meaning as those commonly understood by one of ordinary skill in the art. In certain embodiments, abbreviations are as defined in *J. Org. Chem.* 2007, 72, 23A. All publications and patents referred to herein are incorporated by reference herein in their entireties.

A. Definitions

As used in the specification and the accompanying claims, the indefinite articles "a" and "an" and the definite article "the" include plural as well as singular referents, unless the context clearly dictates otherwise.

As used herein, and unless otherwise indicated, the term "alkyl" refers to a linear or branched saturated monovalent hydrocarbon radical, wherein the alkyl may optionally be substituted with one or more substituents. In certain embodiments, the alkyl is a linear saturated monovalent hydrocarbon radical that has 1 to 20 ($C_{1-20}$), 1 to 15 ($C_{1-15}$), 1 to 12 ($C_{1-12}$), 1 to 10 ($C_{1-10}$), or 1 to 6 ($C_{1-6}$) carbon atoms, or branched saturated monovalent hydrocarbon radical of 3 to 20 ($C_{3-20}$), 3 to 15 ($C_{3-15}$), 3 to 12 ($C_{3-12}$), 3 to 10 ($C_{3-10}$), or 3 to 6 ($C_{3-6}$) carbon atoms. As used herein, linear $C_{1-6}$ and branched $C_{3-6}$ alkyl groups are also referred as "lower alkyl." Examples of alkyl groups include, but are not limited to, methyl, ethyl, propyl (including all isomeric forms, e.g., n-propyl and isopropyl), butyl (including all isomeric forms, e.g, n-butyl, isobutyl, and t-butyl), pentyl (including all isomeric forms), and hexyl (including all isomeric forms). For example, $C_{1-6}$ alkyl refers to a linear saturated monovalent hydrocarbon radical of 1 to 6 carbon atoms or a branched saturated monovalent hydrocarbon radical of 3 to 6 carbon atoms. In certain embodiments, the alkyl is optionally substituted as described herein elsewhere.

As used herein, and unless otherwise specified, the term "alkenyl" refers to a linear or branched monovalent hydrocarbon radical, which contains one or more, in one embodiment, one to five, carbon-carbon double bonds. The alkenyl may be optionally substituted with one or more substituents. The term "alkenyl" also encompasses radicals having "cis" and "trans" configurations, or alternatively, "E" and "Z" configurations, as appreciated by those of ordinary skill in the art. For example, $C_{2-6}$ alkenyl refers to a linear unsaturated monovalent hydrocarbon radical of 2 to 6 carbon atoms or a branched unsaturated monovalent hydrocarbon radical of 3 to 6 carbon atoms. In certain embodiments, the alkenyl is a linear monovalent hydrocarbon radical of 2 to 20 ($C_{2-20}$), 2 to 15 ($C_{2-15}$), 2 to 12 ($C_{2-12}$), 2 to 10 ($C_{2-10}$), or 2 to 6 ($C_{2-6}$) carbon atoms, or a branched monovalent hydrocarbon radical of 3 to 20 ($C_{3-20}$), 3 to 15 ($C_{3-15}$), 3 to 12 ($C_{3-12}$), 3 to 10 ($C_{3-10}$), or 3 to 6 ($C_{3-6}$) carbon atoms. Examples of alkenyl groups include, but are not limited to, ethenyl, propen-1-yl, propen-2-yl, allyl, butenyl, and 4-methylbutenyl. In certain embodiments, the alkenyl is optionally substituted as described herein elsewhere.

As used herein, and unless otherwise specified, the term "alkynyl" refers to a linear or branched monovalent hydrocarbon radical, which contains one or more, in one embodiment, one to five, carbon-carbon triple bonds. The alkynyl may be optionally substituted with one or more substituents. In certain embodiments, the alkynyl is a linear monovalent hydrocarbon radical of 2 to 20 ($C_{2-20}$), 2 to 15 ($C_{2-15}$), 2 to 12 ($C_{2-12}$), 2 to 10 ($C_{2-10}$), or 2 to 6 ($C_{2-6}$) carbon atoms, or a branched monovalent hydrocarbon radical of 3 to 20 ($C_{3-20}$), 3 to 15 ($C_{3-15}$), 3 to 12 ($C_{3-12}$), 3 to 10 ($C_{3-10}$), or 3 to 6 ($C_{3-6}$) carbon atoms. Examples of alkynyl groups include, but are not limited to, ethynyl (—C≡CH) and propargyl (—$CH_2$C≡CH). For example, $C_{2-6}$ alkynyl refers to a linear unsaturated monovalent hydrocarbon radical of 2 to 6 carbon atoms or a branched unsaturated monovalent hydrocarbon radical of 3 to 6 carbon atoms. In certain embodiments, the alkynyl is optionally substituted as described herein elsewhere.

As used herein, and unless otherwise specified, the term "cycloalkyl" refers to a cyclic fully or partially saturated bridged and/or non-bridged hydrocarbon radical or ring system, which may be optionally substituted with one or more substituents. In certain embodiments, the cycloalkyl has from 3 to 20 ($C_{3-20}$), from 3 to 15 ($C_{3-15}$), from 3 to 12 ($C_{3-12}$), from 3 to 10 ($C_{3-10}$), or from 3 to 7 ($C_{3-7}$) carbon atoms. Examples of cycloalkyl groups include, but are not limited to, cyclopropyl, cyclobutyl, cyclopentyl, cyclohexyl, cycloheptyl, decalinyl, and adamantyl. In certain embodiments, the cycloalkyl is optionally substituted as described herein elsewhere.

As used herein, and unless otherwise specified, the term "heteroalkyl" refers to a stable straight or branched chain, or cyclic hydrocarbon radical, or combinations thereof, consisting of the stated number of carbon atoms and from one or more, in one embodiment, one to three, heteroatoms selected from the group consisting of O, N, Si, and S, and wherein the nitrogen and sulfur atoms are optionally oxidized and the nitrogen heteroatom can optionally be quaternized. In one embodiment, the heteroatom(s) O, N and S can be placed at any interior position of the heteroalkyl group. In one embodiment, the heteroatom Si can be placed at any position of the heteroalkyl group (e.g., interior or terminal position), including the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms can be consecutive, such as, for example, —$CH_2$—NH—O—$CH_3$ and —$CH_2$—O—Si($CH_3$)$_3$. In certain embodiments, the heteroalkyl is optionally substituted as described herein elsewhere.

As used herein, and unless otherwise specified, the term "alkoxyl" refers to a stable straight or branched chain, or cyclic hydrocarbon radical, or combinations thereof, consisting of the stated number of carbon atoms and from one or more, in one embodiment, one to three, O atoms. Examples of alkoxyl include, but are not limited to, —O—$CH_3$, —O—$CF_3$, —O—$CH_2$—$CH_3$, —O—$CH_2$—$CH_2$—$CH_3$, —O—CH—($CH_3$)$_2$, and —O—$CH_2$—$CH_2$—O—$CH_3$. In one embodiment, the alkoxyl is optionally substituted as described herein elsewhere.

As used herein, and unless otherwise specified, the term "aminoalkyl" refers to a stable straight or branched chain, or cyclic hydrocarbon radical, or combinations thereof, consisting of the stated number of carbon atoms and from one or more, in one embodiment, one to three, N atoms. Examples of aminoalkyl include, but are not limited to, —NH—$CH_3$, —N($CH_3$)$_2$, —NH—$CH_2$—$CH_3$, —N($CH_3$)—$CH_2$—$CH_3$, —NH—CH—($CH_3$)$_2$, —$CH_2$—$CH_2$—NH—$CH_3$, and —$CH_2$—$CH_2$—N($CH_3$)$_2$. In one embodiment, the aminoalkyl is optionally substituted as described herein elsewhere. In some embodiments, the aminoalkyl is optionally substituted with one or more halo.

As used herein, and unless otherwise specified, the term "aryl" refers to an optionally substituted monocyclic or multicyclic radical or ring system that contains at least one aromatic hydrocarbon ring. In certain embodiments, the aryl has from 6 to 20, from 6 to 15, or from 6 to 10 ring atoms. Examples of aryl groups include, but are not limited to, phenyl, naphthyl, fluorenyl, azulenyl, anthryl, phenanthryl, pyrenyl, biphenyl, and terphenyl. In certain embodiments, aryl also refers to bicyclic, tricyclic, or tetracyclic carbon rings, where one of the rings is aromatic and the other(s) of the rings may be saturated, partially unsaturated, or aromatic, for example, dihydronaphthyl, indenyl, indanyl, or tetrahydronaphthyl (tetralinyl). In certain embodiments, aryl may be a bicyclic, tricyclic, or tetracyclic ring system, where at least one of the rings is aromatic and one or more of the ring(s) is/are saturated or partially unsaturated containing one or more heteroatoms independently selected from O, S, and N. In certain embodiments, the aryl is optionally substituted with one or more substituents as described herein elsewhere.

As used herein, and unless otherwise specified, the term "arylalkyl" or "aralkyl" refers to a monovalent alkyl group substituted with aryl. Example of aralkyl includes, but is not limited to, benzyl. In certain embodiments, both alkyl and aryl may be optionally substituted with one or more substituents as described herein elsewhere.

As used herein, and unless otherwise specified, the term "cycloalkylalkyl" refers to a monovalent alkyl group substituted with cycloalkyl. In certain embodiments, both the alkyl and cycloalkyl may be optionally substituted with one or more substituents as described herein elsewhere.

As used herein, and unless otherwise specified, the term "heteroaryl" refers to an optionally substituted monocyclic or multicyclic radical or ring system which contains at least one aromatic ring having one or more heteroatoms independently selected from O, S, and N. In one embodiment, each ring of a heteroaryl group can contain one or two O atoms, one or two S atoms, and/or one to four N atoms, provided that the total number of heteroatoms in each ring is four or less and each ring contains at least one carbon atom. In certain embodiments, the heteroaryl has from 5 to 20, from 5 to 15, or from 5 to 10 ring atoms. In certain embodiments, heteroaryl also refers to bicyclic, tricyclic, or tetracyclic rings, where one of the rings is aromatic having one or more heteroatoms independently selected from O, S, and N, and the other(s) of the rings may be saturated, partially unsaturated, or aromatic and may be carbocyclic or contain one or more heteroatoms independently selected from O, S, and N. Examples of monocyclic heteroaryl groups include, but are not limited to, furanyl, imidazolyl, isothiazolyl, isoxazolyl, oxadiazolyl, oxazolyl, pyrazinyl, pyrazolyl, pyridazinyl, pyridyl, pyrimidinyl, pyrrolyl, thiadiazolyl, thiazolyl, thienyl, tetrazolyl, triazinyl, and triazolyl. Examples of bicyclic heteroaryl groups include, but are not limited to, benzofuranyl, benzimidazolyl, benzoisoxazolyl, benzopyranyl, benzothiadiazolyl, benzothiazolyl, benzothienyl, benzotriazolyl, benzoxazolyl, furopyridyl, imidazopyridinyl, imidazothiazolyl, indolizinyl, indolyl, indazolyl, isobenzofuranyl, isobenzothienyl, isoindolyl, isoquinolinyl, isothiazolyl, naphthyridinyl, oxazolopyridinyl, phthalazinyl, pteridinyl, purinyl, pyridopyridyl, pyrrolopyridyl, quinolinyl, quinoxalinyl, quinazolinyl, thiadiazolopyrimidyl, and thienopyridyl. Examples of tricyclic heteroaryl groups include, but are not limited to, acridinyl, benzindolyl, carbazolyl, dibenzofuranyl, perimidinyl, phenanthrolinyl, phenanthridinyl, phenarsazinyl, phenazinyl, phenothiazinyl, phenoxazinyl, and xanthenyl. In certain embodiments, the heteroaryl is optionally substituted with one or more substituents as described herein elsewhere.

As used herein, and unless otherwise specified, the term "heterocycloalkyl" or "heterocyclyl" refers to an optionally substituted monocyclic or multicyclic radical or ring system which contains at least one non-aromatic ring having one or more heteroatoms independently selected from O, S, and N, and the remaining ring atoms are carbon atoms. In certain embodiments, the heterocyclyl or heterocycloalkyl group has from 3 to 20, from 3 to 15, from 3 to 10, from 3 to 8, from 4 to 7, or from 5 to 6 ring atoms. In certain embodiments, the heterocyclyl or heterocycloalkyl is a monocyclic, bicyclic, tricyclic, or tetracyclic ring system, which may include a fused or bridged ring system, and in which the nitrogen or sulfur atoms may be optionally oxidized, the nitrogen atoms may be optionally quaternized, the ring carbon atoms may be optionally substituted with oxo, and some rings may be partially or fully saturated, or aromatic. The heterocycloalkyl or heterocyclyl may be attached to the main structure at a heteroatom or a carbon atom which results in the creation of a stable compound. Examples include, but are not limited to, azepinyl, benzodioxanyl, benzodioxolyl, benzofuranonyl, benzopyranonyl, benzopyranyl, benzotetrahydrofuranyl, benzotetrahydrothienyl, benzothiopyranyl, benzoxazinyl, β-carbolinyl, chromanyl, chromonyl, cinnolinyl, coumarinyl, decahydroisoquinolinyl, dihydrobenzisothiazinyl, dihydrobenzisoxazinyl, dihydrofuryl, dihydroisoindolyl, dihydropyranyl, dihydropyrazolyl, dihydropyrazinyl, dihydropyridinyl, dihydropyrimidinyl, dihydropyrrolyl, dioxolanyl, 1,4-dithianyl, furanonyl, imidazolidinyl, imidazolinyl, indolinyl, isobenzotetrahydrofuranyl, isobenzotetrahydrothienyl, isochromanyl, isocoumarinyl, isoindolinyl, isothiazolidinyl, isoxazolidinyl, morpholinyl, octahydroindolyl, octahydroisoindolyl, oxazolidinonyl, oxazolidinyl, oxiranyl, piperazinyl, piperidinyl, 4-piperidonyl, pyrazolidinyl, pyrazolinyl, pyrrolidinyl, pyrrolinyl, quinuclidinyl, tetrahydrofuryl, tetrahydroisoquinolinyl, tetrahydropyranyl, tetrahydrothienyl, thiamorpholinyl, thiazolidinyl, tetrahydroquinolinyl, and 1,3,5-trithianyl. In certain embodiments, when the heterocyclyl or heterocycloalkyl ring contains one or more O, the heterocyclyl or heterocycloalkyl may also be referred to as "cycloalkoxyl." In certain embodiments, the heterocyclyl or heterocycloalkyl is optionally substituted with one or more substituents as described herein elsewhere.

As used herein, and unless otherwise specified, the term "halogen", "halide" or "halo" refers to fluorine, chlorine, bromine, and iodine.

As used herein, and unless otherwise specified, the term "hydrogen" encompasses proton ($^1$H), deuterium ($^2$H), tritium ($^3$H), and/or mixtures thereof. In a compound described herein, one or more positions occupied by hydrogen may be enriched with deuterium and/or tritium. Such isotopically enriched analogs may be prepared from suitable isotopically labeled starting material obtained from a commercial source or prepared using known literature procedures.

The term "combination treatment," as used herein, encompasses administration of two or more agents to a subject so that both agents and/or their metabolites are present in the subject at the same time. Combination treatment can include simultaneous administration in separate compositions, administration at different times in separate compositions, or administration in a composition in which both agents are present.

As used herein, and unless otherwise specified, the term "optionally substituted" is intended to mean that a group, such as an alkyl, alkenyl, alkynyl, cycloalkyl, heteroalkyl, aryl, aralkyl, cycloalkylalkyl, heteroaryl, or heterocyclyl, may be substituted with one or more substituents independently selected from, e.g., (a) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl, each optionally substituted with one or more, in one embodiment, one, two, three, or four, substituents $Q^1$; and (b) halo, cyano (—CN), nitro (—NO$_2$), —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O) NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$) NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —SR$^a$, —S(O)R$^a$, —S(O)$_2$R$^a$, —S(O) NR$^b$R$^c$, and —S(O)$_2$NR$^b$R$^c$, wherein each R$^a$, R$^b$, R$^c$, and R$^d$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more, in one embodiment, one, two, three, or four, substituents $Q^1$; or (iii) R$^b$ and R$^c$ together with the N atom to which they are attached form heteroaryl or heterocyclyl, optionally substituted with one or more, in one embodiment, one, two, three, or four, substituents $Q^1$. As used herein, all groups that can be substituted are "optionally substituted," unless otherwise specified.

In one embodiment, each $Q^1$ is independently selected from the group consisting of (a) cyano, halo, and nitro; and (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl; and (c) —C(O)R$^e$, —C(O)OR$^e$, —C(O)NR$^f$R$^g$, —C(NR$^e$) NR$^f$R$^g$, —OC(O)R$^e$, —OC(O)OR$^e$, —OC(O)NR$^f$R$^g$, —OC (=NR$^e$)NR$^f$R$^g$, —OS(O)R$^e$, —OS(O)$_2$R$^e$, —OS(O)NR$^f$R$^g$, —OS(O)$_2$NR$^f$R$^g$, —NR$^f$R$^g$, —NR$^e$C(O)R$^h$, —NR$^e$C(O) OR$^h$, —NR$^e$C(O)NR$^f$R$^g$, —NR$^e$C(=NR$^h$)NR$^f$R$^g$, —NR$^e$S (O)R$^h$, —NR$^e$S(O)$_2$R$^h$, —NR$^e$S(O)NR$^f$R$^g$, —NR$^e$S(O)$_2$ NR$^f$R$^g$, —S(O)R$^e$, —S(O)$_2$R$^e$, —S(O)NR$^f$R$^g$, and —S(O)$_2$ NR$^f$R$^g$; wherein each R$^e$, R$^f$, R$^g$, and R$^h$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (iii) R$^f$ and R$^g$ together with the N atom to which they are attached form heteroaryl or heterocyclyl.

As used herein, and unless otherwise specified, the term "pharmaceutically acceptable salts" refers to salts prepared from pharmaceutically acceptable non-toxic acids, including inorganic acids and organic acids. Suitable non-toxic acids include inorganic and organic acids, such as, including but not limited to, acetic, alginic, anthranilic, benzenesulfonic, benzoic, camphorsulfonic, citric, ethenesulfonic, formic, fumaric, furoic, gluconic, glutamic, glucorenic, galacturonic, glycidic, hydrobromic, hydrochloric, isethionic, lactic, maleic, malic, mandelic, methanesulfonic, mucic, nitric, pamoic, pantothenic, phenylacetic, propionic, phosphoric, salicylic, stearic, succinic, sulfanilic, sulfuric, tartaric acid, and p-toluenesulfonic.

As used herein, and unless otherwise specified, the term "solvate" refers to a compound provided herein or a salt thereof, which further includes a stoichiometric or non-stoichiometric amount of solvent bound by non-covalent intermolecular forces. Where the solvent is water, the solvate is a hydrate. In certain embodiments, a compound as disclosed herein may be provided as a solvate. In certain embodiments, a compound as disclosed herein may be provided as a hydrate.

As used herein, and unless otherwise specified, the term "stereoisomer" encompasses all enantiomerically/diastereomerically/stereomerically pure and enantiomerically/diastereomerically/stereomerically enriched compounds provided herein.

As used herein and unless otherwise specified, the term "stereomerically pure" means a composition that comprises one stereoisomer of a compound and is substantially free of other stereoisomers of that compound. For example, a stereomerically pure composition of a compound having one chiral center will be substantially free of the opposite enantiomer of the compound. A stereomerically pure composition of a compound having two chiral centers will be substantially free of other diastereomers of the compound. A typical stereomerically pure compound comprises greater than about 80% by weight of one stereoisomer of the compound and less than about 20% by weight of other stereoisomers of the compound, greater than about 90% by weight of one stereoisomer of the compound and less than about 10% by weight of the other stereoisomers of the compound, greater than about 95% by weight of one stereoisomer of the compound and less than about 5% by weight of the other stereoisomers of the compound, greater than about 97% by weight of one stereoisomer of the compound and less than about 3% by weight of the other stereoisomers of the compound, or greater than about 99% by weight of one stereoisomer of the compound and less than about 1% by weight of the other stereoisomers of the compound.

As used herein and unless otherwise indicated, the term "stereomerically enriched" means a composition that comprises greater than about 55% by weight of one stereoisomer of a compound, greater than about 60% by weight of one stereoisomer of a compound, greater than about 70% by weight, or greater than about 80% by weight of one stereoisomer of a compound.

As used herein, and unless otherwise indicated, the term "enantiomerically pure" means a stereomerically pure composition of a compound having one chiral center. Similarly, the term "enantiomerically enriched" means a stereomerically enriched composition of a compound having one chiral center.

In certain embodiments, as used herein, and unless otherwise specified, "optically active" and "enantiomerically active" refer to a collection of molecules, which has an enantiomeric excess or diastereomeric excess of no less than about 50%, no less than about 70%, no less than about 80%, no less than about 90%, no less than about 91%, no less than about 92%, no less than about 93%, no less than about 94%, no less than about 95%, no less than about 96%, no less than about 97%, no less than about 98%, no less than about 99%, no less than about 99.5%, or no less than about 99.8%. In certain embodiments, the compound comprises about 95% or more of the desired enantiomer or diastereomer and about 5% or less of the less preferred enantiomer or diastereomer based on the total weight of the racemate in question.

In describing an optically active compound, the prefixes R and S are used to denote the absolute configuration of the molecule about its chiral center(s). The (+) and (−) are used to denote the optical rotation of the compound, that is, the direction in which a plane of polarized light is rotated by the optically active compound. The (−) prefix indicates that the compound is levorotatory, that is, the compound rotates the plane of polarized light to the left or counterclockwise. The (+) prefix indicates that the compound is dextrorotatory, that is, the compound rotates the plane of polarized light to the right or clockwise. However, the sign of optical rotation, (+) and (−), is not related to the absolute configuration of the molecule, R and S.

As used herein, and unless otherwise specified, the term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 30%, 25%, 20%, 15%, 10%, 9%, 8%, 7%, 6%, 5%, 4%, 3%, 2%, 1%, 0.5%, 0.1%, or 0.05% of a given value or range.

As used herein, and unless otherwise specified, the term "pharmaceutically acceptable carrier," "pharmaceutically acceptable excipient," "physiologically acceptable carrier," or "physiologically acceptable excipient" refers to a pharmaceutically-acceptable material, composition, or vehicle, such as a liquid or solid filler, diluent, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, *Remington: The Science and Practice of Pharmacy,* 21st Edition, Lippincott Williams & Wilkins: Philadelphia, Pa., 2005; *Handbook of Pharmaceutical Excipients,* 5th Edition, Rowe et al., Eds., The Pharmaceutical Press and the American Pharmaceutical Association: 2005; and *Handbook of Pharmaceutical Additives,* 3rd Edition, Ash and Ash Eds., Gower Publishing Company: 2007; *Pharmaceutical Preformulation and Formulation,* 2nd Edition, Gibson Ed., CRC Press LLC: Boca Raton, Fla., 2009.

As used herein, and unless otherwise specified, the terms "active ingredient" and "active substance" refer to a compound, which is administered, alone or in combination with one or more pharmaceutically acceptable excipients, to a subject for treating, preventing, or ameliorating one or more symptoms of a condition, disorder, or disease. As used herein, "active ingredient" and "active substance" may be an optically active isomer of a compound described herein.

As used herein, and unless otherwise specified, the terms "drug" and "therapeutic agent" refer to a compound, or a pharmaceutical composition thereof, which is administered to a subject for treating, preventing, managing, or ameliorating one or more symptoms of a condition, disorder, or disease.

As used herein, and unless otherwise indicated, the terms "treat," "treating" and "treatment" refer to the eradication or amelioration of a disease or disorder, or of one or more symptoms associated with the disease or disorder. In one embodiment, such symptoms are those known to a person of skill in the art to be associated with the disease or disorder being treated. In certain embodiments, the terms refer to minimizing the spread or worsening of the disease or disorder resulting from the administration of one or more prophylactic or therapeutic agents to a subject with such a disease or disorder. In some embodiments, the terms refer to the administration of a compound provided herein, with or without other additional active agent, after the onset of symptoms of the particular disease.

As used herein, and unless otherwise indicated, the terms "prevent," "preventing" and "prevention" refer to the prevention of the onset, recurrence or spread of a disease or disorder, or of one or more symptoms associated with the disease or disorder. In one embodiment, such symptoms are those known to a person of skill in the art to be associated with the disease or disorder being prevented. In certain embodiments, the terms refer to the treatment with or administration of a compound provided herein, with or without other additional active compound, prior to the onset of symptoms, particularly to patients at risk of disease or disorders provided herein. The terms encompass the inhibition or reduction of a symptom of the particular disease. Patients with familial history of a disease in particular are candidates for preventive regimens in certain embodiments. In addition, patients who have a history of recurring symptoms are also potential candidates for the prevention. In this regard, the term "prevention" may be interchangeably used with the term "prophylactic treatment."

As used herein, and unless otherwise specified, the terms "manage," "managing," and "management" refer to preventing or slowing the progression, spread or worsening of a disease or disorder, or of one or more symptoms associated with the disease or disorder. In one embodiment, such symptoms are those known to a person of skill in the art to be associated with the disease or disorder being managed.

Often, the beneficial effects that a subject derives from a prophylactic and/or therapeutic agent do not result in a cure of the disease or disorder. In this regard, the term "managing" encompasses treating a patient who had suffered from the particular disease in an attempt to prevent or minimize the recurrence of the disease.

As used herein, and unless otherwise specified, a "therapeutically effective amount" of a compound is an amount sufficient to provide a therapeutic benefit in the treatment or management of a disease or disorder, or to delay or minimize one or more symptoms associated with the disease or disorder. A therapeutically effective amount of a compound means an amount of therapeutic agent, alone or in combination with other therapies, which provides a therapeutic benefit in the treatment or management of the disease or disorder. The term "therapeutically effective amount" can encompass an amount that improves overall therapy, reduces or avoids symptoms or causes of disease or disorder, or enhances the therapeutic efficacy of another therapeutic agent.

As used herein, and unless otherwise specified, a "prophylactically effective amount" of a compound is an amount sufficient to prevent a disease or disorder, or prevent its recurrence. A prophylactically effective amount of a compound means an amount of therapeutic agent, alone or in combination with other agents, which provides a prophylactic benefit in the prevention of the disease. The term "prophylactically effective amount" can encompass an amount that improves overall prophylaxis or enhances the prophylactic efficacy of another prophylactic agent.

As used herein, and unless otherwise specified, the term "subject" is defined herein to include animals such as mammals, including, but not limited to, primates (e.g., humans), cows, sheep, goats, horses, dogs, cats, rabbits, rats, mice and the like. In specific embodiments, the subject is a human.

As used herein, and unless otherwise specified, the term "neurological disorder" refers to any condition of the central or peripheral nervous system of a mammal. The term "neurological disorder" includes, but is not limited to, neurodegenerative diseases (e.g., Alzheimer's disease, Parkinson's disease and amyotrophic lateral sclerosis), neuropsychiatric diseases (e.g., schizophrenia and anxieties, such as general anxiety disorder), and affective disorders (e.g., depression, bipolar disorder, manic conditions, and attention deficit disorder). Exemplary neurological disorders include, but are not limited to, MLS (cerebellar ataxia), Huntington's disease, Down syndrome, multi-infarct dementia, status epilecticus, contusive injuries (e.g., spinal cord injury and head injury), viral infection induced neurodegeneration, (e.g., AIDS, encephalopathies), epilepsy, benign forgetfulness, closed head injury, sleep disorders, major depressive disorder, dysthymia, seasonal affective disorder, dementias, movement disorders, psychosis, alcoholism, post-traumatic stress disorder, and the like. "Neurological disorder" also includes any condition associated with the disorder. For instance, a method of treating a neurodegenerative disorder includes methods of treating loss of memory and/or loss of cognition associated with a neurodegenerative disorder. An exemplary method would also include treating or preventing loss of neuronal function characteristic of neurodegenerative disorder. "Neurological disorder" also includes any disease or condition that is implicated, at least in part, in monoamine (e.g., norepinephrine) signaling pathways (e.g., cardiovascular disease).

As used herein, and unless otherwise specified, the terms "psychosis," "schizophrenia," "obsessive-compulsive disorder," "substance abuse," "anxiety," "eating disorders," "migraine," and other CNS or neurological disorders described herein elsewhere are used herein in a manner consistent with their accepted meanings in the art. See, e.g., *Diagnostic and Statistical Manual of Mental Disorders, 4th* Ed., American Psychiatric Association (1997) (DSM-IV™).

As used herein, and unless otherwise specified, the term "seizure" refers to a neurological disorder and may be used interchangeably with "convulsion," although there are many types of seizure, some of which have subtle or mild symptoms instead of convulsions. In one embodiment, the term "seizure" as used herein is intended to encompass "convulsion." In some embodiments, seizures may be caused by disorganized and sudden electrical activity in the brain. In some embodiments, convulsions are a rapid and uncontrollable shaking during which the muscles contract and relax repeatedly. Unless otherwise specified, the terms "convulsion" and "seizure" are used herein in accordance with the accepted meanings as found in the *Diagnostic and Statistical Manual of Mental Disorders, 4th* Ed., American Psychiatric Association (1997) (DSM-IV™).

As used herein, and unless otherwise specified, the term "affective disorder" includes depression, attention deficit disorder, attention deficit disorder with hyperactivity, bipolar disorder, and manic disorder, and the like.

As used herein, and unless otherwise specified, the term "depression" includes all forms of depression, including, but not limited to, major depressive disorder (MDD) or unipolar depressive disorder, dysthymia, seasonal affective disorder (SAD), and bipolar depressive disorder. "Major depressive disorder" is used herein interchangeably with "unipolar depression", "unipolar depressive disorder", and "major depression." "Depression" may also include any condition commonly associated with depression, such as all forms of fatigue (e.g., chronic fatigue syndrome) and cognitive deficits.

Unless otherwise specified, the terms "bipolar disorder" and "manic disorder" are used herein in accordance with the accepted meanings as found in the *Diagnostic and Statistical Manual of Mental Disorders, 4th* Ed., American Psychiatric Association (1997) (DSM-IV™).

Unless otherwise specified, the terms "attention deficit disorder" (ADD), and "attention deficit disorder with hyperactivity" (ADDH) or "attention deficit hyperactivity disorder" (ADHD), are used herein in accordance with the accepted meanings as found in the *Diagnostic and Statistical Manual of Mental Disorders, 4th* Ed., American Psychiatric Association (1997) (DSM-IV™).

As used herein, and unless otherwise specified, the term "pain" refers to an unpleasant sensory and emotional experience. Unless otherwise specified, the term "pain," as used herein, refers to all categories of pain, including pain that is described in terms of stimulus or nerve response, e.g., somatic pain (normal nerve response to a noxious stimulus) and neuropathic pain (abnormal response of a injured or altered sensory pathway, often without clear noxious input); pain that is categorized temporally, e.g., chronic pain and acute pain; pain that is categorized in terms of its severity, e.g., mild, moderate, or severe; and pain that is a symptom or a result of a disease state or syndrome, e.g., inflammatory pain, cancer pain, AIDS pain, arthropathy, migraine, trigeminal neuralgia, cardiac ischaemia, and diabetic peripheral neuropathic pain (See, e.g., Harrison's Principles of Internal Medicine, pp. 93-98 (Wilson et al., eds., 12th ed. 1991); Williams et al., *J. of Med. Chem.* 42: 1481-1485 (1999), herein each incorporated by reference in their entirety). "Pain" is also meant to include mixed etiology pain, dual mechanism pain, allodynia, causalgia, central pain, hyperesthesia, hyperpathia, dysesthesia, and hyperalgesia. In one embodiment, the term "pain" includes pain resulting from dysfunction of the nervous system: organic pain states that share clinical features of neuropathic pain and possible common pathophysiology mechanisms, but are not initiated by an identifiable lesion in any part of the nervous system.

Unless otherwise specified, the term "somatic pain," as used herein, refers to a normal nerve response to a noxious stimulus such as injury or illness, e.g., trauma, burn, infection, inflammation, or disease process such as cancer, and includes both cutaneous pain (e.g., skin, muscle or joint derived) and visceral pain (e.g., organ derived).

Unless otherwise specified, the term "neuropathic pain," as used herein, refers to a heterogeneous group of neurological conditions that result from damage to the nervous system. The term also refers to pain resulting from injury to or dysfunctions of peripheral and/or central sensory pathways, and from dysfunctions of the nervous system, where the pain often occurs or persists without an obvious noxious input. This includes pain related to peripheral neuropathies as well as central neuropathic pain. Common types of peripheral neuropathic pain include diabetic neuropathy (also called diabetic peripheral neuropathic pain, or DN, DPN, or DPNP), post-herpetic neuralgia (PHN), and trigeminal neuralgia (TGN). Central neuropathic pain, involving damage to the brain or spinal cord, can occur following stroke, spinal cord injury, and as a result of multiple sclerosis, and is also encompassed by the term. Other types of pain that are meant to be included in the definition of neuropathic pain include, but are not limited to, neuropathic cancer pain, HIV/AIDS induced pain, phantom limb pain, and complex regional pain syndrome. Unless otherwise specified, the term also encompasses the common clinical features of neuropathic pain including, but not limited to, sensory loss, allodynia (non-noxious stimuli produce pain), hyperalgesia and hyperpathia (delayed perception, summation, and painful after sensation). Pain is often a combination of nociceptive and neuropathic types, for example, mechanical spinal pain and radiculopathy or myelopathy.

As used herein, and unless otherwise specified, the term "acute pain" refers to the normal, predicted physiological response to a noxious chemical, thermal or mechanical stimulus typically associated with invasive procedures, trauma and disease. It is generally time-limited, and may be viewed as an appropriate response to a stimulus that threatens and/or produces tissue injury. The term also refers to pain which is marked by short duration or sudden onset.

As used herein, and unless otherwise specified, the term "chronic pain" encompasses the pain occurring in a wide range of disorders, for example, trauma, malignancies and chronic inflammatory diseases such as rheumatoid arthritis. Chronic pain may last more than about six months. In addition, the intensity of chronic pain may be disproportionate to the intensity of the noxious stimulus or underlying process. The term also refers to pain associated with a chronic disorder, or pain that persists beyond resolution of an underlying disorder or healing of an injury, and that is often more intense than the underlying process would predict. It may be subject to frequent recurrence.

As used herein, and unless otherwise specified, the term "inflammatory pain" is pain in response to tissue injury and the resulting inflammatory process. Inflammatory pain is adaptive in that it elicits physiologic responses that promote healing. However, inflammation may also affect neuronal function. Inflammatory mediators, including $PGE_2$ induced by the COX2 enzyme, bradykinins, and other substances, bind to receptors on pain-transmitting neurons and alter their function, increasing their excitability and thus increasing pain sensation. Much chronic pain has an inflammatory component. The term also refers to pain which is produced as a symptom or a result of inflammation or an immune system disorder.

As used herein, and unless otherwise specified, the term "visceral pain" refers to pain which is located in an internal organ.

As used herein, and unless otherwise specified, the term "mixed etiology pain" refers to pain that contains both inflammatory and neuropathic components.

As used herein, and unless otherwise specified, the term "dual mechanism pain" refers to pain that is amplified and maintained by both peripheral and central sensitization.

As used herein, and unless otherwise specified, the term "causalgia" refers to a syndrome of sustained burning, allodynia, and hyperpathia after a traumatic nerve lesion, often combined with vasomotor and sudomotor dysfunction and later trophic changes. As used herein, and unless otherwise specified, the term "central pain" refers to pain initiated by a primary lesion or dysfunction in the central nervous system.

As used herein, and unless otherwise specified, the term "hyperesthesia" refers to increased sensitivity to stimulation, excluding the special senses.

As used herein, and unless otherwise specified, the term "hyperpathia" refers to a painful syndrome characterized by an abnormally painful reaction to a stimulus, especially a repetitive stimulus, as well as an increased threshold. It may occur with allodynia, hyperesthesia, hyperalgesia, or dysesthesia.

As used herein, and unless otherwise specified, the term "dysesthesia" refers to an unpleasant abnormal sensation, whether spontaneous or evoked. In certain embodiments, dysesthesia include hyperalgesia and allodynia.

As used herein, and unless otherwise specified, the term "hyperalgesia" refers to an increased response to a stimulus that is normally painful. It reflects increased pain on suprathreshold stimulation.

As used herein, and unless otherwise specified, the term "allodynia" refers to pain due to a stimulus that does not normally provoke pain.

As used herein, and unless otherwise specified, the term "diabetic peripheral neuropathic pain" (DPNP), also called diabetic neuropathy, DN or diabetic peripheral neuropathy), refers to chronic pain caused by neuropathy associated with diabetes mellitus. The classic presentation of DPNP is pain or tingling in the feet that can be described not only as "burning" or "shooting" but also as severe aching pain. Less commonly, patients may describe the pain as itching, tearing, or like a toothache. The pain may be accompanied by allodynia and hyperalgesia and an absence of symptoms, such as numbness.

As used herein, and unless otherwise specified, the term "post-herpetic neuralgia", also called "postherpetic neuralgia" (PHN), refers to a painful condition affecting nerve fibers and skin. Without being limited by a particular theory, it is a complication of shingles, a second outbreak of the varicella zoster virus (VZV), which initially causes chickenpox.

As used herein, and unless otherwise specified, the term "neuropathic cancer pain" refers to peripheral neuropathic pain as a result of cancer, and can be caused directly by infiltration or compression of a nerve by a tumor, or indirectly by cancer treatments such as radiation therapy and chemotherapy (chemotherapy-induced neuropathy).

As used herein, and unless otherwise specified, the term "HIV/AIDS peripheral neuropathy" or "HIV/AIDS related neuropathy" refers to peripheral neuropathy caused by HIV/AIDS, such as acute or chronic inflammatory demyelinating neuropathy (AIDP and CIDP, respectively), as well as peripheral neuropathy resulting as a side effect of drugs used to treat HIV/AIDS.

As used herein, and unless otherwise specified, the term "phantom limb pain" refers to pain appearing to come from where an amputated limb used to be. Phantom limb pain can also occur in limbs following paralysis (e.g., following spinal cord injury). "Phantom limb pain" is usually chronic in nature.

As used herein, and unless otherwise specified, the term "trigeminal neuralgia" (TN) refers to a disorder of the fifth cranial (trigeminal) nerve that causes episodes of intense, stabbing, electric-shock-like pain in the areas of the face where the branches of the nerve are distributed (lips, eyes, nose, scalp, forehead, upper jaw, and lower jaw). It is also known as the "suicide disease".

As used herein, and unless otherwise specified, the term "complex regional pain syndrome" (CRPS), formerly known as "reflex sympathetic dystrophy" (RSD), refers to a chronic pain condition whose key symptom is continuous, intense pain out of proportion to the severity of the injury, which gets worse rather than better over time. The term encompasses type 1 CRPS, which includes conditions caused by tissue injury other than peripheral nerve, and type 2 CRPS, in which the syndrome is provoked by major nerve injury, and is sometimes called causalgia.

As used herein, and unless otherwise specified, the term "fibromyalgia" refers to a chronic condition characterized by diffuse or specific muscle, joint, or bone pain, along with fatigue and a range of other symptoms. Previously, fibromyalgia was known by other names such as fibrositis, chronic muscle pain syndrome, psychogenic rheumatism and tension myalgias.

B. Compounds

In one embodiment, provided herein is a compound of formula (I):

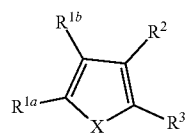

(I)

or a pharmaceutically acceptable salt thereof, wherein:
X is selected from S and O;
one of $R^{1a}$ and $R^{1b}$ is a heterocyclic or heteroaryl ring; and the other of $R^{1a}$ and $R^{1b}$ is selected from hydrogen, halo, cyano, alkyl, alkoxyl, alkenyl, alkynyl, cycloalkyl, cycloalkylalkyl, aryl, aralkyl, heterocyclyl, and heteroaryl; or
$R^{1a}$ is a heterocyclic or heteroaryl ring; and taken together, $R^{1b}$ and $R^2$ and the atoms to which they are attached form a cycloalkyl, aryl, heterocyclic or heteroaryl ring; and
$R^2$ and $R^3$ are each independently selected from hydrogen, halo, cyano, alkyl, alkoxyl, alkenyl, alkynyl, cycloalkyl, cycloalkylalkyl, aryl, aralkyl, heterocyclyl, and heteroaryl; or, taken together, $R^2$ and $R^3$ and the atoms to which they are attached form a cycloalkyl, aryl, heterocyclic or heteroaryl ring.

In one embodiment, provided herein is a compound of formula (I), as defined herein elsewhere, or a pharmaceutically acceptable salt thereof, wherein:
X is selected from S and O;
one of $R^{1a}$ and $R^{1b}$ is a heterocyclic or heteroaryl ring; and the other of $R^{1a}$ and $R^{1b}$ is selected from hydrogen, halo, alkyl, and aryl; or
$R^{1a}$ is a heterocyclic or heteroaryl ring; and taken together, $R^{1b}$ and $R^2$ and the atoms to which they are attached form a cycloalkyl or aryl ring; and
$R^2$ and $R^3$ are each independently selected from hydrogen, halo, alkyl, and aryl; or, taken together, $R^2$ and $R^3$ and the atoms to which they are attached form a cycloalkyl or aryl ring.

In one embodiment, X is S or O. In one embodiment, X is S. In one embodiment, X is O.

In one embodiment, $R^{1a}$ is a heterocyclic or heteroaryl ring; and $R^{1b}$ is selected from hydrogen, halo, cyano, alkyl, alkoxyl, alkenyl, alkynyl, cycloalkyl, cycloalkylalkyl, aryl, aralkyl, heterocyclyl, and heteroaryl. In one such embodiment, $R^{1b}$ is selected from hydrogen, halogen, alkyl, and aryl. In one such embodiment, $R^{1b}$ is selected from hydrogen, F, Cl, Br, $(C_1$-$C_4)$alkyl, and phenyl.

In one embodiment, $R^{1a}$ is a heterocyclic ring and $R^{1b}$ is hydrogen. In one embodiment, $R^{1a}$ is a heterocyclic ring and $R^{1b}$ is halo. In one embodiment, $R^{1a}$ is a heterocyclic ring and $R^{1b}$ is cyano. In one embodiment, $R^{1a}$ is a heterocyclic ring and $R^{1b}$ is alkyl. In one embodiment, $R^{1a}$ is a heterocyclic ring and $R^{1b}$ is alkoxyl. In one embodiment, $R^{1a}$ is a heterocyclic ring and $R^{1b}$ is alkenyl. In one embodiment, $R^{1a}$ is a heterocyclic ring and $R^{1b}$ is alkynyl. In one embodiment, $R^{1a}$ is a heterocyclic ring and $R^{1b}$ is cycloalkyl. In one embodiment, $R^{1a}$ is a heterocyclic ring and $R^{1b}$ is cycloalkylalkyl. In one embodiment, $R^{1a}$ is a heterocyclic ring and $R^{1b}$ is aryl. In one embodiment, $R^{1a}$ is a heterocyclic ring and $R^{1b}$ is aralkyl. In one embodiment, $R^{1a}$ is a heterocyclic ring and $R^{1b}$ is heterocyclyl. In one embodiment, $R^{1a}$ is a heterocyclic ring and $R^{1b}$ is heteroaryl.

In one embodiment, $R^{1a}$ is a heteroaryl ring and $R^{1b}$ is hydrogen. In one embodiment, $R^{1a}$ is a heteroaryl ring and $R^{1b}$ is halo. In one embodiment, $R^{1a}$ is a heteroaryl ring and $R^{1b}$ is cyano. In one embodiment, $R^{1a}$ is a heteroaryl ring and $R^{1b}$ is alkyl. In one embodiment, $R^{1a}$ is a heteroaryl ring and $R^{1b}$ is alkoxyl. In one embodiment, $R^{1a}$ is a heteroaryl ring and $R^{1b}$ is alkenyl. In one embodiment, $R^{1a}$ is a heteroaryl ring and $R^{1b}$ is alkynyl. In one embodiment, $R^{1a}$ is a heteroaryl ring and $R^{1b}$ is cycloalkyl. In one embodiment, $R^{1a}$ is a heteroaryl ring and $R^{1b}$ is cycloalkylalkyl. In one embodiment, $R^{1a}$ is a heteroaryl ring and $R^{1b}$ is aryl. In one embodiment, $R^{1a}$ is a heteroaryl ring and $R^{1b}$ is aralkyl. In one embodiment, $R^{1a}$ is a heteroaryl ring and $R^{1b}$ is heterocyclyl. In one embodiment, $R^{1a}$ is a heteroaryl ring and $R^{1b}$ is heteroaryl.

In one embodiment, $R^{1b}$ is a heterocyclic or heteroaryl ring; and $R^{1a}$ is selected from hydrogen, halo, cyano, alkyl, alkoxyl, alkenyl, alkynyl, cycloalkyl, cycloalkylalkyl, aryl, aralkyl, heterocyclyl, and heteroaryl. In one such embodiment, $R^{1a}$ is selected from hydrogen, halogen, alkyl, and aryl. In one such embodiment, $R^{1a}$ is selected from hydrogen, F, Cl, Br, $(C_1$-$C_4)$alkyl, and phenyl.

In one embodiment, $R^{1b}$ is a heterocyclic ring and $R^{1a}$ is hydrogen. In one embodiment, $R^{1b}$ is a heterocyclic ring and $R^{1a}$ is halo. In one embodiment, $R^{1b}$ is a heterocyclic ring and $R^{1a}$ is cyano. In one embodiment, $R^{1b}$ is a heterocyclic ring and $R^{1a}$ is alkyl. In one embodiment, $R^{1b}$ is a heterocyclic ring and $R^{1a}$ is alkoxyl. In one embodiment, $R^{1b}$ is a heterocyclic ring and $R^{1a}$ is alkenyl. In one embodiment, $R^{1b}$ is a heterocyclic ring and $R^{1a}$ is alkynyl. In one embodiment, $R^{1b}$ is a heterocyclic ring and $R^{1a}$ is cycloalkyl. In one embodiment, $R^{1b}$ is a heterocyclic ring and $R^{1a}$ is cycloalkylalkyl. In one embodiment, $R^{1b}$ is a heterocyclic ring and $R^{1a}$ is aryl. In one embodiment, $R^{1b}$ is a heterocyclic ring and $R^{1a}$ is aralkyl. In one embodiment, $R^{1b}$ is a heterocyclic ring and $R^{1a}$ is heterocyclyl. In one embodiment, $R^{1b}$ is a heterocyclic ring and $R^{1a}$ is heteroaryl.

In one embodiment, $R^{1b}$ is a heteroaryl ring and $R^{1a}$ is hydrogen. In one embodiment, $R^{1b}$ is a heteroaryl ring and $R^{1a}$ is halo. In one embodiment, $R^{1b}$ is a heteroaryl ring and $R^{1a}$ is cyano. In one embodiment, $R^{1b}$ is a heteroaryl ring and $R^{1a}$ is alkyl. In one embodiment, $R^{1b}$ is a heteroaryl ring and $R^{1a}$ is alkoxyl. In one embodiment, $R^{1b}$ is a heteroaryl ring and $R^{1a}$ is alkenyl. In one embodiment, $R^{1b}$ is a heteroaryl ring and $R^{1a}$ is alkynyl. In one embodiment, $R^{1b}$ is a heteroaryl ring and $R^{1a}$ is cycloalkyl. In one embodiment, $R^{1b}$ is a heteroaryl ring and $R^{1a}$ is cycloalkylalkyl. In one embodiment, $R^{1b}$ is a heteroaryl ring and $R^{1a}$ is aryl. In one embodiment, $R^{1b}$ is a heteroaryl ring and $R^{1a}$ is aralkyl. In one embodiment, $R^{1b}$ is a heteroaryl ring and $R^{1a}$ is heterocyclyl. In one embodiment, $R^{1b}$ is a heteroaryl ring and $R^{1a}$ is heteroaryl.

In one embodiment, $R^{1a}$ is a heterocyclic or heteroaryl ring; and taken together, $R^{1b}$ and $R^2$ and the atoms to which they are attached form a cycloalkyl, aryl, heterocyclic or heteroaryl ring.

In one embodiment, $R^{1a}$ is a heterocyclic ring; and taken together, $R^{1b}$ and $R^2$ and the atoms to which they are attached form a cycloalkyl, aryl, heterocyclic or heteroaryl ring. In one embodiment, $R^{1a}$ is a heterocyclic ring; and taken together, $R^{1b}$ and $R^2$ and the atoms to which they are attached form a cycloalkyl ring. In one embodiment, $R^{1a}$ is a heterocyclic ring; and taken together, $R^{1b}$ and $R^2$ and the atoms to which they are attached form an aryl ring. In one embodiment, $R^{1a}$ is a heterocyclic ring; and taken together, $R^{1b}$ and $R^2$ and the atoms to which they are attached form a heterocyclic ring. In one embodiment, $R^{1a}$ is a heterocyclic ring; and taken together, $R^{1b}$ and $R^2$ and the atoms to which they are attached form a heteroaryl ring.

In one embodiment, $R^{1a}$ is a heteroaryl ring; and taken together, $R^{1b}$ and $R^2$ and the atoms to which they are attached form a cycloalkyl, aryl, heterocyclic or heteroaryl ring. In one embodiment, $R^{1a}$ is a heteroaryl ring; and taken together, $R^{1b}$ and $R^2$ and the atoms to which they are attached form a cycloalkyl ring. In one embodiment, $R^{1a}$ is a heteroaryl ring; and taken together, $R^{1b}$ and $R^2$ and the atoms to which they are attached an aryl ring. In one embodiment, $R^{1a}$ is a heteroaryl ring; and taken together, $R^{1b}$ and $R^2$ and the atoms to which they are attached form an a heterocyclic ring. In one embodiment, $R^{1a}$ is a heteroaryl ring; and taken together, $R^{1b}$ and $R^2$ and the atoms to which they are attached form a heteroaryl ring.

In one embodiment, the ring formed by $R^{1b}$ and $R^2$ is a cycloalkyl or aryl ring. In one embodiment, the ring formed by $R^{1b}$ and $R^2$ is a cyclopentyl, cyclohexyl or phenyl ring. In one embodiment, the ring formed by $R^{1b}$ and $R^2$ is cyclopentyl, cyclohexyl or phenyl, each of which is optionally substituted with halo, alkyl, or alkoxyl. In one embodiment, the ring formed by $R^{1b}$ and $R^2$ is cyclopentyl, cyclohexyl, or phenyl, each of which is optionally substituted with F, Cl, Br, $(C_1-C_4)$alkyl or $(C_1-C_4)$alkoxyl. In one embodiment, the ring formed by $R^{1b}$ and $R^2$ is an optionally substituted cyclohexyl. In one embodiment, the ring formed by $R^{1b}$ and $R^2$ is unsubstituted cyclohexyl. In one embodiment, the ring formed by $R^{1b}$ and $R^2$ is an optionally substituted aryl ring (e.g., phenyl). In one embodiment, the ring formed by $R^{1b}$ and $R^2$ is an unsubstituted phenyl ring. In one embodiment, the ring formed by $R^{1b}$ and $R^2$ is a monosubstituted phenyl ring (e.g., 3-chlorophenyl or 4-chlorophenyl).

In one embodiment, $R^2$ and $R^3$ are each independently selected from hydrogen, halo, cyano, alkyl, alkoxyl, alkenyl, alkynyl, cycloalkyl, cycloalkylalkyl, aryl, aralkyl, heterocyclyl, and heteroaryl.

In one embodiment, $R^2$ is hydrogen. In one embodiment, $R^2$ is halo (e.g., chloro). In one embodiment, $R^2$ is cyano. In one embodiment, $R^2$ is alkyl (e.g., methyl or ethyl). In one embodiment, $R^2$ is alkoxyl. In one embodiment, $R^2$ is alkenyl. In one embodiment, $R^2$ is alkynyl. In one embodiment, $R^2$ is cycloalkyl. In one embodiment, $R^2$ is cycloalkylalkyl. In one embodiment, $R^2$ is aryl (e.g., phenyl). In one embodiment, $R^2$ is aralkyl. In one embodiment, $R^2$ is heterocyclyl. In one embodiment, $R^2$ is heteroaryl. In one embodiment, $R^2$ is selected from hydrogen, halogen, alkyl, and aryl. In one embodiment, $R^2$ is selected from hydrogen, F, Cl, Br, $(C_1-C_4)$alkyl, and phenyl.

In one embodiment, $R^3$ is hydrogen. In one embodiment, $R^3$ is halo (e.g., fluoro or bromo). In one embodiment, $R^3$ is cyano. In one embodiment, $R^3$ is alkyl (e.g., methyl or ethyl). In one embodiment, $R^3$ is alkoxyl. In one embodiment, $R^3$ is alkenyl. In one embodiment, $R^3$ is alkynyl. In one embodiment, $R^3$ is cycloalkyl. In one embodiment, $R^3$ is cycloalkylalkyl. In one embodiment, $R^3$ is aryl (e.g., phenyl or 4-fluorophenyl). In one embodiment, $R^3$ is aralkyl. In one embodiment, $R^3$ is heterocyclyl. In one embodiment, $R^3$ is heteroaryl. In one embodiment, $R^3$ is selected from hydrogen, halogen, alkyl, and aryl. In one embodiment, $R^3$ is selected from hydrogen, F, Cl, Br, $(C_1-C_4)$alkyl, and phenyl.

In one embodiment; taken together, $R^2$ and $R^3$ and the atoms to which they are attached form a cycloalkyl, aryl, heterocyclic or heteroaryl ring. In one embodiment, $R^2$ and $R^3$ and the atoms to which they are attached form a cycloalkyl ring. In one embodiment, taken together, $R^2$ and $R^3$ and the atoms to which they are attached form an aryl ring. In one embodiment, taken together, $R^2$ and $R^3$ and the atoms to which they are attached form a heterocyclic ring. In one embodiment, taken together, $R^2$ and $R^3$ and the atoms to which they are attached form a heteroaryl ring.

In one embodiment, the ring formed by $R^2$ and $R^3$ is a cycloalkyl or aryl ring. In one embodiment, the ring formed by $R^2$ and $R^3$ is a cyclopentyl, cyclohexyl or phenyl ring. In one embodiment, the ring formed by $R^2$ and $R^3$ is a cyclopentyl, cyclohexyl or phenyl ring, each of which is optionally substituted with halo, alkyl or alkoxyl. In one embodiment, the ring formed by $R^2$ and $R^3$ is a cyclopentyl, cyclohexyl or phenyl ring, each of which is optionally substituted with F, Cl, Br, $(C_1-C_4)$alkyl or $(C_1-C_4)$alkoxyl.

In one embodiment, the ring formed by $R^2$ and $R^3$ is an optionally substituted cyclopenyl. In one embodiment, the ring formed by $R^2$ and $R^3$ is unsubstituted cyclopentyl. In one embodiment, the ring formed by $R^2$ and $R^3$ is an optionally substituted cyclohexyl. In one embodiment, the ring formed by $R^2$ and $R^3$ is unsubstituted cyclohexyl. In one embodiment, the ring formed by $R^2$ and $R^3$ is an optionally substituted aryl (e.g., phenyl). In one embodiment, the ring formed by $R^2$ and $R^3$ is unsubstituted phenyl. In one embodiment, the ring formed by $R^2$ and $R^3$ is monosubstituted phenyl (e.g., 2-chlorophenyl, 3-chlorophenyl, 4-chlorophenyl, 3-fluorophenyl, 4-fluorophenyl, 4-methylphenyl or 4-methoxyphenyl). In one embodiment, the ring formed by $R^2$ and $R^3$ is disubstituted phenyl (e.g., 3,4-dichlorophenyl).

In one embodiment, one of $R^{1a}$ and $R^{1b}$ is selected from a dihydropyrimidine, dihydroquinazoline, and pyrimidine group.

In one embodiment, $R^{1a}$ is selected from a dihydropyrimidine and pyrimidine group. In one embodiment, $R^{1a}$ is a dihydropyrimidine group. In one embodiment, $R^{1a}$ is a pyrimidine group.

In one embodiment, $R^{1b}$ is selected from a dihydropyrimidine, and pyrimidine group. In one embodiment, $R^{1b}$ is a dihydropyrimidine group. In one embodiment, $R^{1b}$ is a pyrimidine group.

In one embodiment, one of $R^{1a}$ and $R^{1b}$ is selected from a 1,6-dihydropyrimidine, a 1,4-dihydropyrimidine and a pyrimidine.

In one embodiment, $R^{1a}$ is a 1,6-dihydropyrimidine, a 1,4-dihydropyrimidine, or a pyrimidine. In one embodiment, $R^{1a}$ is a 1,6-dihydropyrimidine. In one embodiment, $R^{1a}$ is a 1,4-dihydropyrimidine. In one embodiment, $R^{1a}$ is a pyrimidine.

In one embodiment, $R^{1b}$ is a 1,6-dihydropyrimidine, a 1,4-dihydropyrimidine, and a pyrimidine. In one embodiment, $R^{1b}$ is a 1,6-dihydropyrimidine. In one embodiment, $R^{1b}$ is a 1,4-dihydropyrimidine. In one embodiment, $R^{1b}$ is a pyrimidine.

In one embodiment, one of $R^{1a}$ and $R^{1b}$ is a heterocyclic or heteroaryl ring; and the other of $R^{1a}$ and $R^{1b}$ is selected from hydrogen, halo, cyano, alkyl, alkoxyl, alkenyl, alkynyl, cycloalkyl, cycloalkylalkyl, aryl, aralkyl, heterocyclyl, and heteroaryl; provided that the other of $R^{1a}$ and $R^{1b}$ is not a 1,6-dihydropyrimidine, a 1,4-dihydropyrimidine, or a pyrimidine ring.

In one embodiment, one of $R^{1a}$ and $R^{1b}$ is a 1,6-dihydropyrimidine, a 1,4-dihydropyrimidine, or a pyrimidine ring; and the other of $R^{1a}$ and $R^{1b}$ is selected from hydrogen, halo, cyano, alkyl, alkoxyl, alkenyl, alkynyl, cycloalkyl, cycloalkylalkyl, aryl, aralkyl, heterocyclyl, and heteroaryl; provided that the other of $R^{1a}$ and $R^{1b}$ is not a 1,6-dihydropyrimidine, a 1,4-dihydropyrimidine, or a pyrimidine ring.

In one embodiment, either $R^{1a}$ and $R^{1b}$ is selected from a dihydropyrimidine and pyrimidine group; and the other of $R^{1a}$ and $R^{1b}$ is selected from hydrogen, halo, cyano, alkyl, alkoxyl, alkenyl, alkynyl, cycloalkyl, cycloalkylalkyl, aryl, and aralkyl; or $R^{1a}$ is selected from a dihydropyrimidine and a pyrimidine; and taken together, $R^{1b}$ and $R^2$ and the atoms to which they are attached form an optionally substituted 4 to 7 membered cycloalkyl, aryl, heterocyclic or heteroaryl ring, preferably a cycloalkyl or aryl ring.

In one embodiment, $R^{1a}$ is hydrogen. In one embodiment, $R^{1a}$ is alkyl (e.g., methyl or ethyl). In one embodiment, $R^{1a}$ is halo (e.g., fluoro or chloro). In one embodiment, $R^{1a}$ is aryl (e.g., phenyl, 2-chlorophenyl, 3-chlorophenyl, 4-chlorophenyl or 4-fluorophenyl). In one embodiment, $R^{1a}$ is heterocyclyl.

In one embodiment, $R^{1a}$ is selected from:

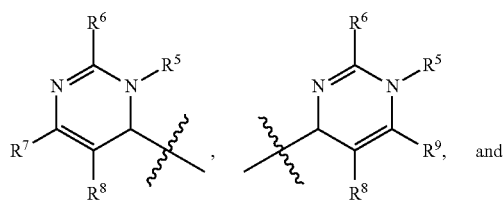

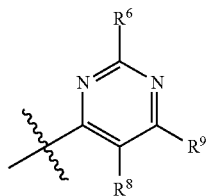

wherein $R^5$ is selected from hydrogen, alkyl, and cycloalkyl; $R^6$, $R^7$, $R^8$ and $R^9$ are each independently selected from hydrogen, halo, cyano, amino, alkylamino, alkyl, alkoxyl, alkenyl, alkynyl, cycloalkyl, cycloalkylalkyl, aryl, aralkyl, zheterocyclyl, and heteroaryl; or $R^7$ and $R^8$ together with the atoms to which they are attached form an aryl, heteroaryl, cycloalkyl, or heterocyclyl ring.

In one embodiment, $R^5$ is selected from hydrogen and $(C_1-C_4)$alkyl.

In one embodiment, $R^6$, $R^7$, $R^8$, $R^9$ are each independently selected from hydrogen, halogen, alkyl, alkoxyl, amino, alkylamino, cycloalkyl and aryl.

In one embodiment, $R^{1a}$ is represented by the following structure:

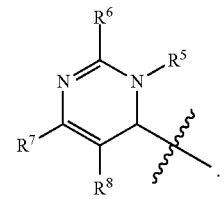

In one embodiment, $R^7$ and $R^8$ are each independently selected from hydrogen, halo, cyano, amino, alkylamino, alkyl, alkoxyl, alkenyl, alkynyl, cycloalkyl, and aryl.

In one embodiment, $R^5$ is hydrogen or alkyl; and $R^6$, $R^7$, and $R^8$ are each independently selected from hydrogen, halo, amino, alkylamino, alkyl, alkoxyl, cycloalkyl, and aryl.

In one embodiment, $R^5$ is hydrogen. In one embodiment, $R^5$ is alkyl (e.g., methyl or ethyl).

In one embodiment, $R^6$ is hydrogen. In one embodiment, $R^6$ is alkyl (e.g., methyl, ethyl or isopropyl). In one embodiment, $R^6$ is alkoxy (e.g., methoxy). In one embodiment, $R^6$ is cycloalkyl (e.g., cyclopropyl). In one embodiment, $R^6$ is halo (e.g., chloro). In one embodiment, $R^6$ is amino. In one embodiment, $R^6$ is alkylamino (e.g., dimethylamino or methylamino). In one embodiment, $R^6$ is aryl (e.g., phenyl, 4-fluorophenyl or 3-fluorophenyl). In one embodiment, $R^7$ is hydrogen. In one embodiment, $R^7$ is alkyl (e.g., methyl). In one embodiment, $R^7$ is cycloalkyl (e.g., cyclopropyl). In one embodiment, $R^8$ is hydrogen. In one embodiment, $R^8$ is halo (e.g., chloro or fluoro). In one embodiment, $R^8$ is alkyl (e.g., methyl, ethyl or isopropyl). In one embodiment, $R^8$ is cycloalkyl (e.g., cyclopropyl). In one embodiment, $R^8$ is alkoxy (e.g., methoxy). In one embodiment, $R^8$ is aryl (e.g., phenyl, 4-fluorophenyl or 3-chlorophenyl).

Specific examples include, but are not limited to, the following compounds:
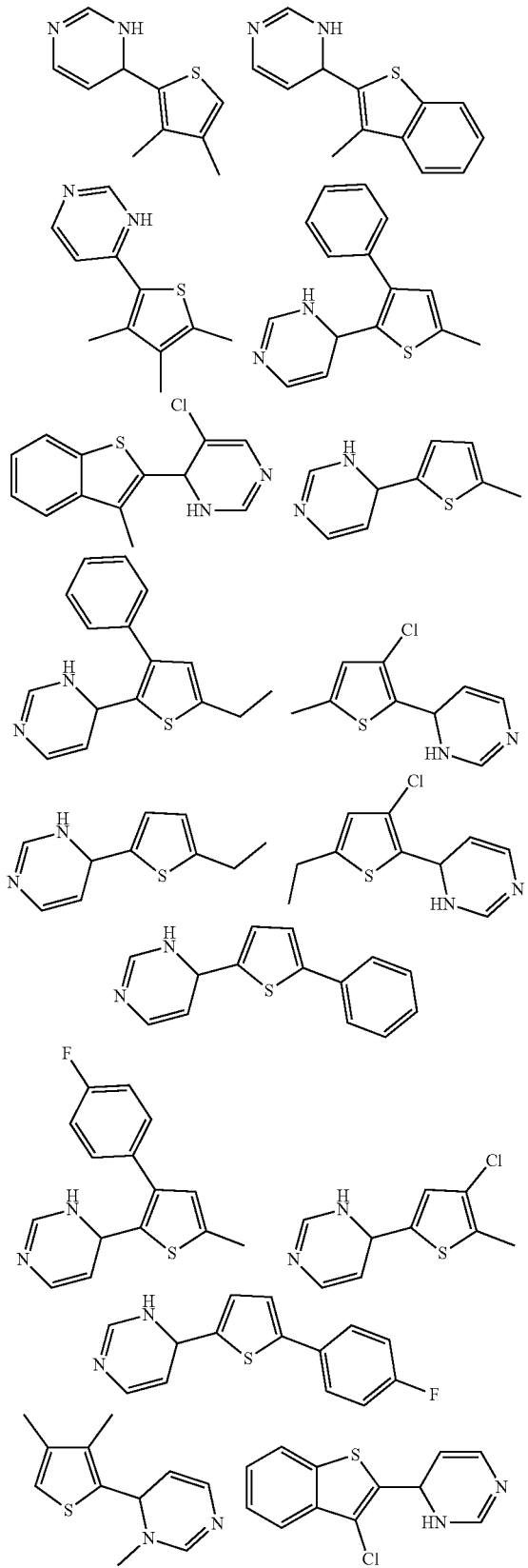
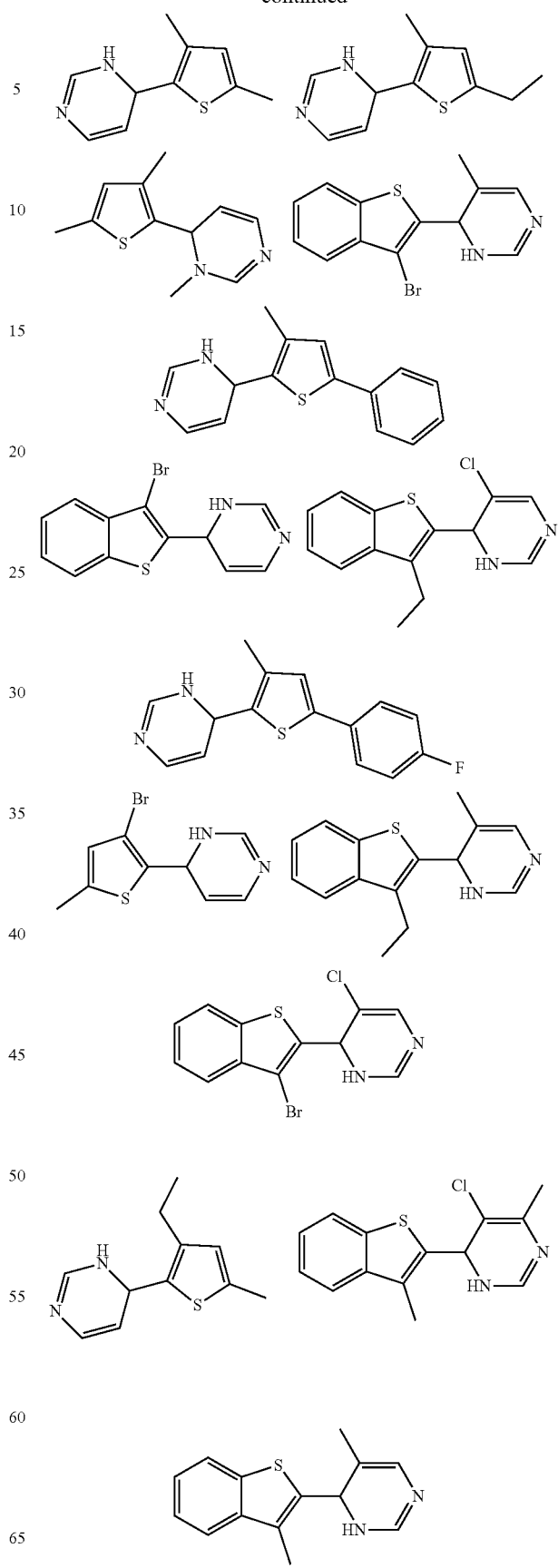

-continued
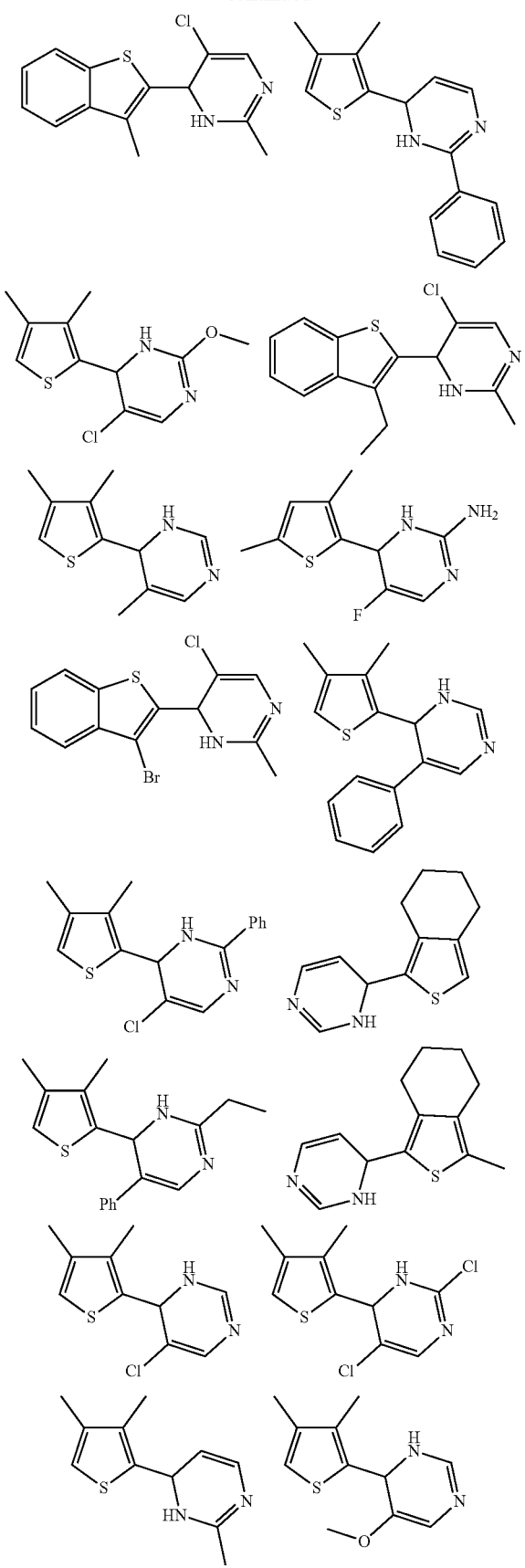
-continued
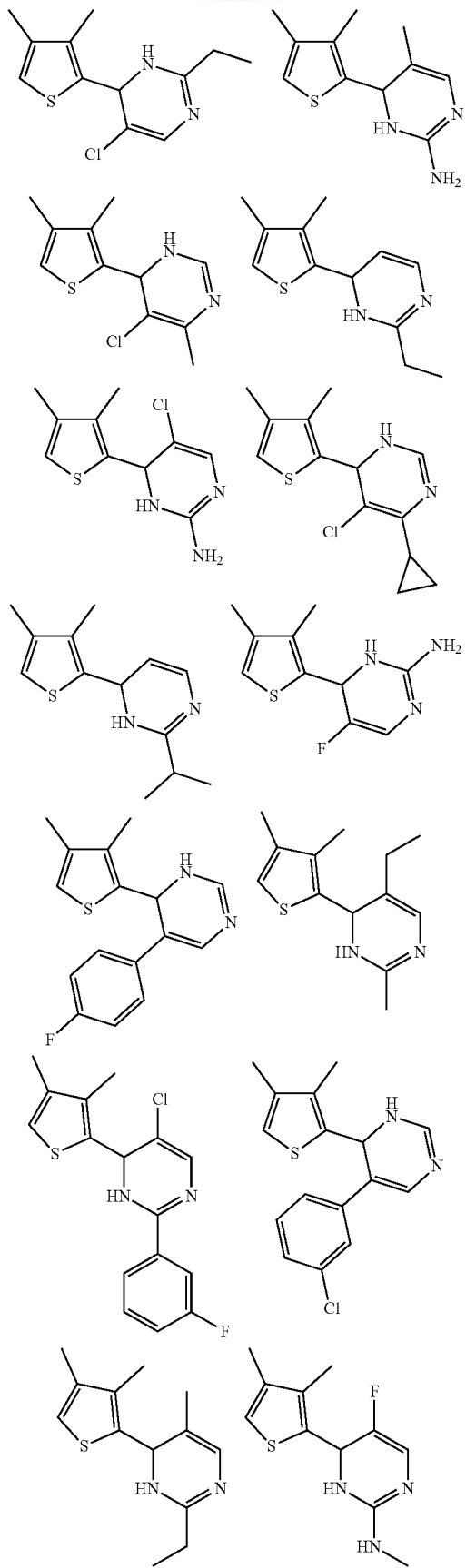

-continued
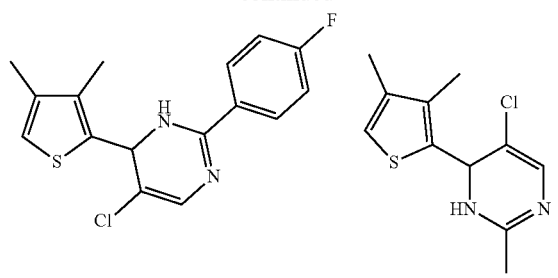
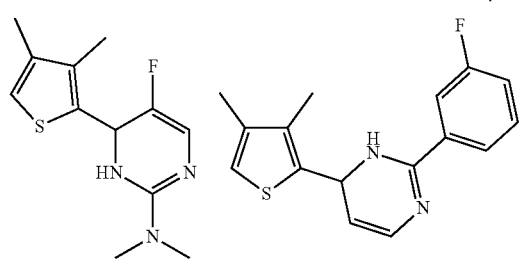
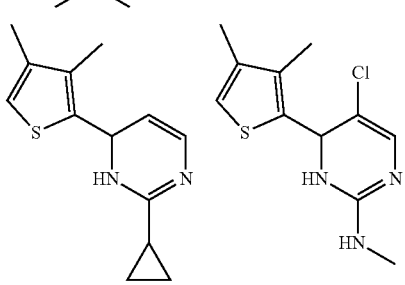
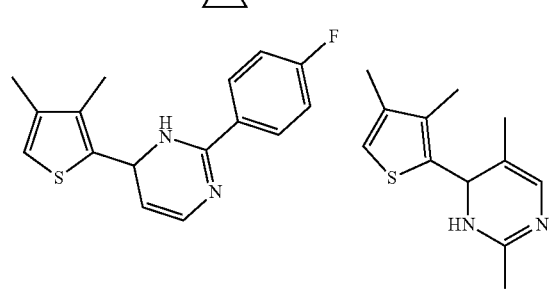
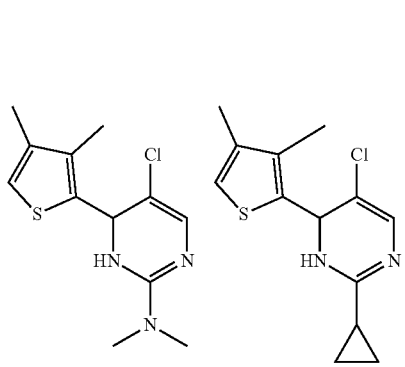
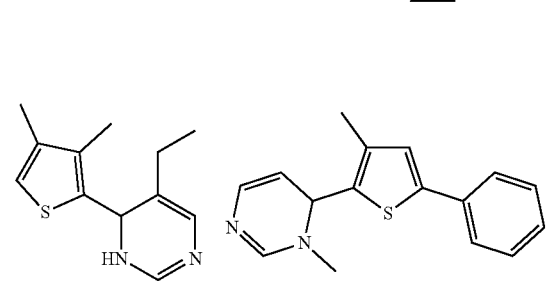
-continued
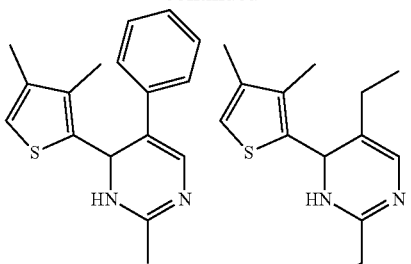
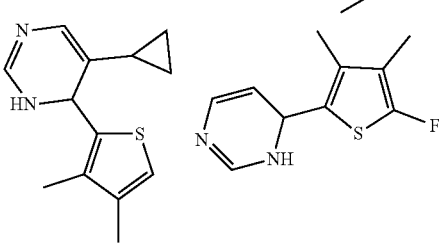
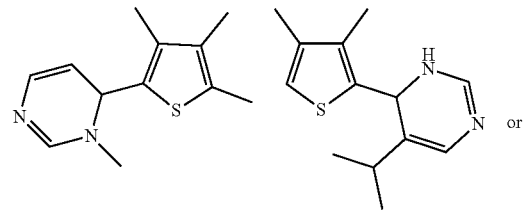
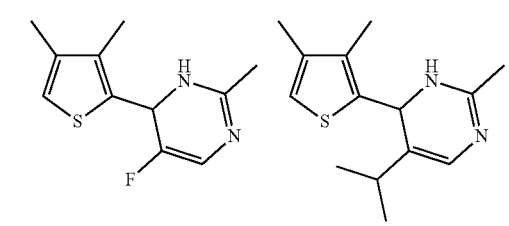
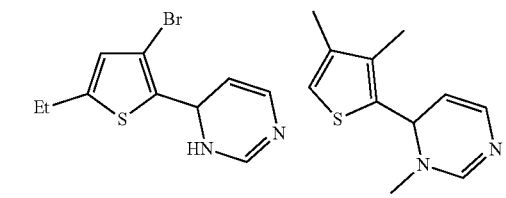
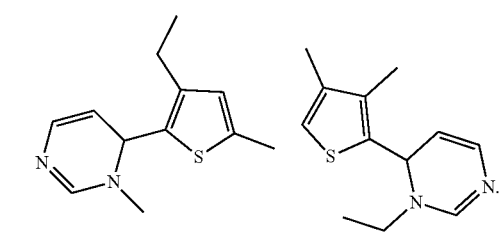
In one embodiment, $R^7$ and $R^8$ together with the atoms to which they are attached form an aryl, cycloalkyl, heterocyclyl, or heteroaryl ring.

In one embodiment, $R^{1a}$ is selected from:

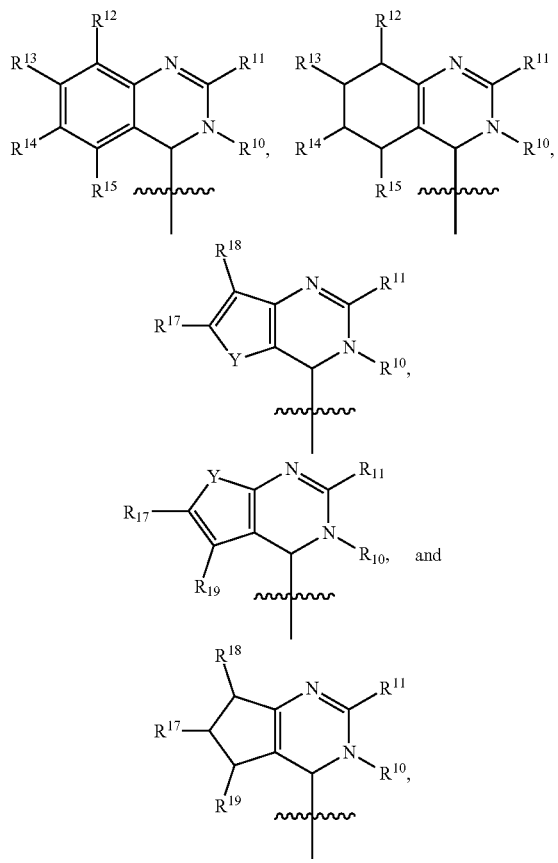

Y is S or O;
$R^{10}$ is hydrogen or alkyl; and
$R^{11}$, $R^{12}$, $R^{13}$, $R^{14}$, $R^{15}$, $R^{16}$, $R^{17}$, $R^{18}$, and $R^{19}$ are each independently selected from hydrogen, halo, amino, alkylamino, alkyl, alkoxyl, cycloalkyl, and aryl.

In one embodiment, $R^{10}$ is hydrogen or $(C_1-C_4)$ alkyl.

In one embodiment, $R^{11}$, $R^{12}$, $R^{13}$, $R^{14}$, $R^{15}$, $R^{16}$, $R^{17}$, $R^{18}$, and $R^{19}$ are each independently selected from hydrogen, halo, alkyl, alkoxyl, amino, alkylamino, aryl, or cycloalkyl.

In one embodiment, $R^{1a}$ is

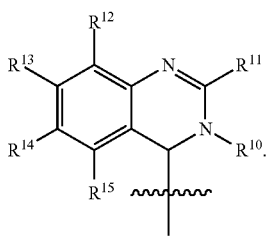

In one embodiment, $R^{10}$ is hydrogen.
In one embodiment, $R^{11}$ is hydrogen.
In one embodiment, $R^{12}$, $R^{13}$, $R^{14}$ and $R^{15}$ are each hydrogen.

In one embodiment, $R^{1a}$ is

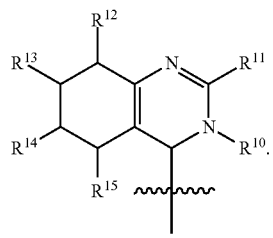

In one embodiment, $R^{10}$ is hydrogen.
In one embodiment, $R^{11}$ is hydrogen. In one embodiment, $R^{11}$ is alkyl (e.g., methyl).
In one embodiment, $R^{12}$, $R^{13}$, $R^{14}$ and $R^{15}$ are each hydrogen.
In one embodiment, $R^{1a}$ is

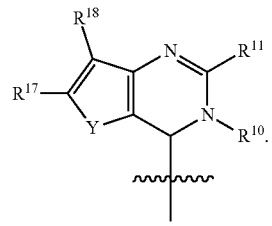

In one embodiment, Y is S.
In one embodiment, $R^{10}$, $R^{11}$, $R^{17}$ and $R^{18}$ are each hydrogen.
In one embodiment, $R^{1a}$ is

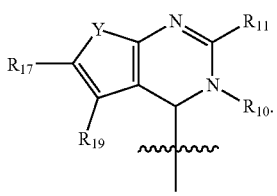

In one embodiment, $R^{10}$, $R^{11}$, $R^{17}$ and $R^{19}$ are each hydrogen.
In one embodiment, $R^{1a}$ is

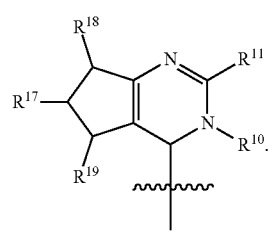

In one embodiment, $R^{11}$ is hydrogen. In one embodiment, $R^{11}$ is $(C_1-C_4)$ alkyl (e.g., methyl).
In one embodiment, $R^{10}$, $R^{17}$, $R^{18}$ and $R^{19}$ are each hydrogen.
In one embodiment, $R^{10}$ is hydrogen or alkyl; and $R^{11}$, $R^{12}$, $R^{13}$, $R^{14}$, $R^{15}$, $R^{16}$, $R^{17}$, $R^{18}$, and $R^{19}$ are each independently selected from hydrogen, halo (e.g., chloro, fluoro or bromo), and alkyl (e.g., methyl).

Specific examples include, but are not limited to, the following compounds:

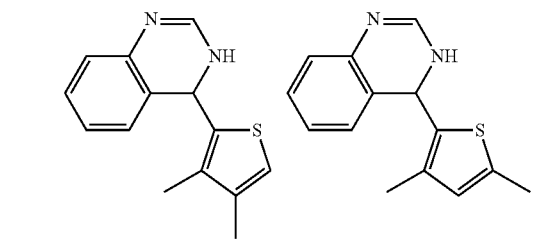
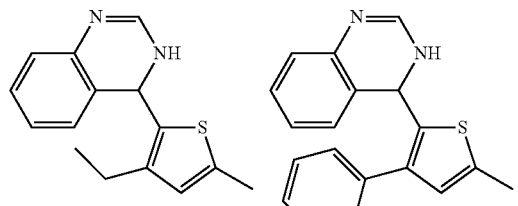
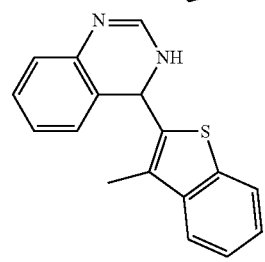
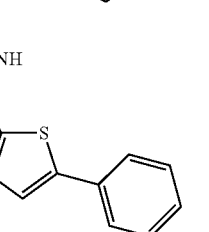
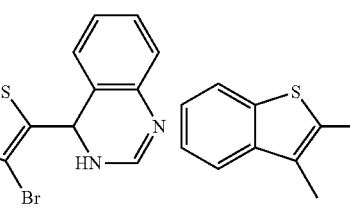
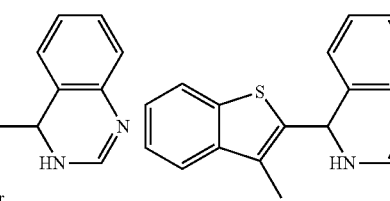
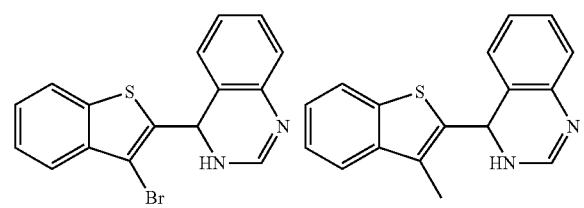

-continued

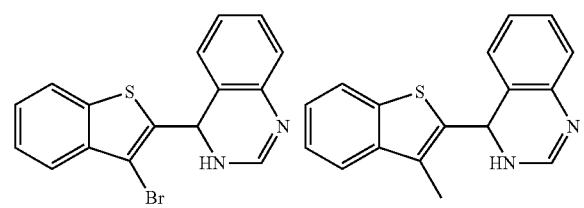
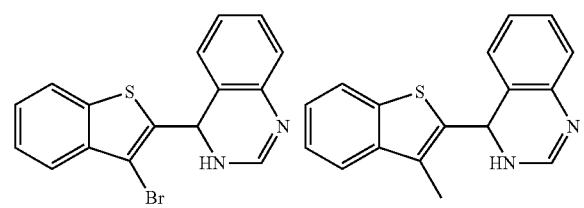
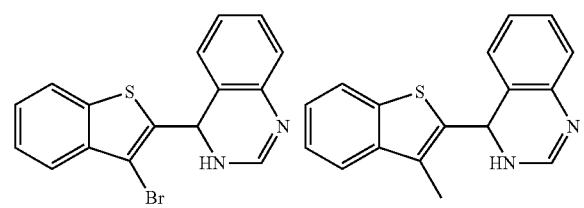
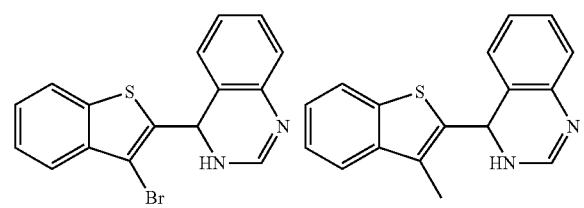

In one embodiment, $R^{1a}$ is represented by the following structure:

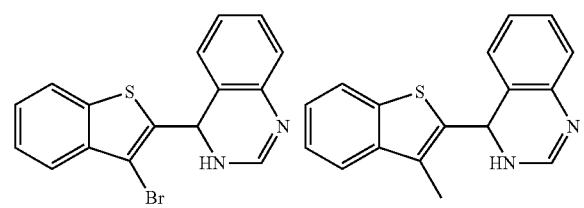

In one embodiment, $R^5$ is hydrogen or alkyl; and $R^6$, $R^8$ and $R^9$ are each independently selected from hydrogen, halo, amino, alkylamino, alkyl, alkoxyl, cycloalkyl, and aryl.

In one embodiment, $R^5$ is alkyl (e.g., ethyl, 2-methoxyethyl or 2-hydroxyethyl).

In one embodiment, $R^6$, $R^8$ and $R^9$ are hydrogen.

Specific examples include, but are not limited to, the following compounds:

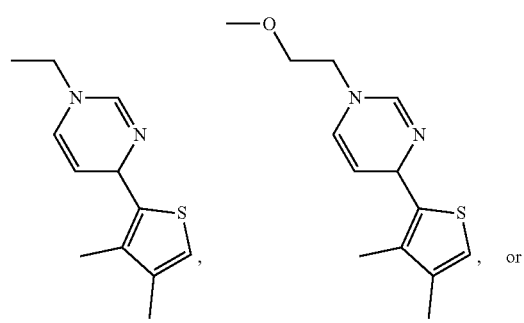

In one embodiment, $R^1$-a is represented by the following structure:

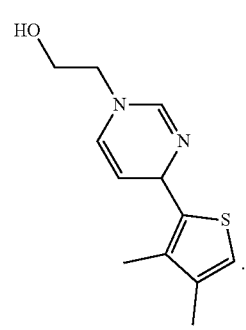

In one embodiment, $R^6$, $R^8$ and $R^9$ are each independently selected from hydrogen, halo, amino, alkylamino, alkyl, alkoxyl, cycloalkyl, and aryl.

In one embodiment, $R^6$ is hydrogen. In one embodiment, $R^6$ is aryl (e.g., phenyl).

In one embodiment, $R^8$ and $R^9$ are hydrogen.

Specific examples include, but are not limited to, the following compounds:

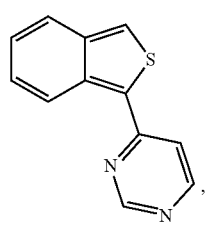 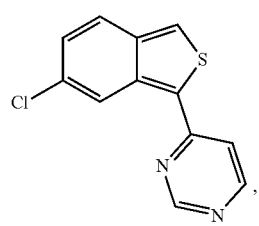

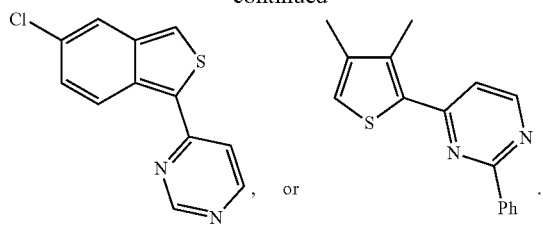

In one embodiment, $R^{1a}$ is selected from the following:

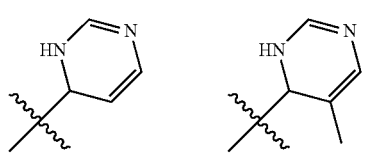

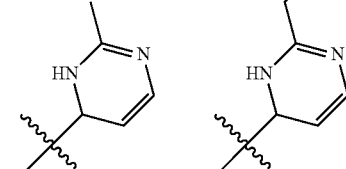

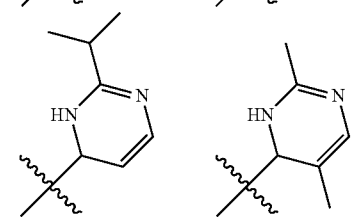

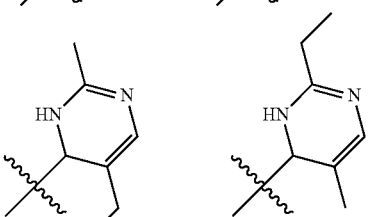

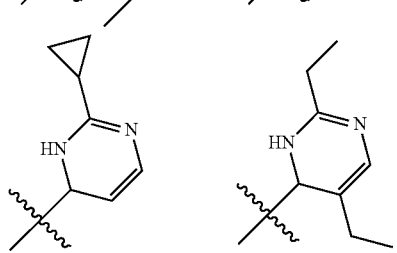

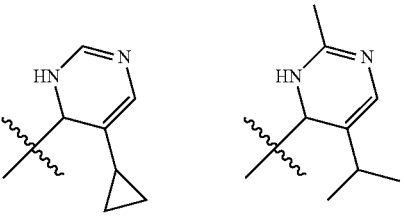

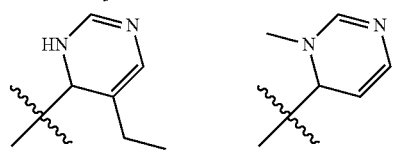

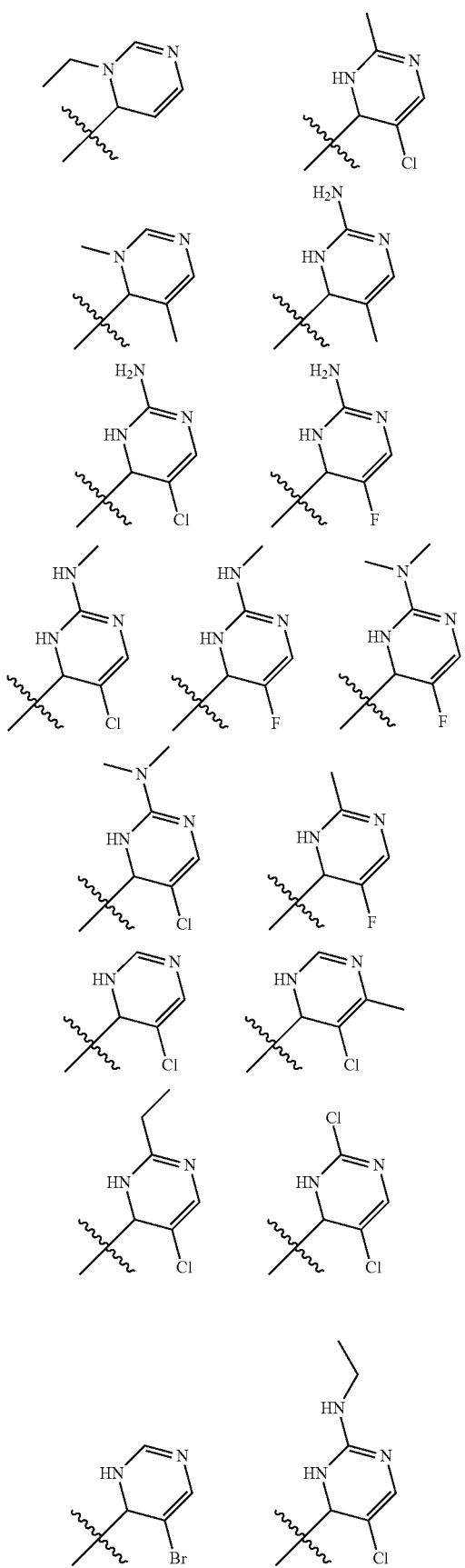
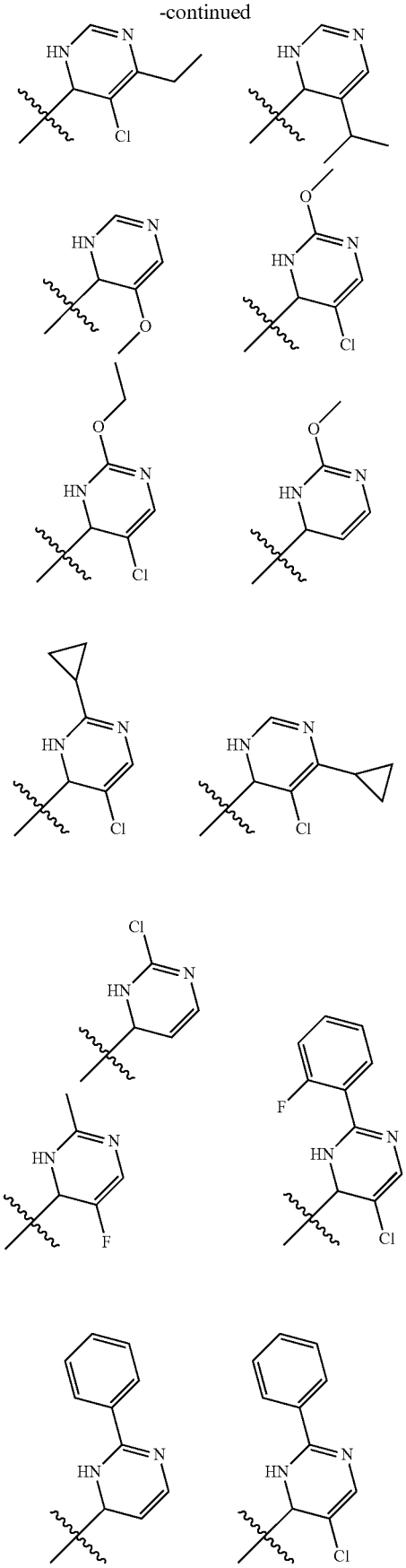

-continued

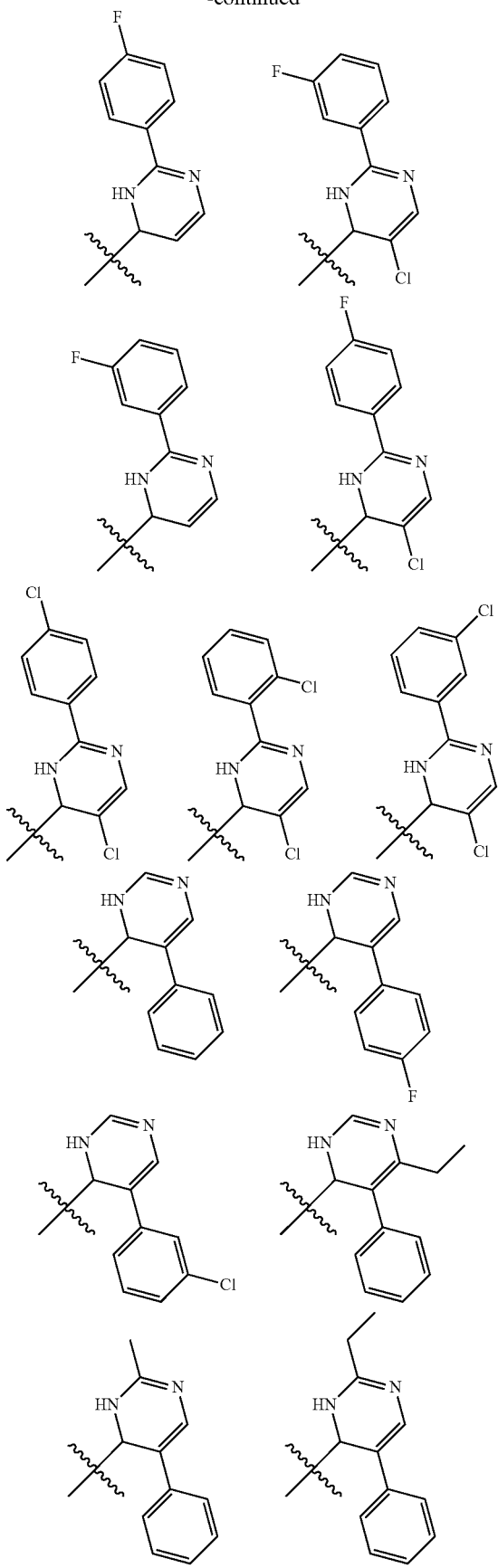

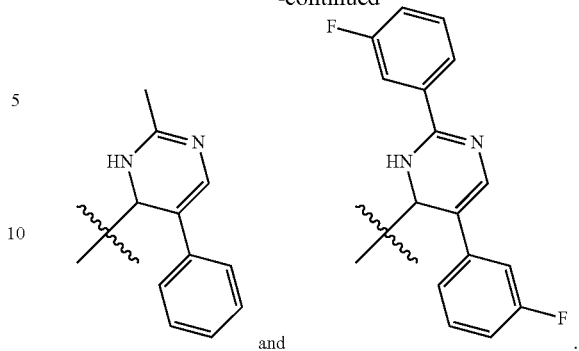

and

In one embodiment, $R^{1b}$ is hydrogen. In one embodiment, $R^{1b}$ is alkyl (e.g., methyl or ethyl). In one embodiment, $R^{1b}$ is halo (e.g., fluoro, chloro or bromo). In one embodiment, $R^{1b}$ is aryl (e.g., phenyl or 4-fluorophenyl).

In one embodiment, $R^{1b}$ is selected from:

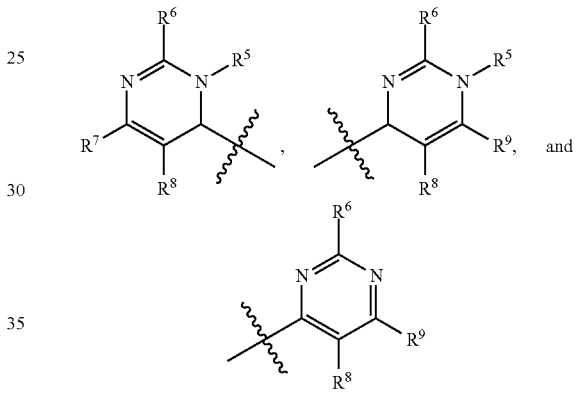

wherein $R^5$ is selected from hydrogen, alkyl, and cycloalkyl; $R^6$, $R^7$, $R^8$ and $R^9$ are each independently selected from hydrogen, halo, cyano, amino, alkylamino, alkyl, alkoxyl, alkenyl, alkynyl, cycloalkyl, cycloalkylalkyl, aryl, aralkyl, heterocyclyl, and heteroaryl; or $R^7$ and $R^8$ together with the atoms to which they are attached form an aryl, heteroaryl, cycloalkyl, or heterocyclyl ring.

In one embodiment, $R^{1b}$ is represented by the following structure:

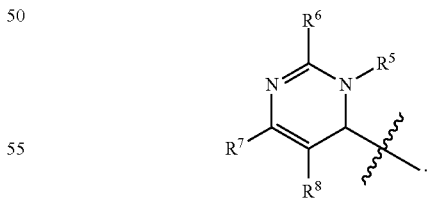

In one embodiment, $R^7$ and $R^8$ are each independently selected from hydrogen, halo, cyano, amino, alkylamino, alkyl, alkoxyl, alkenyl, alkynyl, cycloalkyl, and aryl.

In one embodiment, $R^5$ is hydrogen or alkyl; and $R^6$, $R^7$, $R^8$ and $R^9$ are each independently selected from hydrogen, halo, amino, alkylamino, alkyl, alkoxyl, cycloalkyl, and aryl.

In one embodiment, $R^5$ is hydrogen. In one embodiment, $R^5$ is ($C_1$-$C_4$) alkyl (e.g., methyl or ethyl).

In one embodiment, $R^6$ is hydrogen. In one embodiment, $R^6$ is ($C_1$-$C_4$) alkyl (e.g., methyl, ethyl or isopropyl). In one embodiment, $R^6$ is ($C_1$-$C_4$) alkoxyl (e.g., methoxy or ethoxy). In one embodiment, $R^6$ is amino. In one embodiment, $R^6$ is alkylamino (e.g., methylamino, ethylamino or dimethylamino). In one embodiment, $R^6$ is cycloalkyl (e.g., cyclopropyl). In one embodiment, $R^6$ is halo (e.g., chloro). In one embodiment, $R^6$ is aryl (e.g., phenyl, 2-chlorophenyl, 3-chlorophenyl, 4-chlorophenyl, 2-fluorophenyl, 3-fluorophenyl or 4-fluorophenyl).

In one embodiment, $R^7$ is hydrogen. In one embodiment, $R^7$ is ($C_1$-$C_4$) alkyl (e.g., methyl or ethyl).

In one embodiment, $R^8$ is hydrogen. In one embodiment, $R^8$ is ($C_1$-$C_4$) alkyl (e.g., methyl, ethyl or isopropyl). In one embodiment, $R^8$ is halo (e.g., fluoro, chloro or bromo). In one embodiment, $R^8$ is ($C_1$-$C_4$) alkoxy (e.g., methoxy). In one embodiment, $R^8$ is cycloalkyl (e.g., cyclopropyl). In one embodiment, $R^8$ is aryl (e.g., phenyl, 2-fluorophenyl or 3-fluorophenyl).

Specific examples include, but are not limited to, the following compounds:

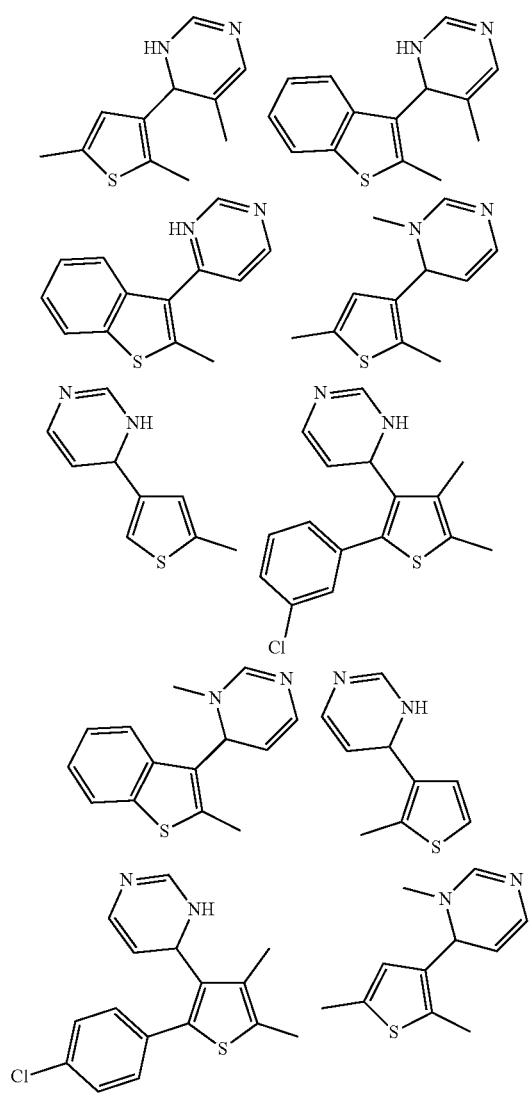

-continued

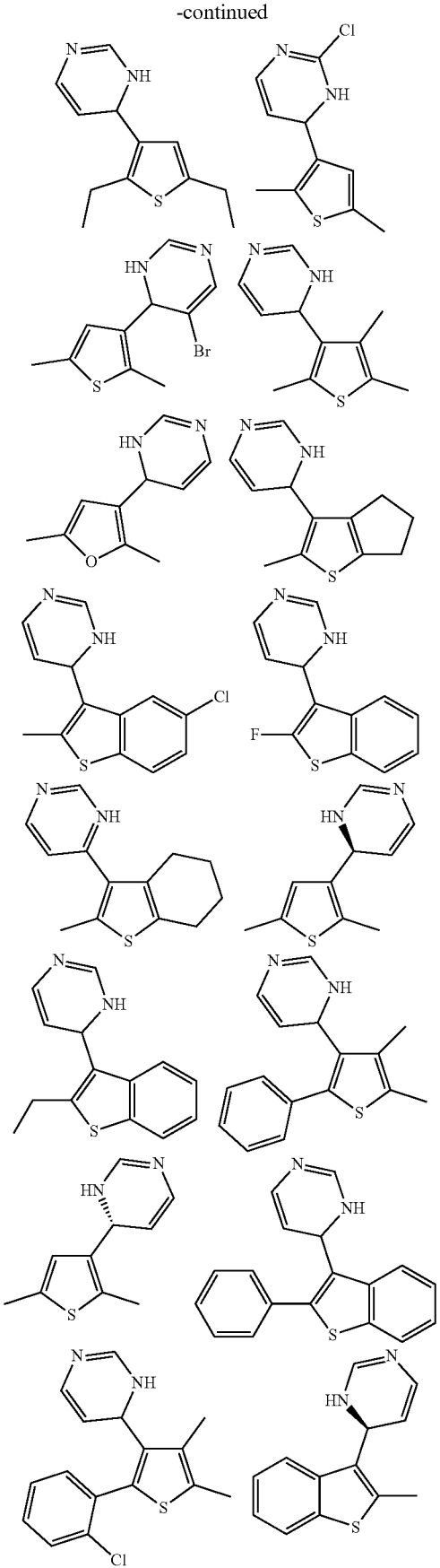

-continued
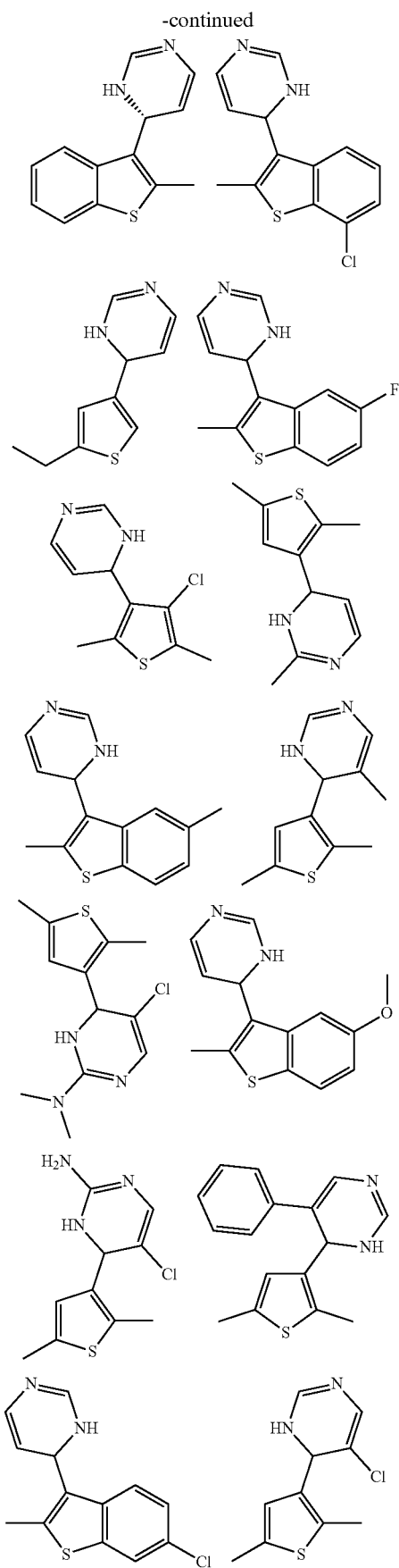
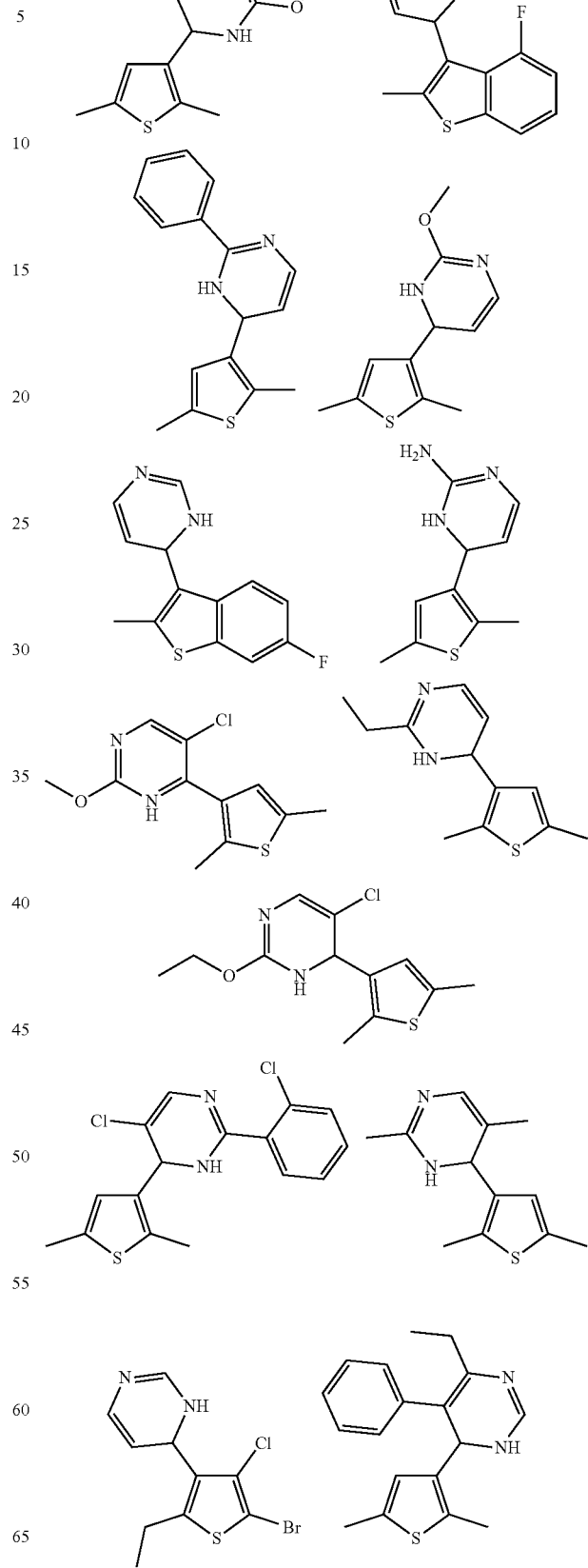

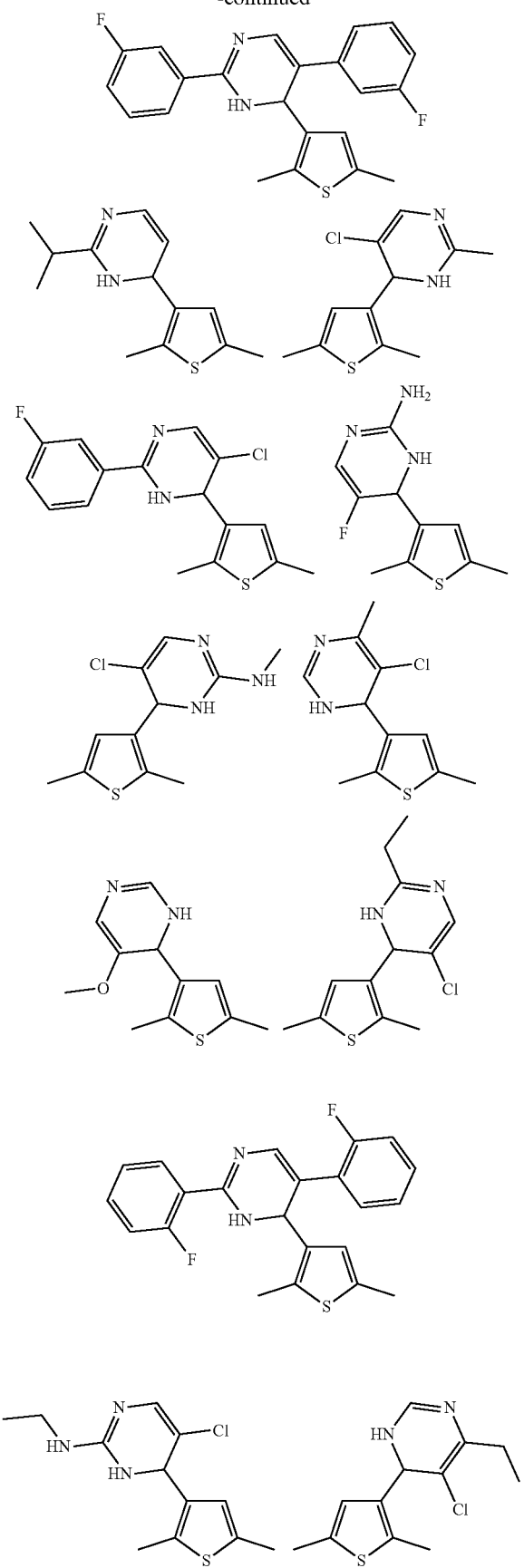
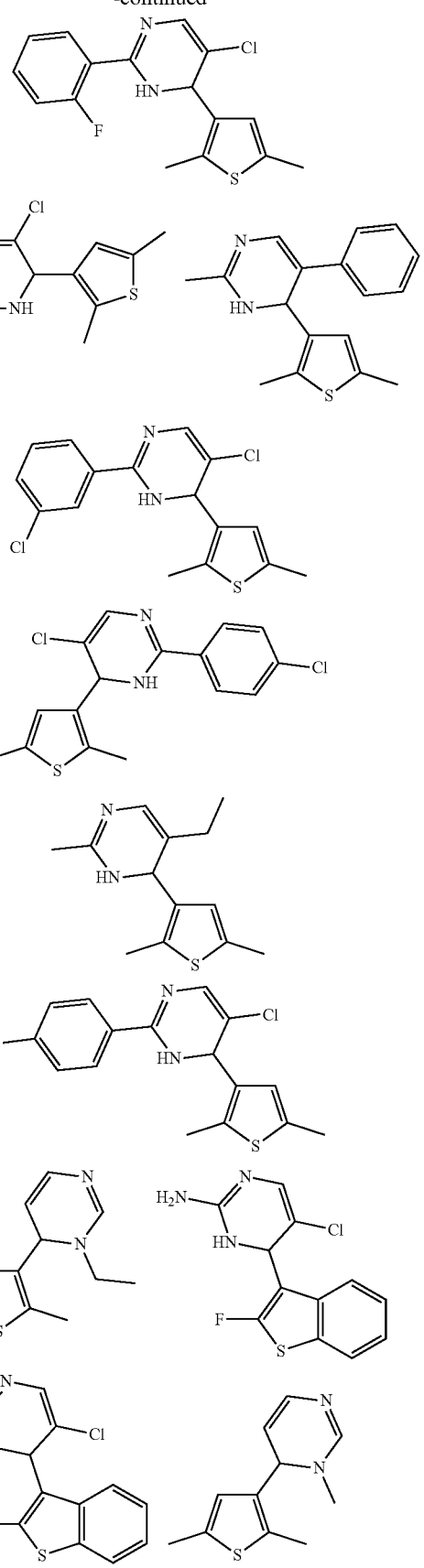

-continued

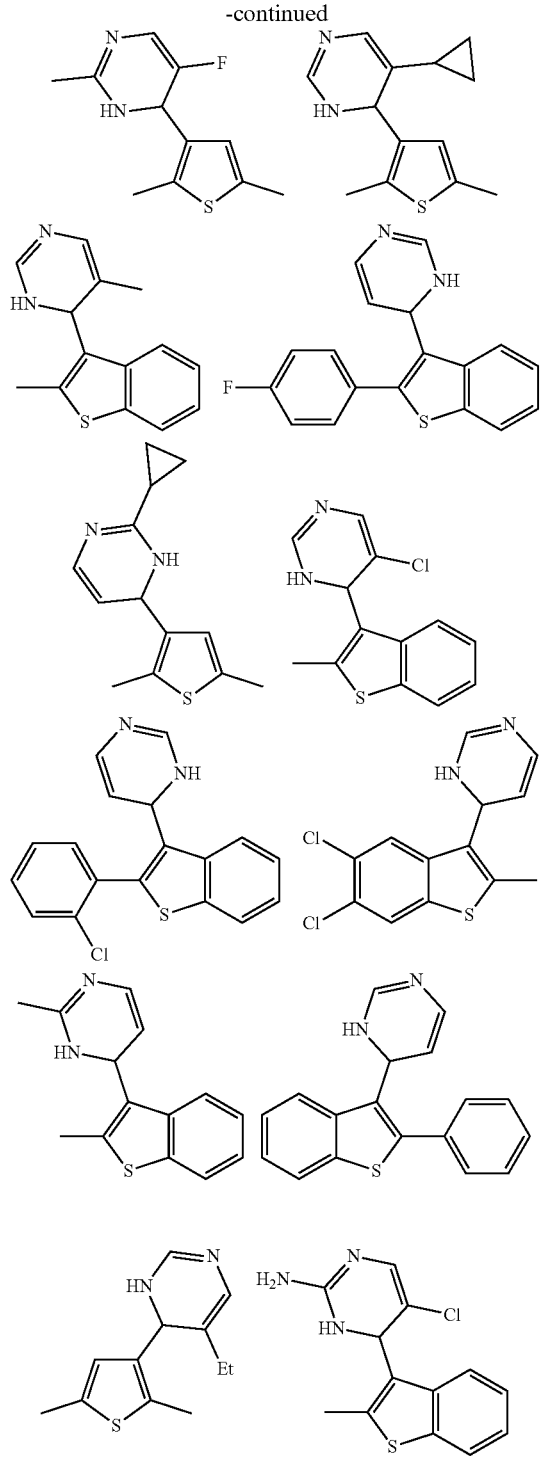

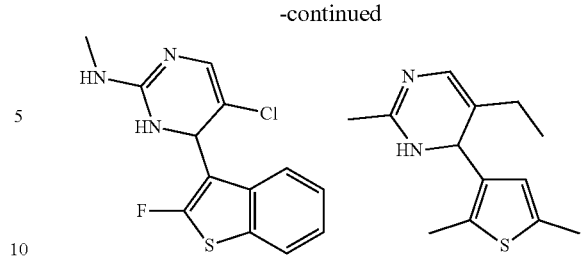

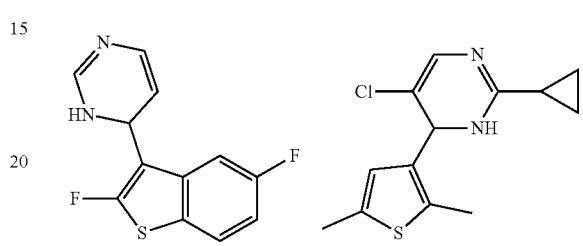

In one embodiment, $R^7$ and $R^8$ together with the atoms to which they are attached form an aryl, cycloalkyl, heterocyclyl, or heteroaryl ring.

In one embodiment, $R^{1b}$ is selected from:

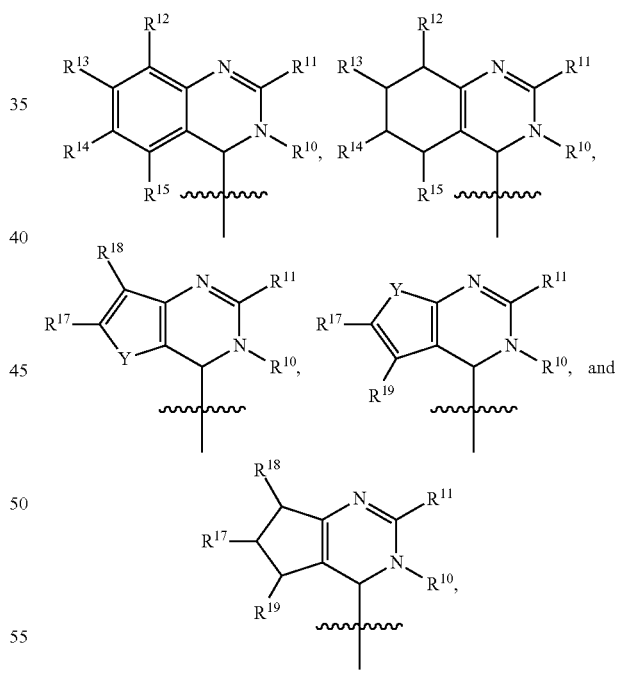

Y is S or O;

$R^{10}$ is hydrogen or alkyl; and $R^{11}$, $R^{12}$, $R^{13}$, $R^{14}$, $R^{15}$, $R^{16}$, $R^{17}$, $R^{18}$, and $R^{19}$ are each independently selected from hydrogen, halo, amino, alkylamino, alkyl, alkoxyl, cycloalkyl, and aryl.

In one embodiment, $R^{10}$ is hydrogen or alkyl; and $R^{11}$, $R^{12}$, $R^{13}$, $R^{14}$, $R^{15}$, $R^{16}$, $R^{17}$, $R^{18}$, and $R^{19}$ are each independently selected from hydrogen, halo, and alkyl.

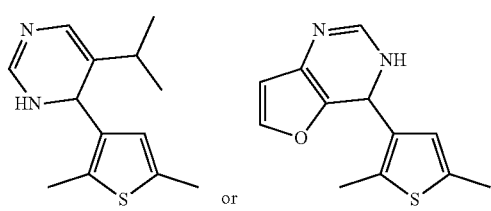

or

In one embodiment, $R^{1b}$ is

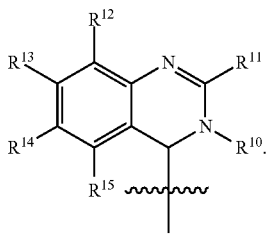

In one embodiment, $R^{11}$ is hydrogen. In one embodiment, $R^{11}$ is ($C_1$-$C_4$) alkyl (e.g., methyl).
In one embodiment, $R^{10}$ and $R^{15}$ are each hydrogen.
In one embodiment, $R^{12}$ is hydrogen. In one embodiment, $R^{12}$ is halo (e.g., fluoro).
In one embodiment, $R^{13}$ is hydrogen. In one embodiment, $R^{13}$ is halo (e.g., fluoro or chloro).
In one embodiment, $R^{14}$ is hydrogen. In one embodiment, $R^{14}$ is halo (e.g., chloro).
In one embodiment, $R^{1b}$ is

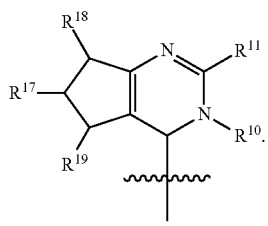

In one embodiment, $R^{11}$ is hydrogen. In one embodiment, $R^{11}$ is ($C_1$-$C_4$) alkyl (e.g., methyl).
In one embodiment, $R^{10}$, $R^{17}$, $R^{18}$ and $R^{19}$ are each hydrogen.
In one embodiment, $R^{1b}$ is

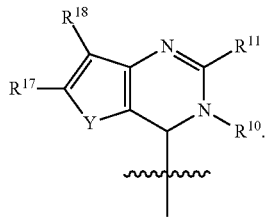

In one embodiment, Y is O. In one embodiment, Y is S.
In one embodiment, $R^{10}$, $R^{11}$, $R^{17}$ and $R^{18}$ are each hydrogen.
In one embodiment, $R^{1b}$ is

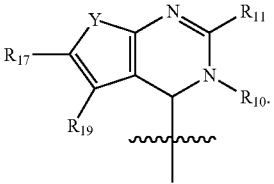

In one embodiment, Y is S.
In one embodiment, $R^{10}$, $R^{11}$, $R^{17}$ and $R^{19}$ are each hydrogen.
In one embodiment, $R^{1b}$ is

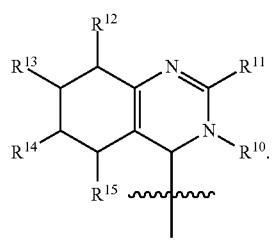

In one embodiment, $R^{11}$ is hydrogen. In one embodiment, $R^{11}$ is ($C_1$-$C_4$) alkyl (e.g., methyl).
In one embodiment, $R^{10}$, $R^{12}$, $R^{13}$, $R^{14}$ and $R^{15}$ are each hydrogen.

Specific examples include, but are not limited to, the following compounds:

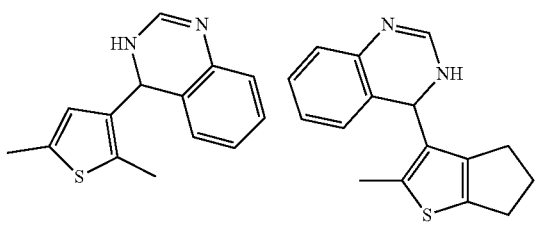

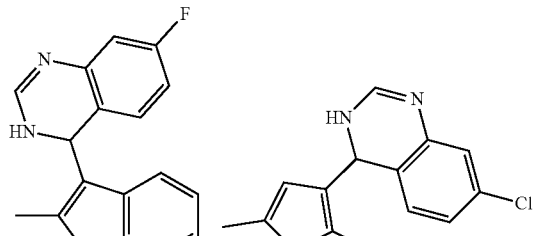

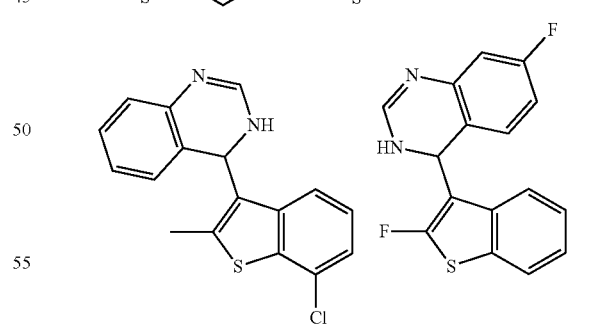

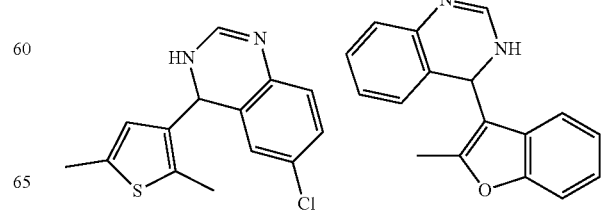

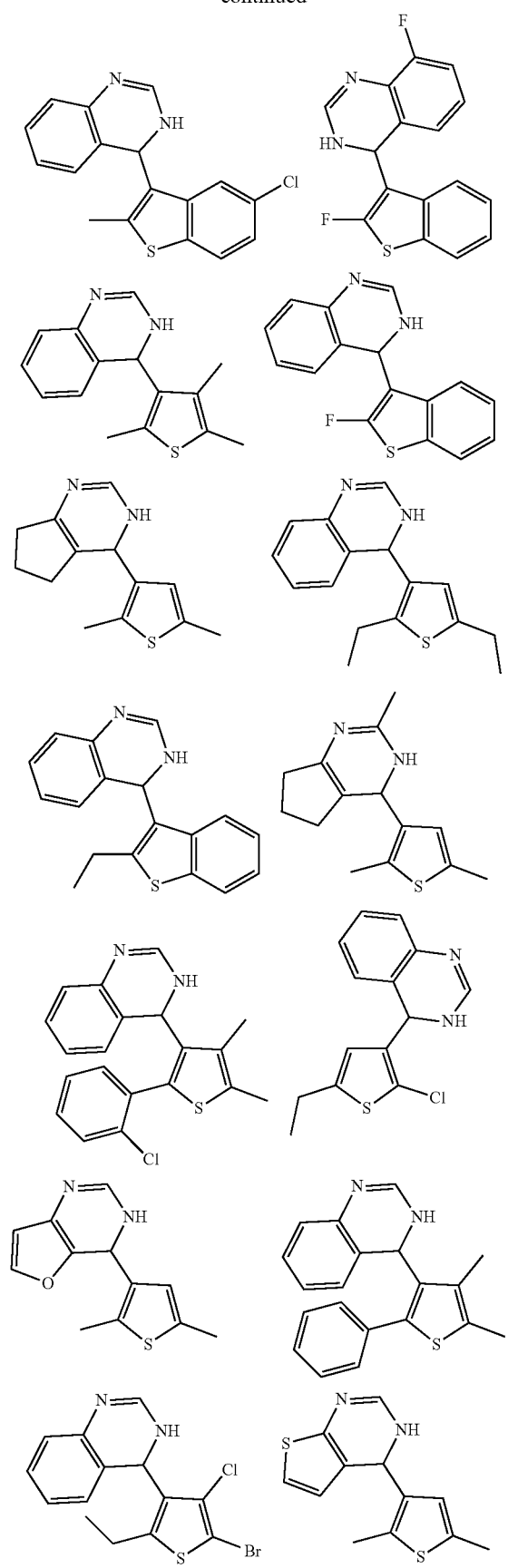
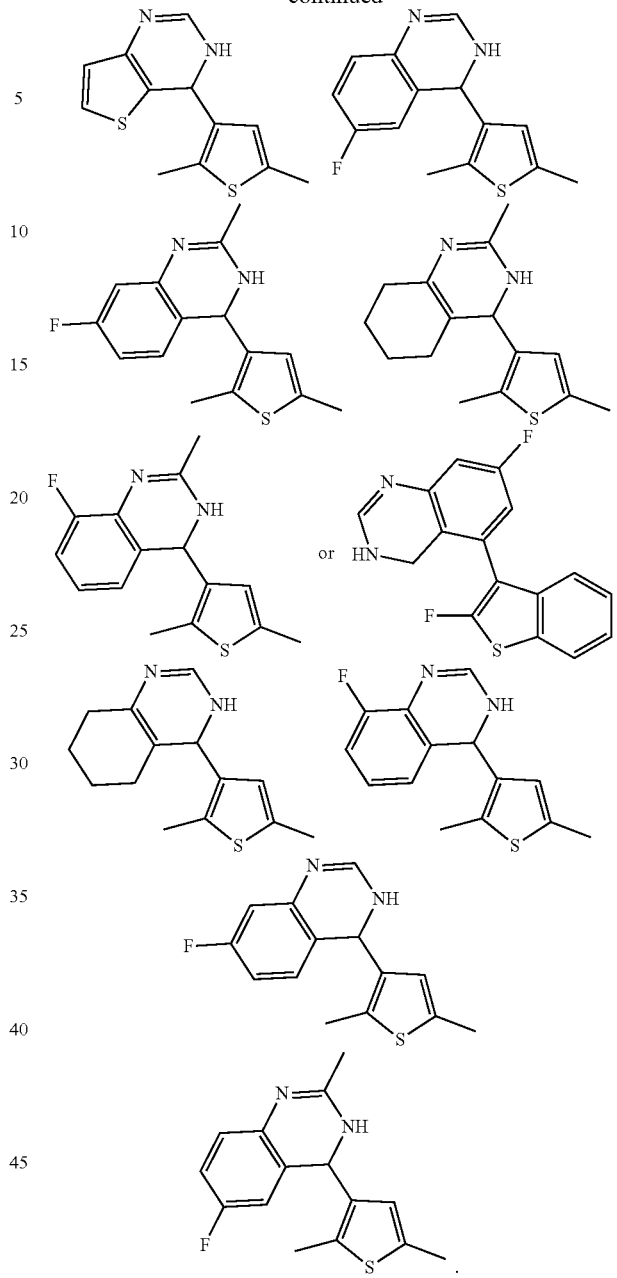
In one embodiment, $R^{1b}$ is represented by the following structure:
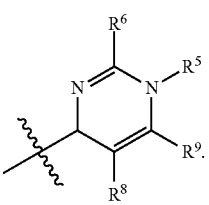
In one embodiment, $R^5$ is hydrogen or alkyl; and $R^6$, $R^8$ and $R^9$ are each independently selected from hydrogen, halo, amino, alkylamino, alkyl, alkoxyl, cycloalkyl, and aryl.

In one embodiment, $R^5$ is hydrogen. In one embodiment, $R^5$ is alkyl (e.g., methyl or 2-(pyrrolidin-2,5-dionyl)ethane).

In one embodiment, $R^6$ is hydrogen. In one embodiment, $R^9$ is hydrogen. In one embodiment, $R^8$ is hydrogen. In one embodiment, $R^8$ is $(C_1-C_4)$ alkyl (e.g., methyl).

Specific examples include, but are not limited to, the following compounds:

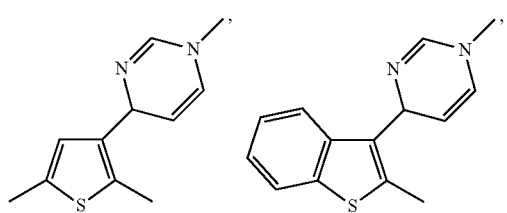

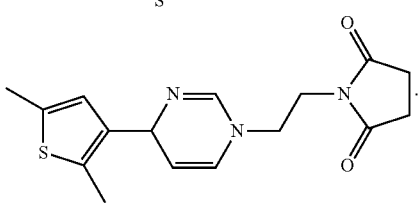

In one embodiment, $R^{1b}$ is represented by the following structure:

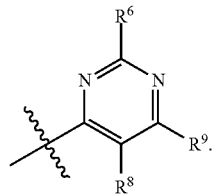

In one embodiment, $R^6$, $R^8$ and $R^9$ are each independently selected from hydrogen, halo, amino, alkylamino, alkyl, alkoxyl, cycloalkyl, and aryl.

In one embodiment, $R^6$, $R^8$ and $R^9$ are each hydrogen.

Specific examples include, but are not limited to, the following compound:

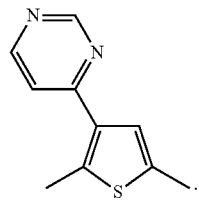

In one embodiment, $R^{1b}$ is selected from the following:

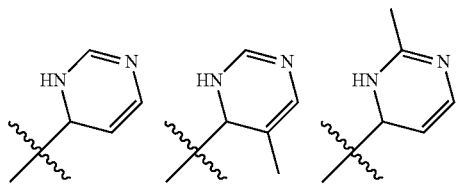
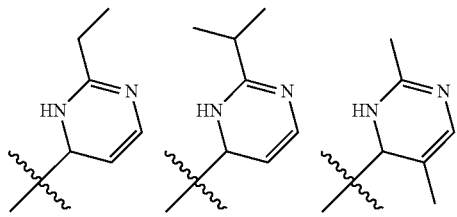
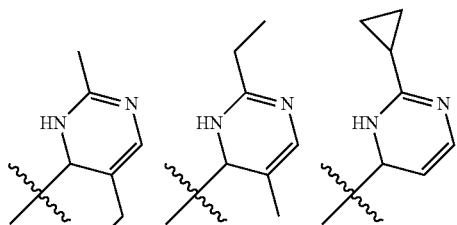
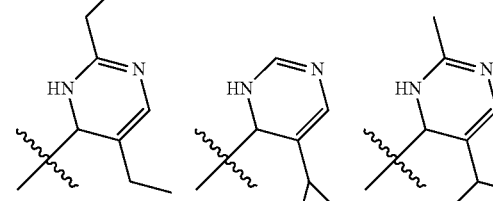
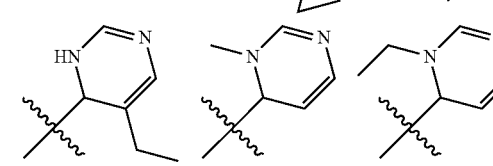
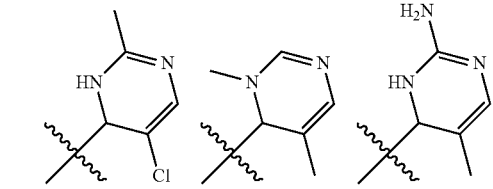
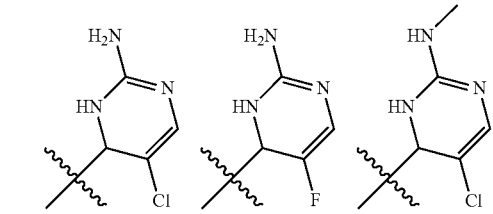
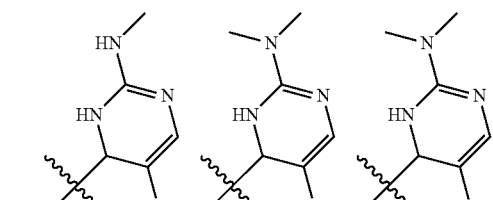

-continued
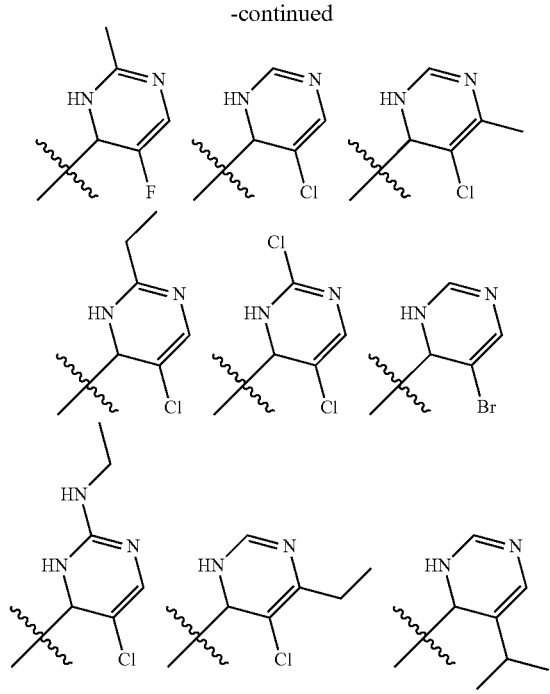
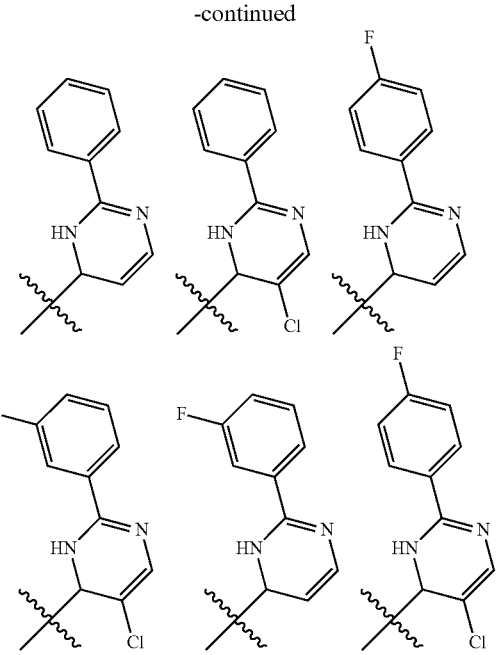
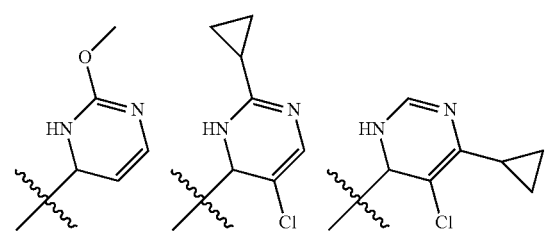
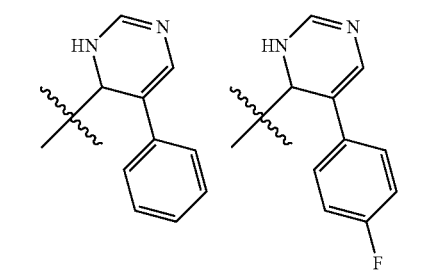
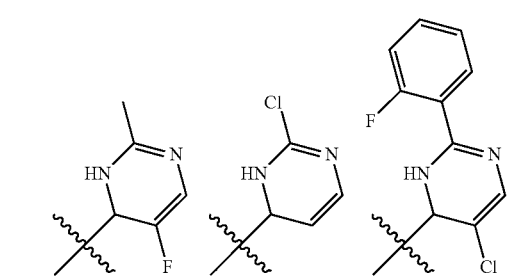

-continued

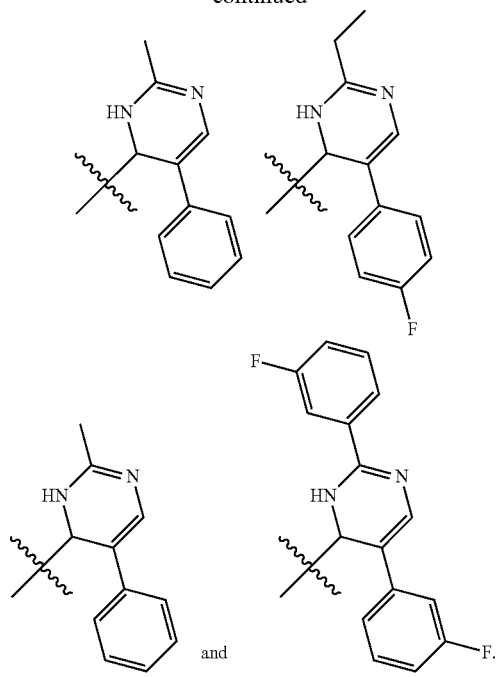

and

It should be noted that if there is a discrepancy between a depicted structure and a chemical name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it or mixtures thereof. Where the compound provided herein contains an alkenyl or alkenylene group, the compound may exist as one of or a mixture of geometric cis/trans (or Z/E) isomers. Where structural isomers are inter-convertible, the compound may exist as a single tautomer or a mixture of tautomers. This can take the form of proton tautomerism in the compound that contains, for example, an imino, keto, or oxime group; or so-called valence tautomerism in the compound that contains, for example, an aromatic moiety. It follows that a single compound may exhibit more than one type of isomerism.

The compounds provided herein may be enantiomerically pure or diastereomerically pure, such as a single enantiomer or a single diastereomer, or be stereoisomeric mixtures, such as a mixture of enantiomers and/or diastereomers, e.g., a racemic or enantioenriched mixture of two enantiomers; or a mixture of two or more diastereomers. In some instances, for compounds that undergo epimerization in vivo, one of skill in the art will recognize that administration of a compound in its (R) form is equivalent to administration of the compound in its (S) form, and vice versa. Conventional techniques for the preparation/isolation of individual enantiomers or diastereomers include synthesis from a suitable optically pure precursor, asymmetric synthesis from achiral starting materials, or resolution of a stereomeric mixture, for example, by chiral chromatography, recrystallization, resolution, diastereomeric salt formation, or derivatization into diastereomeric adducts followed by separation.

When the compound provided herein contains an acidic or basic moiety, it may also be provided as a pharmaceutically acceptable salt (See, Berge et al., *J. Pharm. Sci.* 1977, 66, 1-19; and "Handbook of Pharmaceutical Salts, Properties, and Use," Stahl and Wermuth, Ed.; Wiley-VCH and VHCA, Zurich, 2002).

Suitable acids for use in the preparation of pharmaceutically acceptable salts include, but are not limited to, acetic acid, 2,2-dichloroacetic acid, acylated amino acids, adipic acid, alginic acid, ascorbic acid, aspartic acid, L-aspartic acid, benzenesulfonic acid, benzoic acid, 4-acetamidobenzoic acid, boric acid, camphoric acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexanesulfamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, gluconic acid, D-gluconic acid, glucuronic acid, D-glucuronic acid, glutamic acid, L-glutamic acid, α-oxoglutaric acid, glycolic acid, hippuric acid, hydrobromic acid, hydrochloric acid, hydroiodic acid, isoethonic acid; (+)-L-lactic acid, (±)-DL-lactic acid, lactobionic acid, lauric acid, maleic acid, malic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, pyroglutamic acid, pyroglutamic acid, L-pyroglutamic acid, saccharic acid, salicylic acid, 4-amino-salicylic acid, sebacic acid, stearic acid, succinic acid, sulfuric acid, tannic acid, tartaric acid, (+)-L-tartaric acid, thiocyanic acid, p-toluenesulfonic acid, undecylenic acid, and valeric acid.

Suitable bases for use in the preparation of pharmaceutically acceptable salts, including, but not limited to, inorganic bases, such as magnesium hydroxide, calcium hydroxide, potassium hydroxide, potassium carbonate, zinc hydroxide, sodium hydroxide, or ammonia; and organic bases, such as primary, secondary, tertiary, and quaternary, aliphatic and aromatic amines, including L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methyl-glucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, secondary amines, triethanolamine, trimethylamine, triethylamine, N-methyl-D-glucamine, 2-amino-2-(hydroxymethyl)-1,3-propanediol, and tromethamine.

Unless otherwise specified, the term "compound" referred to herein, such as, e.g., a compound of formula (I) is intended to encompass one or more of the following, a stereoisomer or a mixture of two or more stereoisomers, a solid form (e.g., a crystal form or an amorphous form) or a mixture of two or more solid forms thereofthereof. In certain embodiments, the term "compound" referred to herein is intended to encompass a pharmaceutical acceptable form of the compound, including but not limited to, a free base, a stereoisomer or a mixture of two or more stereoisomers, a solid form (e.g., a crystal form or an amorphous form) or a mixture of two or more solid forms.

The compound provided herein may also be provided as a prodrug, which is a functional derivative of the compound, for example, of Formula (I) and is readily convertible into the parent compound in vivo. Prodrugs are often useful because, in some situations, they may be easier to administer than the parent compound. They may, for instance, be bioavailable by oral administration whereas the parent compound is not. The prodrug may also have enhanced solubility in pharmaceutical compositions over the parent compound. A prodrug may be converted into the parent drug by various mechanisms, including enzymatic processes and metabolic hydrolysis. See Harper, *Progress in Drug Research* 1962, 4, 221-294; Morozowich et al. in "Design of Biopharmaceutical Properties through Prodrugs and Analogs," Roche Ed., APHA Acad. Pharm. Sci. 1977; "Bioreversible Carriers in Drug in Drug Design, Theory and Application," Roche Ed., APHA Acad. Pharm. Sci. 1987; "Design of Prodrugs," Bundgaard, Elsevier, 1985; Wang et al., *Curr. Pharm. Design* 1999, 5, 265-287; Pauletti et al., *Adv. Drug. Delivery Rev.* 1997, 27, 235-256; Mizen et al., *Pharm. Biotech.* 1998, 11, 345-365; Gaignault et al., *Pract. Med. Chem.* 1996, 671-696; Asgharnejad in "Transport Processes in Pharmaceutical Systems," Amidon et al., Ed., Marcell Dekker, 185-218, 2000; Balant et al., *Eur. J. Drug Metab. Pharmacokinet.* 1990, 15, 143-53; Balimane and Sinko, *Adv. Drug Delivery Rev.* 1999, 39, 183-209; Browne, *Clin. Neuropharmacol.* 1997, 20, 1-12; Bundgaard, *Arch. Pharm. Chem.* 1979, 86, 1-39; Bundgaard, *Controlled Drug Delivery* 1987, 17, 179-96; Bundgaard, *Adv. Drug Delivery Rev.* 1992, 8, 1-38; Fleisher et al., *Adv. Drug Delivery Rev.* 1996, 19, 115-130; Fleisher et al., *Methods Enzymol.* 1985, 112, 360-381; Farquhar et al., *J. Pharm. Sci.* 1983, 72, 324-325; Freeman et al., *J. Chem. Soc., Chem. Commun.* 1991, 875-877; Friis and Bundgaard, *Eur. J. Pharm. Sci.* 1996, 4, 49-59; Gangwar et al., *Des. Biopharm. Prop. Prodrugs Analogs*, 1977, 409-421; Nathwani and Wood, *Drugs* 1993, 45, 866-94; Sinhababu and Thakker, *Adv. Drug Delivery Rev.* 1996, 19, 241-273; Stella et al., *Drugs* 1985, 29, 455-73; Tan et al., *Adv. Drug Delivery Rev.* 1999, 39, 117-151; Taylor, *Adv. Drug Delivery Rev.* 1996, 19, 131-148; Valentino and Borchardt, *Drug Discovery Today* 1997, 2, 148-155; Wiebe and Knaus, *Adv. Drug Delivery Rev.* 1999, 39, 63-80; and Waller et al., *Br. J. Clin. Pharmac.* 1989, 28, 497-507.

C. Methods of Treatment, Prevention, and/or Management

1. In Vivo Assays

In one embodiment, provided herein is a method of administering a compound provided herein, or a pharmaceutically acceptable salt or stereoisomer thereof, in a disease model that is known in the art. In one embodiment, the disease model is an animal model. In one embodiment, provided herein is a method of administering a compound provided herein, or a pharmaceutically acceptable salt or stereoisomer thereof, in an animal model that is predictive of efficacy in the treatment of certain diseases in human. The method comprises administering a compound provided herein, or a pharmaceutically acceptable salt or stereoisomer thereof, in a subject. In one embodiment, the method comprises administering a therapeutically effective amount of a compound provided herein, or a pharmaceutically acceptable salt or stereoisomer thereof, in a subject. In one embodiment, the method comprises treatment of a test subject (e.g., a mouse or rat) with a compound provided herein, or a pharmaceutically acceptable salt or stereoisomer thereof. In one embodiment, the method comprises treatment of a test subject (e.g., a mouse or rat) with a compound provided herein, or a pharmaceutically acceptable salt or stereoisomer thereof, as well as a reference compound, either in separate animal groups (e.g., administer a reference compound in a control group and administer a compound provided herein in a test group) or in the same animal group (e.g., as combination therapy). In one embodiment, the in vivo activity of the compound provided herein is dose dependent.

In one embodiment, the compounds provided herein are active in animal models of psychosis such as Pre-Pulse Inhibition (PPI) and PCP-induced hyperlocomotion. These two models have been used in the development of several antipsychotics, including olanzapine (Bakshi and Geyer, Psychopharmacology 1995, 122, 198-201) and quetapine (Swedlow et al., *J. Pharm. Exp. Ther.*, 1996, 279, 1290-99), and are predictive of efficacy in human psychotic patients. In one embodiment, compounds that are active in in vivo models of psychosis are further optimized to improve the potency in the in vivo assays and drug-like properties such as, e.g., solubility and lipophilicity. Given the exact molecular basis of certain diseases such as schizophrenia are poorly understood, this approach allows the use of predictive and well-validated animal models to develop compounds with established efficacy without focusing on specific molecular targets that may or may not translate to human efficacy in the clinic.

2. Treatment, Prevention, and/or Management

In one embodiment, provided herein is a method of treating, preventing, and/or managing various disorders, including, but not limited to, neurological disorders. In one embodiment, provided herein is a method of treating, preventing, and/or managing one or more symptoms of a neurological disorder. In one embodiment, the method comprises administering to a subject (e.g., human) a therapeutically or prophylactically effective amount of a composition or a compound provided herein or a pharmaceutically acceptable salt or stereoisomer thereof. In one embodiment, the subject is a human. In one embodiment, the subject is an animal. In one embodiment, the compounds provided herein are highly brain penetrable in the subject. In certain embodiments, the efficacious concentration of a compound provided herein is less than 10 nM, less than 100 nM, less than 1 µM, less than 10 µM, less than 100 µM, or less than 1 mM. In one embodiment, a compound's activity may be assessed in various art-recognized animal models as described herein elsewhere or known in the literature.

In one embodiment, without being limited by a particular theory, the treatment, prevention, and/or management is done by administering a compound provided herein that has shown in vivo efficacy in an animal model predictive of antipsychotic activity in humans. The phenotypic approach to develop antipsychotics has been used in psychopharmacology, with the antipsychotic chlorpromazine developed in this way. The phenotypic approach may also offer advantages over compounds developed by traditional in vitro based drug discovery approach, because the compounds developed using the phenotypic approach have established pharmaceutical properties and in vivo activity, rather than activity toward a given molecular target, which may be less predictive and lead to attrition at later stages of, for example, clinical development.

In one embodiment, provided herein is a method of treating, preventing, and/or managing a neurological disorder, including schizophrenia, schizophrenia spectrum disorder, acute schizophrenia, chronic schizophrenia, NOS schizophrenia, schizoid personality disorder, schizotypal personality disorder, delusional disorder, psychosis, psychotic disorder, brief psychotic disorder, shared psychotic disorder, psychotic disorder due to a general medical condition, drug-induced psychosis (e.g., cocaine, alcohol, amphetamine), psychoaffective disorder, aggression, delirium, Parkinson's psychosis, excitative psychosis, Tourette's syndrome, organic or NOS psychosis, seizure, agitation, post-traumatic stress disorder, behavior disorder, neurodegenerative disease, Alzheimer's disease, Parkinson's disease, dyskinesias, Huntington's disease, dementia, mood disorder, anxiety, affective disorders (e.g., depression, e.g., major depressive disorder and dysthymia; bipolar disorder, e.g., biopolar depressive disorder; manic disorder; seasonal affective disorder; and attention deficit disorder (ADD) and attention deficit hyperactivity disorder (ADHD)), obsessive-compulsive disorder, vertigo, epilepsy, pain (e.g., neuropathic pain, sensitization accompanying neuropathic pain, and inflammatory pain), fibromyalgia, migraine, cognitive impairment, cognitive impairment associated with schizophrenia (CIAS), movement disorder, restless leg syndrome (RLS), multiple sclerosis, sleep disorder, sleep apnea, narcolepsy, excessive daytime sleepiness, jet lag, drowsy side effect of medications, insomnia, substance abuse or dependency (e.g., nicotine, cocaine), addiction, eating disorder, sexual dysfunction, hypertension, emesis, Lesche-Nyhane disease, Wilson's disease, autism, Huntington's chorea, and premenstrual dysphoria, comprising administering to a subject an effective amount of a compound provided herein, or a pharmaceutically acceptable salt or stereoisomer thereof.

In one embodiment, provided herein is a method of treating, preventing, and/or managing a disorder related to psychosis, schizophrenia, ADHD, mood disorder or affective disorder such as depression and anxiety, comprising administering to a subject an effective amount of a compound provided herein. For example, without being limited by a particular theory, the compounds provided herein may improve the gating deficits of DBA/2 mice seen in the pre-pulse inhibition (PPI) test and reverse the methamphetamine-induced hyperlocomotor activity. Without being limited to a particular theory, the compounds provided herein may: 1) reverse the amphetamine-induced hyper-locomotor activity; 2) be useful as antipsychotic agents and dosed sparing; 3) improve attention and modulate impulsivity; 4) improve learning parameters in ADHD; 5) enhance learning ability and reduce anxiety in behavioral tests; and/or 6) have an anti-depressant effect.

In another embodiment, provided herein is a method of treating, preventing, and/or managing a disorder related to cognitive impairments, such as Alzheimer's disease, Parkinson's disease, schizophrenia, cognitive impairment associated with schizophrenia (CIAS), and attention deficit hyperactivity disorder (ADHD), and the like, comprising administering to a subject an effective amount of a compound provided herein. For example, without being limited by a particular theory, the compounds provided herein may have pro-cognitive effects, such as passive avoidance, novel object recognition, social recognition, and attention-set shifting. Further, without being limited by a particular theory, the compounds provided herein may improve social memory, increase the acquisition of an environment, and reverse scopolamine-induced deficits. The compounds provided herein may also reverse scopolamine-induced deficits in a passive avoidance memory test.

In another embodiment, provided herein is a method of treating, preventing, and/or managing a disorder associated with excessive daytime sleepiness, such as, narcolepsy, Parkinson's disease, multiple sclerosis, shift workers, jet lag, relief of side effects of other medications, and the like, comprising administering to a subject an effective amount of a compound provided herein. For example, without being limited by a particular theory, the compounds provided herein may have wake promoting effects.

In another embodiment, provided herein is a method of treating, preventing, and/or managing a sleeping disorder, such as insomnia, comprising administering to a subject an effective amount of a compound provided herein. For example, without being limited by a particular theory, the compounds provided herein may improve wakefulness and lead to an improved sleep pattern, and therefore the compounds provided herein may be useful in treating insomnia.

In another embodiment, provided herein is a method of treating, preventing, and/or managing substance abuse, comprising administering to a subject an effective amount of a compound provided herein. For example, without being limited by a particular theory, the compounds provided herein may alter methamphetamine self-administration in rats, and therefore the compounds provided herein may ameliorate the craving for addictive drugs.

In another embodiment, provided herein is a method of using the compounds provided herein as psycho-stimulants, which may lack the abuse liabilities generally associated with other classes of psycho-stimulants. Without being limited by a particular theory, the compounds provided herein may increase the levels of histamine, dopamine, norepinephrine, and/or acetylcholine in the prefrontal cortical area, which is consistent with their pro-cognitive effects and their wake promoting effects seen in animal models. For example, the compounds provided herein may increase dopamine in the frontal cortex but not the striatum. The compounds provided herein may not induce increased locomotor activity or sensitization that is associated with other psycho-stimulus.

In another embodiment, provided herein is a method of treating, preventing, and/or managing a disorder such as seizure, epilepsy, vertigo, and pain, comprising administering to a subject an effective amount of a compound provided herein. For example, without being limited by a particular theory, the compounds provided herein may be protective against pentylene-tetrazole (PTZ) and electrical-induced seizures. The compounds provided herein may increase the seizure threshold in humans. The compounds provided herein may decrease electrical discharge from afferent neurons in an inner ear preparation. Further, without being limited by a particular theory, the compounds provided herein may increase the threshold for neuropathic pain, which is shown in models such as the chronic constriction injure (CCI) model, herpes virus-induced model, and capsaicin-induced allodynia model. Therefore, in some embodiments, the compounds provided herein are employed for their analgesic effects to treat, prevent, and/or manage disorders involving pain and the sensitization that accompanies many neuropathic pain disorders.

In another embodiment, provided herein is a method of treating, preventing, and/or managing a movement disorder, such as Parkinson's disease, restless leg syndrome (RLS), and Huntington's disease, comprising administering to a subject an effective amount of a compound provided herein.

In some embodiments, a compound provided herein is active in at least one model, which can be used to measure the activity of the compound and estimate the efficacy in treating a neurological disorder. For example, when the model is for psychosis (e.g., PCP Hyperactivity Model or Prepulse Inhibition of Startle Model), a compound is active when the compound reduces PCP induced hyperactivity in mice by a statistically signicant amount compared to a vehicle, or when the compound reverses the disruption of prepulse inhibition (PPI) induced by PCP in mice.

In other embodiments, provided herein is a method of effecting a therapeutic effect as described herein elsewhere. The method comprises administering to a subject (e.g., a mammal) a therapeutically effective amount of a compound or composition provided herein. The particular therapeutic effects may be measured using any model system known in the art and described herein, such as those involving an animal model of a disease.

In some embodiments, the neurological disorder is: depression (e.g., major depressive disorder or dysthymia); bipolar disorder, seasonal affective disorder; cognitive deficit; fibromyalgia; pain (e.g., neuropathic pain); sleep related disorder (e.g., sleep apnea, insomnia, narcolepsy, cataplexy) including those sleep disorders which are produced by psychiatric conditions; chronic fatigue syndrome; attention deficit disorder (ADD); attention deficit hyperactivity disorder (ADHD); restless leg syndrome; schizophrenia; anxieties (e.g., general anxiety disorder, social anxiety disorder, panic disorder); obsessive compulsive disorder; post-traumatic stress disorder; seasonal affective disorder (SAD); premenstrual dysphoria; post-menopausal vasomotor symptoms (e.g., hot flashes, night sweats); neurodegenerative disease (e.g., Parkinson's disease, Alzheimer's disease and amyotrophic lateral sclerosis); manic disorder; dysthymic disorder; cyclothymic disorder; obesity; and substance abuse or dependency (e.g., cocaine addiction, nicotine addiction). In another embodiment, the compounds provided herein are useful to treat, prevent, and/or manage two or more conditions/disorders, which are co-morbid, such as psychosis and depression.

Neurological disorders may also include cerebral function disorders, including without limitation, senile dementia, Alzheimer's type dementia, cognition, memory loss, amnesia/amnestic syndrome, epilepsy, disturbances of consciousness, coma, lowering of attention, speech disorder, Lennox syndrome, autism, and hyperkinetic syndrome.

Neuropathic pain includes, without limitation, post herpetic (or post-shingles) neuralgia, reflex sympathetic dystrophy/causalgia or nerve trauma, phantom limb pain, carpal tunnel syndrome, and peripheral neuropathy (such as diabetic neuropathy or neuropathy arising from chronic alcohol use).

Other exemplary diseases and conditions that may be treated, prevented, and/or managed using the methods, compounds, and/or compositions provided herein include, but are not limited to: obesity; migraine or migraine headache; and sexual dysfunction, in men or women, including without limitation sexual dysfunction caused by psychological and/or physiological factors, erectile dysfunction, premature ejaculation, vaginal dryness, lack of sexual excitement, inability to obtain orgasm, and psycho-sexual dysfunction, including without limitation, inhibited sexual desire, inhibited sexual excitement, inhibited female orgasm, inhibited male orgasm, functional dyspareunia, functional vaginismus, and atypical psychosexual dysfunction.

In one embodiment, the neurological disorder is excessive daytime sleepiness. In another embodiment, the neurological disorder is a cognitive impairment. In another embodiment, the neurological disorder is a mood disorder. In another embodiment, the neurological disorder is an affective disorder. In another embodiment, the neurological disorder is a movement disorder. In another embodiment, the neurological disorder is schizophrenia. In another embodiment, the neurological disorder is an attention disorder. In another embodiment, the neurological disorder is an anxiety disorder. In another embodiment, the neurological disorder is seizure. In another embodiment, the neurological disorder is psychosis. In another embodiment, the neurological disorder is epilepsy. In another embodiment, the neurological disorder is vertigo. In another embodiment, the neurological disorder is pain. In another embodiment, the neurological disorder is neuropathic pain. In another embodiment, the neuropathic pain is diabetic neuropathy.

In one embodiment, the neurological disorder is a neurodegenerative disease. In one embodiment, the neurodegenerative disease is Parkinson's disease. In another embodiment, the neurodegenerative disorder is Alzheimer's disease.

In one embodiment, the compounds described herein treat, prevent, and/or manage a neurological disorder of the central nervous system, without causing addiction to said compounds.

Any suitable route of administration can be employed for providing the patient with a therapeutically or prophylactically effective dose of an active ingredient. For example, oral, mucosal (e.g., nasal, sublingual, buccal, rectal, vaginal), parenteral (e.g., intravenous, intramuscular), transdermal, and subcutaneous routes can be employed. Exemplary routes of administration include oral, transdermal, and mucosal. Suitable dosage forms for such routes include, but are not limited to, transdermal patches, ophthalmic solutions, sprays, and aerosols. Transdermal compositions can also take the form of creams, lotions, and/or emulsions, which can be included in an appropriate adhesive for application to the skin or can be included in a transdermal patch of the matrix or reservoir type as are conventional in the art for this purpose. An exemplary transdermal dosage form is a "reservoir type" or "matrix type" patch, which is applied to the skin and worn for a specific period of time to permit the penetration of a desired amount of active ingredient. The patch can be replaced with a fresh patch when necessary to provide constant administration of the active ingredient to the patient.

The amount to be administered to a patient to treat, prevent, and/or manage the disorders described herein will depend upon a variety of factors including the activity of the particular compound employed, or the ester, salt or amide thereof, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount required. For example, the physician or veterinarian could start doses of the compounds employed at levels lower than that required in order to achieve the desired therapeutic effect and gradually increase the dosage until the desired effect is achieved.

In general, a suitable daily dose of a compound provided herein will be that amount of the compound which is the lowest dose effective to produce a therapeutic or prophylactic effect. Such an effective dose will generally depend upon the factors described above. Generally, oral, intravenous, intracerebroventricular and subcutaneous doses of the compounds provided herein for a patient will range from about 0.005 mg per kilogram to about 5 mg per kilogram of body weight per day. In one embodiment, the oral dose of a compound provided herein will range from about 10 mg to about 300 mg per day. In another embodiment, the oral dose of a compound provided herein will range from about 20 mg to about 250 mg per day. In another embodiment, the oral dose of a compound provided herein will range from about 100 mg to about 300 mg per day. In another embodiment, the oral dose of a compound provided herein will range from about 10 mg to about 100 mg per day. In another embodiment, the oral dose of a compound provided herein will range from about 25 mg to about 50 mg per day. In another embodiment, the oral dose of a compound provided herein will range from about 50 mg to about 200 mg per day. Each of the above-recited dosage ranges may be formulated as a single or multiple unit dosage formulations.

In some embodiments, the compounds disclosed herein may be used in a combination treatment with one or more second active agents to treat, prevent, and/or manage disorders described herein. In one embodiment, the one or more second active agents are selected from antidepressants, agents useful in the treatment of Parkinson's disease and antipsychotics. Exemplary antipsychotics include, but are not limited to atypical antipsychotics such as amisulpride, aripiprazole, asenapine, blonanserin, clotiapine, clozapine, iloperidone, lurasidone, mosapramine, olanzapine, paliperidone, perospirone, quetiapine, remoxipride, risperidone, sertindole, sulpiride, ziprasidone, and zotepine. Exemplary antidepressants include, but are not limited to citalopram, excitalopram, fluoxetine, fluvoxamine, paroxetine, sertraline, vilazodone, desvenlafaxine, duloxetine, milnacipran, vanlafaxine, mianserin, mirtazapine, atomoxetine, mazindol, reboxetine, viloxazine, bupropion, agomelatine, amitriptyline, clomipramine, doxepin, imipramine, timipramine, desipramine, nortriptyline, protriptyline, isocarboxazid, moclobemide, phenelzine, selegiline, tranylcypromine, buspirone, gepirone, nefazodone, tandospirone and trazodone. Exemplary treatments for Parkinson's disease include, but are not limited to carbidopa, levodopa, entacapone, bromocriptine, pergolide, pramipexole, ropinirole, rotogotine, tolcapone, selegiline, rasagiline, benzotropine, trihexylphenidyl and amantadine.

3. Pharmaceutical Compositions and Dosage Forms

Pharmaceutical compositions can be used in the preparation of individual, single unit dosage forms. Pharmaceutical compositions and dosage forms provided herein comprise a compound provided herein, or a pharmaceutically acceptable salt, stereoisomer, clathrate, or prodrug thereof. Pharmaceutical compositions and dosage forms can further comprise one or more excipients.

Pharmaceutical compositions and dosage forms provided herein can also comprise one or more additional active ingredients. Examples of optional second, or additional, active ingredients are also disclosed herein.

Single unit dosage forms provided herein are suitable for oral, mucosal (e.g., nasal, sublingual, vaginal, buccal, or rectal), parenteral (e.g., subcutaneous, intravenous, bolus injection, intramuscular, or intra-arterial), topical (e.g., eye drops or other ophthalmic preparations), transdermal or transcutaneous administration to a patient. Examples of dosage forms include, but are not limited to: tablets; caplets; capsules, such as soft elastic gelatin capsules; cachets; troches; lozenges; dispersions; suppositories; powders; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; eye drops or other ophthalmic preparations suitable for topical administration; and sterile solids (e.g., crystalline or amorphous solids) that can be reconstituted to provide liquid dosage forms suitable for parenteral administration to a patient.

The composition, shape, and type of dosage forms will typically vary depending on their use. For example, a dosage form used in the acute treatment of a disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. These and other ways in which specific dosage forms are used will vary from one another and will be readily apparent to those skilled in the art. See, e.g., *Remington's Pharmaceutical Sciences*, 18th Ed., Mack Publishing, Easton Pa. (1990).

In one embodiment, pharmaceutical compositions and dosage forms comprise one or more excipients. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form. For example, the decomposition of some active ingredients may be accelerated by some excipients such as lactose, or when exposed to water. Active ingredients that comprise primary or secondary amines are particularly susceptible to such accelerated decomposition. Consequently, provided are pharmaceutical compositions and dosage forms that contain little, if any, lactose other mono- or disaccharides. As used herein, the term "lactose-free" means that the amount of lactose present, if any, is insufficient to substantially increase the degradation rate of an active ingredient.

Lactose-free compositions can comprise excipients that are well known in the art and are listed, for example, in the *U.S. Pharmacopeia* (USP) 25-NF20 (2002). In general, lactose-free compositions comprise active ingredients, a binder/filler, and a lubricant in pharmaceutically compatible and pharmaceutically acceptable amounts. In one embodiment, lactose-free dosage forms comprise active ingredients, microcrystalline cellulose, pre-gelatinized starch, and/or magnesium stearate.

Also provided are anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, *Drug Stability: Principles & Practice*, 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are, in one embodiment, packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

Also provided are pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

Like the amounts and types of excipients, the amounts and specific types of active ingredients in a dosage form may differ depending on factors such as, but not limited to, the route by which it is to be administered to patients. In one embodiment, dosage forms comprise a compound provided herein in an amount of from about 0.10 to about 500 mg. In other embodiments, dosage forms comprise a compound provided herein in an amount of about 0.1, 1, 2, 5, 7.5, 10, 12.5, 15, 17.5, 20, 25, 50, 100, 150, 200, 250, 300, 350, 400, 450, or 500 mg.

In other embodiments, dosage forms comprise a second active ingredient in an amount of 1 to about 1000 mg, from about 5 to about 500 mg, from about 10 to about 350 mg, or from about 50 to about 200 mg. Of course, the specific amount of the second active agent will depend on the specific agent used, the diseases or disorders being treated or managed, and the amount(s) of a compound provided herein, and any optional additional active agents concurrently administered to the patient.

In one embodiment, pharmaceutical compositions and dosage forms described herein include one or more second active agents to treat, prevent, and/or manage disorders described herein. In one embodiment, the one or more second active agents are selected from antidepressants, agents useful in the treatment of Parkinson's disease and antipsychotics.

(a) Oral Dosage Forms

Pharmaceutical compositions that are suitable for oral administration can be provided as discrete dosage forms, such as, but not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, *Remington's The Science and Practice of Pharmacy*, 21st Ed., Lippincott Williams & Wilkins (2005).

Oral dosage forms provided herein are prepared by combining the active ingredients in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

In one embodiment, oral dosage forms are tablets or capsules, in which case solid excipients are employed. In another embodiment, tablets can be coated by standard aqueous or non-aqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms provided herein include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. A specific example of a binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Examples of fillers suitable for use in the pharmaceutical compositions and dosage forms provided herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions is, in one embodiment, present in from about 50 to about 99 weight percent of the pharmaceutical composition or dosage form.

Disintegrants may be used in the compositions to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients may be used to form solid oral dosage forms. The amount of disintegrant used varies based upon the type of formulation, and is readily discernible to those of ordinary skill in the art. In one embodiment, pharmaceutical compositions comprise from about 0.5 to about 15 weight percent of disintegrant, or from about 1 to about 5 weight percent of disintegrant.

Disintegrants that can be used in pharmaceutical compositions and dosage forms include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, and mixtures thereof.

Lubricants that can be used in pharmaceutical compositions and dosage forms include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants may be used in an amount of less than about 1 weight percent of the pharmaceutical compositions or dosage forms into which they are incorporated.

In one embodiment, a solid oral dosage form comprises a compound provided herein, and optional excipients, such as anhydrous lactose, microcrystalline cellulose, polyvinylpyrrolidone, stearic acid, colloidal anhydrous silica, and gelatin.

(b) Controlled Release Dosage Forms

Active ingredients provided herein can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active agents provided herein. In one embodiment, provided are single unit dosage forms suitable for oral administration such as, but not limited to, tablets, capsules, gelcaps, and caplets that are adapted for controlled-release.

In one embodiment, controlled-release pharmaceutical products improve drug therapy over that achieved by their non-controlled counterparts. In another embodiment, the use of a controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

In another embodiment, the controlled-release formulations are designed to initially release an amount of drug (active ingredient) that promptly produces the desired therapeutic or prophylactic effect, and gradually and continually release of other amounts of drug to maintain this level of therapeutic or prophylactic effect over an extended period of time. In one embodiment, in order to maintain a constant level of drug in the body, the drug can be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

(c) Parenteral Dosage Forms

Parenteral dosage forms can be administered to patients by various routes including, but not limited to, subcutaneous, intravenous (including bolus injection), intramuscular, and intra-arterial. In some embodiments, administration of a parenteral dosage form bypasses patients' natural defenses against contaminants, and thus, in these embodiments, parenteral dosage forms are sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms. For example, cyclodextrin and its derivatives can be used to increase the solubility of a compound provided herein. See, e.g., U U.S. Pat. No. 5,134,127, which is incorporated herein by reference.

(d) Topical and Mucosal Dosage Forms

Topical and mucosal dosage forms provided herein include, but are not limited to, sprays, aerosols, solutions, emulsions, suspensions, eye drops or other ophthalmic preparations, or other forms known to one of skill in the art. See, e.g., *Remington's The Science and Practice of Pharmacy,* 21st Ed., Lippincott Williams & Wilkins (2005); and *Introduction to Pharmaceutical Dosage Forms,* 4th ed., Lea & Febiger, Philadelphia (1985). Dosage forms suitable for treating mucosal tissues within the oral cavity can be formulated as mouthwashes or as oral gels.

Suitable excipients (e.g., carriers and diluents) and other materials that can be used to provide topical and mucosal dosage forms encompassed herein are well known to those skilled in the pharmaceutical arts, and depend on the particular tissue to which a given pharmaceutical composition or dosage form will be applied. In one embodiment, excipients include, but are not limited to, water, acetone, ethanol, ethylene glycol, propylene glycol, butane-1,3-diol, isopropyl myristate, isopropyl palmitate, mineral oil, and mixtures thereof to form solutions, emulsions or gels, which are non-toxic and pharmaceutically acceptable. Moisturizers or humectants can also be added to pharmaceutical compositions and dosage forms. Examples of additional ingredients are well known in the art. See, e.g., *Remington's The Science and Practice of Pharmacy*, 21st Ed., Lippincott Williams & Wilkins (2005).

The pH of a pharmaceutical composition or dosage form may also be adjusted to improve delivery of one or more active ingredients. Also, the polarity of a solvent carrier, its ionic strength, or tonicity can be adjusted to improve delivery. Compounds such as stearates can also be added to pharmaceutical compositions or dosage forms to alter the hydrophilicity or lipophilicity of one or more active ingredients so as to improve delivery. In other embodiments, stearates can serve as a lipid vehicle for the formulation, as an emulsifying agent or surfactant, or as a delivery-enhancing or penetration-enhancing agent. In other embodiments, salts, solvates, prodrugs, clathrates, or stereoisomers of the active ingredients can be used to further adjust the properties of the resulting composition.

4. Kits

In one embodiment, active ingredients provided herein are not administered to a patient at the same time or by the same route of administration. In another embodiment, provided are kits which can simplify the administration of appropriate amounts of active ingredients.

In one embodiment, a kit comprises a dosage form of a compound provided herein. Kits can further comprise one or more second active ingredients as described herein, or a pharmacologically active mutant or derivative thereof, or a combination thereof.

In other embodiments, kits can further comprise devices that are used to administer the active ingredients. Examples of such devices include, but are not limited to, syringes, drip bags, patches, and inhalers.

Kits can further comprise cells or blood for transplantation as well as pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

V. EXAMPLES

Certain embodiments are illustrated by the following non-limiting examples.

A. General Procedures for Compound Synthesis

In the examples below, unless otherwise indicated, all temperatures are set forth in degrees Celsius and all parts and percentages are by weight. Reagents may be purchased from commercial suppliers, such as Sigma-Aldrich® Chemical Company, and may be used without further purification unless otherwise indicated. Reagents may also be prepared following standard literature procedures known to those skilled in the art. Solvents may be purchased from Sigma-Aldrich® in Sure-Seal® bottles and used as received. All solvents may be purified using standard methods known to those skilled in the art, unless otherwise indicated.

The reactions set forth below were done generally at ambient temperature, unless otherwise indicated. Unless otherwise specified, generally the reaction flasks were fitted with rubber septa for introduction of substrates and reagents via syringe. Analytical thin layer chromatography (TLC) was performed using glass-backed silica gel pre-coated plates and eluted with appropriate solvent ratios (v/v). Reactions were assayed by TLC or LCMS, and terminated as judged by the consumption of starting material. Visualization of the TLC plates was done with UV light (254 wavelength) or with an appropriate TLC visualizing solvent, such as basic aqueous $KMnO_4$ solution activated with heat. Flash column chromatography (see, e.g., Still et al., J. Org. Chem., 43: 2923 (1978)) was performed using, for example, silica gel 60 or various MPLC systems (such as Biotage® or ISCO® separation systems).

The compound structures in the examples below were confirmed by one or more of the following methods: proton nuclear magnetic resonance spectroscopy, mass spectroscopy, elemental microanalysis, and melting point. Proton nuclear magnetic resonance CH NMR) spectra were determined using a NMR spectrometer operating at a certain field strength. Chemical shifts are reported in parts per million (ppm, δ) downfield from an internal standard, such as TMS. Alternatively, $^1$H NMR spectra were referenced to signals from residual protons in deuterated solvents, for example, as follows: $CDCl_3$=7.25 ppm; DMSO-$d_6$=2.49 ppm; $C_6D_6$=7.16 ppm; $CD_3OD$=3.30 ppm. Peak multiplicities are designated, for example, as follows: s, singlet; d, doublet; dd, doublet of doublets; t, triplet; dt, doublet of triplets; q, quartet; br, broadened; and m, multiplet. Coupling constants are given in Hertz (Hz). Mass spectra (MS) data were obtained using a mass spectrometer with APCI or ESI ionization.

1. 6-(2-fluorobenzo[b]thiophen-3-yl)-1,6-dihydropyrimidine

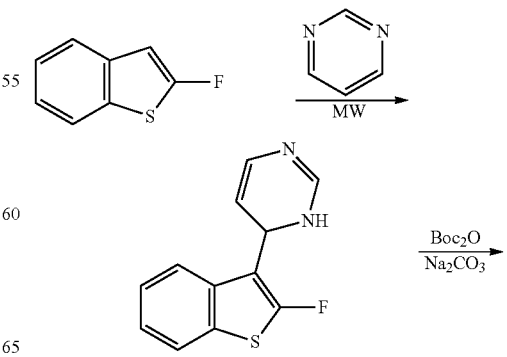

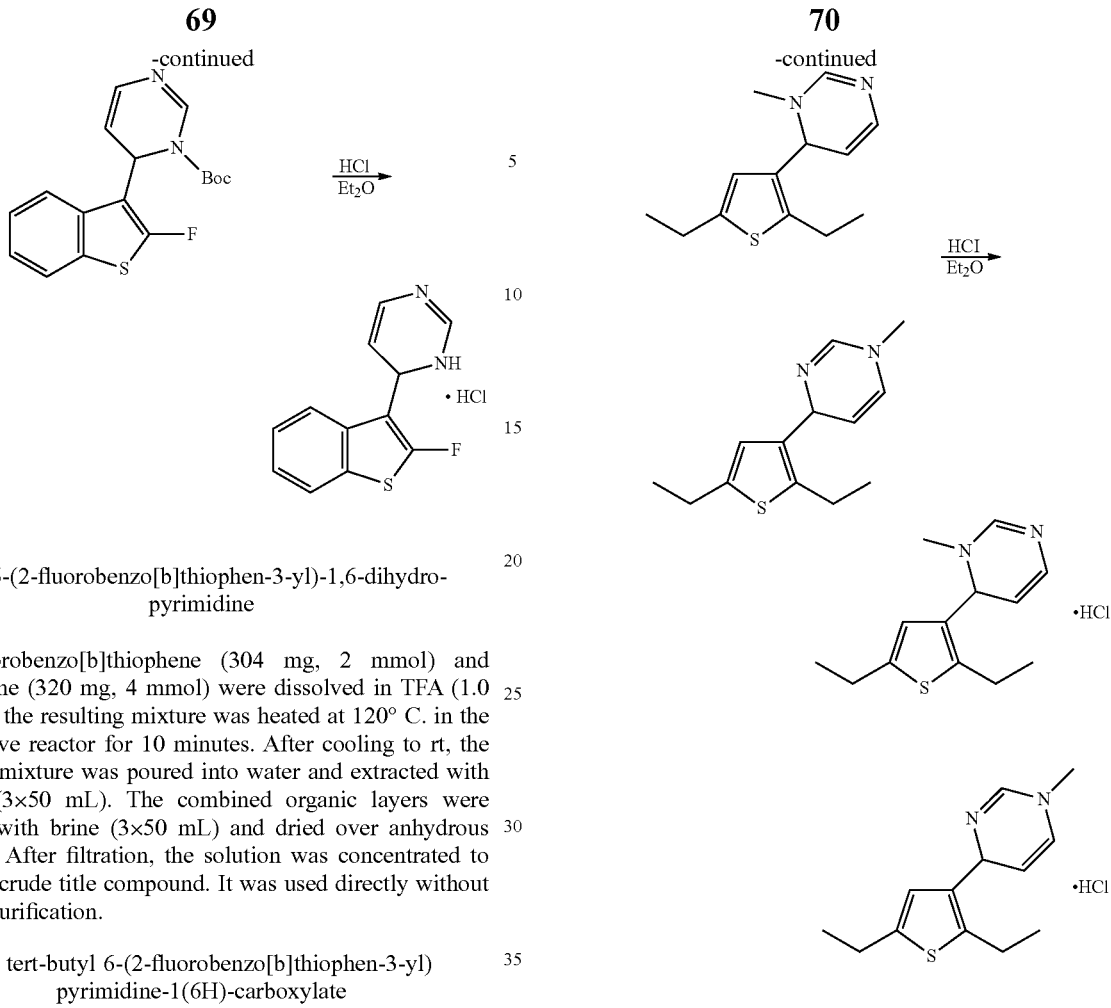

(a) 6-(2-fluorobenzo[b]thiophen-3-yl)-1,6-dihydro-pyrimidine

2-Fluorobenzo[b]thiophene (304 mg, 2 mmol) and pyrimidine (320 mg, 4 mmol) were dissolved in TFA (1.0 mL) and the resulting mixture was heated at 120° C. in the microwave reactor for 10 minutes. After cooling to rt, the reaction mixture was poured into water and extracted with EtOAc (3×50 mL). The combined organic layers were washed with brine (3×50 mL) and dried over anhydrous $Na_2SO_4$. After filtration, the solution was concentrated to give the crude title compound. It was used directly without further purification.

(b) tert-butyl 6-(2-fluorobenzo[b]thiophen-3-yl) pyrimidine-1(6H)-carboxylate

A solution of 6-(2-fluorobenzo[b]thiophen-3-yl)-1,6-dihydropyrimidine in water was treated with $Na_2CO_3$ until pH reached 9. A solution of $Boc_2O$ in dry EtOAc (20 mL) was then added dropwise. After the starting material was consumed completely as shown by TLC, the reaction mixture was extracted with EtOAc (3×50 mL), washed with brine (3×50 mL), and dried over anhydrous $Na_2SO_4$. After filtration and concentration, the crude product was purified by column chromatography to give the title compound.

(c) HCl salt of tert-butyl 6-(2-fluorobenzo[b]thiophen-3-yl) pyrimidine-1(6H)

A solution of tert-butyl 6-(2-fluorobenzo[b]thiophen-3-yl) pyrimidine-1(6H) in $Et_2O$ was treated with gaseous HCl at 0° C. for 10 minutes. The precipitated solid was collected by vacuum filtration and dried to give the desired product.

2. 6-(2,5-diethylthiophen-3-yl)-1-methyl-1,6-dihydropyrimidine and 4-(2,5-diethylthiophen-3-yl)-1-methyl-1,4-dihydropyrimidine (a) 6-(2,5-diethylthiophen-3-yl)-1-methyl-1,6-dihydropyrimidine and 4-(2,5-diethylthiophen-3-yl)-1-methyl-1,4-dihydropyrimidine 2,5-Diethylthiophene (280 mg, 2 mmol) and 1-methylpyrimidin-1-ium iodide (888 mg, 4 mmol) was dissolved in TFA (1.0 mL) and the mixture was heated at 120° C. in the microwave reactor for 10 minutes. After cooling to room temperature, the reaction mixture was poured into water and extracted with EtOAc (3×50 mL). The combined organic layers were washed with brine (3×50 mL) and dried over anhydrous $Na_2SO_4$. After filtration and concentration, the crude product was purified by preparative HPLC to give the title compound.

(b) Preparation of HCl salt

A solution of above product in $Et_2O$ was treated with gaseous HCl at 0° C. for 10 minutes. The precipitated solid was collected by vacuum filtration and dried to give the desired product.

3. 6-(2,5-difluorobenzo[b]thiophen-3-yl)-1,6-dihydropyrimidine

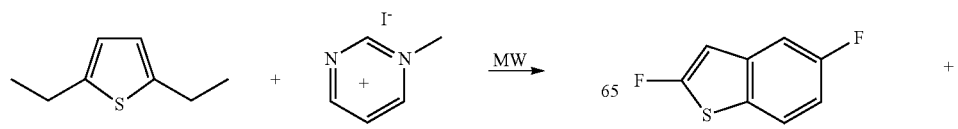

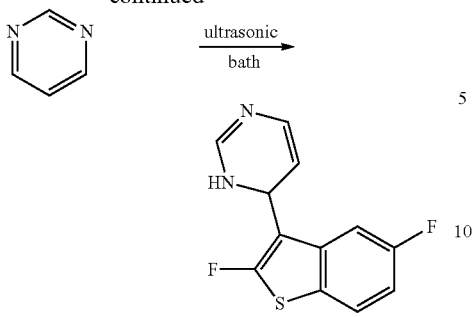

(a) 6-(2,5-difluorobenzo[b]thiophen-3-yl)-1,6-dihydropyrimidine 2,5-difluorobenzo[b]thiophene (340 mg, 2 mmol) and pyrimidine (320 mg, 4 mmol) were dissolved in TFA (1.0 mL) and the resulting mixture was put in the ultrasonic reactor for 4 hours. The reaction mixture was then poured into water and extracted with EtOAc (3×50 mL). The combined organic layers were washed with brine (3×50 mL) and dried over anhydrous $Na_2SO_4$. After filtration, the solution was concentrated to give the crude title compound.

4. Generic Thiophene Synthesis6-(2-phenylbenzo[b]thiophen-3-yl)-1,6-dihydropyrimidine

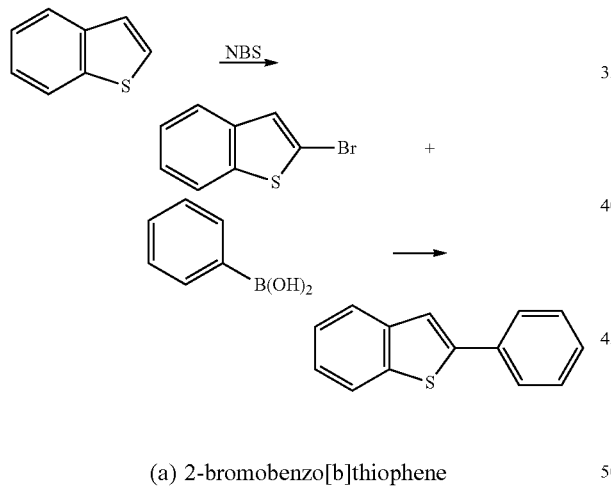

(a) 2-bromobenzo[b]thiophene

To a solution of benzo[b]thiophene (1.34 g, 10 mmol) in AcOH (10 mL) and DCM (25 mL) was added NBS (1.78 g, 10 mmol) in portions. After stirring overnight at room temperature, the reaction mixture was treated with $Na_2SO_3$ and water, followed by extraction with EtOAc. The combined organic layers were washed with brine and dried over anhydrous $Na_2SO_4$. After filtration and concentration, the crude product was purified by column chromatography to give the title compound (b) 2-phenylbenzo[b]thiophene A 100 mL round-bottomed flask was charged with 2-bromobenzo[b]thiophene (1.06 g, 5 mmol), phenylboronic acid (1.22 g, 10 mmol), $PPh_3$ (265 mg, 1 mmol) and $Pd(OAc)_2$ (224 mg, 1 mmol) in dioxide (50 mL) under nitrogen at room temperature. After stirring for 30 minutes, $Na_2CO_3$ (159 mg, 7.5 mmol) and $H_2O$ (10 mL) were added. The resulting mixture was heated at reflux for 3 h. After cooling to rt, the reaction mixture was poured into water and extracted with EtOAc (3×50 mL). The combined organic layers were washed with brine (3×50 mL) and dried over anhydrous $Na_2SO_4$. After filtration and concentration, the crude product was purified by column chromatography to give the title compound.

5. 3-chloro-2,5-dimethylthiophene

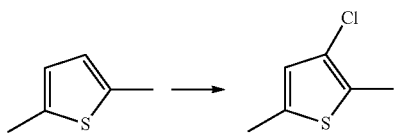

(a) 3-chloro-2,5-dimethylthiophene

To a solution of 2,5-dimethylthiophene (3.36 g, 30 mmol) in HOAc (50 mL) at 0° C. was added NCS (4.42 g, 33 mmol) in one portion. The reaction mixture was warmed gradually to room temperature and stirred overnight. The mixture was then treated with $Na_2SO_3$ and water, followed by extraction with EtOAc. The combined organic layers were washed with brine and dried over anhydrous $Na_2SO_4$. After filtration and concentration, the crude product was purified by column chromatography to give the title compound.

6. 2-methyl-5,6-dihydro-4H-cyclopenta[b]thiophene

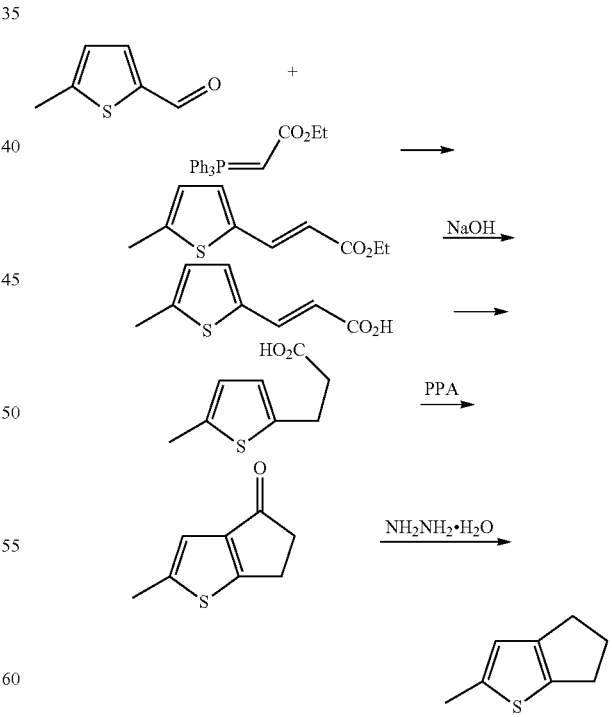

(a) (E)-ethyl 3-(5-methylthiophen-2-yl) acrylate

To a solution of 5-methylthiophene-2-carbaldehyde (63 g, 0.5 mol) in $CH_2Cl_2$ (200 mL) was added triphenylphosphorane (191.4 g, 0.55 mol) at room temperature and stirred overnight. After concentration, the crude product was purified by column chromatography to give the title compound.

(b) (E)-3-(5-methylthiophen-2-yl) acrylic acid

To a solution of (E)-ethyl 3-(5-methylthiophen-2-yl)acrylate (80 g, 408 mmol) in methanol (2000 mL) was added NaOH (130 g, 3.25 mol) and water (2000 mL) at room temperature. The mixture was heated to 50° C. and stirred for 0.5 h. After the starting material was consumed completely as shown by TLC, the reaction mixture was concentrated. The crude product was used directly without further purification.

(c) 3-(5-methylthiophen-2-yl) propanoic acid

To a solution of (E)-3-(5-methylthiophen-2-yl)acrylic acid (20 g, 119 mmol) was dissolved in water (1000 mL) was added a catalytic amount of Pd/C. A vacuum was applied and the reaction mixture was back filled with hydrogen gas three times. The resulting mixture was stirred under atmospheric $H_2$. After the reduction was complete, the reaction mixture was filtered and the filter cake was washed with water. The filtrate was acidified to pH 2, extracted with EtOAc, and dried over anhydrous $Na_2SO_4$. The solvent was removed under reduced pressure to give the title compound.

(d) 2-methyl-5,6-dihydro-4H-cyclopenta[b]thiophen-4-one

To a solution of 3-(5-methylthiophen-2-yl) propanoic acid (20 g, 117 mmol) in DCE (200 mL) was added PPA (300 g) and the resulting mixture was refluxed overnight. After concentration, the reaction mixture was treated with solid $NaCO_3$, followed by addition of water. After stirring for 30 minutes, the mixture was extracted with EtOAc and the organic layer was washed with brine and dried over anhydrous $Na_2SO_4$. After filtration and concentration, the crude product was purified by column chromatography to give the title compound.

(e) 2-methyl-5,6-dihydro-4H-cyclopenta[b]thiophene

To a solution of 2-methyl-5,6-dihydro-4H-cyclopenta[b]thiophen-4-one (5 g, 33 mmol) in ethylene glycol (10 mL) and water (2 mL) was added KOH (7.4 g, 132 mmol) and hydrazine hydrate (50 mL). The resulting mixture was then refluxed for 48 h. After cooling to rt, the reaction was quenched with water and extracted with EtOAc. The organic layer was then washed with brine and dried over anhydrous $Na_2SO_4$. After filtration and concentration, the crude product was purified by column chromatography to give the title compound.

7. 2,3,4-trimethylthiophene

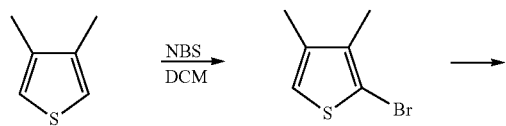

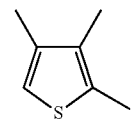

(a) 2-bromo-3,4-dimethylthiophene

To a solution of 3,4-dimethylthiophene (2 g, 17.8 mmol) in DCM (100 mL) was added NBS (3.2 g, 17.8 mmol) and the mixture was stirred overnight at rt. After concentration, the crude product was purified by column chromatography to give the title compound.

(b) 2,3,4-trimethylthiophene

To a solution of 2-bromo-3,4-dimethylthiophene (1 g, 5.2 mmol) in THF (50 mL) under $N_2$ at −60° C. was added n-BuLi (2.1 mL, 5.2 mmol, 2.5 M in hexane) dropwise. After stirring at −78° C. for 1 h, the reaction mixture was allowed to warm to −20° C. and stirred for 0.5 h. The reaction mixture was then cooled to −78° C. and $CH_3I$ (1.5 g, 10 mmol) was added. The reaction mixture was then warmed gradually to rt and stirred overnight. The mixture was poured into water, extracted with ethyl ether (3×100 mL), and the combined organic layers were dried over anhydrous $Na_2SO_4$. After concentration, the crude product was purified by column chromatography to give the title compound.

8. 2,3-dimethyl-5-phenylthiophene

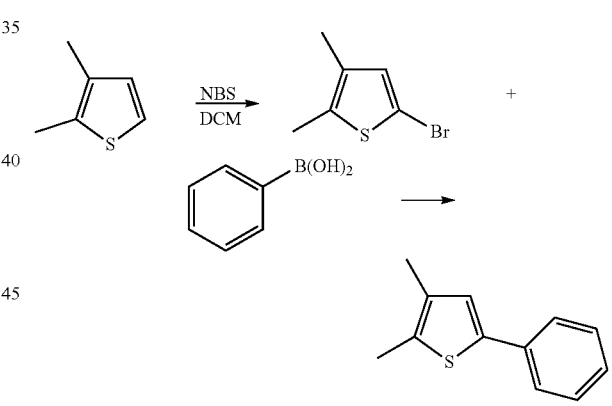

(a) 5-bromo-2,3-dimethylthiophene

To a solution of 2,3-dimethylthiophene (2.24 g, 2 mmol) in DCM (50 mL) was added NBS (3.56 g, 2 mmol) and the mixture was stirred overnight. After concentration, the crude product was purified by column chromatography to give the title compound.

(b) 2,3-dimethyl-5-phenylthiophene

To a solution of 5-bromo-2,3-dimethylthiophene (1.9 g, 1 mmol) in water (10 mL) and 1,4-dioxane (25 mL) was added $Pd(OAc)_2$ (22.4 mg, 0.1 mmol), triphenylphosphine (118 mg, 0.45 mmol), phenylboronic acid (244 mg, 2 mmol) and $Na_2CO_3$ (318 mg, 3 mmol). The reaction mixture was refluxed for 4 h. The mixture was then poured into water and extracted with diethyl ether (3×20 mL). The combined organic layers were then dried over anhydrous Na$_2$SO$_4$. After filtration and concentration, the crude product was purified by column chromatography to give the title compound.

9. 2-phenylthiophene

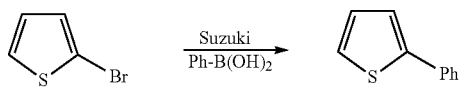 [SMILES: "Ph-B(OH)2" ; Brc1cccs1 ; c1ccc(-c2cccs2)cc1]

(a) 2-phenylthiophene

A solution of 4-bromo-2-methylthiophene (3.6 g, 20.3 mmol), phenylboronic acid (5.0 g, 40.7 mmol), Pd (OAc)$_2$ (456 mg, 2.03 mmol), PPh$_3$ (2.4 g, 9.1 mmol) and Na$_2$CO$_3$ (6.5 g, 60.9 mmol) in dioxane (10 mL) and water (10 mL) was refluxed under N$_2$ for 12 h. After cooling to rt, the reaction mixture was extracted with EtOAc several times. The combined organic layers were washed with brine and dried over anhydrous Na$_2$SO$_4$. After filtration and concentration, the crude product was purified by column chromatography to give the title compound.

10. 2,4-dimethylthiophene

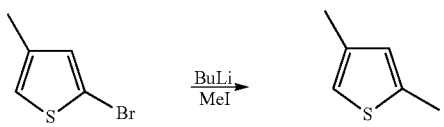

(a) 2,4-dimethylthiophene

To a solution of 4-bromo-2-methylthiophene (5 g, 28.25 mmol) and Ni(dppf)Cl$_2$ (46 mg, 0.085 mmol) in ether (20 mL) under nitrogen atmosphere was added MeMgBr (4.2 g, 35.3 mmol) slowly and the reaction mixture was heated at reflux for 24 h. After cooling to rt, the reaction was diluted with water and extracted with ether (50 mL×3). The combined organic layers were washed with brine and dried over anhydrous MgSO$_4$. After filtration and concentration, the crude product was purified by column chromatography to give the title compound.

11. 2-ethyl-4-methylthiophene

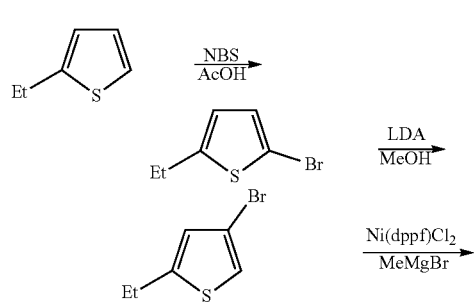

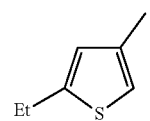

(a) 2-bromo-5-ethylthiophene

To a solution of 2-ethylthiophene (5 g, 44.6 mmol) in CHCl$_3$ and AcOH (1:1, 60 mL) at 0° C. was added NBS (8.7 g, 49.6 mmol) in and the resulting mixture was stirred for 3 h. After the starting material was consumed completely as shown by TLC, the reaction was quenched with saturated sodium carbonate and extracted with CHCl$_3$. The combined organic layers were washed with brine and dried over anhydrous MgSO$_4$. After filtration and concentration, the crude product was purified by column chromatography to give the title compound.

(b) 3-bromo-5-ethylthiophene

To a solution of 2-bromo-5-ethylthiophene (4 g, 21.05 mmol) in anhydrous THF (50 mL) at −70° C. under nitrogen atmosphere was added LDA (42.1 mmol) dropwise and the resulting mixture was stirred for 2 h. MeOH (120 mL) was then added to the reaction and stirring was continued for another 1 h. The temperature was then allowed to warm to room temperature and the reaction mixture was quenched with saturated sodium carbonate and extracted with EtOAc (200 mL×3). The combined organic layers were washed with brine and dried over anhydrous MgSO$_4$. After filtration and concentration, the crude product was purified by column chromatography to give the title compound.

(c) 2-ethyl-4-methylthiophene

To a solution of 4-bromo-2-ethylthiophene (5 g, 28.25 mmol) and Ni(dppf)Cl$_2$ (46 mg, 0.085 mmol) in anhydrous ether (20 mL) under nitrogen atmosphere was added MeMgBr (4.2 g, 35.3 mmol) slowly. The reaction solution was then heated at reflux for 24 h. After cooling to room temperature, the reaction was diluted with water and extracted with ether (20 mL×3). The combined organic layers were washed with brine and dried over anhydrous MgSO$_4$. After filtration and concentration, the crude product was purified by column chromatography to give the title compound.

12. 2-fluorobenzo[b]thiophene

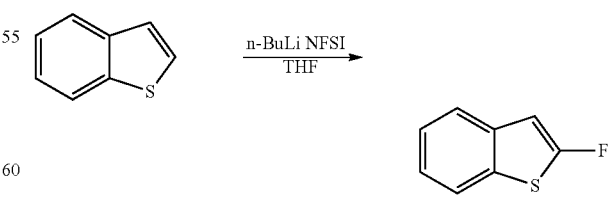

(a) 2-fluorobenzo[b]thiophene

To a solution of benzo[b]thiophene (1.34 g, 10 mmol) in anhydrous THF (100 mL) at −78° C. was added butyl lithium (4.4 mL, 11 mmol, 2.5 M in hexane) dropwise. After stirring at −78° C. for 30 minutes, N-fluorobenzenesulfonimide (NFSI, 6.3 g, 20 mmol) was added. The reaction mixture was stirred at −78° C. for 30 minutes. The mixture was warmed gradually to room temperate and stirred for two days followed by quenching with water and extracting with ether (3×50 mL). The combined organic layers were dried over Na₂SO₄ and concentrated to give a crude product that was purified by column chromatography to provide the title compound.

13. 2-ethylbenzo[b]thiophene

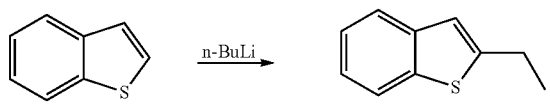

(a) 2-ethylbenzo[b]thiophene

To a solution of benzo[b]thiophene (1.34 g, 10 mmol) in anhydrous THF (100 mL) at −78° C. was added butyl lithium (4.4 mL, 11 mmol, 2.5 M in hexane) dropwise. After stirring at −78° C. for 30 minutes, diethyl sulfate (2.34 g, 15 mmol) was added dropwise. The reaction mixture was then warmed to room temperature and stirred for two days. The mixture was quenched with water and extracted with diethyl ether. The organic layer was dried over Na₂SO₄ and concentrated to give a crude product. The crude product was purified by column chromatography to provide the title compound.

14. 5-chloro-2-methylbenzo[b]thiophene

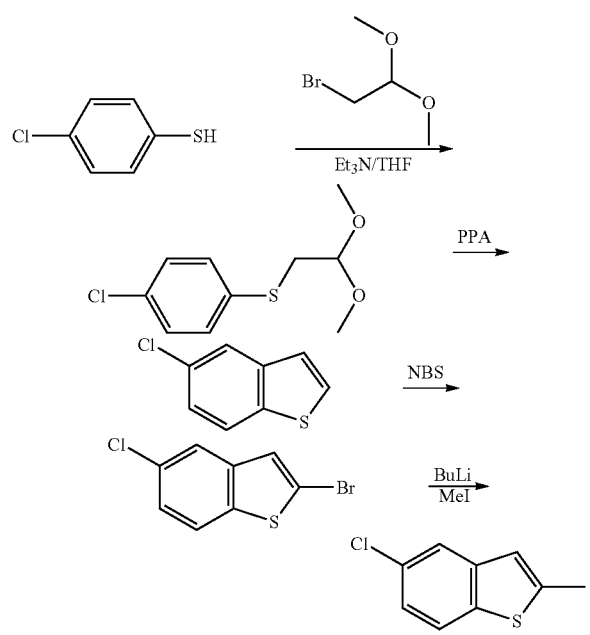

(a) (4-chlorophenyl)(2,2-dimethoxyethyl)sulfane

To a solution of 4-chlorobenzenethiol (100 mmol) and K₂CO₃ (13.8 g, 100 mmol) in DMF (150 mL) at 0° C. was added 2-bromo-1,1-dimethoxyethane (18.7 g, 110 mmol). After the benzenethiol was consumed completely as shown by TLC, water (200 mL) was added and extracted with EtOAc (3×100 mL). The combined organic layers were washed with brine (3×50 mL) and dried over anhydrous Na₂SO₄. After filtration and concentration, the crude product was purified by column chromatography to give the title compound.

(b) 5-chlorobenzo[b]thiophene (4-chlorophenyl)(2,2-dimethoxyethyl)sulfane (95 mmol) was dissolved in chlorobenzene (50 mL). The resulting mixture was added dropwise to boiling polyphosphoric acid (200 g) in chlorobenzene (100 mL) over 10 minutes. The mixture was then poured into ice water (500 mL) and Na₂CO₃ was added until the pH 8. The mixture was then extracted with EtOAc (3×100 mL), and the combined organic layers were washed with brine (3×50 mL) and dried over anhydrous Na₂SO₄. After filtration and concentration, the crude product was purified by column chromatography to give the title compound.

(c) 2-bromo-5-chlorobenzo[b]thiophene

To a solution of 5-chlorobenzo[b]thiophene (30 mmol) in AcOH (10 mL) and DCM (50 mL) at room temperature was added NBS (30 mmol) in one portion. After stirring overnight, the reaction mixture was treated with Na₂SO₃ and water, followed by extraction with EtOAc. The combined organic layers were washed with brine and dried over anhydrous Na₂SO₄. After filtration and concentration, the crude product was purified by column chromatography to give the title compound (d) 5-chloro-2-methylbenzo[b]thiophene To a solution of 2-bromo-5-chlorobenzo[b]thiophene (25 mmol) in dry THF (100 mL) under nitrogen at −78° C. was added butyl lithium (10 mL, 2.5 M in hexane) dropwise. The resulting mixture was stirred at −78° C. for 30 minutes. It was then warmed to −20° C. and iodomethane (7.1 g, 50 mmol) was added. After stirring at −20° C. for 30 minutes, the reaction mixture was poured into water and extracted with ether (3×50 mL). The combined organic layers were washed with brine (3×50 mL) and dried over anhydrous Na₂SO₄. After concentration, the crude product was purified by column chromatography to give the title compound.

15. 3-chlorobenzo[b]thiophene

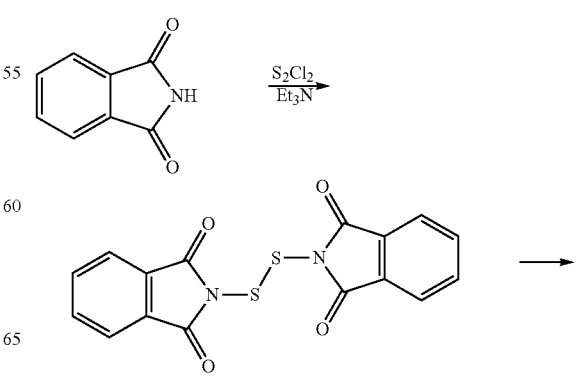

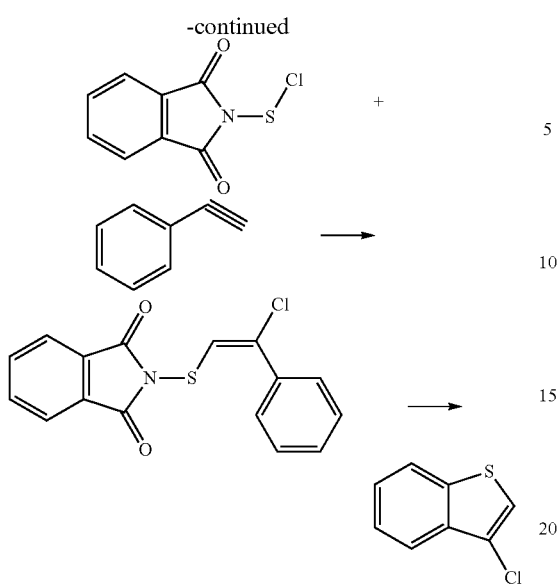

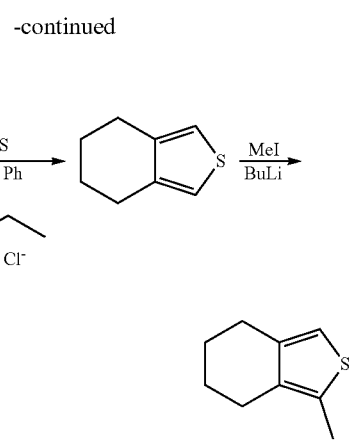

(a) 4,5,6,7-tetrahydrobenzo[c]thiophene was synthesized according to: *J. Org. Chem.* 2006, 71, 3154-3158

(a) 3-chlorobenzo[b]thiophene was synthesized according to: *J. Org. Chem.* 1987, 52, 169-172

18. benzo[c]thiophene 16. 6-(3-chloro-5-methylthiophen-2-yl)-1,6-dihydro-pyrimidine4-chloro-2-methylthiophene

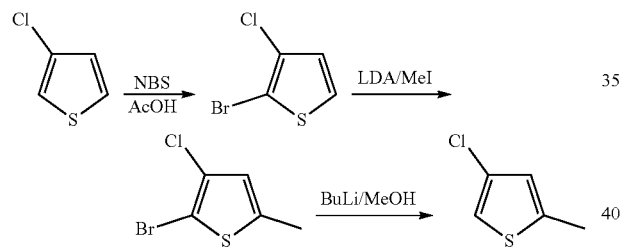

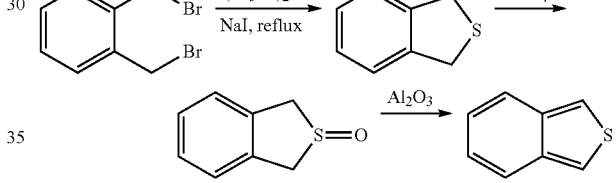

(a) benzo[c]thiophene was synthesized according to: *J. Org. Chem.* 1985, 50, 4969-4971

(a) The title compound was synthesized according to: WO 2011/069063

19. 5-chlorobenzo[c]thiophene 17. 4,5,6,7-tetrahydrobenzo[c]thiophene

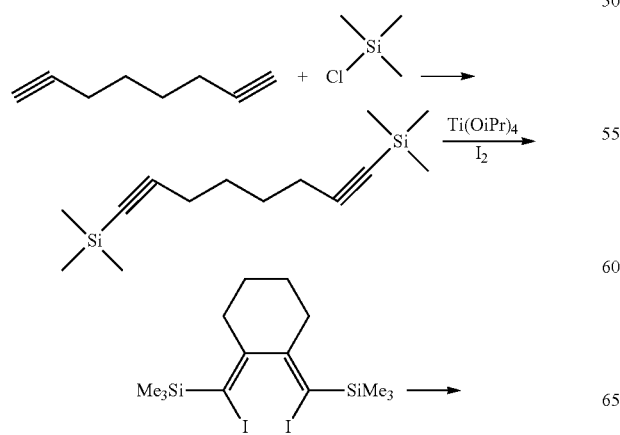

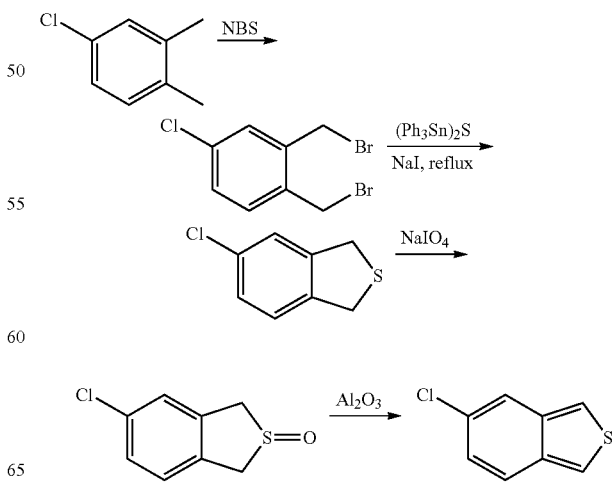

(a) 5-chlorobenzo[c]thiophene was synthesized according to: *J. Org. Chem.* 1985, 50, 4969-4971

Generic Pyrimidine Synthetic Schemes 20. 1-ethylpyrimidin-1-ium bromide

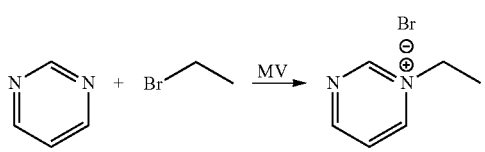

(a) 1-ethylpyrimidin-1-ium bromide

In a 5 mL microwave reaction tube, bromoethane (2 mL) and pyrimidine (320 mg, 4 mmol) was added and the resulting mixture was heated at 80° C. in the microwave reactor for 20 minutes. After cooling to rt, the reaction mixture was filtered and the filter cake was washed with ether and dried under vacuum to give the crude title compound.

21. 5-chloro-2-methylpyrimidine

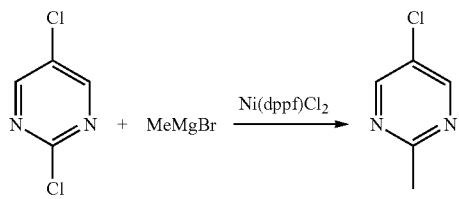

(a) 5-chloro-2-methylpyrimidine

To a solution of 2,5-dichloropyrimidine (5 mmol) and Ni(dppf)Cl$_2$ (0.25 mmol) in ether (30 mL) was added MeMgBr (6 mmol, 1M in THF) dropwise under nitrogen atmosphere and the resulting mixture was refluxed overnight. After cooling to rt, water (20 mL) was added and the mixture was extracted with ether (3×35 mL). The combined organic layers were washed with brine and dried over anhydrous Na$_2$SO$_4$. After filtration and concentration, the crude product was purified by column chromatography to give the title compound.

22. 5-chloro-4-methylpyrimidine

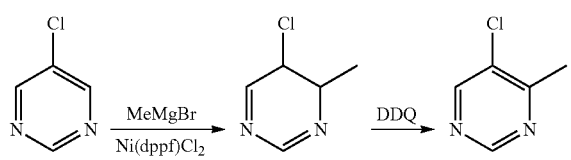

(a) 5-chloro-4-methyl-4,5-dihydropyrimidine

To a solution of 5-chloropyrimidine (5 mmol) and Ni(dppf)Cl$_2$ (0.25 mmol) in ether (30 mL) was added MeMgBr (6 mmol, 1M in THF) dropwise under nitrogen atmosphere and the resulting mixture was refluxed overnight. After cooling to rt, water (20 mL) was added and the mixture was extracted with ether (3×35 mL). The combined organic layers were washed with brine, dried over anhydrous Na$_2$SO$_4$. After filtration and concentration, the crude product was purified by column chromatography to give the title compound.

(b) 5-chloro-4-methylpyrimidine

To a solution of 5-chloro-4-methyl-4,5-dihydropyrimidine (2 g) in THF (30 mL) was added DDQ (1 g) dropwise at 0° C. and the resulting mixture was stirred for 6 hours. After the 5-chloro-4-methyl-4,5-dihydropyrimidine was consumed completely as shown by TLC, water (30 mL) was added and the mixture was extracted with EtOAc (3×50 mL). The combined organic layers were washed with brine and dried over anhydrous Na$_2$SO$_4$. After filtration and concentration, the crude product was purified by column chromatography to give the title compound.

23. 5-phenylpyrimidine

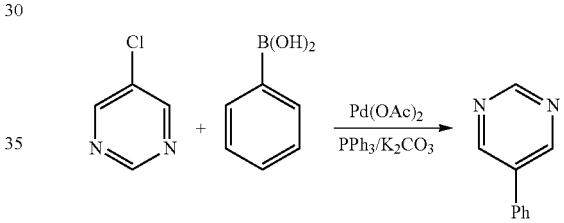

(a) 5-phenylpyrimidine

A 100 mL round-bottom flask was charged with 5-chloropyrimidine (5 mmol), phenylboronic acid (1.22 g, 10 mmol), PPh$_3$ (265 mg, 1 mmol) and Pd(OAc)$_2$ (224 mg, 1 mmol) in dioxide (50 mL) under nitrogen at room temperature. After stirring for 30 minutes, Na$_2$CO$_3$ (159 mg, 7.5 mmol) and H$_2$O (10 mL) were added and the resulting mixture was heated at reflux for 3 h. After cooling to rt, the reaction mixture was poured into water and extracted with EtOAc (3×50 mL). The combined organic layers were washed with brine (3×50 mL) and dried over anhydrous Na$_2$SO$_4$. After filtration and concentration, the crude product was purified by column chromatography to give the title compound.

24. 2-methoxypyrimidine

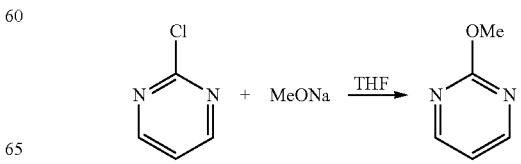

(a) 2-methoxypyrimidine

A solution of 5-chloropyrimidine (5 mmol) and MeONa (5.5 mmol) in THF (30 mL) was stirred overnight at 150° C. After cooling to rt, the solvent was removed and water (20 mL) was added to the residue. The resulting mixture was extracted with EtOAc (3×35 mL). The combined organic layers were washed with brine, and dried over anhydrous $Na_2SO_4$. After filtration and concentration, the crude product was purified by column chromatography to give the title compound.

25. 5-chloro-N-ethylpyrimidin-2-amine

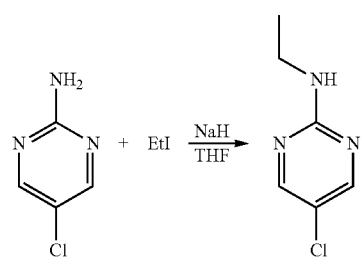

(a) 5-chloro-N-ethylpyrimidin-2-amine

To a solution of 5-chloropyrimidin-2-amine (6 mmol) in THF (30 mL) was added NaH (6.6 mmol) in four portions at 0° C. The resulting mixture was stirred for 1 hour. After that, MeI (6 mmol) was added to the reaction mixture dropwise at 0° C. and stirred for another 2 hours. After the 5-chloropyrimidin-2-amine was consumed completely by LC-MS, water (30 mL) was added to the reaction mixture and the mixture was extracted with EtOAc (3×50 mL). The combined organic layers were washed with brine, dried over anhydrous $Na_2SO_4$. After filtration and concentration, the crude product was purified by column chromatography to give the title compound.

26. 5,6,7,8-tetrahydroquinazoline

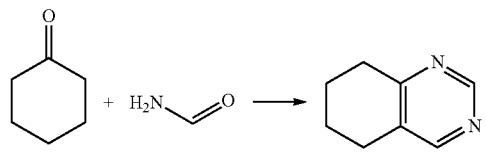

(a) 5,6,7,8-tetrahydroquinazoline was synthesized according to: *Heterocycles* 2005, 65, 2593-2603

27. thieno[3,2-d]pyrimidine

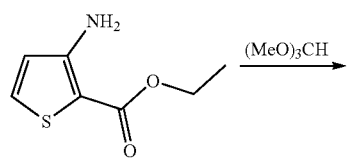

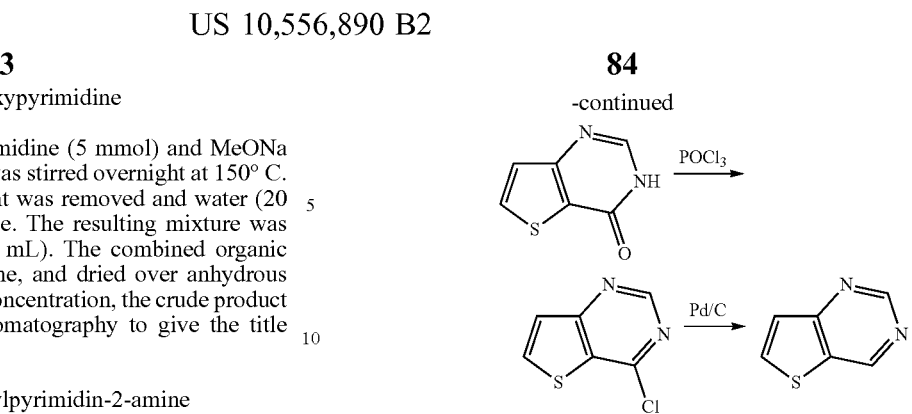

(a) The substituted pyrimidine was synthesized according to: *Heterocycles,* 1994 Vol. 39, No. 2

28. Ethylpyrrolidine-2,5-dione pyridinium bromide

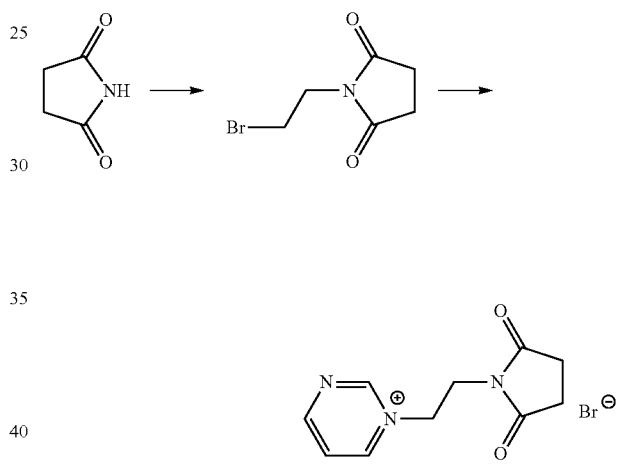

(a) The substituted pyrimidinium was synthesized according to: *J. Het. Chem.* 2008, 45, 1371-1375; *Tetrahedron Lett.* 2007, 48, 1571-1575

29. 6,7-dihydro-5H-cyclopenta[d]pyrimidine

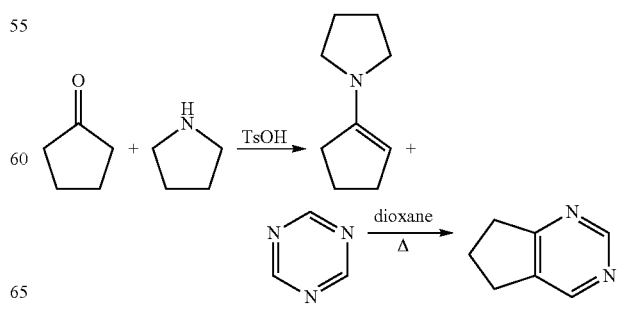

(a) The substituted pyrimidine was synthesized according to: *J. Org. Chem.* 1986, 51, 5100-5105; *J. Org. Chem.* 1982, 47, 2673-2675

30. 2-methyl-6,7-dihydro-5H-cyclopenta[d]pyrimidine

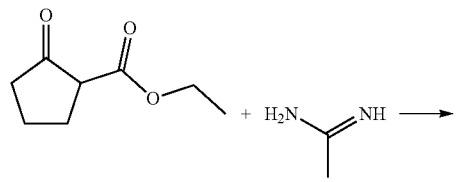

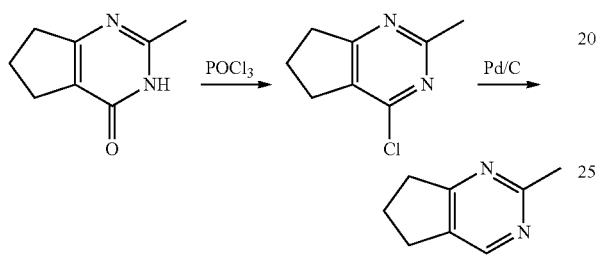

(a) The substituted pyrimidine was synthesized according to: *J. Am. Chem. Soc.* 1959, 3108-3104

31. 5-isopropyl-2-methylpyrimidine

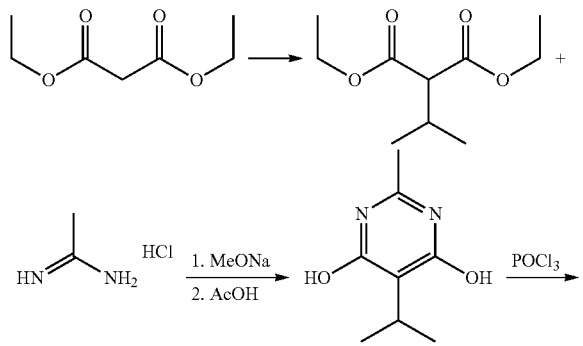

-continued

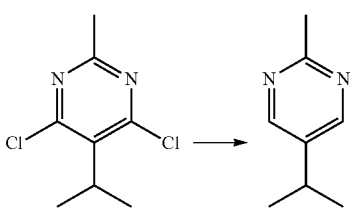

(a) The substituted pyrimidine was synthesized according to: WO 2005/95357

32. 7-fluoroquinazoline

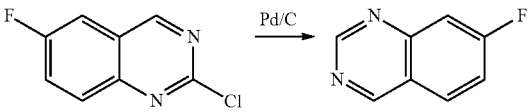

(a) The substituted quinazoline was synthesized according to: WO 2005/35518; WO 2006/66950; *J. Am. Chem. Soc.* 2006, 128, 14255

Data

| Tabular Data | | | |
|---|---|---|---|
| No. | Structure | Methods | Data |
| 1 |  | 1 | MS (ESI+): m/z 207 |

-continued

| No. | Structure | Methods | Data |
|---|---|---|---|
| 2 | 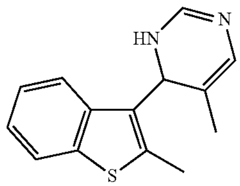 [SMILES: CC1=CN=CNC1c1c(C)sc2ccccc12] | 1 | ¹H NMR (400 MHz, MeOD): δ 8.11 (s, 1H), 7.85 (t, J = 6.5 Hz, 2H), 7.41-7.32 (m, 2H), 6.28 (s, 1H), 6.02 (brs, 1H), 2.63 (s, 3H), 1.47 (s, 3H). |
| 3 | 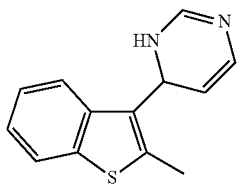 [SMILES: Cc1sc2ccccc2c1C1C=CN=CN1] | 1 | MS (ESI+): m/z 229 (MH⁺); ¹H NMR (300 MHz, MeOD): δ 8.21 (s, 1H), 7.93-7.85 (dd, J = 16.91 Hz, 7.49 Hz, 2H), 7.45-7.34 (m, 2H), 6.47-6.45 (d, J = 8.22 Hz, 1H), 6.13-6.12 (t, J = 2.40 Hz, 1H), 5.30-5.26 (dd, J = 8.25 Hz, J = 2.88 Hz, 1H), 2.64 (s, 3H). |
| 4 | 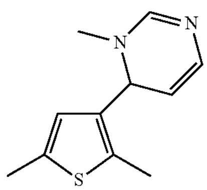 | 21, 3 | ¹H NMR (400 MHz, MeOD): δ 8.15 (s, 1H), 6.75 (s, 1H), 6.37 (d, J = 8.0 Hz, 1H), 5.47 (dd, J = 4.0, 1.5 Hz, 1H), 5.23 (dd, J = 8.0, 4.0 Hz, 1H), 3.06 (s, 3H), 2.42 (s, 3H), 2.39 (s, 3H). |
| 5 | 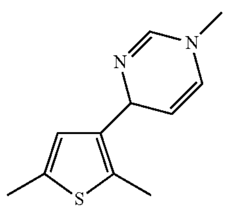 | 21, 3 | ¹H NMR (400 MHz, MeOD): δ 8.06 (s, 1H), 6.78 (s, 1H), 6.30 (dt, J = 10.0, 1.5 Hz, 1H), 5.47 (dd, J = 3.5, 1.5 Hz, 1H), 5.33 (dd, J = 8.0, 3.5 Hz, 1H), 3.33 (s, 3H), 2.39 (s, 3H), 2.38 (s, 3H). |
| 6 | 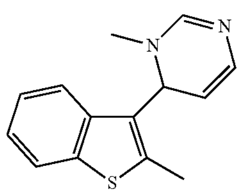 [SMILES: Cc1sc2ccccc2c1C1C=CN=CN1C] | 21, 3 | ¹H NMR (400 MHz, MeOD): δ 8.53 (s, 1H), 8.19 (s, 1H), 7.85 (t, J = 8.0 Hz, 2H), 7.43-7.33 (m, 2H), 6.45 (d, J = 8.0 Hz, 6.05 (brs, 1H), 5.23 (dd, J = 8.0, 3.2 Hz, 1H), 2.93 (s, 3H), 2.2.64 (s, 3H). |
| 7 | 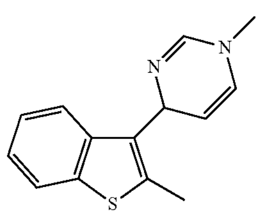 [SMILES: Cc1sc2ccccc2c1C1C=CN(C)C=N1] | 21, 3 | ¹H NMR (400 MHz, MeOD): δ 8.49 (brs, 1H), 8.17 (s, 1H), 7.88 (d, J = 8.0 Hz, 1H), 7.82 (d, J = 7.5 Hz, 1H), 7.79-7.31 (m, 2H), 6.38 (d, J = 8.0 Hz, 1H), 6.04 (brs, 1H), 5.34 (dd, J = 8.0, 3.0 Hz, 1H), 3.41 (s, 3H), 2.61 (s, 3H). |
| 8 | 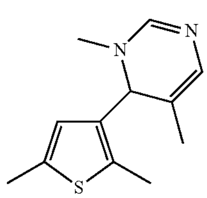 | 21, 3 | ¹H NMR (400 MHz, MeOD): δ 8.11 (s, 1H), 6.67 (s, 1H), 6.21 (s, 1H), 5.33 (s, 1H), 3.04 (s, 3H), 2.44 (s, 3H), 2.41 (s, 3H), 1.53 (s, 3H). |

-continued

| No. | Structure | Methods | Data |
|---|---|---|---|
| 9 | 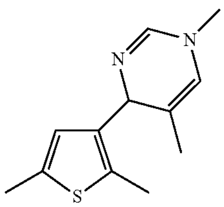 | 21, 3 | $^1$H NMR (400 MHz, MeOD): δ 8.38, (s, 1H), 8.02 (s, 1H), 6.70 (s, 1H), 6.15 (s, 1H), 5.35 (s, 1H), 3.31 (s, 3H), 2.41 (s, 3H), 2.39 (s, 3H), 1.55 (s, 3H). |
| 10 | 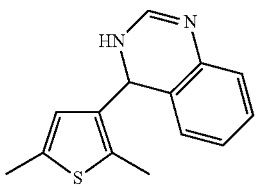 [SMILES: Cc1cc(C2NC=Nc3ccccc32)c(C)s1] | 1 | $^1$H NMR (400 MHz, CDCl$_3$): δ 8.33 (s, 1H), 7.25 (dd, J = 8.0, 1.5 Hz, 1H), 7.16 (s, 1H), 6.92 (d, J = 8.0 Hz, 1H), 6.52 (s, 1H), 6.18 (s, 1H), 2.47 (s, 3H), 2.35 (s, 3H). |
| 11 | 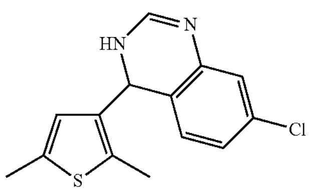 [SMILES: Cc1cc(C2NC=Nc3cc(Cl)ccc32)c(C)s1] | 33, 1 | $^1$H NMR (400 MHz, CDCl$_3$): δ 8.58 (brs, 1H), 7.41 (s, 1H), 7.13 (d, J = 8.0 Hz, 1H), 6.79 (d, J = 8.0 Hz, 1H), 6.31 (s, 1H), 5.98 (s, 1H), 2.46 (s, 3H), 2.23 (s, 3H). |
| 12 | 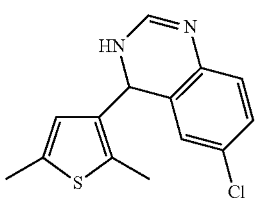 [SMILES: Cc1cc(C2NC=Nc3ccc(Cl)cc32)c(C)s1] | 33, 1 | $^1$H NMR (400 MHz, MeOD): δ 8.57 (brs, 1H), 7.38 (d, J = 8.0 Hz, 1H), 7.21 (d, J = 8.0 Hz, 1H), 6.80 (s, 1H), 6.30 (s, 1H), 5.93 (s, 1H), 2.47 (s, 3H), 2.23 (s, 3H). |
| 13 | 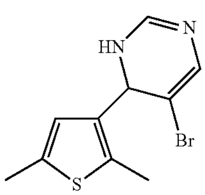 | 1 | $^1$H NMR (400 MHz, MeOD): δ 8.18 (s, 1H), 6.82 (s, 1H), 6.75 (s, 1H), 5.63 (s, 1H), 2.42 (s, 3H), 2.40 (s, 3H). |
| 14 | 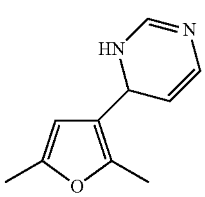 | 1 | $^1$H NMR (400 MHz, MeOD): δ 8.02 (s, 1H), 6.34 (d, J = 8.0 Hz, 1H), 6.04 (s, 1H), 5.36 (s, 1H), 5.19 (dd, J = 8.0, 3.5 Hz, 1H), 2.23 (s, 3H), 2.20 (s, 3H). |
| 15 | 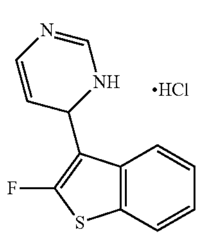 [SMILES: Fc1sc2ccccc2c1C1C=CN=CN1 ; Cl] | 13, 1 | MS (ESI+): m/z 233 (MH+); $^1$H NMR (300 MHz, MeOD): δ 8.26 (s, 1H), 7.89-7.85 (t, J = 6.77 Hz, 2H), 7.53-7.42 (m, 2H), 6.51-6.48 (d, J = 8.37 Hz, 1H), 6.05 (s, 1H), 5.39-5.36 (dd, J = 8.00 Hz, J = 2.93 Hz, 1H). |

| No. | Structure | Methods | Data |
|---|---|---|---|
| 16 | 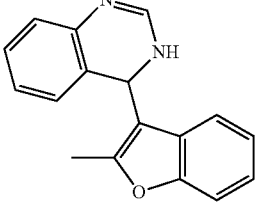 | 1 | MS (ESI+): m/z 263 |
| 17 | 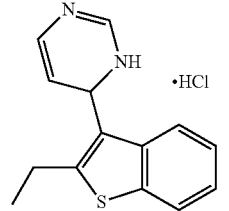 [SMILES: CCc1sc2ccccc2c1C1C=CN=CN1 ; Cl] | 14, 1 | MS (ESI+): m/z 243 (MH$^+$); $^1$H NMR (300 MHz, MeOD): δ 8.21 (s, 1H), 7.94-7.87 (m, 2H), 7.43-7.34 (m, 2H), 6.47-6.44 (d, J = 8.25 Hz, 1H), 6.14-6.12 (t, J = 2.37 Hz, 1H), 5.29-5.26 (dd, J = 8.22 Hz, J = 2.82 Hz, 1H), 3.09-3.02 (q, 2H), 1.42-1.37 (t, J = 7.53 Hz, 3H). |
| 18 | 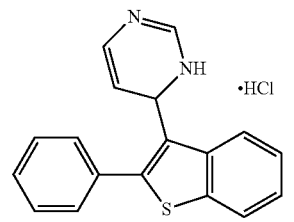 [SMILES: C1=CC(c2c(-c3ccccc3)sc3ccccc23)NC=N1 ; Cl] | 5, 1 | MS (ESI+): m/z 291 (MH$^+$); $^1$H NMR (300 MHz, MeOD): δ 8.13-8.05 (m, 2H), 7.99-7.83 (m, 2H), 7.80-7.74 (m, 1H), 7.54 (m, 4H), 7.49-7.46 (m, 1H), 6.40-6.37 (d, J = 8.85 Hz, 1H), 6.08-5.98 (m, 1H), 5.37-5.34 (dd, J = 8.35 Hz, J = 5.37 Hz, 1H). |
| 19 | 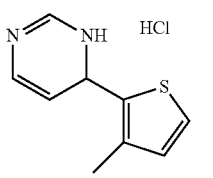 | 1 | MS (ESI+): m/z 193 (MH$^+$); $^1$H NMR (300 MHz, DMSO-d$_6$): δ 11.38 (s, 1H), 10.95 (s, 1H), 8.23 (s, 1H), 7.21 (s, 1H), 6.50-6.47 (d, J = 7.95 Hz, 1H), 5.80 (d, J = 3.27 Hz, 1H), 5.32-5.28 (m, 1H), 2.11 (s, 6H). |
| 20 | 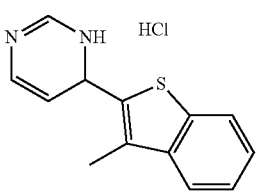 [SMILES: Cc1c(C2C=CN=CN2)sc2ccccc12 ; Cl] | 1 | MS (ESI+): m/z 229 (MH$^+$); $^1$H NMR (300 MHz, MeOD): δ 8.17 (s, 1H), 7.90-7.88 (d, J = 7.08 Hz, 1H), 7.84-7.81 (d, J = 7.65 Hz, 1H), 7.48-7.42 (m, 2H), 6.51-6.48 (d, J = 7.98 Hz, 1H), 6.13-6.12 (d, J = 3.15 Hz, 1H), 5.48-5.44 (dd, J = 8.01 Hz, J = 3.42 Hz, 1H), 2.48 (s, 3H). |
| 21 | 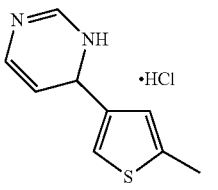 | 1 | MS (ESI+): m/z 179 (MH$^+$); $^1$H NMR (300 MHz, MeOD): δ 8.09 (s, 1H), 6.97-6.96 (d, J = 3.45 Hz, 1H), 6.75-6.74 (m, 1H), 6.46-6.43 (d, J = 8.07 Hz, 1H), 5.70-5.69 (d, J = 2.70 Hz, 1H), 5.44-5.40 (dd, J = 8.04 Hz, J = 3.63 Hz, 1H), 2.50 (s, 3H). |

-continued

| No. | Structure | Methods | Data |
|---|---|---|---|
| 22 | (structure) ·HCl | 1 | MS (ESI+): m/z 179 (MH+); $^1$H NMR (300 MHz, MeOD): δ 8.09 (s, 1H), 6.96-6.94 (d, J = 3.45 Hz, 1H), 6.75-6.74 (d, J = 1.17 Hz, 1H), 6.45-6.43 (d, J = 8.10 Hz, 1H), 5.70-5.69 (d, J = 3.54 Hz, 1H), 5.44-5.40 (dd, J = 8.10 Hz, J = 0.78 Hz, 1H), 2.50 (s, 3H). |
| 23 | (structure) ·HCl | 1 | MS (ESI+): m/z 221 (MH+); $^1$H NMR (300 MHz, MeOD): δ 8.06 (s, 1H), 6.82 (s, 1H), 6.37-6.34 (d, J = 8.19 Hz, 1H), 5.56-5.54 (dd, J = 3.24 Hz, J = 1.41 Hz, 1H), 5.25-5.22 (dd, J = 8.16 Hz, J = 3.33 Hz, 1H), 2.87-2.76 (m, 4H), 1.31-1.25 (m, 6H). |
| 24 | (structure) ·HCl | 1 | MS (ESI+): m/z 206 (MH+); $^1$H NMR (300 MHz, MeOD): δ 8.09 (s, 1H), 6.34-6.31 (d, J = 8.31 Hz, 1H), 5.74-5.72 (t, J = 2.37 Hz, 1H), 5.17-5.13 (dd, J = 8.28 Hz, J = 2.88 Hz, 1H), 2.41 (s, 3H), 2.29 (s, 3H), 2.18 (s, 3H). |
| 25 | (structure) ·HCl | 1 | MS (ESI+): m/z 192 (MH+); $^1$H NMR (300 MHz, MeOD): δ 9.40 (s, 1H), 8.94-8.91 (dd, J = 6.54 Hz, 0.9 Hz, 1H), 8.18-8.16 (d, J = 6.54 Hz, 1H), 7.41 (s, 1H), 2.87 (s, 3H), 2.49 (s, 3H). |
| 26 | (structure) ·HCl | 7, 1 | MS (ESI+): m/z 219 (MH+); $^1$H NMR (300 MHz, MeOD): δ 8.09 (s, 1H), 6.35-6.32 (d, J = 8.22 Hz, 1H), 5.64-5.63 (q, 1H), 5.18-5.14 (dd, J = 7.47 Hz, 2.49 Hz, 1H), 2.86-2.71 (m, 4H), 2.52-2.47 (m, 2H), 2.43 (s, 3H). |
| 27 | (structure) ·HCl | 7, 1 | MS (ESI+): m/z 233 (MH+); $^1$H NMR (300 MHz, MeOD): δ 8.07 (s, 1H), 6.33-6.30 (d, J = 8.16 Hz, 1H), 5.70-5.68 (t, J = 2.34 Hz, 1H), 5.16-5.13 (dd, J = 7.68 Hz, 2.31 Hz, 1H), 2.75-2.55 (m, 4H), 2.42 (s, 3H), 1.84-1.83 (m, 4H). |
| 28 | (structure) | 8, 1 | MS (ESI+): m/z 207 (MH+); $^1$H NMR (300 MHz, MeOD): δ 8.05 (s, 1H), 6.42-6.40 (d, J = 8.16 Hz, 1H), 5.83-5.81 (dd, J = 3.60 Hz, 1.50 Hz, 1H), 5.36-5.32 (m, 1H), 2.35 (s, 3H), 2.14 (s, 3H), 2.00 (s, 3H). |

-continued

| No. | Structure | Methods | Data |
|---|---|---|---|
| 29 | 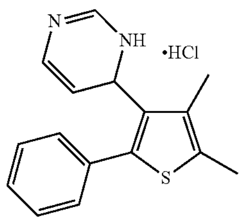 [SMILES: Cc1sc(-c2ccccc2)c(C2C=CN=CN2)c1C ; Cl] | 9, 1 | MS (ESI+): m/z 269 (MH⁺); ¹H NMR (300 MHz, MeOD): δ 7.96 (s, 1H), 7.49-7.36 (m, 5H), 6.26-6.24 (d, J = 8.19 Hz, 1H), 5.71-5.69 (t, J = 2.40 Hz, 1H), 5.24-5.21 (dd, J = 8.24 Hz, J = 2.78 Hz, 1H), 2.41 (s, 3H), 2.32 (s, 3H). |
| 30 | 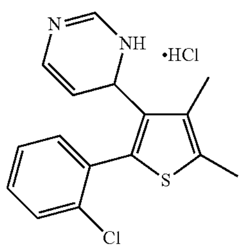 [SMILES: Cc1sc(-c2ccccc2Cl)c(C2C=CN=CN2)c1C ; Cl] | 9, 1 | MS (ESI+): m/z 303 (MH⁺); ¹H NMR (300 MHz, MeOD): δ 8.12 (s, 1H), 7.59-7.53 (dd, J = 8.01 Hz, J = 1.26 Hz, 2H), 7.44-7.39 (d, J = 7.44 Hz, 2H), 7.28-7.23 (t, J = 7.77 Hz, 1H), 5.22 (s, 1H), 5.02-5.00 (d, J = 6.90 Hz, 1H), 2.39 (s, 3H), 2.27 (s, 3H). |
| 31 | 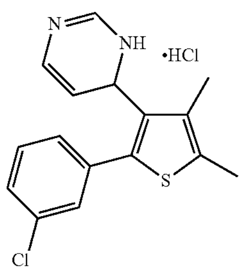 [SMILES: Cc1sc(-c2cccc(Cl)c2)c(C2C=CN=CN2)c1C ; Cl] | 9, 1 | MS (ESI+): m/z 303 (MH⁺); ¹H NMR (300 MHz, MeOD): δ 8.19-8.16 (m, 1H), 7.97 (s, 1H), 7.79 (m, 1H), 7.46-7.35 (m, 2H), 6.27-6.24 (d, J = 8.04 Hz, 1H), 5.69 (s, 1H), 5.25-5.22 (m, 1H), 2.31 (s, 3H), 2.25 (s, 3H). |
| 32 | 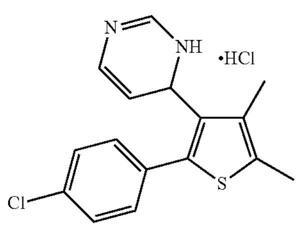 [SMILES: Cc1sc(-c2ccc(Cl)cc2)c(C2C=CN=CN2)c1C ; Cl] | 9, 1 | MS (ESI+): m/z 303 (MH⁺); ¹H NMR (300 MHz, MeOD): δ 7.98 (s, 1H), 7.48-7.42 (m, 2H), 7.38-7.35 (m, 2H), 6.27-6.24 (d, J = 8.31 Hz, 1H), 5.69-5.68 (t, J = 2.37 Hz, 1H), 5.24-5.21 (dd, J = 8.22 Hz, 2.10 Hz, 1H), 2.41 (s, 3H), 2.31 (s, 3H). |
| 33 | 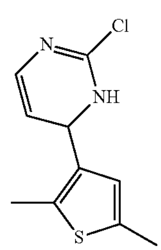 | 9, 1 | MS (ESI+): m/z 227 |
| 34 | 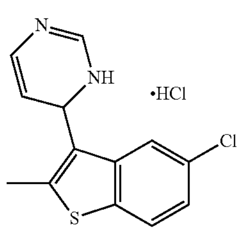 [SMILES: Cc1sc2ccc(Cl)cc2c1C1C=CN=CN1 ; Cl] | 15, 1 | MS (ESI+): m/z 263 (MH⁺); ¹H NMR (300 MHz, MeOD): δ 8.26 (s, 1H), 7.90 (s, 1H), 7.87-7.84 (d, J = 8.58 Hz, 1H), 7.38-7.34 (dd, J = 8.58 Hz, J = 1.92 Hz, 1H), 6.51-6.48 (d, J = 7.83 Hz, 1H), 6.13-6.11 (t, J = 2.37 Hz, 1H), 5.30-5.27 (dd, J = 8.18 Hz, J = 2.48 Hz, 1H), 2.66 (s, 3H). |

-continued

| No. | Structure | Methods | Data |
|---|---|---|---|
| 35 | ·HCl | 1 | MS (ESI+): m/z 179 (MH$^+$); $^1$H NMR (300 MHz, CDCl$_3$): δ 7.32 (s, 1H), 6.78-6.77 (d, J = 3.36 Hz, 1H), 6.63-6.62 (m, 1H), 6.25-6.23 (d, J = 7.71 Hz, 1H), 5.40-5.36 (d, J = 3.42 Hz, 1H), 4.96-4.93 (m, 1H), 2.47 (s, 3H). |
| 36 | ·HCl | 1 | MS (ESI+): m/z 193 (MH$^+$); $^1$H NMR (300 MHz, CDCl$_3$): δ 7.51-7.25 (m, 1H), 6.87-6.81 (m, 1H), 6.64-6.62 (m, 1H), 6.26-6.23 (m, 1H), 5.43-5.36 (m, 1H), 4.96-4.93 (m, 1H), 2.84-2.76 (m, 2H), 1.30-1.26-2.76 (m, 3H). |
| 37 | ·HCl | 10, 1 | MS (ESI+): m/z 241 (MH$^+$); $^1$H NMR (300 MHz, MeOD): δ 8.14 (s, 1H), 7.66-7.65 (m, 2H), 7.63-7.33 (m, 4H), 7.18-7.17 (d, J = 3.9 Hz, 1H), 6.51-6.49 (d, J = 8.10 Hz, 1H), 5.80-5.78 (m, 1H), 5.52-5.48 (m, 1H). |
| 38 | ·HCl | 10, 1 | MS (ESI+): m/z 259 (MH$^+$); $^1$H NMR (300 MHz, MeOD): δ 8.14 (s, 1H), 7.69-7.64 (m, 2H), 7.33-7.31 (d, J = 3.72 Hz, 1H), 7.19-7.14 (m, 3H), 6.52-6.49 (d, J = 8.10 Hz, 1H), 5.80-5.78 (m, 1H), 5.52-5.48 (m, 1H). |
| 39 | ·HCl | 11, 1 | MS (ESI+): m/z 194 (MH$^+$); $^1$H NMR (300 MHz, MeOD): δ 8.08 (s, 1H), 6.59 (s, 1H), 6.44-6.41 (d, J = 8.10 Hz, 1H), 5.79-5.78 (m, 1H), 5.37-5.33 (m, 1H), 2.43 (s, 3H), 2.21 (s, 3H). |
| 40 | ·HCl | 12, 1 | MS (ESI+): m/z 207 (MH$^+$); $^1$H NMR (300 MHz, MeOD): δ 8.07 (s, 1H), 6.63 (s, 1H), 6.43-6.41 (d, J = 8.16 Hz, 1H), 5.80-5.78 (m, 1H), 5.38-5.34 (m, 1H), 2.84-2.77 (m, 2H), 2.22 (s, 3H), 1.30-1.22 (m, 3H). |
| 41 | ·HCl | 9, 1 | MS (ESI+): m/z 255 (MH$^+$); $^1$H NMR (300 MHz, MeOD): δ 8.13 (s, 1H), 7.67-7.61 (d, J = 7.14 Hz, 2H), 7.45-7.34 (m, 3H), 7.23 (s, 1H), 6.50-6.47 (d, J = 8.19 Hz, 1H) 5.89-5.88 (d, J = 2.22 Hz, 1H), 5.46-5.42 (m, 1H), 2.32 (s, 3H). |

-continued

Tabular Data

| No. | Structure | Methods | Data |
|---|---|---|---|
| 42 | 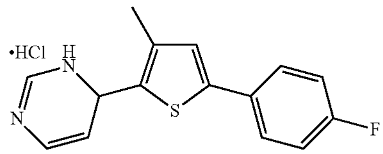 [SMILES: Cl ; Cc1cc(-c2ccc(F)cc2)sc1C1C=CN=CN1] | 9, 1 | MS (ESI+): m/z 273 (MH$^+$); $^1$H NMR (300 MHz, MeOD): δ 7.63-7.58 (m, 2H), 7.46 (s, 1H), 7.19-7.08 (m, 3H), 6.33-6.30 (d, J = 7.83 Hz, 1H), 5.62.-5.61 (d, J = 3.15 Hz, 1H), 5.08-5.02 (m, 1H), 2.27 (s, 3H). |
| 43 | 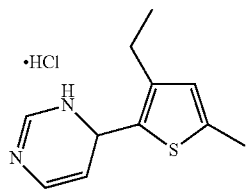 | 11, 1 | MS (ESI+): m/z 207 (MH$^+$); $^1$H NMR (300 MHz, CDCl$_3$): δ 7.10 (s, 1H), 6.55 (s, 1H), 6.24-6.22 (d, J = 7.47 Hz, 1H), 5.47-5.46 (m, 1H), 5.84.-4.80 (m, 1H), 2.61-2.53 (m, 2H), 2.44 (s, 3H), 1.22-1.17 (t, J = 7.56 Hz, 3H). |
| 44 | 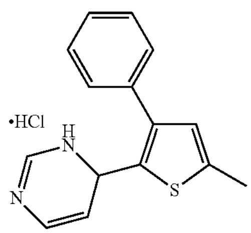 [SMILES: Cl ; Cc1cc(-c2ccccc2)c(C2C=CN=CN2)s1] | 12, 5, 1 | MS (ESI+): m/z 255 (MH$^+$); $^1$H NMR (300 MHz, MeOD): δ 8.06 (s, 1H), 7.50-7.36 (m, 5H), 6.80 (s, 1H), 6.40-6.37 (d, J = 8.13 Hz, 1H), 5.77.-5.75 (m, 1H), 5.43-5.39 (m, 1H), 2.54 (s, 3H). |
| 45 | 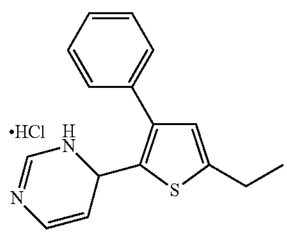 [SMILES: Cl ; CCc1cc(-c2ccccc2)c(C2C=CN=CN2)s1] | 12, 5, 1 | MS (ESI+): m/z 269 (MH$^+$); $^1$H NMR (300 MHz, CDCl$_3$): δ 7.45-7.32 (m, 5H), 7.20-7.16 (s, 1H), 6.74 (s, 1H), 6.24-6.17 (m, 1H), 5.52.-5.50 (m, 1H), 4.84-4.80 (m, 1H), 2.92-2.81 (m, 2H), 1.36-1.31 (t, J = 7.52 Hz, 3H). |
| 46 | 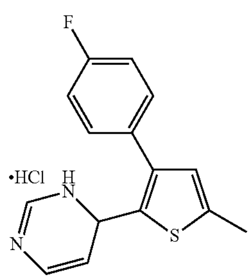 [SMILES: Cl ; Cc1cc(-c2ccc(F)cc2)c(C2C=CN=CN2)s1] | 12, 5, 1 | MS (ESI+): m/z 273 (MH$^+$); $^1$H NMR (300 MHz, CDCl$_3$): δ 7.52-7.41 (m, 2H), 7.24-7.04 (m, 3H), 6.88 (s, 1H), 6.19-6.16 (d, J = 7.71 Hz, 1H), 5.43.-5.42 (m, 1H), 4.78-4.74 (m, 1H), 2.49 (s, 3H). |
| 47 | 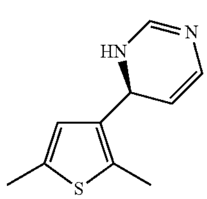 | 1, chiral purification | (ESI+): m/z 193 (MH$^+$); $^1$H NMR (400 MHz, CDCl$_3$): δ 8.33 (s, 1H), 6.63 (s, 1H), 6.19 (d, J = 8.1 Hz, 1H), 5.34 (dd, J = 3.3, 1.1 Hz, 1H), 5.04 (dd, J = 8.1, 3.3 Hz, 1H), 2.37 (s, 3H), 2.33 (s, 3H) |
| 48 | 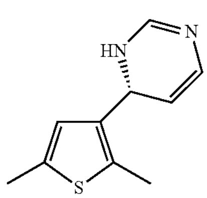 | 1, chiral purification | (ESI+): m/z 193 (MH$^+$); $^1$H NMR (400 MHz, CDCl$_3$): δ 8.33 (s, 1H), 6.63 (s, 1H), 6.19 (d, J = 8.1 Hz, 1H), 5.34 (dd, J = 3.3, 1.1 Hz, 1H), 5.04 (dd, J = 8.1, 3.3 Hz, 1H), 2.37 (s, 3H), 2.33 (s, 3H) |

-continued

| No. | Structure | Methods | Data |
|---|---|---|---|
| 49 | 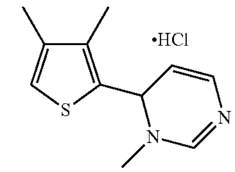 | 3 | MS (ESI+): m/z 207 |
| 50 | 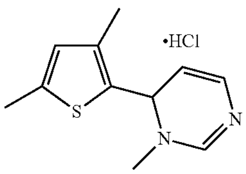 | 11, 3 | MS (ESI+): m/z 207 (MH$^+$); $^1$H NMR (300 MHz, MeOD): δ 8.17 (s, 1H), 6.61-6.59 (m, 1H), 6.45-6.38 (m, 1H), 5.75-5.73 (m, 1H), 5.37-5.33 (m, 1H), 3.15 (s, 3H), 2.45 (s, 3H), 2.24 (s, 3H). |
| 51 | 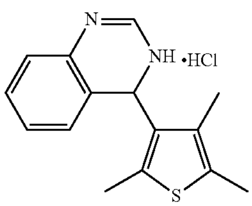 [SMILES: Cc1sc(C)c(C2NC=Nc3ccccc32)c1C ; Cl] | 1 | MS (ESI+): m/z 257 (MH$^+$); $^1$H NMR (300 MHz, MeOD): δ 8.29 (s, 1H), 7.38-7.33 (m, 1H), 7.25-7.20 (td, J = 7.61 Hz, 1.05 Hz, 1H), 7.11-7.08 (d, J = 7.89 Hz, 1H), 6.83-6.81 (d, J = 7.71 Hz, 1H), 6.38 (s, 1H), 2.41 (s, 3H), 2.27 (s, 3H), 1.93 (s, 3H). |
| 52 | 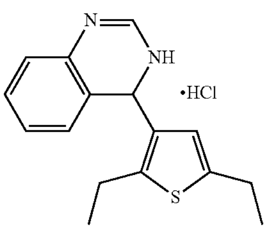 [SMILES: CCc1cc(C2NC=Nc3ccccc32)c(CC)s1 ; Cl] | 1 | MS (ESI+): m/z 271 (MH$^+$); $^1$H NMR (300 MHz, MeOD): δ 8.26 (s, 1H), 7.39-7.34 (t, J = 7.68 Hz, 1H), 7.27-7.22 (m, 1H), 7.15-7.13 (d, J = 7.89 Hz, 1H), 6.94-6.91 (d, J = 7.71 Hz, 1H), 6.55 (s, 1H), 6.21 (s, 1H), 2.98-2.89 (m, 2H), 2.78-2.70 (q, 2H), 1.36 (t, J = 7.53 Hz, 3H), 1.24-1.19 (t, J = 7.53 Hz, 3H). |
| 53 | 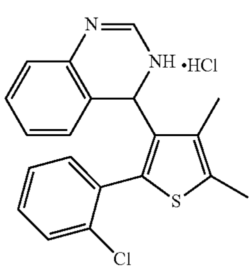 [SMILES: Cc1sc(-c2ccccc2Cl)c(C2NC=Nc3ccccc32)c1C ; Cl] | 9, 1 | MS (ESI+): m/z 353 (MH$^+$); $^1$H NMR (300 MHz, MeOD): δ 8.13 (s, 1H), 7.50-7.39 (m, 3H), 7.32-7.18 (m, 3H), 6.92-6.90 (m, 2H), 6.04 (s, 1H), 2.91 (s, 3H), 2.10 (s, 3H). |
| 54 | 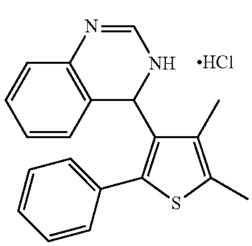 [SMILES: Cc1sc(-c2ccccc2)c(C2NC=Nc3ccccc32)c1C ; Cl] | 9, 1 | MS (ESI+): m/z 319 (MH$^+$); $^1$H NMR (300 MHz, MeOD): δ 8.17 (s, 1H), 7.42-7.25 (m, 6H), 7.24-7.20 (td, J = 7.60 Hz, 1.07 Hz, 1H), 7.03-7.00 (d, J = 7.84 Hz, 1H), 6.85-6.83 (d, J = 7.74 Hz, 1H), 6.28 (s, 1H), 2.38 (s, 3H), 2.00 (s, 3H). |

-continued

| No. | Structure | Methods | Data |
|---|---|---|---|
| 55 | 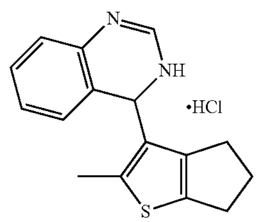 [SMILES: Cc1sc2c(c1C1NC=Nc3ccccc31)CCC2 ; Cl] | 7, 1 | MS (ESI+): m/z 269 (MH⁺); ¹H NMR (300 MHz, MeOD): δ 8.29 (s, 1H), 7.39-7.33 (t, J = 7.41 Hz, 1H), 7.27-7.22 (t, J = 7.74 Hz, 1H), 7.13-7.10 (d, J = 7.92 Hz, 1H), 6.93-6.90 (d, J = 7.65 Hz, 1H), 6.29 (s, 1H), 2.82-2.71 (m, 2H), 2.56 (s, 3H), 2.47-2.23 (m, 3H), 2.07-1.97 (m, 1H). |
| 56 | 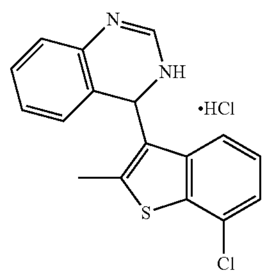 [SMILES: Cc1sc2c(Cl)cccc2c1C1NC=Nc2ccccc21 ; Cl] | 15, 1 | MS (ESI+): m/z 313 (MH⁺); ¹H NMR (300 MHz, MeOD): δ 8.41 (s, 1H), 7.49-7.46 (m, 1H), 7.41-7.35 (m, 2H), 7.32-7.27 (m, 1H), 7.21-7.17 (m, 2H), 6.86-6.84 (d, J = 8.07 Hz, 1H), 6.74 (s, 1H), 2.71 (s, 3H). |
| 57 | 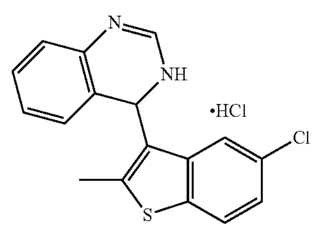 [SMILES: Cc1sc2ccc(Cl)cc2c1C1NC=Nc2ccccc21 ; Cl] | 15, 1 | MS (ESI+): m/z 313 (MH⁺); ¹H NMR (300 MHz, MeOD): δ 8.43 (s, 1H), 7.86-7.83 (d, J = 8.58 Hz, 1H), 7.50 (brs, 1H), 7.43-7.38 (t, J = 8.13 Hz, 1H), 7.33-7.29 (dd, J = 8.58 Hz, 1.92 Hz, 1H), 7.24-7.18 (m, 2H), 6.87-6.84 (d, J = 7.68 Hz, 1H), 6.74 (s, 1H), 2.67 (s, 3H). |
| 58 | 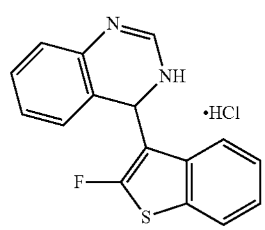 [SMILES: Fc1sc2ccccc2c1C1NC=Nc2ccccc21 ; Cl] | 13, 1 | MS (ESI+): m/z 283 (MH⁺); ¹H NMR (300 MHz, MeOD): δ 8.45 (s, 1H), 7.89-7.83 (m, 1H), 7.63-7.59 (m 1H), 7.43-7.39 (m, 3H), 7.26-7.21 (m, 2H), 7.03-7.01 (d, J = 7.74 Hz, 1H), 6.73 (s, 1H). |
| 59 | 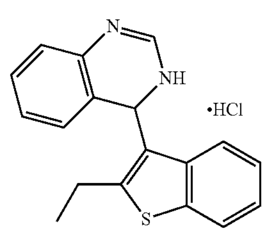 [SMILES: CCc1sc2ccccc2c1C1NC=Nc2ccccc21 ; Cl] | 14, 1 | MS (ESI+): m/z 293 (MH⁺); ¹H NMR (300 MHz, MeOD): δ 8.38 (s, 1H), 7.88-7.86 (m, 1H), 7.55-7.44 (brs, 1H), 7.40-7.33 (m, 1H), 7.31-7.26 (m, 2H), 7.21-7.15 (m, 2H), 6.84-6.81 (d, J = 7.71 Hz, 1H), 6.74 (s, 1H), 3.12-3.09 (m, 2H), 1.45-1.40 (t, J = 7.34 Hz, 3H). |
| 60 | 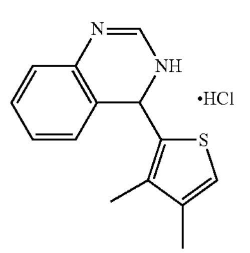 [SMILES: Cc1csc(C2NC=Nc3ccccc32)c1C ; Cl] | 1 | MS (ESI+): m/z 243 (MH⁺); ¹H NMR (300 MHz, MeOD): δ 8.30 (s, 1H), 7.42-7.38 (m, 1H), 7.30-7.25 (m, 1H), 7.17-7.15 (d, J = 7.92 Hz, 1H), 7.07-7.03 (m, 2H), 6.53 (s, 1H), 2.76 (s, 3H), 2.19 (s, 3H). |

| No. | Structure | Methods | Data |
|---|---|---|---|
| 61 | 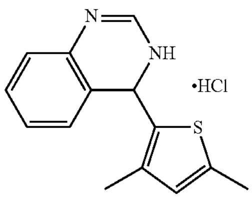 [SMILES: Cc1cc(C)c(C2NC=Nc3ccccc32)s1 ; Cl] | 11, 1 | MS (ESI+): m/z 243 (MH+); 1H NMR (300 MHz, MeOD): δ 8.29 (s, 1H), 7.42-7.37 (m, 1H), 7.30-7.25 (m, 1H), 7.17-7.14 (d, J = 7.92 Hz, 1H), 7.07-7.04 (d, J = 7.65 Hz, 1H), 6.59 (s, 1H), 6.46 (s, 1H), 2.39 (s, 3H), 2.28 (s, 3H) |
| 62 | 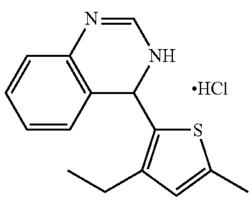 [SMILES: CCc1cc(C)sc1C1NC=Nc2ccccc21 ; Cl] | 11, 1 | MS (ESI+): m/z 257 (MH+); 1H NMR (300 MHz, MeOD): δ 8.28 (s, 1H), 7.42-7.37 (m, 1H), 7.30-7.25 (m, 1H), 7.16-7.13 (d, J = 7.92 Hz, 1H), 7.05-7.02 (d, J = 7.71 Hz, 1H), 6.71 (s, 1H), 6.47 (s, 1H), 2.74-2.62 (m, 2H), 2.41 (s, 3H), 1.27-1.22 (t, J = 7.56 Hz, 3H). |
| 63 | 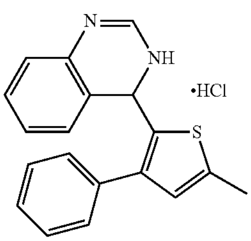 [SMILES: Cc1cc(-c2ccccc2)c(C2NC=Nc3ccccc32)s1 ; Cl] | 12, 1 | MS (ESI+): m/z 305 (MH+); 1H NMR (300 MHz, MeOD): δ 8.23 (s, 1H), 7.50-7.34 (m, 6H), 7.27-7.21 (m, 1H), 7.10-7.07 (d, J = 7.92 Hz, 1H), 6.96-6.94 (d, J = 7.56 Hz, 1H), 6.79 (s, 1H), 6.40 (s, 1H), 2.49 (s, 3H). |
| 64 | 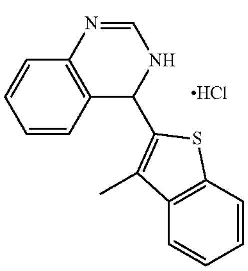 [SMILES: Cc1c(C2NC=Nc3ccccc32)sc2ccccc12 ; Cl] | 1 | MS (ESI+): m/z 279 (MH+); 1H NMR (300 MHz, MeOD): δ 8.39 (s, 1H), 7.86-7.80 (m, 2H), 7.48-7.37 (m, 3H), 7.31-7.26 (m, 1H), 7.22-7.19 (d, J = 7.92 Hz, 1H), 7.11-7.09 (d, J = 7.68 Hz, 1H), 6.79 (s, 1H), 2.61 (s, 3H). |
| 65 | 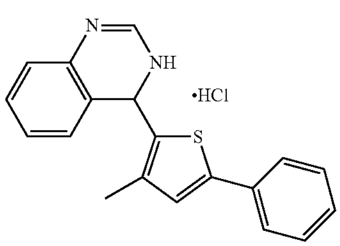 | 9, 1 | MS (ESI+): m/z 243 (MH+); 1H NMR (300 MHz, CDCl3): δ 7.33 (m, 3H), 7.18-7.13 (m, 3H), 7.06-6.93 (m, 3H), 6.84-6.82 (m, 1H), 6.75-6.73 (m, 1H), 6.13-6.08 (m, 1H), 2.14 (s, 3H). |
| 66 | 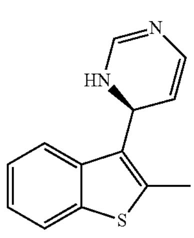 [SMILES: Cc1sc2ccccc2c1[C@@H]1C=CN=CN1] | 1, chiral purification | MS (ESI+): m/z 229 (MH+); 1H NMR (300 MHz, MeOD): δ 8.21 (s, 1H), 7.93-7.85 (dd, J = 16.91 Hz, 7.49 Hz, 2H), 7.45-7.34 (m, 2H), 6.47-6.45 (d, J = 8.22 Hz, 1H), 6.13-6.12 (t, J = 2.40 Hz, 1H), 5.30-5.26 (dd, J = 8.25 Hz, J = 2.88 Hz, 1H), 2.64 (s, 3H). |

-continued

| No. | Structure | Methods | Data |
|---|---|---|---|
| 67 | 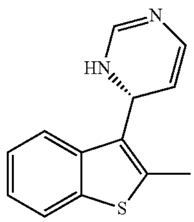 [SMILES: Cc1sc2ccccc2c1[C@H]1C=CN=CN1] | 1, chiral purification | MS (ESI+): m/z 229 (MH+); $^1$H NMR (300 MHz, MeOD): δ 8.21 (s, 1H), 7.93-7.85 (dd, J = 16.91 Hz, 7.49 Hz, 2H), 7.45-7.34 (m, 2H), 6.47-6.45 (d, J = 8.22 Hz, 1H), 6.13-6.12 (t, J = 2.40 Hz, 1H), 5.30-5.26 (dd, J = 8.25 Hz, J = 2.88 Hz, 1H), 2.64 (s, 3H). |
| 68 | 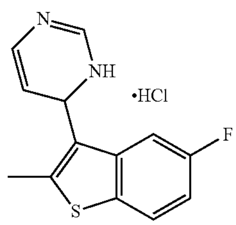 [SMILES: Cc1sc2ccc(F)cc2c1C1C=CN=CN1 ; Cl] | 15, 1 | MS (ESI+): m/z 247 (MH+); $^1$H NMR (300 MHz, MeOD): δ 8.24 (s, 1H), 7.88-7.84 (dd, J = 9.10 Hz, 5.10 Hz, 1H), 7.62-7.58 (dd, J = 10.50 Hz, 2.40 Hz, 1H), 7.20-7.14 (td, J = 8.82 Hz, 2.32 Hz, 1H), 6.50-6.47 (d, J = 8.13 Hz, 1H), 6.11-6.10 (m, 1H), 5.30-5.26 (dd, J = 8.19 Hz, 2.64 Hz, 1H), 2.65 (s, 3H). |
| 69 | 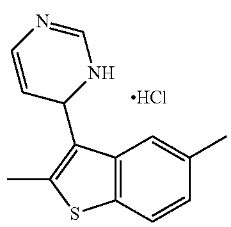 | 15, 1 | MS (ESI+): m/z 243 (MH+); $^1$H NMR (300 MHz, MeOD): δ 8.21 (s, 1H), 7.74-7.68 (m, 2H), 7.23-7.20 (d, J = 6.49 Hz, 1H), 6.47-6.45 (d, J = 7.35 Hz, 1H), 6.11-6.09 (m, 1H), 5.29-5.25 (dd, J = 8.37 Hz, 2.37 Hz, 1H), 2.63 (s, 3H), 2.48 (s, 3H). |
| 70 | 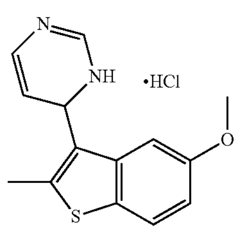 | 15, 1 | MS (ESI+): m/z 259 (MH+); $^1$H NMR (300 MHz, MeOD): δ 8.09 (s, 1H), 7.74 (s, 1H), 7.37-7.36 (m, 1H), 7.04-7.02 (m, 1H), 6.46-6.44 (d, J = 8.13 Hz, 1H), 5.83-5.81 (dd, J = 3.65 Hz, 1.10 Hz, 1H), 5.38-5.34 (dd, J = 8.12 Hz, 3.68 Hz, 1H), 4.00 (s, 3H), 2.59 (s, 3H). |
| 71 | 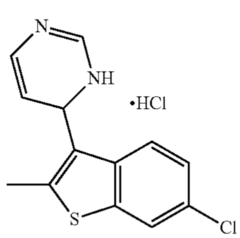 [SMILES: Cc1sc2cc(Cl)ccc2c1C1C=CN=CN1 ; Cl] | 15, 1 | MS (ESI+): m/z 263.5 (MH+); $^1$H NMR (300 MHz, MeOD): δ 8.22 (s, 1H), 7.92-7.86 (m, 2H), 7.44-7.40 (m, 1H), 6.48-6.45 (d, J = 8.46 Hz, 1H), 6.11 (m, 1H), 5.28-5.26 (m, 1H), 2.64 (s, 3H). |
| 72 | 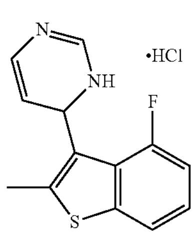 [SMILES: Cc1sc2cccc(F)c2c1C1C=CN=CN1 ; Cl] | 15, 1 | MS (ESI+): m/z 247 (MH+); $^1$H NMR (300 MHz, MeOD): δ 8.21 (s, 1H), 7.93-7.88 (m, 1H), 7.66-7.62 (dd, J = 8.76 Hz, 2.43 Hz, 1H), 7.25-7.19 (td, J = 8.97 Hz, 2.46 Hz, 1H), 6.48-6.45 (dd, J = 8.15 Hz, 0.60 Hz, 1H), 6.12-6.10 (m, 1H), 5.29-5.26 (m, 1H), 2.63 (s, 3H). |

-continued

| No. | Structure | Methods | Data |
|---|---|---|---|
| 73 | 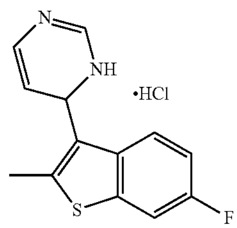 [SMILES: Cc1sc2cc(F)ccc2c1C1C=CN=CN1 ; Cl] | 15, 1 | MS (ESI+): m/z 247 (MH⁺); ¹H NMR (300 MHz, MeOD): δ 8.14 (s, 1H), 7.69-7.66 (d, J = 8.22 Hz, 1H), 7.39-7.32 (m, 1H), 7.18-7.11 (dd, J = 12.60 Hz, 7.86 Hz, 1H), 6.38-6.35 (dd, J = 8.25 Hz, 1.80 Hz, 1H), 6.31-6.30 (m, 1H), 5.28-5.25 (dd J = 8.40 Hz, J = 1.80 Hz, 1H), 2.65 (s, 3H). |
| 74 | 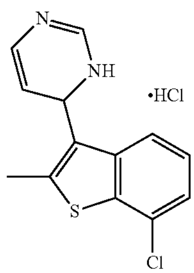 [SMILES: Cc1sc2c(Cl)cccc2c1C1C=CN=CN1 ; Cl] | 15, 1 | MS (ESI+): m/z 263 (MH⁺); ¹H NMR (300 MHz, MeOD): δ 8.23 (s, 1H), 7.90-7.87 (dd, J = 7.35 Hz, 1.38 Hz, 1H), 7.48-7.40 (m, 2H), 6.49-6.46 (d, J = 8.04 Hz, 1H), 5.31-5.27 (dd, J = 8.12 Hz, J = 2.36 Hz, 1H), 2.65 (s, 3H). |
| 75 | 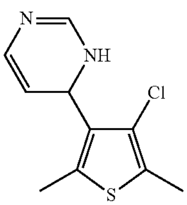 | 6, 1 | MS (ESI+): m/z 226 (MH⁺); ¹H NMR (300 MHz, MeOD): δ 8.12 (s, 1H), 6.37-6.34 (d, J = 8.43 Hz, 1H), 5.82-5.80 (m, 1H), 5.17-5.13 (dd, J = 7.53 Hz, J = 2.31 Hz, 1H), 2.46 (s, 3H), 2.36 (s, 3H). |
| 76 | 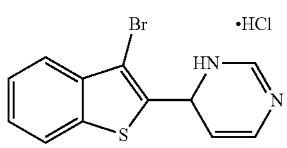 [SMILES: Cl ; Brc1c(C2C=CN=CN2)sc2ccccc12] | 16, 1 | MS (ESI+): m/z 293 (MH⁺); ¹H NMR (300 MHz, MeOD): δ 8.25 (s, 1H), 8.00-7.97 (m, 1H), 7.91-7.88 (m, 1H), 7.60-7.50 (m, 2H), 6.56 (d, J = 8.13 Hz, 1H), 6.18-6.17 (m, 1H), 5.52-5.48 (dd, J = 3.06 Hz, J = 7.59 Hz, 1H), |
| 77 | 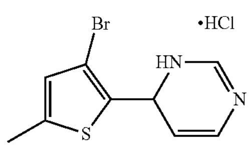 | 12, 1 | MS (ESI+): m/z 257 (MH⁺); ¹H NMR (300 MHz, MeOD): δ 8.14 (s, 1H), 6.81 (s, 1H), 6.49-6.46 (d, J = 8.04 Hz, 1H), 5.85-5.83 (dd, J = 3.60 Hz, J = 1.38 Hz, 1H), 5.40-5.36 (m, 1H), 2.51 (s, 3H). |
| 78 | 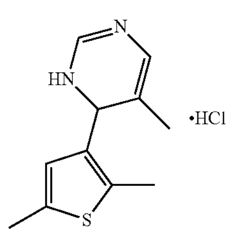 | 1 | MS (ESI+): m/z 207 (MH⁺); ¹H NMR (300 MHz, MeOD): δ 8.03 (s, 1H), 6.71 (s, 1H), 6.21 (s, 1H), 5.42 (s, 1H), 2.42 (s, 3H), 2.40 (s, 3H), 1.55 (s, 3H). |

-continued
| No. | Structure | Methods | Data |
|---|---|---|---|
| 79 | 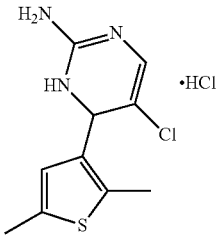 | 1 | MS (ESI+): m/z 243 (MH⁺); ¹H NMR (300 MHz, MeOD): δ 6.62 (s, 1H), 6.56 (s, 1H), 5.31 (s, 1H), 2.42 (s, 3H), 2.40 (s, 3H). |
| 80 | 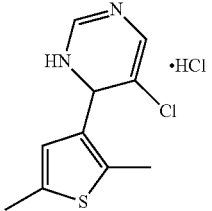 | 1 | MS (ESI+): m/z 228 (MH⁺); ¹H NMR (300 MHz, MeOD): δ 8.22 (s, 1H), 6.77-6.75 (d, J = 5.16 Hz, 2H), 5.66 (s, 1H), 2.44 (s, 3H), 2.42 (s, 3H). |
| 81 | 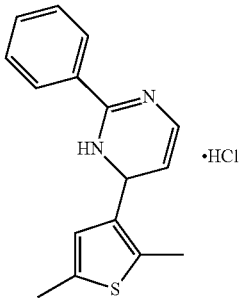 [SMILES: Cc1cc(C2C=CN=C(c3ccccc3)N2)c(C)s1 ; Cl] | 1 | MS (ESI+): m/z 269 (MH⁺); ¹H NMR (300 MHz, MeOD): δ 7.82-7.73 (m, 3H), 7.68-7.63 (m, 2H), 6.81 (s, 1H), 6.53-6.50 (dd, J = 8.01 Hz, J = 1.29 Hz, 1H), 5.66-5.64 (dd, J = 3.69 Hz, J = 1.31 Hz, 1H), 5.39-5.35 (dd, J = 8.10 Hz, 3.9 Hz, 1H), 2.45 (s, 3H), 2.41 (s, 3H). |
| 82 | 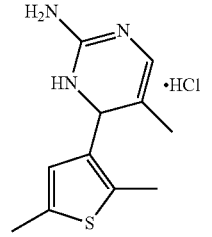 | 1 | MS (ESI+): m/z 222 (MH⁺); ¹H NMR (300 MHz, MeOD): δ 6.58 (s, 1H), 6.07 (s, 1H), 5.10 (s, 1H), 2.40 (s, 3H), 2.38 (s, 3H), 1.53 (s, 3H). |
| 83 | 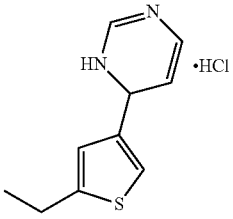 | 1 | MS (ESI+): m/z 193 (MH⁺); ¹H NMR (300 MHz, MeOD): δ 8.13 (s, 1H), 6.85 (s, 1H), 6.49-6.46 (d, J = 8.13 Hz, 1H), 5.86-5.85 (dd, J = 3.63 Hz, J = 1.41 Hz, 1H), 5.41-5.37 (m, 1H), 2.91-2.83 (m, 2H), 1.33-1.28 (t, J = 7.53 Hz, 3H). |
| 84 | 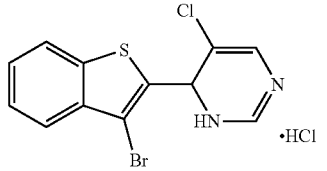 [SMILES: ClC1=CN=CNC1c1sc2ccccc2c1Br ; Cl] | 16, 1 | MS (ESI+): m/z 329 (MH⁺); ¹H NMR (300 MHz, MeOD): δ 8.36 (s, 1H), 7.91-8.01 (m, 2H), 7.62-7.56 (m, 2H), 6.93 (s, 1H), 6.32 (s, 1H). |

| No. | Structure | Methods | Data |
|---|---|---|---|
| 85 | 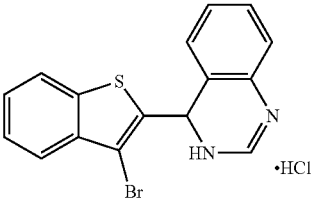 [SMILES: Brc1c(C2NC=Nc3ccccc32)sc2ccccc12 ; Cl] | 16, 1 | MS (ESI+): m/z 343 (MH$^+$); $^1$H NMR (300 MHz, MeOD): δ 8.44 (s, 1H), 7.90-7.93 (td, J = 8.64 Hz, J = 1.02 Hz, 2H), 7.43-7.60 (m, 3H), 7.28-7.34 (td, 7.61 Hz, 1H), 7.16-7.24 (m, 2H), 6.85 (s, 1H). |
| 86 | 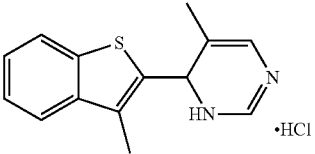 [SMILES: CC1=CN=CNC1c1sc2ccccc2c1C ; Cl] | 1 | MS (ESI+): m/z 243 (MH$^+$); $^1$H NMR (300 MHz, MeOD): δ 8.13 (s, 1H), 7.81-7.89 (m, 2H), 7.39-7.49 (m, 2H), 6.33 (s, 1H), 6.01 (s, 1H), 2.52 (s, 3H), 1.67 (s, 3H). |
| 87 | 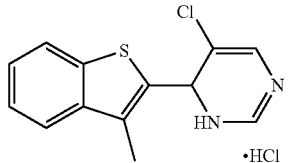 [SMILES: Cc1c(C2NC=NC=C2Cl)sc2ccccc12 ; Cl] | 1 | MS (ESI+): m/z 263 (MH$^+$); $^1$H NMR (300 MHz, MeOD): δ 8.31 (s, 1H), 7.83-7.91 (m, 2H), 7.42-7.50 (m, 2H), 6.87 (s, 1H), 6.27 (s, 1H), 2.53 (s, 3H). |
| 88 | 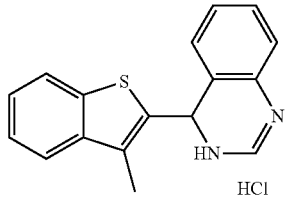 [SMILES: Cc1c(C2NC=Nc3ccccc32)sc2ccccc12 ; Cl] | 1 | MS (ESI+): m/z 279 (MH$^+$); $^1$H NMR (300 MHz, MeOD): δ 8.37 (s, 1H), 7.80-7.86 (m, 2H), 7.37-7.48 (m, 3H), 7.26-7.31 (t, J = 7.49 Hz, 1H), 7.19-7.21 (d, J = 7.89 Hz, 1H), 7.09-7.12 (d, J = 7.71 Hz, 1H), 6.79 (s, 1H), 2.60 (s, 3H). |
| 89 | 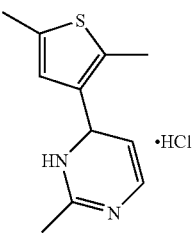 | 1 | MS (ESI+): m/z 207 (MH$^+$); $^1$H NMR (300 MHz, MeOD): δ 6.75 (s, 1H), 6.32-6.35 (dd, J = 8.09, J = 1.34, 1H), 5.48-5.50 (m, 1H), 5.17-5.21 (dd, J = 8.09 Hz, J = 3.38 Hz, 1H), 2.40 (s, 6H), 2.24 (s, 3H). |
| 90 | 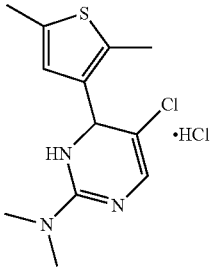 [SMILES: Cc1cc(C2NC(N(C)C)=NC=C2Cl)c(C)s1 ; Cl] | 26, 1 | MS (ESI+): m/z 270 (MH$^+$); $^1$H NMR (300 MHz, MeOD): δ 6.63 (s, 1H), 6.52 (s, 1H), 5.31 (s, 1H), 3.10 (s, 6H), 2.43 (s, 3H), 2.39 (s, 3H). |
| 91 | 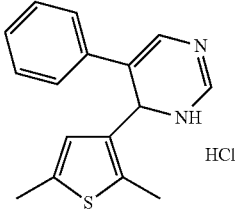 [SMILES: Cc1cc(C2NC=NC=C2c2ccccc2)c(C)s1 ; Cl] | 24, 1 | MS (ESI+): m/z 269 (MH$^+$); $^1$H NMR (300 MHz, MeOD): δ 8.15 (s, 1H), 7.31-7.34 (m, 5H), 6.82 (s, 1H), 6.74 (s, 1H), 5.99 (s, 1H), 2.44 (s, 3H), 2.34 (s, 3H). |

-continued

| No. | Structure | Methods | Data |
|---|---|---|---|
| 92 | 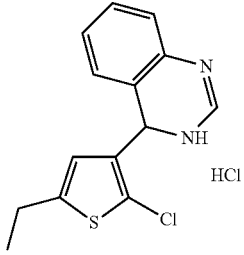 [SMILES: CCc1cc(C2NC=Nc3ccccc32)c(Cl)s1 ; Cl] | 12, 1 | MS (ESI+): m/z 277 (MH$^+$); $^1$H NMR (300 MHz, MeOD): δ 8.35 (s, 1H), 7.42-7.47 (t, J = 7.62 Hz, 1H), 7.18-7.22 (m, 2H), 6.39 (s, 1H), 2.76-2.84 (q, 2H), 1.20-1.25 (t, J = 7.53 Hz, 3H). |
| 93 | 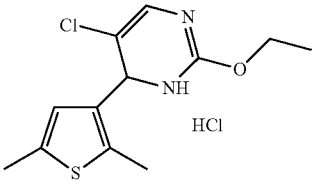 [SMILES: CCOC1=NC=C(Cl)C(c2cc(C)sc2C)N1 ; Cl] | 25, 1 | MS (ESI+): m/z 271 (MH$^+$); $^1$H NMR (300 MHz, MeOD): δ 6.75 (s, 1H), 6.59 (s, 1H), 5.56 (s, 1H), 4.35-4.57 (m, 2H), 2.43 (s, 3H), 2.41 (s, 3H), 1.43-1.47 (t, J = 6.38 Hz, 3H). |
| 94 | 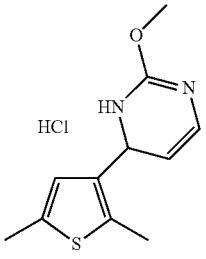 | 25, 1 | MS (ESI+): m/z 223 (MH$^+$); $^1$H NMR (300 MHz, MeOD): δ 6.74 (s, 1H), 6.28-6.31 (d, J = 7.8 Hz, 1H), 5.53-5.54 (m, 1H), 5.14-5.22 (m, 1H), 4.10 (s, 3H), 2.40 (s, 6H). |
| 95 | 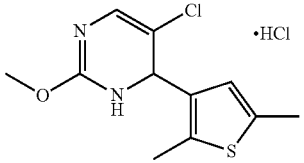 | 25, 1 | MS (ESI+): m/z 257 (MH$^+$); $^1$H NMR (300 MHz, MeOD): δ 6.76 (s, 1H), 6.60 (s, 1H), 5.58 (s, 1H), 4.12 (s, 3H), 2.43 (s, 3H), 2.41 (s, 3H). |
| 96 | 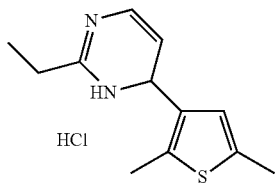 | 1 | MS (ESI+): m/z 221 (MH$^+$); $^1$H NMR (300 MHz, MeOD): δ 6.73 (s, 1H), 6.33-6.36 (d, J = 8.07 Hz, 1H), 5.48-5.50 (m, 1H), 5.18-5.22 (dd, J = 8.06 Hz, J = 3.38 Hz, 1H), 2.40 (s, 6H), 1.26-1.31 (t, J = 7.64 Hz, 3H). |
| 97 | 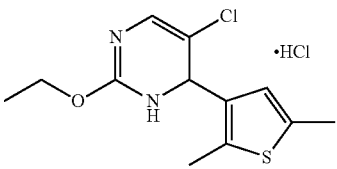 [SMILES: CCOC1=NC=C(Cl)C(c2cc(C)sc2C)N1 ; Cl] | 25, 1 | MS (ESI+): m/z 271 (MH$^+$); $^1$H NMR (300 MHz, MeOD): δ 6.75 (s, 1H), 6.59 (s, 1H), 6.57 (s, 1H), 4.35-4.55 (m, 2H), 2.43 (s, 3H), 2.41 (s, 3H), 1.43-1.47 (t, J = 6.38 Hz, 3H). |
| 98 | 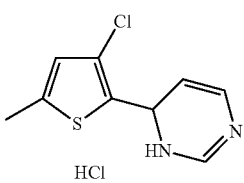 | 17, 1 | MS (ESI+): m/z 213 (MH$^+$); $^1$H NMR (300 MHz, MeOD): δ 8.11 (s, 1H), 7.11 (s, 1H), 6.47-6.50 (d, J = 8.04 Hz, 1H), 5.68-5.69 (m, 1H), 5.40-5.44 (m, 1H), 2.42 (s, 3H), |

-continued

Tabular Data

| No. | Structure | Methods | Data |
|---|---|---|---|
| 99 | 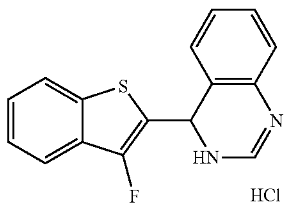 [SMILES: Fc1c(C2NC=Nc3ccccc32)sc2ccccc12 ; Cl] | 16, 1 | MS (ESI+): m/z 283 (MH+); $^1$H NMR (300 MHz, MeOD): δ 8.44 (s, 1H), 7.84-7.87 (m, 2H), 7.60-7.63 (m, 1H), 7.39-7.43 (m, 3H), 7.20-7.26 (m, 2H), 7.01-7.04 (d, J = 7.62 Hz, 1H), 6.73 (s, 1H). |
| 100 | 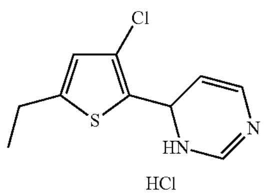 | 17, 1 | MS (ESI+): m/z 227 (MH+); $^1$H NMR (300 MHz, MeOD): δ 8.12 (s, 1H), 7.02 (s, 1H), 6.48-6.51 (d, J = 8.04 Hz, 1H), 5.70-5.71 (d, J = 3.0 Hz, 1H), 5.41-5.45 (m, 1H), 2.81-2.88 (q, 2H), 1.30-1.25 (t, J = 7.52 Hz, 3H). |
| 101 | 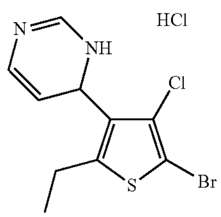 | 17, 1 | MS (ESI+): m/z 307 (MH+); $^1$H NMR (300 MHz, MeOD): δ 8.17 (s, 1H), 6.52-6.54 (d, J = 8.10 Hz, 1H), 5.91-5.95 (dd, J = 8.10 Hz, 3.60 Hz, 1H), 5.38-5.42 (m, 1H), 2.83-2.96 (m, 2H), 1.27-1.32 (t, J = 7.51 Hz, 3H). |
| 102 | 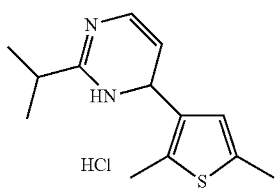 [SMILES: Cc1cc(C2C=CN=C(C(C)C)N2)c(C)s1 ; Cl] | 22, 1 | MS (ESI+): m/z 235 (MH+); $^1$H NMR (300 MHz, MeOD): δ 6.71 (s, 1H), 6.32-6.35 (d, J = 8.10 Hz, 1H), 5.48-5.49 (m, 1H), 5.20-5.24 (dd, J = 8.10 Hz, 3.3 Hz, 1H), 2.71-2.81 (m, 1H), 2.41 (s, 6H), 1.32 (s, 3H), 1.30 (s, 3H). |
| 103 | 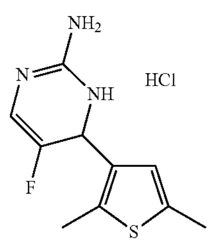 | 1 | MS (ESI+): m/z 226 (MH+); $^1$H NMR (300 MHz, MeOD): δ 6.65 (s, 1H), 6.43-6.45 (d, J = 6.21 Hz, 1H), 5.50-5.51 (d, J = 2.64 Hz, 1H), 2.41 (s, 3H), 2.40 (s, 3H). |
| 104 | 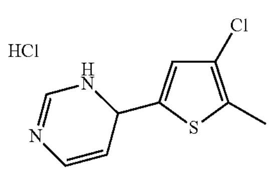 | 1 | MS (ESI+): m/z 213 (MH+); $^1$H NMR (300 MHz, MeOD): δ 8.12 (s, 1H), 7.01 (s, 1H), 6.47-6.50 (d, J = 8.10 Hz, 1H), 5.69-5.70 (d, J = 2.79 Hz, 1H), 5.40-5.44 (dd, J = 8.06 Hz, J = 3.67 Hz, 1H), 2.42 (s, 3H). |
| 105 | 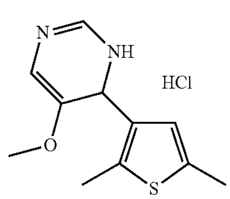 | 1 | MS (ESI+): m/z 223 (MH+); $^1$H NMR (300 MHz, MeOD): δ 7.97 (s, 1H), 6.64 (s, 1H), 6.04 (s, 1H), 5.50 (s, 1H), 3.63 (s, 3H), 2.40 (s, 3H), 2.39 (s, 3H). |

-continued

| No. | Structure | Methods | Data |
|---|---|---|---|
| 106 | 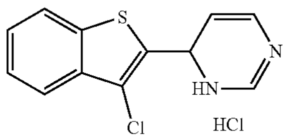 [SMILES: Clc1c(C2C=CN=CN2)sc2ccccc12 ; Cl] | 16, 1 | MS (ESI+): m/z 249 (MH$^+$); $^1$H NMR (300 MHz, MeOD): δ 8.25 (s, 1H), 7.89-7.99 (m, 2H), 7.51-7.59 (m, 2H), 6.54-6.57 (d, J = 8.07 Hz, 1H), 6.16-6.18 (dd, J = 3.56 Hz, J = 1.31 Hz, 1H), 5.47-5.51 (dd, J = 7.53 Hz, J = 3.60 Hz, 1H). |
| 107 | 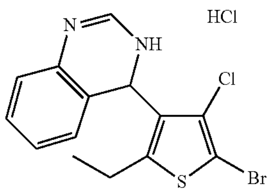 [SMILES: CCc1sc(Br)c(Cl)c1C1NC=Nc2ccccc21 ; Cl] | 17, 1 | MS (ESI+): m/z 357 (MH$^+$); $^1$H NMR (300 MHz, MeOD): δ 8.38 (s, 1H), 7.42-7.47 (t, J = 7.65 Hz, 1H), 7.30-7.35 (t, J = 7.58 Hz, 1H), 7.13-7.21 (m, 2H), 6.61-6.63 (d, J = 6.03 Hz, 1H), 2.82-2.93 (m, 2H), 1.20-1.28 (t, J= 7.53 Hz, 3H). |
| 108 | 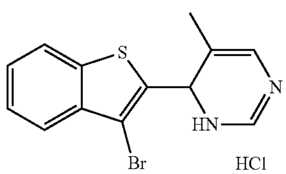 [SMILES: CC1=CN=CNC1c1sc2ccccc2c1Br ; Cl] | 17, 1 | MS (ESI+): m/z 307 (MH$^+$); $^1$H NMR (300 MHz, MeOD): δ 8.19 (s, 1H), 7.89-7.99 (m, 2H), 7.53-7.58 (m, 2H), 6.37 (m, 1H), 6.09 (m, 1H), 1.69 (s, 3H). |
| 109 | 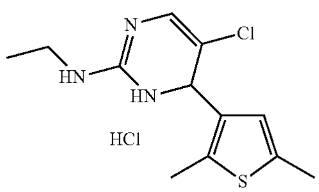 [SMILES: CCNC1=NC=C(Cl)C(c2cc(C)sc2C)N1 ; Cl] | 26, 1 | MS (ESI+): m/z 270 (MH$^+$); $^1$H NMR (300 MHz, MeOD): δ 6.62 (s, 1H), 6.53 (s, 1H), 5.30 (s, 1H), 3.23-3.30 (q, 2H), 2.24 (s, 3H), 2.39 (s, 3H), 1.21-1.25 (t, J = 7.22 Hz, 3H). |
| 110 | 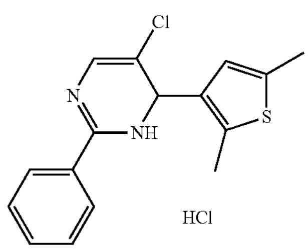 [SMILES: Cc1cc(C2NC(c3ccccc3)=NC=C2Cl)c(C)s1 ; Cl] | 22, 1 | MS (ESI+): m/z 303 (MH$^+$); $^1$H NMR (300 MHz, MeOD): δ 7.73-7.80 (m, 3H), 6.63-6.68 (m, 2H), 6.85 (s, 1H), 6.82 (s, 1H), 5.75 (s, 1H), 2.49 (s, 3H), 2.42 (s, 3H). |
| 111 | 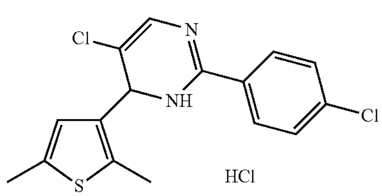 [SMILES: Cc1cc(C2NC(c3ccc(Cl)cc3)=NC=C2Cl)c(C)s1 ; Cl] | 22, 1 | MS (ESI+): m/z 337 (MH$^+$); $^1$H NMR (300 MHz, MeOD): δ 7.70-7.76 (m, 4H), 6.83-6.86 (m, 2H), 5.76 (s, 1H), 2.48 (s, 3H), 2.42 (s, 3H). |
| 112 | 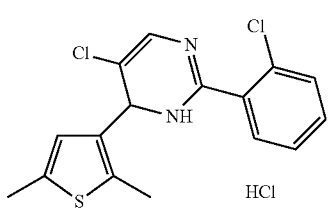 [SMILES: Cc1cc(C2NC(c3ccccc3Cl)=NC=C2Cl)c(C)s1 ; Cl] | 22, 1 | MS (ESI+): m/z 337 (MH$^+$); $^1$H NMR (300 MHz, MeOD): δ 7.67-7.74 (m, 3H), 7.55-7.62 (m, 1H), 7.12 (s, 1H), 6.91 (s, 1H), 5.82 (s, 1H), 2.41 (s, 3H), 2.40 (s, 3H). |

-continued

| No. | Structure | Methods | Data |
|---|---|---|---|
| 113 | 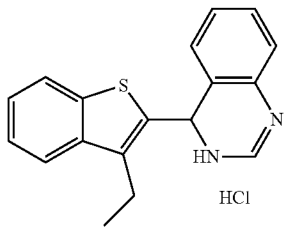 [SMILES: CCc1c(C2NC=Nc3ccccc32)sc2ccccc12 ; Cl] | 16, 1 | MS (ESI+): m/z 293 (MH+); ¹H NMR (300 MHz, MeOD): δ 8.38 (s, 1H), 7.86-7.88 (m, 1H), 7.46-7.55 (m, 1H), 7.18-7.40 (m, 5H), 6.81-6.84 (d, J = 7.74 Hz, 1H), 6.74 (s, 1H), 3.09-3.12 (m, 2H), 1.38-1.45 (m, 3H). |
| 114 | 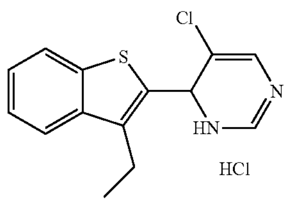 [SMILES: CCc1c(C2NC=NC=C2Cl)sc2ccccc12 ; Cl] | 16, 1 | MS (ESI+): m/z 277 (MH+); ¹H NMR (300 MHz, MeOD): δ 8.33 (s, 1H), 7.89-7.92 (d, J = 7.32 Hz, 1H), 7.80-7.83 (d, J = 7.59 Hz, 1H), 7.36-7.47 (m, 2H), 6.87 (s, 1H), 6.28 (s, 1H), 3.04-3.12 (q, 2H), 1.40-1.46 (t, J = 7.53 Hz, 3H). |
| 115 | 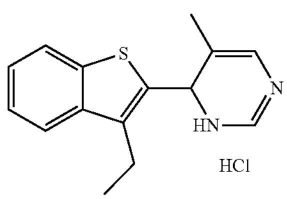 [SMILES: CCc1c(C2NC=NC=C2C)sc2ccccc12 ; Cl] | 16, 1 | MS (ESI+): m/z 257 (MH+); ¹H NMR (300 MHz, MeOD): δ 8.15 (s, 1H), 7.87-7.90 (d, J = 7.26 Hz, 2H), 7.36-7.42 (m, 2H), 6.31 (s, 1H), 6.06 (s, 1H), 3.04-3.17 (q, 2H), 1.49 (s, 3H), 1.39-1.44 (t, J = 7.41 Hz, 2H). |
| 116 | 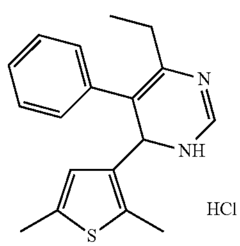 [SMILES: CCC1=C(c2ccccc2)C(c2cc(C)sc2C)NC=N1 ; Cl] | 24, 23, 1 | MS (ESI+): m/z 297 (MH+); ¹H NMR (300 MHz, MeOD): δ 8.22 (s, 1H), 7.30 (m, 3H), 7.01-7.02 (m, 2H), 6.81 (s, 1H), 5.55 (s, 1H), 2.40 (s, 3H), 2.10-2.17 (q, 2H), 1.96 (s, 3H), 1.08-1.13 (t, J = 7.40 Hz, 3H). |
| 117 | 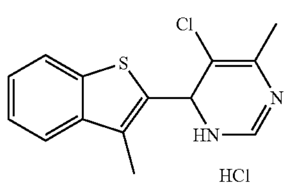 [SMILES: CC1=C(Cl)C(c2sc3ccccc3c2C)NC=N1 ; Cl] | 23, 1 | MS (ESI+): m/z 277 (MH+); ¹H NMR (300 MHz, MeOD): δ 8.32 (s, 1H), 7.81-7.89 (m, 2H), 7.43-7.47 (m, 2H), 6.20 (s, 1H), 2.52 (s, 3H), 2.14 (s, 3H). |
| 118 | 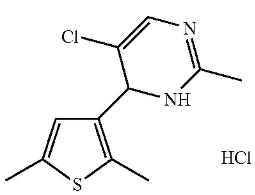 | 22, 1 | MS (ESI+): m/z 241 (MH+); ¹H NMR (300 MHz, MeOD): δ 6.76 (s, 1H), 6.70 (s, 1H), 5.60 (s, 1H), 2.43 (s, 3H), 2.42 (s, 3H), 2.28 (s, 3H). |
| 119 | 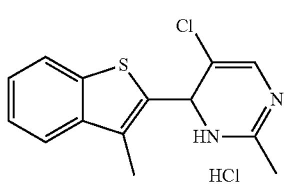 [SMILES: CC1=NC=C(Cl)C(c2sc3ccccc3c2C)N1 ; Cl] | 22, 16, 1 | MS (ESI+): m/z 277 (MH+); ¹H NMR (300 MHz, MeOD): δ 7.82-7.91 (m, 2H), 7.42-7.50 (m, 2H), 6.74 (s, 1H), 6.21 (s, 1H), 2.52 (s, 3H), 2.33 (s, 3H). |

-continued

| No. | Structure | Methods | Data |
|---|---|---|---|
| 120 | 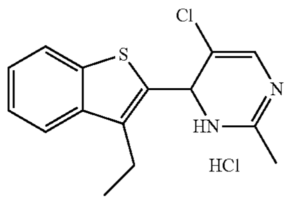 [SMILES: CCc1c(C2NC(C)=NC=C2Cl)sc2ccccc12 ; Cl] | 22, 16, 1 | MS (ESI+): m/z 291 (MH+); $^1$H NMR (300 MHz, MeOD): δ 7.89-7.92 (d, J = 7.17 Hz, 1H), 7.77-7.80 (d, J = 7.71 Hz, 1H), 7.36-7.46 (m, 2H), 6.84 (s, 1H), 6.21 (s, 1H), 3.03-3.11 (q, 2H), 2.31 (s, 3H), 1.41-1.46 (t, J = 7.56, 3H). |
| 121 | 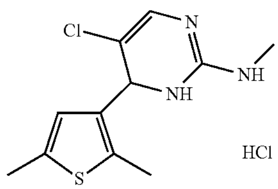 | 26, 1 | MS (ESI+): m/z 256 (MH+); $^1$H NMR (300 MHz, MeOD): δ 6.62 (s, 1H), 6.53 (s, 1H), 4.84 (s, 1H), 2.88 (s, 3H), 2.42 (s, 3H), 2.39 (s, 3H). |
| 122 | 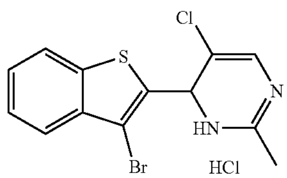 [SMILES: CC1=NC=C(Cl)C(c2sc3ccccc3c2Br)N1 ; Cl] | 22, 16, 1 | MS (ESI+): m/z 343 (MH+); $^1$H NMR (300 MHz, MeOD): δ 7.90-8.0 (m, 2H), 7.55-7.59 (m, 2H), 6.89 (s, 1H), 6.26 (s, 1H), 2.34 (s, 3H). |
| 123 | 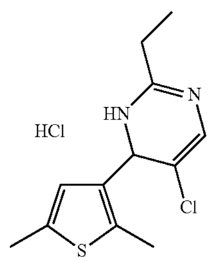 [SMILES: CCC1=NC=C(Cl)C(c2cc(C)sc2C)N1 ; Cl] | 22, 16, 1 | MS (ESI+): m/z 255 (MH+); $^1$H NMR (300 MHz, MeOD): δ 6.73 (s, 1H), 6.71 (s, 1H), 5.60 (s, 1H), 2.53-2.55 (q, 2H), 2.44 (s, 3H), 2.42 (s, 3H), 1.27-1.32 (t, J = 7.67, 3H). |
| 124 | 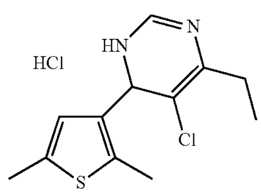 [SMILES: CCC1=C(Cl)C(c2cc(C)sc2C)NC=N1 ; Cl] | 23, 1 | MS (ESI+): m/z 255 (MH+); $^1$H NMR (300 MHz, MeOD): δ 8.21 (s, 1H), 6.70 (s, 1H), 5.59 (s, 1H), 2.36-2.50 (m, 8H), 1.18-1.21 (t, J = 7.56, 3H). |
| 125 | 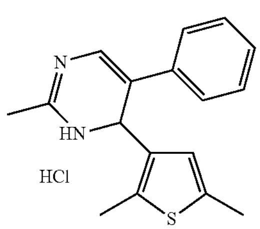 [SMILES: CC1=NC=C(c2ccccc2)C(c2cc(C)sc2C)N1 ; Cl] | 24, 22, 1 | MS (ESI+): m/z 283 (MH+); $^1$H NMR (300 MHz, MeOD): δ 7.28-7.33 (m, 5H), 6.81 (s, 1H), 6.71 (s, 1H), 5.95 (s, 1H), 2.45 (s, 3H), 2.33 (s, 3H), 2.32 (s, 3H). |
| 126 | 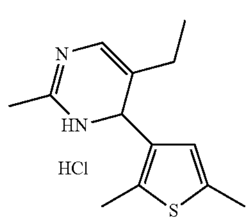 | 32, 1 | MS (ESI+): m/z 235 (MH+); $^1$H NMR (300 MHz, MeOD): δ 6.67 (s, 1H), 6.17 (s, 1H), 5.38 (s, 1H), 2.46-2.54 (q, 2H), 2.43 (s, 3H), 2.40 (s, 3H), 1.54 (s, 3H), 1.25-1.30 (t, J = 7.67 Hz, 3H). |

| No. | Structure | Methods | Data |
|---|---|---|---|
| 127 | (structure) HCl | 32, 1 | MS (ESI+): m/z 221 (MH+); ¹H NMR (300 MHz, MeOD): δ 6.68 (s, 1H), 6.16 (s, 1H), 5.37 (s, 1H), 2.42 (s, 3H), 2.39 (s, 3H), 2.23 (s, 3H), 1.53 (s, 3H). |
| 128 | (structure) HCl | 24, 22, 1 | MS (ESI+): m/z 381 (MH+); ¹H NMR (300 MHz, MeOD): δ 7.69-7.70 (m, 1H), 7.55-7.60 (m, 3H), 7.31-7.39 (m, 1H), 7.15-7.24 (m, 2H), 7.02-7.08 (m, 2H), 6.80 (s, 1H), 6.09 (s, 1H), 2.51 (s, 3H), 2.37 (s, 3H). |
| 129 | (structure) HCl | 22, 1 | MS (ESI+): m/z 321 (MH+); ¹H NMR (300 MHz, MeOD): δ 7.66-7.72 (m, 1H), 7.54-7.60 (m, 3H), 6.85-6.86 (m, 2H), 5.77 (s, 1H), 2.49 (s, 3H), 2.43 (s, 3H). |
| 130 | (structure) HCl | 23, 1 | MS (ESI+): m/z 221 (MH+); ¹H NMR (300 MHz, MeOD): δ 8.81 (s, 1H), 6.71 (s, 1H), 5.58 (s, 1H), 2.43 (s, 3H), 2.41 (s, 3H), 2.09 (s, 3H). |
| 131 | (structure) HCl | 24, 22, 1 | MS (ESI+): m/z 381 (MH+); ¹H NMR (300 MHz, MeOD): δ 7.70-7.84 (m, 2H), 7.29-7.50 (m, 4H), 7.11-7.18 (m, 2H), 6.84-6.85 (m, 2H), 6.13 (s, 1H), 2.36 (s, 6H). |
| 132 | (structure) HCl | 22, 1 | MS (ESI+): m/z 321 (MH+); ¹H NMR (300 MHz, MeOD): δ 7.76-7.82 (m, 1H), 7.68-7.73 (t, J = 7.34 Hz, 1H), 7.39-7.49 (m, 2H), 6.88 (s, 1H), 6.85 (s, 1H), 5.80 (s, 1H), 2.48 (s, 3H), 2.44 (s, 3H). |
| 133 | (structure) HCl | 22, 1 | MS (ESI+): m/z 337 (MH+); ¹H NMR (300 MHz, MeOD): δ 7.80-7.83 (m, 2H), 7.64-7.67 (m, 2H), 6.84 (s, 2H), 5.76 (s, 1H), 2.48 (s, 3H), 2.43 (s, 3H). |

-continued

Tabular Data

| No. | Structure | Methods | Data |
|---|---|---|---|
| 134 | 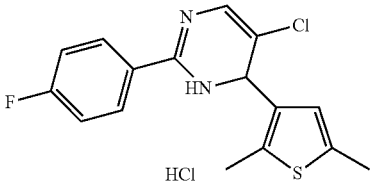 [SMILES: Cc1cc(C2NC(c3ccc(F)cc3)=NC=C2Cl)c(C)s1 ; Cl] | 22, 1 | MS (ESI+): m/z 321 (MH$^+$); $^1$H NMR (300 MHz, MeOD): δ 7.80-7.84 (m, 2H), 7.39-7.44 (t, J = 8.69 Hz, 2H), 6.82-6.85 (d, J = 9.81 Hz, 2H), 5.75 (s, 1H), 2.49 (s, 3H), 2.42 (s, 3H). |
| 135 | 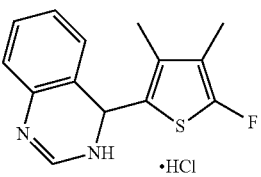 [SMILES: Cc1c(F)sc(C2NC=Nc3ccccc32)c1C ; Cl] | 8, 1 | MS (ESI+): m/z 261 (MH$^+$); $^1$H NMR (300 MHz, MeOD): δ 8.28 (s, 1H), 7.40-7.38 (m, 1H), 7.34-7.25 (m, 1H), 7.18-7.15 (d, J = 7.92 Hz, 1H), 7.10-7.08 (d, J = 7.71 Hz, 1H), 6.55-6.54 (m, 1H), 2.23 (s, 3H), 2.03 (s, 3H). |
| 136 | 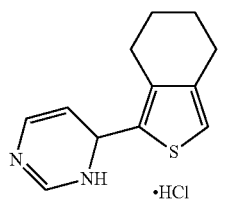 [SMILES: C1=CC(c2scc3c2CCCC3)NC=N1 ; Cl] | 18, 1 | MS (ESI+): m/z 219 (MH$^+$); $^1$H NMR (300 MHz, MeOD): δ 8.07 (s, 1H), 7.07 (s, 1H), 6.44-6.41 (d, J = 8.13 Hz, 1H), 5.80-5.79 (d, J = 2.10 Hz, 1H), 5.38-5.34 (dd, J = 8.42 Hz, J = 3.30 Hz, 1H), 2.81-2.65 (m, 4H), 1.85-1.76 (m, 4H). |
| 137 | 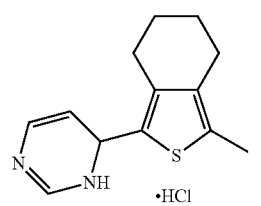 [SMILES: Cc1sc(C2C=CN=CN2)c2c1CCCC2 ; Cl] | 18, 1 | MS (ESI+): m/z 233 (MH$^+$); $^1$H NMR (300 MHz, MeOD): δ 8.04 (s, 1H), 6.41-6.38 (d, J = 8.07 Hz, 1H), 5.74-5.72 (m, 1H), 5.35-5.31 (m, 1H), 2.70-2.65 (m, 2H), 2.54-2.49 (m, 2H), 2.31 (s, 3H), 1.78-1.76 (m, 4H). |
| 138 | 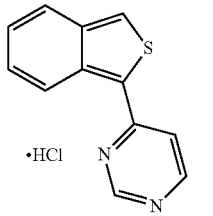 [SMILES: c1ccc2c(-c3ccncn3)scc2c1 ; Cl] | 19, 1 | MS (ESI+): m/z 213 (MH$^+$); $^1$H NMR (300 MHz, MeOD): δ 9.09 (s, 1H), 8.71-8.69 (d, J = 5.61 Hz, 1H), 8.57-8.54 (d, J = 9.00 Hz, 1H), 8.26 (s, 1H), 7.96-7.94 (dd, J = 5.64 Hz, J = 1.23 Hz, 1H), 7.75-7.72 (d, J = 8.73 Hz, 1H), 7.37-7.32 (m, 1H), 7.22-7.17 (m, 1H). |
| 139 | 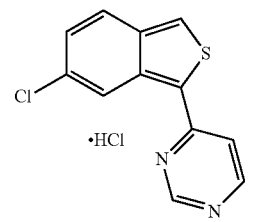 [SMILES: Clc1ccc2csc(-c3ccncn3)c2c1 ; Cl] | 20, 1 | MS (ESI+): m/z 247 (MH$^+$); $^1$H NMR (300 MHz, MeOD): δ 9.34 (s, 1H), 8.91-8.89 (d, J = 6.06 Hz, 2H), 8.79-8.77 (d, J = 6.39 Hz, 1H), 8.28-8.26 (d, J = 6.84 Hz, 1H), 7.91-7.88 (d, J = 9.09 Hz, 1H), 7.38-7.34 (d, J = 9.08 Hz, J = 1.70 Hz, 1H). |
| 140 | 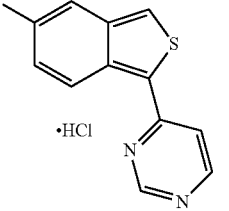 | 20, 1 | MS (ESI+): m/z 248 (MH$^+$); $^1$H NMR (300 MHz, MeOD): δ 9.31 (s, 1H), 8.82-8.74 (m, 3H), 8.30-8.27 (d, J = 6.69 Hz, 1H), 7.94-7.93 (d, J = 1.65 Hz, 1H), 7.53-7.50 (dd, J = 9.39 Hz, J = 1.92 Hz, 1H). |

-continued

| No. | Structure | Methods | Data |
|---|---|---|---|
| 141 | 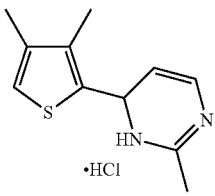 | 1 | MS (ESI+): m/z 207 (MH$^+$); $^1$H NMR (300 MHz, MeOD): δ 7.10 (s, 1H), 6.42-6.39 (dd, J = 8.04 Hz, J = 1.35 Hz, 1H), 5.83-5.82 (m, 1H), 5.34-5.30 (dd, J = 8.06 Hz, J = 3.53 Hz, 1H), 2.24 (s, 3H), 2.19 (s, 3H), 2.17 (s, 3H). |
| 142 | 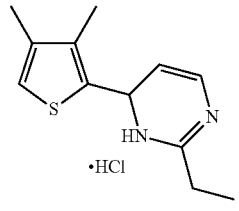 | 1 | MS (ESI+): m/z 221 (MH$^+$); $^1$H NMR (300 MHz, MeOD): δ 7.10 (s, 1H), 6.42-6.39 (dd, J = 8.04 Hz, J = 1.31 Hz, 1H), 5.83-5.82 (d, J = 2.64 Hz, 1H), 5.35-5.31 (dd, J = 8.04 Hz, J = 3.67 Hz, 1H), 2.54-2.46 (q, 2H), 2.19 (s, 3H), 2.17 (s, 3H), 1.31-1.25 (t, J = 7.67 Hz, 3H). |
| 143 | 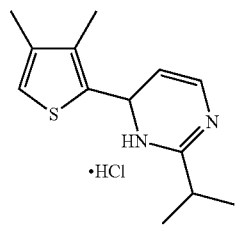 [SMILES: Cc1csc(C2C=CN=C(C(C)C)N2)c1C ; Cl] | 1 | MS (ESI+): m/z 235 (MH$^+$); $^1$H NMR (300 MHz, MeOD): δ 7.09 (s, 1H), 6.41-6.39 (d, J = 7.77 Hz, 1H), 5.83-5.82 (s, 1H), 5.35-5.34 (d, J = 4.80 Hz, 1H), 2.86-2.77 (m, 1H), 2.19 (s, 3H), 2.17 (s, 3H), 1.32-1.30 (m, 6H). |
| 144 | 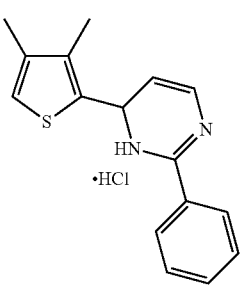 [SMILES: Cc1csc(C2C=CN=C(c3ccccc3)N2)c1C ; Cl] | 1 | MS (ESI+): m/z 269 (MH$^+$); $^1$H NMR (300 MHz, MeOD): δ 7.78-7.76 (m, 3H), 7.67-7.62 (m, 2H), 7.10 (s, 1H), 6.62-6.59 (d, J = 7.71 Hz, 1H), 5.99-5.98 (d, J = 3.27 Hz, 1H), 5.53-5.49 (dd, J = 7.50 Hz, J = 3.63 Hz, 1H), 2.25 (s, 3H), 2.149 (s, 3H). |
| 145 | 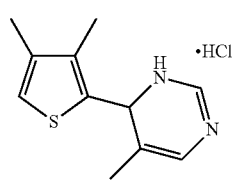 | 1 | MS (ESI+): m/z 207 (MH$^+$); $^1$H NMR (300 MHz, MeOD): δ 8.05 (s, 1H), 7.11 (s, 1H), 6.27 (s, 1H), 5.75 (s, 1H), 2.21 (s, 3H), 2.18 (s, 3H), 1.62 (s, 3H). |
| 146 | 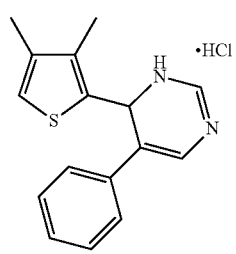 [SMILES: Cc1csc(C2NC=NC=C2c2ccccc2)c1C ; Cl] | 24, 1 | MS (ESI+): m/z 269 (MH$^+$); $^1$H NMR (300 MHz, MeOD): δ 8.18 (s, 1H), 7.39-7.30 (m, 5H), 7.04 (s, 1H), 6.39 (s, 1H), 6.35 (s, 1H), 2.25 (s, 3H), 2.14 (s, 3H). |

-continued

| No. | Structure | Methods | Data |
|---|---|---|---|
| 147 | 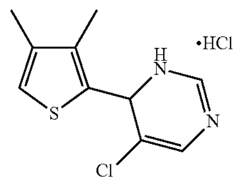 | 1 | MS (ESI+): m/z 228 (MH+); $^1$H NMR (300 MHz, MeOD): δ 8.24 (s, 1H), 7.17 (s, 1H), 6.80 (s, 1H), 6.00 (s, 1H), 2.22 (s, 3H), 2.19 (s, 3H). |
| 148 | 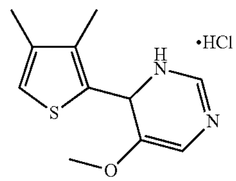 | 1 | MS (ESI+): m/z 223 (MH+); $^1$H NMR (300 MHz, MeOD): δ 7.99 (s, 1H), 7.06 (s, 1H), 6.05 (s, 1H), 5.84 (s, 1H), 3.64 (s, 3H), 2.18 (s, 3H), 2.16 (s, 3H). |
| 149 | 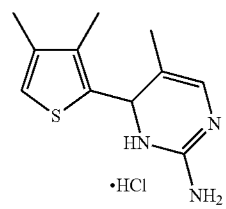 | 1 | MS (ESI+): m/z 222 (MH+); $^1$H NMR (300 MHz, MeOD): δ 7.01 (s, 1H), 6.10 (s, 1H), 5.42 (s, 1H), 2.19 (s, 3H), 2.16 (s, 3H), 1.60 (s, 3H). |
| 150 | 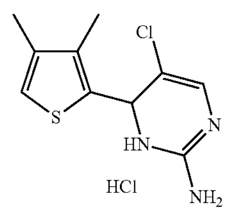 | 1 | MS (ESI+): m/z 243 (MH+); $^1$H NMR (300 MHz, MeOD): δ 7.06 (s, 1H), 6.58 (s, 1H), 5.64 (s, 1H), 2.20 (s, 3H), 2.17 (s, 3H). |
| 151 | 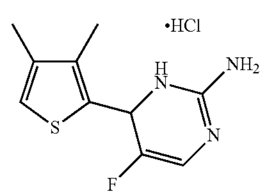 | 1 | MS (ESI+): m/z 226 (MH+); $^1$H NMR (300 MHz, MeOD): δ 7.07 (s, 1H), 6.50-6.46 (d, J = 6.06 Hz, 1H), 5.85-5.83. (d, J = 3.42 Hz, 1H), 2.19 (s, 3H), 2.17 (s, 3H). |
| 152 | 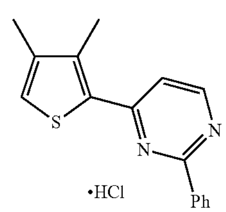 [SMILES: Cc1csc(-c2ccnc(-c3ccccc3)n2)c1C ; Cl] | 1 | MS (ESI+): m/z 267 (MH+); $^1$H NMR (300 MHz, MeOD): δ 8.83-8.81 (d, J = 6.39 Hz, 1H), 8.38-8.35 (m, 2H), 7.95-7.93 (d, J = 6.42 Hz, 1H), 7.75-7.63 (m, 4H), 2.71 (s, 3H), 2.31 (s, 3H). |
| 153 | 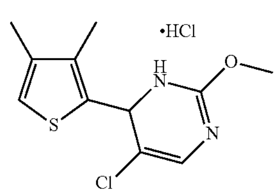 | 25, 1 | MS (ESI+): m/z 258 (MH+); $^1$H NMR (300 MHz, CDCl$_3$): δ 6.91 (s, 1H), 6.45 (s, 1H), 5.56. (s, 1H), 3.77 (s, 3H), 2.11 (s, 3H), 2.07 (s, 3H). |

-continued

| No. | Structure | Methods | Data |
|---|---|---|---|
| 154 | 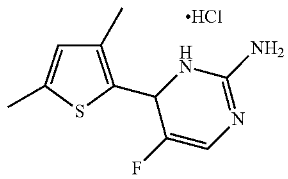 | 11, 1 | MS (ESI+): m/z 226 (MH+); 1H NMR (300 MHz, MeOD): δ 6.57 (s, 1H), 6.47-6.45 (d, J = 6.06 Hz, 1H), 5.76-5.75. (d, J = 3.36 Hz, 1H), 2.21 (s, 3H), 2.43 (s, 3H). |
| 155 | 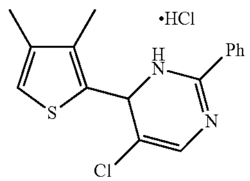 | 22, 1 | MS (ESI+): m/z 267 (MH+); 1H NMR (300 MHz, MeOD): δ 7.67-7.64 (m, 2H), 7.51-7.41 (m, 3H), 6.95 (s, 1H), 6.58 (s, 1H), 5.69 (s, 1H), 2.22 (s, 3H), 2.17 (s, 3H). |
| 156 | 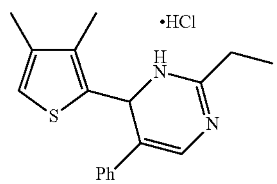 [SMILES: CCC1=NC=C(c2ccccc2)C(c2scc(C)c2C)N1 ; Cl] | 24, 22, 1 | MS (ESI+): m/z 297 (MH+); 1H NMR (300 MHz, MeOD): δ 7.37-7.28 (m, 5H), 7.02 (s, 1H), 6.88 (s, 1H), 6.29 (s, 1H), 2.62-2.55 (q, 2H), 2.26 (s, 3H), 2.13 (s, 3H), 1.32-1.27 (t, J = 7.67 Hz, 3H). |
| 157 | 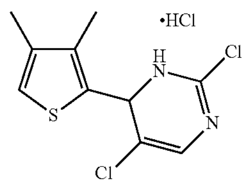 | 1 | MS (ESI+): m/z 261 (MH+); 1H NMR (300 MHz, MeOD): δ 7.20 (s, 1H), 6.86 (s, 1H), 6.13 (s, 1H), 2.23 (s, 3H), 2.20 (s, 3H). |
| 158 | 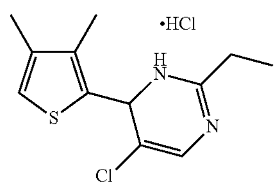 [SMILES: CCC1=NC=C(Cl)C(c2scc(C)c2C)N1 ; Cl] | 22, 1 | MS (ESI+): m/z 255 (MH+); 1H NMR (300 MHz, MeOD): δ 7.15 (s, 1H), 6.76 (s, 1H), 5.94 (s, 1H), 2.59-2.52 (q, 2H), 2.22 (s, 3H), 2.19 (s, 3H), 1.32-1.27 (t, J = 7.65 Hz, 3H). |
| 159 | 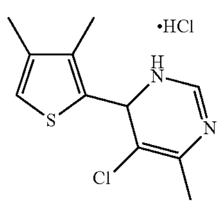 | 23, 1 | MS (ESI+): m/z 241 (MH+); 1H NMR (300 MHz, MeOD): δ 8.21 (s, 1H), 7.13 (s, 1H), 5.93 (s, 1H), 2.21 (s, 3H), 2.18 (s, 3H), 2.11 (s, 3H). |
| 160 | 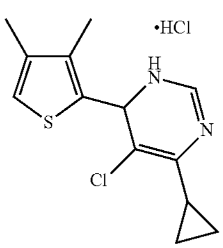 [SMILES: Cc1csc(C2NC=NC(C3CC3)=C2Cl)c1C ; Cl] | 23, 1 | MS (ESI+): m/z 267 (MH+); 1H NMR (300 MHz, MeOD): δ 8.12 (s, 1H), 7.13 (s, 1H), 5.92 (s, 1H), 2.21 (s, 3H), 2.18 (s, 3H), 2.01-1.91 (m, 1H), 1.06-1.02 (m, 2H), 0.87-0.83 (m, 2H). |

-continued

Tabular Data

| No. | Structure | Methods | Data |
|-----|-----------|---------|------|
| 161 | •HCl | 24, 1 | MS (ESI+): m/z 287 (MH$^+$); $^1$H NMR (300 MHz, MeOD): δ 8.18 (s, 1H), 7.42-7.37 (m, 2H), 7.10-7.04 (m, 3H), 6.90 (s, 1H), 6.32 (s, 1H), 2.25 (s, 3H), 2.14 (s, 3H). |
| 162 | •HCl | 24, 1 | MS (ESI+): m/z 303 (MH$^+$); $^1$H NMR (300 MHz, MeOD): δ 8.21 (s, 1H), 7.41 (s, 1H), 7.31-7.29 (m, 3H), 7.06 (s, 1H), 6.99 (s, 1H), 6.37 (s, 1H), 2.25 (s, 3H), 2.14 (s, 3H). |
| 163 | •HCl | 22, 1 | MS (ESI+): m/z 321 (MH$^+$); $^1$H NMR (300 MHz, MeOD): δ 7.83-7.78 (m, 2H), 7.45-7.39 (m, 2H), 7.17 (s, 1H), 6.91 (s, 1H), 6.08 (s, 1H), 2.27 (s, 3H), 2.21 (s, 3H). |
| 164 | •HCl | 22, 1 | MS (ESI+): m/z 287 (MH$^+$); $^1$H NMR (300 MHz, MeOD): δ 7.73-7.68 (m, 1H), 7.58-7.51 (m, 3H), 7.13 (s, 1H), 6.58-6.55 (m, 1H), 5.99-5.98 (m, 1H), 5.54-5.51 (m, 1H), 2.24 (s, 3H), 2.20 (s, 3H). |
| 165 | •HCl | 22, 1 | MS (ESI+): m/z 287 (MH$^+$); $^1$H NMR (300 MHz, MeOD): δ 7.82-7.77 (m, 2H), 7.44-7.38 (m, 2H), 7.12 (s, 1H), 6.59-6.56 (m, 1H), 5.97-5.96 (m, 1H), 5.53-5.49 (m, 1H), 2.24 (s, 3H), 2.20 (s, 3H). |
| 166 | •HCl | 21, 1 | MS (ESI+): m/z 221 (MH$^+$); $^1$H NMR (300 MHz, MeOD): δ 8.22 (s, 1H), 7.11 (s, 1H), 6.55-6.52 (d, J = 8.16 Hz, 1H), 5.84 (s, 1H), 5.53-5.49 (dd, J = 8.12 Hz, J = 3.53 Hz, 1H), 3.73-3.66 (q, 2H), 2.19 (s, 3H), 2.17 (s, 3H), 1.32-1.27 (t, J = 6.77 Hz, 3H). |

-continued

| No. | Structure | Methods | Data |
|---|---|---|---|
| 167 | ·HCl | 21, 1 | MS (ESI+): m/z 251 (MH+); ¹H NMR (300 MHz, MeOD): δ 8.12 (s, 1H), 7.11 (s, 1H), 6.53-6.50 (d, J = 8.07 Hz, 1H), 5.83 (s, 1H), 5.50-5.46 (dd, J = 8.12 Hz, J = 3.53 Hz, 1H), 3.86-3.78 (m, 2H), 3.70-3.59 (m, 2H), 3.42 (s, 3H), 2.19 (s, 3H), 2.17 (s, 3H). |
| 168 | ·HCl | 21, 1 | MS (ESI+): m/z 237 (MH+); ¹H NMR (300 MHz, MeOD): δ 8.09 (s, 1H), 7.12 (s, 1H), 6.51-6.48 (d, J = 8.22 Hz, 1H), 5.85-5.84 (m, 1H), 5.50-5.46 (dd, J = 8.12 Hz, J = 3.53 Hz, 1H), 3.79-3.76 (m, 2H), 3.71-3.68 (m, 2H), 2.19 (s, 3H), 2.18 (s, 3H). |
| 169 | ·HCl | 22, 1 | MS (ESI+): m/z 267 (MH+); ¹H NMR (300 MHz, MeOD): δ 7.14 (s, 1H), 6.67 (s, 1H), 5.86 (s, 1H), 2.21 (s, 3H), 2.108 (s, 3H), 1.93-1.87 (m, 1H), 1.36-1.23 (m, 4H). |
| 170 | ·HCl | 24, 1 | MS (ESI+): m/z 283 (MH+); ¹H NMR (300 MHz, MeOD): δ 7.37-7.29 (m, 5H), 7.02 (s, 1H), 6.89 (s, 1H), 6.29 (s, 1H), 2.03 (s, 3H), 2.26 (s, 3H), 2.14 (s, 3H). |
| 171 | ·HCl | 31, 1 | MS (ESI+): m/z 261 (MH+); ¹H NMR (300 MHz, MeOD): δ 7.06 (s, 1H), 5.57 (s, 1H), 2.23 (s, 3H), 2.19 (s, 3H), 2.17 (s, 3H), 1.85-1.66 (m, 8H). |

-continued

Tabular Data

| No. | Structure | Methods | Data |
|---|---|---|---|
| 172 | 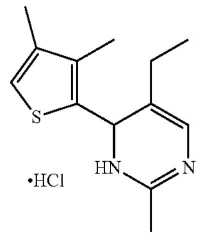 [SMILES: CCC1=CN=C(C)NC1c1scc(C)c1C ; Cl] | 32, 1 | MS (ESI+): m/z 235 (MH$^+$); $^1$H NMR (300 MHz, MeOD): δ 7.09 (s, 1H), 6.20 (s, 1H), 5.73 (s, 1H), 2.22 (s, 3H), 2.21 (s, 3H), 2.17 (s, 3H), 1.96-1.94 (q, 2H), 1.06-1.01 (t, J = 7.44 Hz, 3H). |
| 173 | 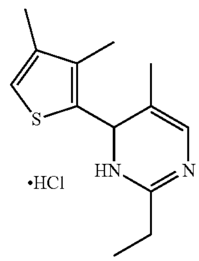 [SMILES: CCC1=NC=C(C)C(c2scc(C)c2C)N1 ; Cl] | 32, 1 | MS (ESI+): m/z 235 (MH$^+$); $^1$H NMR (300 MHz, MeOD): δ 7.10 (s, 1H), 6.22 (s, 1H), 5.70 (s, 1H), 2.53-2.45 (q, 2H), 2.24 (s, 3H), 2.18 (s, 3H), 1.61 (s, 3H), 1.29-1.24 (t, J = 7.67 Hz, 3H). |
| 174 | 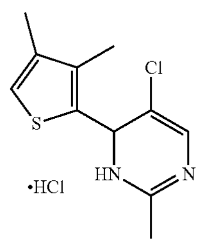 | 22, 1 | MS (ESI+): m/z 241 (MH$^+$); $^1$H NMR (300 MHz, MeOD): δ 7.15 (s, 1H), 6.76 (s, 1H), 5.94 (s, 1H), 2.29 (s, 3H), 2.22 (s, 3H), 2.18 (s, 3H). |
| 175 | 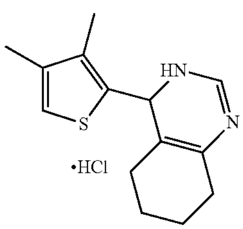 [SMILES: Cc1csc(C2NC=NC3=C2CCCC3)c1C ; Cl] | 30, 1 | MS (ESI+): m/z 247 (MH$^+$); $^1$H NMR (300 MHz, MeOD): δ 8.04 (s, 1H), 7.08 (s, 1H), 5.63 (s, 1H), 2.24-2.23 (m, 2H), 2.20 (s, 3H), 2.16 (s, 3H), 1.86-1.67 (m, 6H). |
| 176 | 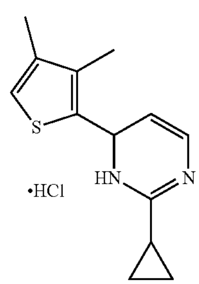 [SMILES: Cc1csc(C2C=CN=C(C3CC3)N2)c1C ; Cl] | 22, 1 | MS (ESI+): m/z 233 (MH$^+$); $^1$H NMR (300 MHz, MeOD): δ 7.08 (s, 1H), 6.35-6.32 (dd, J = 7.97 Hz, J = 1.25 Hz, 1H), 5.76-5.75 (d, J = 3.93 Hz, 1H), 5.35-5.31 (m, 1H), 2.17 (s, 6H), 1.88-1.83 (m, 1H), 1.30-1.25 (m, 4H). |
| 177 | 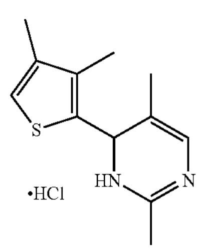 | 22, 1 | MS (ESI+): m/z 221 (MH$^+$); $^1$H NMR (300 MHz, MeOD): δ 7.10 (s, 1H), 6.22 (s, 1H), 5.69 (s, 1H), 2.22 (s, 3H), 2.21 (s, 3H), 2.18 (s, 3H), 1.61 (s, sH). |

-continued
| No. | Structure | Methods | Data |
|---|---|---|---|
| 178 | 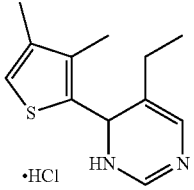 | 24, 1 | MS (ESI+): m/z 221 (MH$^+$); $^1$H NMR (300 MHz, MeOD): δ 8.05 (s, 1H), 7.10 (s, 1H), 6.26 (s, 1H), 5.79 (s, 1H), 2.22 (s, 3H), 2.17 (s, 3H), 1.97-1.95 (q, 2H), 1.06-1.02 (t, J = 7.43 Hz, 3H). |
| 179 | 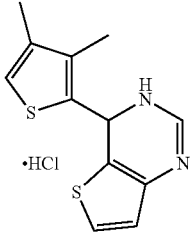 [SMILES: Cc1csc(C2NC=Nc3ccsc32)c1C ; Cl] | 28, 1 | MS (ESI+): m/z 249 (MH$^+$); $^1$H NMR (300 MHz, MeOD): δ 8.29 (s, 1H), 7.59-7.57 (d, J = 5.37 Hz, 1H), 7.10 (s, 1H), 6.95-6.94 (d, J = 5.34 Hz, 1H), 6.79 (s, 1H), 2.34 (s, 3H), 2.18 (s, 3H). |
| 180 | 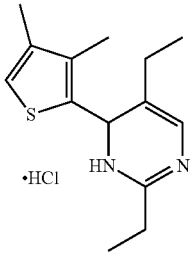 [SMILES: CCC1=CN=C(CC)NC1c1scc(C)c1C ; Cl] | 32, 1 | MS (ESI+): m/z 249 (MH$^+$); $^1$H NMR (300 MHz, MeOD): δ 7.09 (s, 1H), 6.20 (s, 1H), 5.73 (s, 1H), 2.53-2.46 (q, 2H), 2.21 (s, 3H), 2.17 (s, 3H), 1.98-1.91 (q, 2H), 1.29-1.24 (t, J = 7.68 Hz, 3H), 1.06-1.01 (t, J = 7.42 Hz, 3H) |
| 181 | 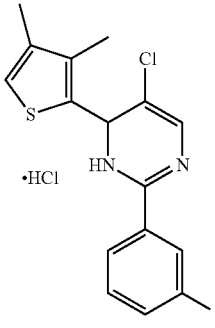 | 22, 1 | MS (ESI+): m/z 321 (MH$^+$); $^1$H NMR (300 MHz, MeOD): δ 7.71-7.67 (m, 1H), 7.60-7.53 (m, 3H), 7.18 (s, 1H), 6.92 (s, 1H), 6.11 (s, 1H), 2.28 (s, 3H), 2.21 (s, 3H). |
| 182 | 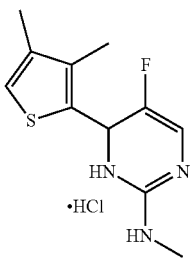 [SMILES: CNC1=NC=C(F)C(c2scc(C)c2C)N1 ; Cl] | 26, 1 | MS (ESI+): m/z 240 (MH$^+$); $^1$H NMR (300 MHz, MeOD): δ 7.06 (s, 1H), 6.47-6.45 (d, J = 5.88 Hz, 1H), 5.85-5.83. (d, J = 3.72 Hz, 1H), 2.92 (s, 3H), 2.19 (s, 3H), 2.17 (s, 3H). |

-continued

| No. | Structure | Methods | Data |
|---|---|---|---|
| 183 | 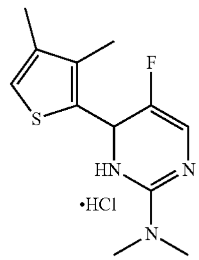 [SMILES: Cc1csc(C2NC(N(C)C)=NC=C2F)c1C ; Cl] | 26, 1 | MS (ESI+): m/z 254 (MH+); ¹H NMR (300 MHz, MeOD): δ 7.05 (s, 1H), 6.46-6.44 (d, J = 5.49 Hz, 1H), 5.85-5.83. (d, J = 4.62 Hz, 1H), 3.12 (s, 6H), 2.20 (s, 3H), 2.17 (s, 3H). |
| 184 | 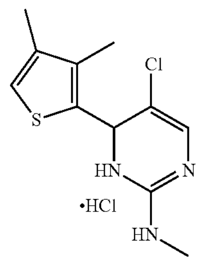 [SMILES: CNC1=NC=C(Cl)C(c2scc(C)c2C)N1 ; Cl] | 26, 1 | MS (ESI+): m/z 256 (MH+); ¹H NMR (300 MHz, MeOD): δ 7.05 (s, 1H), 6.56 (s, 1H), 5.64 (s, 1H), 2.89 (s, 3H), 2.21 (s, 3H), 2.17 (s, 3H). |
| 185 | 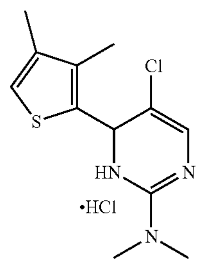 [SMILES: Cc1csc(C2NC(N(C)C)=NC=C2Cl)c1C ; Cl] | 26, 1 | MS (ESI+): m/z 270 (MH+); ¹H NMR (300 MHz, MeOD): δ 7.03 (s, 1H), 6.57 (s, 1H), 5.65. (s, 1H), 3.13 (s, 6H), 2.23 (s, 3H), 2.17 (s, 3H). |
| 186 | 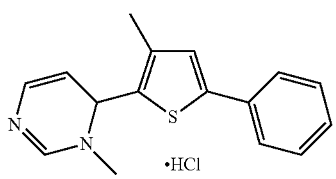 [SMILES: Cc1cc(-c2ccccc2)sc1C1C=CN=CN1C ; Cl] | 21, 9, 3 | MS (ESI+): m/z 269 (MH+); ¹H NMR (300 MHz, MeOD): δ 8.20 (s, 1H), 7.64-7.61 (m, 2H), 7.43-7.33 (m, 3H), 7.24 (s, 1H), 6.51-6.49 (d, J = 8.10 Hz, 1H), 5.84-5.82 (dd, J = 3.90 Hz, J = 1.20 Hz, 1H), 5.46-5.42 (dd, J = 8.10 Hz, J = 3.90 Hz, 1H), 3.20 (s, 3H), 2.36 (s, 3H). |
| 187 | 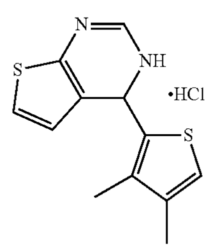 [SMILES: Cc1csc(C2NC=Nc3sccc32)c1C ; Cl] | 28, 1 | MS (ESI+): m/z 249 (MH+); ¹H NMR (300 MHz, MeOD): δ 8.23 (s, 1H), 7.56-7.55 (d, J = 1.50 Hz, 1H), 6.56-6.55 (d, J = 2.10 Hz, 1H), 6.57 (s, 1H), 6.37 (s, 1H), 2.44 (s, 3H), 2.37 (s, 3H). |
| 188 | 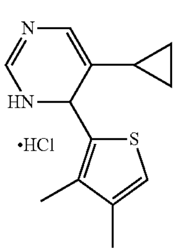 [SMILES: Cc1csc(C2NC=NC=C2C2CC2)c1C ; Cl] | 24, 1 | MS (ESI+): m/z 233 (MH+); ¹H NMR (300 MHz, MeOD): δ 8.04 (s, 1H), 7.10 (s, 1H), 6.21 (s, 1H), 5.80 (s, 1H), 2.24 (s, 3H), 2.18 (s, 3H), 1.25-1.15 (m, 1H), 0.71-0.66 (m, 3H), 0.58-0.43 (m, 1H). |

-continued

| No. | Structure | Methods | Data |
|---|---|---|---|
| 189 | 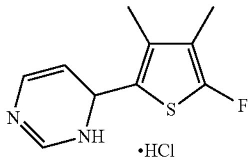 | 8, 13, 1 | MS (ESI+): m/z 211 (MH+); $^1$H NMR (300 MHz, MeOD): δ 8.07 (s, 1H), 6.47-6.44 (d, J = 8.10 Hz, 1H), 5.90-5.87 (m, 1H), 5.39-5.35 (dd, J = 7.50 Hz, J = 3.00 Hz, 1H), 2.19 (s, 3H), 2.03 (m, 3H). |
| 190 | 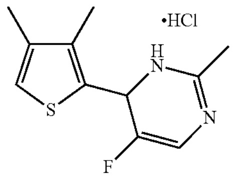 | 1 | MS (ESI+): m/z 225 (MH+); $^1$H NMR (300 MHz, MeOD): δ 7.16 (s, 1H), 6.67-6.65 (d, J = 6.30 Hz, 1H), 6.13 (s, 1H), 2.29 (s, 3H), 2.20 (s, 3H), 2.19 (s, 3H). |
| 191 | 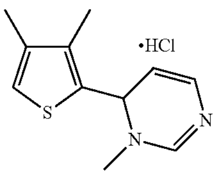 | 21, 3 | MS (ESI+): m/z 207 (MH+); $^1$H NMR (300 MHz, MeOD): δ 8.17 (s, 1H), 7.16 (s, 1H), 6.47-6.44 (d, J = 7.80 Hz, 1H), 5.83-5.82 (d, J = 3.30 Hz, 1H), 5.38-5.35 (m, 1H), 3.13 (s, 3H), 2.28 (s, 3H), 2.21 (s, 3H). |
| 192 | 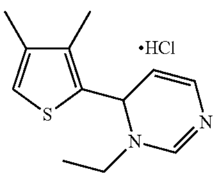 | 21, 3 | MS (ESI+): m/z 221 (MH+); $^1$H NMR (300 MHz, MeOD): δ 8.20 (s, 1H), 7.16 (s, 1H), 6.45-6.43 (d, J = 7.80 Hz, 1H), 5.93-5.91 (d, J = 3.90 Hz, 1H), 5.40-5.36 (dd, J = 8.10 Hz, J = 4.20 Hz, 1H), 3.55-3.47 (m, 2H), 2.14 (s, 3H), 2.06 (s, 3H), 1.40-1.27 (m, 3H). |
| 193 | 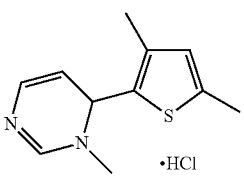 | 21, 11, 3 | MS (ESI+): m/z 207 (MH+); $^1$H NMR (300 MHz, MeOD): δ 8.17 (s, 1H), 6.60 (s, 1H), 6.45-6.43 (d, J = 7.80 Hz, 1H), 5.74-5.73 (d, J = 2.70 Hz, 1H), 5.37-5.33 (dd, J = 7.80 Hz, J = 3.60 Hz, 1H), 3.31 (s, 3H), 2.49 (s, 3H), 2.30 (s, 3H). |
| 194 | 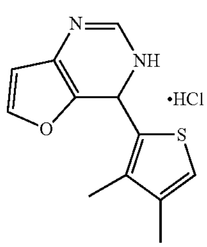 [SMILES: Cc1csc(C2NC=Nc3ccoc32)c1C ; Cl] | 28, 1 | MS (ESI+): m/z 233 (MH+); $^1$H NMR (300 MHz, MeOD): δ 8.25 (s, 1H), 7.59-7.58 (dd, J = 2.10 Hz, J = 0.60 Hz, 1H), 7.11 (s, 1H), 6.73 (s, 1H), 6.58-6.57 (d, J = 2.10 Hz, 1H), 2.23 (s, 3H), 2.18 (s, 3H). |
| 195 | 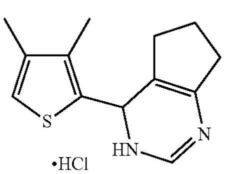 [SMILES: Cc1csc(C2NC=NC3=C2CCC3)c1C ; Cl] | 30, 1 | MS (ESI+): m/z 233 (MH+); $^1$H NMR (300 MHz, MeOD): δ 8.09 (s, 1H), 7.09 (s, 1H), 5.96 (s, 1H), 2.62-2.57 (m, 2H), 2.35-2.30 (m, 2H), 2.18 (s, 3H), 2.17 (s, 3H), 2.21-1.91 (m, 2H). |

-continued

| No. | Structure | Methods | Data |
|---|---|---|---|
| 196 | 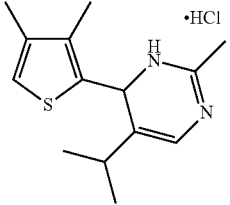 | 32, 1 | MS (ESI+): m/z 249 (MH$^+$); $^1$H NMR (300 MHz, MeOD): δ 7.08 (s, 1H), 6.24 (s, 1H), 5.77 (s, 1H), 2.23 (s, 3H), 2.22 (s, 3H), 2.18 (s, 3H), 2.17-2.13 (m, 1H), 1.07-1.03 (m, 6H). |
| 197 | 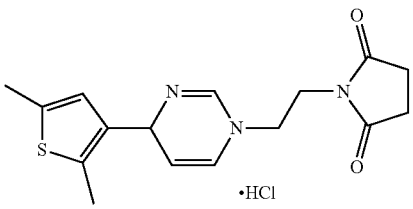 [SMILES: Cc1cc(C2C=CN(CCN3C(=O)CCC3=O)C=N2)c(C)s1 ; Cl] | 29, 3 | MS (ESI+): m/z 318 (MH$^+$); $^1$H NMR (300 MHz, MeOD): δ 8.15 (s, 1H), 6.88 (s, 1H), 6.41-6.38 (dd, J = 8.10 Hz, J = 1.20 Hz, 1H), 5.50-5.48 (dd, J = 3.30 Hz, J = 1.80 Hz, 1H), 5.35-5.31 (dd, J = 8.40 Hz, J = 3.00 Hz, 1H), 3.86-3.82 (m, 2H), 3.78-3.75 (m, 2H), 3.33-3.32 (m, 4H), 2.46 (s, 3H), 2.42 (s, 3H). |
| 198 | 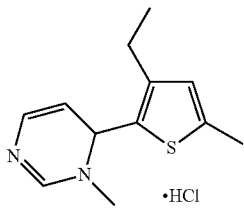 | 21, 11, 3 | MS (ESI+): m/z 221 (MH$^+$); $^1$H NMR (300 MHz, MeOD): δ 8.15 (s, 1H), 6.69 (s, 1H), 6.44-6.43 (d, J = 8.10 Hz, 1H), 5.76-5.74 (dd, J = 3.60 Hz, J = 1.20 Hz, 1H), 5.38-5.34 (dd, J = 7.50 Hz, J = 3.30 Hz, 1H), 3.04 (s, 3H), 2.67-2.60 (q, 2H), 2.50 (s, 3H), 1.25-1.21 (t, J = 7.50 Hz, 3H). |
| 199 | 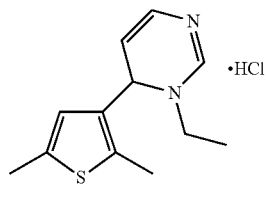 | 21, 3 | MS (ESI+): m/z 221 (MH$^+$); $^1$H NMR (300 MHz, MeOD): δ 8.13 (s, 1H), 6.75 (s, 1H), 6.44-6.41 (d, J = 8.10 Hz, 1H), 5.50-5.49 (m, 1H), 5.40-5.36 (dd, J = 8.10 Hz, J = 3.60 Hz, 1H), 3.68-3.60 (q, 2H), 2.43 (s, 3H), 2.40 (s, 3H), 1.40-1.27 (m, 3H). |
| 200 | 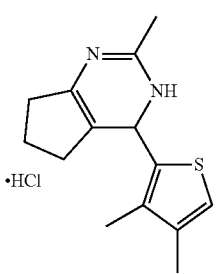 [SMILES: Cl ; CC1=NC2=C(CCC2)C(c2scc(C)c2C)N1] | 31, 1 | MS (ESI+): m/z 247 (MH$^+$); $^1$H NMR (300 MHz, MeOD): δ 7.08 (s, 1H), 5.90 (s, 1H), 2.64-2.53 (m, 2H), 2.34-2.30 (m, 2H), 2.27 (s, 3H), 2.18 (s, 3H), 2.17 (s, 3H), 2.10-1.96 (m, 2H). |
| 201 | 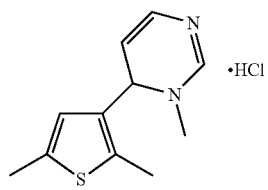 | 21, 3 | MS (ESI+): m/z 207 (MH$^+$); $^1$H NMR (300 MHz, MeOD): δ 8.07 (s, 1H), 6.79 (s, 1H), 6.34-6.30 (m, 1H), 5.49-5.47 (m, 1H), 5.37-5.33 (dd, J = 8.16 Hz, J = 3.36 Hz, 1H), 3.34 (s, 3H), 2.42 (s, 3H), 2.40 (s, 3H). |

-continued

| No. | Structure | Methods | Data |
|---|---|---|---|
| 202 | 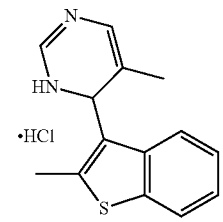 [SMILES: Cl ; CC1=CN=CNC1c1c(C)sc2ccccc12] | 1 | MS (ESI+): m/z 243 (MH⁺); ¹H NMR (300 MHz, MeOD): δ 8.15 (s, 1H), 7.88-7.85 (dd, J = 7.80 Hz, J = 2.40 Hz, 2H), 7.44-7.34 (m, 2H), 6.30 (s, 1H), 6.05 (s, 1H), 2.65 (s, 3H), 1.49 (s, 3H). |
| 203 | 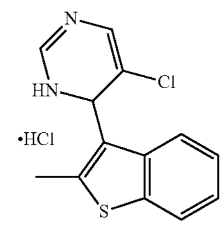 [SMILES: Cl ; Cc1sc2ccccc2c1C1NC=NC=C1Cl] | 1 | MS (ESI+): m/z 263 (MH⁺); ¹H NMR (300 MHz, MeOD): δ 8.32 (s, 1H), 7.89-7.87 (d, J = 7.50 Hz, 1H), 7.82-7.80 (d, J = 7.50 Hz, 1H), 7.46-7.36 (m, 2H), 6.86-6.85 (d, J = 0.6 Hz, 1H), 6.26-6.25 (d, J = 1.2 Hz, 1H), 2.66 (s, 3H). |
| 204 | 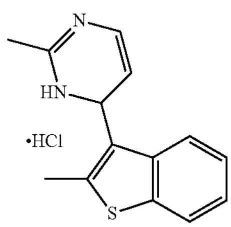 [SMILES: CC1=NC=CC(c2c(C)sc3ccccc23)N1 ; Cl] | 1 | MS (ESI+): m/z 243 (MH⁺); ¹H NMR (300 MHz, MeOD): δ 7.89-7.84 (m, 2H), 7.44-7.33 (m, 2H), 6.45-6.42 (dd, J = 8.10 Hz, J = 1.80 Hz, 1H), 6.09-6.07 (m, 1H), 5.27-5.23 (dd, J = 8.10 Hz, J = 3.00 Hz, 1H), 2.63 (s, 3H), 2.28 (s, 3H). |
| 205 | 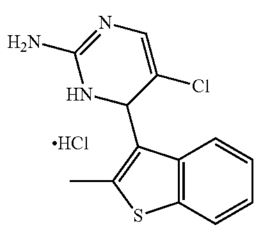 [SMILES: Cc1sc2ccccc2c1C1NC(N)=NC=C1Cl ; Cl] | 1 | MS (ESI+): m/z 278 (MH⁺); ¹H NMR (300 MHz, MeOD): δ 7.85-7.83 (m, 1H), 7.76-7.73 (m, 1H), 7.41-7.32 (m, 2H), 6.66 (s, 1H), 5.91 (s, 1H), 2.64 (s, 3H). |
| 206 | 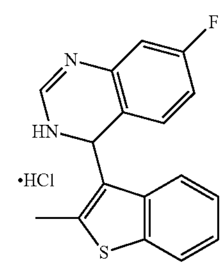 [SMILES: Cl ; Cc1sc2ccccc2c1C1NC=Nc2cc(F)ccc21] | 33, 4 | MS (ESI+): m/z 297 (MH⁺); ¹H NMR (300 MHz, MeOD): δ 8.43 (s, 1H), 7.87-7.84 (m, 1H), 7.52-7.50 (m, 1H), 7.34-7.29 (m, 2H), 6.99-6.84 (m, 3H), 6.70 (s, 1H), 2.67 (s, 3H). |
| 207 | 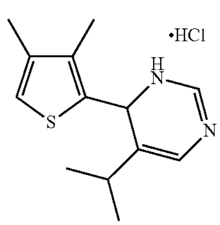 [SMILES: Cc1csc(C2NC=NC=C2C(C)C)c1C ; Cl] | 24, 1 | MS (ESI+): m/z 235 (MH⁺); ¹H NMR (300 MHz, MeOD): δ 8.03 (s, 1H), 7.10 (s, 1H), 6.29 (s, 1H), 5.82 (s, 1H), 2.23 (s, 3H), 2.18 (s, 3H), 2.17-2.14 (m, 1H), 1.09-1.04 (m, 6H). |

-continued

| No. | Structure | Methods | Data |
|---|---|---|---|
| 208 | 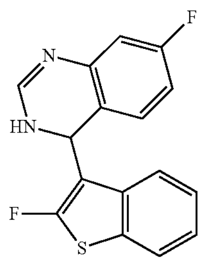 [SMILES: Fc1ccc2c(c1)N=CNC2c1c(F)sc2ccccc12] | 33, 13, 4 | MS (ESI+): m/z 301 (MH$^+$); $^1$H NMR (300 MHz, MeOD): δ 8.50 (s, 1H), 7.88-7.85 (m, 1H), 7.63-7.60 (m, 1H), 7.45-7.41 (m, 2H), 7.09-6.98 (m, 3H), 6.7 (s, 1H) |
| 209 | 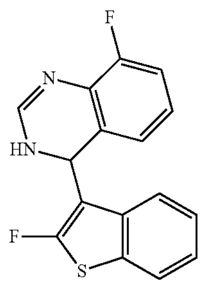 [SMILES: Fc1cccc2c1N=CNC2c1c(F)sc2ccccc12] | 33, 13, 4 | MS (ESI+): m/z 301 (MH$^+$); $^1$H NMR (300 MHz, MeOD): δ 8.46 (s, 1H), 7.88-7.85 (m, 1H), 7.65-7.62 (m, 1H), 7.46-7.39 (m, 2H), 7.30-7.22 (m, 2H), 6.87-6.84 (m, 1H), 6.75 (s, 1H) |
| 210 | 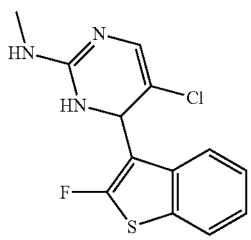 [SMILES: CNC1=NC=C(Cl)C(c2c(F)sc3ccccc23)N1] | 26, 13, 4 | MS (ESI+): m/z 296 (MH$^+$); $^1$H NMR (300 MHz, MeOD): δ 7.87-7.85 (d, J = 7.5 Hz, 1H), 7.76-7.74 (d, J = 7.2 Hz, 1H), 7.48-7.43 (m, 2H), 6.69 (s, 1H), 5.88 (s, 1H), 2.89 (s, 3H) |
| 211 | 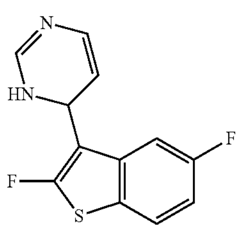 [SMILES: Fc1ccc2sc(F)c(C3C=CN=CN3)c2c1] | 15, 13, 4 | MS (ESI+): m/z 251 (MH$^+$); $^1$H NMR (300 MHz, MeOD): δ 8.25 (s, 1H), 7.91-7.87 (m, 1H), 7.64-7.60 (dd, J = 9.81 Hz, J = 2.46 Hz, 1H), 7.28-7.22 (td, J = 8.97 Hz, J = 2.54 Hz, 1H), 6.52-6.50 (d, J = 8.29 Hz, 1H), 6.03-6.01 (m, 1H), 5.41-5.36 (m, 1H) |
| 212 | 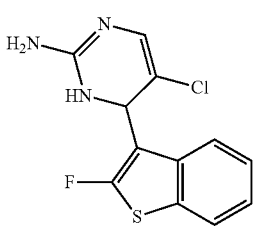 [SMILES: NC1=NC=C(Cl)C(c2c(F)sc3ccccc23)N1] | 13, 1 | MS (ESI+): m/z 282 (MH$^+$); $^1$H NMR (300 MHz, MeOD): δ 7.87-7.84 (d, J = 7.20 Hz, 1H), 7.77-7.75 (d, J = 7.35 Hz, 1H), 7.50-7.40 (m, 2H), 6.70 (s, 1H), 5.87 (s, 1H) |
| 213 | 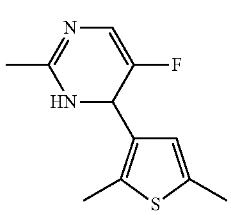 | 1 | MS (ESI+): m/z 225 (MH$^+$); $^1$H NMR (300 MHz, MeOD): δ 8.38 (s, 1H), 7.90-7.82 (dd, J = 10.5 Hz, J = 7.5 Hz, 2H), 7.55-7.46 (m, 2H), 6.90 (s, 1H), 6.20 (s, 1H). |

-continued

| No. | Structure | Methods | Data |
|---|---|---|---|
| 214 | 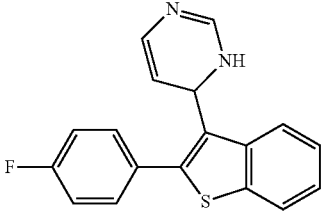 [SMILES: Fc1ccc(-c2sc3ccccc3c2C2C=CN=CN2)cc1] | 5, 1 | MS (ESI+): m/z 309 (MH$^+$); $^1$H NMR (300 MHz, MeOD): δ 8.11 (s, 1H), 7.99-7.96 (m, 1H), 7.51-7.30 (m, 8H), 6.44-6.40 (m, 1H), 5.81-5.80 (m, 1H), 5.48-5.44 (m, 1H) |
| 215 | 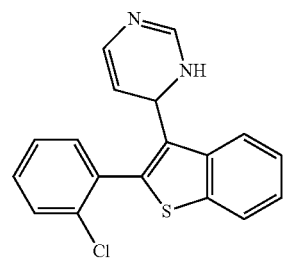 [SMILES: Clc1ccccc1-c1sc2ccccc2c1C1C=CN=CN1] | 5, 1 | MS (ESI+): m/z 325 (MH$^+$); $^1$H NMR (300 MHz, MeOD): δ 8.12 (s, 1H), 8.00-7.97 (d, J = 7.77 Hz, 1H), 7.68-7.65 (m, 1H), 7.58-7.39 (m, 5H), 7.27-7.25 (m, 1H), 6.41-6.38 (d, J = 8.19 Hz, 1H), 5.63-5.62 (m, 1H), 5.44-5.41 (dd, J = 8.13 Hz, J = 3.24 Hz, 2H) |
| 216 | 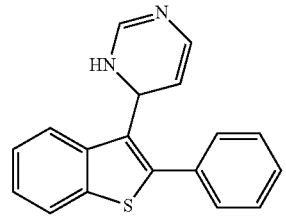 [SMILES: C1=CC(c2c(-c3ccccc3)sc3ccccc23)NC=N1] | 5, 1 | MS (ESI+): m/z 291 (MH$^+$); $^1$H NMR (300 MHz, MeOD): δ 8.08-8.05 (m, 2H), 7.99-7.97 (d, J = 7.17 Hz, 1H), 7.54-7.47 (m, 7H), 6.40-6.37 (d, J = 8.16 Hz, 1H), 6.00-5.99 (t, J = 2.37 Hz, 1H), 5.39-5.36 (dd, J = 8.24 Hz, J = 2.04 Hz, 1H) |
| 217 | 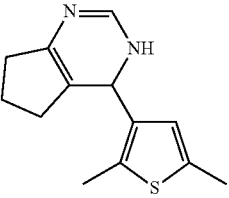 [SMILES: Cc1cc(C2NC=NC3=C2CCC3)c(C)s1] | 30, 1 | MS (ESI+): m/z 233 (MH$^+$); $^1$H NMR (300 MHz, MeOD): δ 8.08 (s, 1H), 6.67 (s, 1H), 5.64 (s, 1H), 2.61-2.56 (m, 2H), 2.42 (s, 6H), 2.39-2.27 (m, 1H), 2.11-1.98 (m, 3H) |
| 218 | 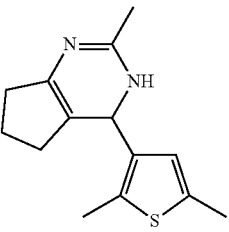 [SMILES: CC1=NC2=C(CCC2)C(c2cc(C)sc2C)N1] | 31, 1 | MS (ESI+): m/z 247 (MH$^+$); $^1$H NMR (300 MHz, MeOD): δ 6.65 (s, 1H), 5.74 (s, 1H), 2.59-2.53 (m, 2H), 2.42 (s, 3H), 2.39 (s, 3H), 2.29 (s, 3H), 2.09-2.01 (m, 4H) |
| 219 | 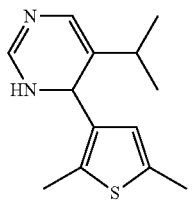 [SMILES: Cc1cc(C2NC=NC=C2C(C)C)c(C)s1] | 1 | MS (ESI+): m/z 235 (MH$^+$); $^1$H NMR (300 MHz, MeOD): δ 8.01 (s, 1H), 6.69 (s, 1H), 6.23 (s, 1H), 5.50 (s, 1H), 2.44 (s, 3H), 2.39 (s, 3H), 2.03-2.02 (m, 1H), 1.06-0.99 (dd, J = 10.2 Hz, J = 6.9 Hz, 6H) |

| No. | Structure | Methods | Data |
|---|---|---|---|
| 220 | 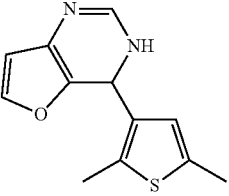 [SMILES: Cc1cc(C2NC=Nc3ccoc32)c(C)s1] | 28, 1 | MS (ESI+): m/z 233 (MH$^+$); $^1$H NMR (300 MHz, MeOD): δ 8.23 (s, 1H), 7.56-7.55 (m, 1H), 6.56-6.55 (m, 1H), 6.37 (s, 1H), 6.38 (s, 1H), 2.44 (s, 3H), 2.39 (s, 3H) |
| 221 | 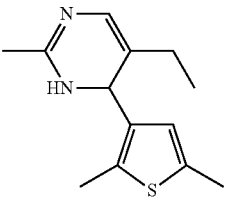 | 32, 1 | MS (ESI+): m/z 235 (MH$^+$); $^1$H NMR (300 MHz, MeOD): δ 6.67 (s, 1H), 6.17 (s, 1H), 5.37 (s, 1H), 2.53-2.42 (q, 2H), 2.40 (s, 3H), 2.39 (s, 3H), 1.54 (s, 3H), 1.30-1.25 (t, J = 8.4 Hz, 3H) |
| 222 | 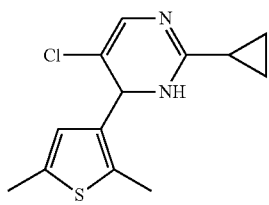 [SMILES: Cc1cc(C2NC(C3CC3)=NC=C2Cl)c(C)s1] | 22, 1 | MS (ESI+): m/z 267 (MH$^+$); $^1$H NMR (300 MHz, MeOD): δ 6.70 (s, 1H), 6.63 (s, 1H), 5.53 (s, 1H), 2.43 (s, 3H), 2.42 (s, 3H), 1.94-1.87 (m, 1H), 1.36-1.27 (m, 3H), 1.19-1.11 (m, 1H) |
| 223 | 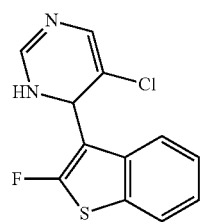 [SMILES: Fc1sc2ccccc2c1C1NC=NC=C1Cl] | 13, 1 | MS (ESI+): m/z 267 (MH$^+$); $^1$H NMR (300 MHz, MeOD): δ 6.78 (s, 1H), 6.61-6.59 (d, J = 6.3 Hz, 1H), 5.78 (s, 1H), 2.42 (s, 3H), 2.27 (s, 3H) |
| 224 | 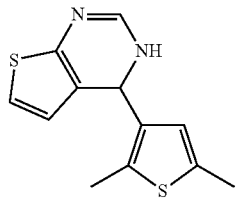 [SMILES: Cc1cc(C2NC=Nc3sccc32)c(C)s1] | 28, 1 | MS (ESI+): m/z 249 (MH$^+$); $^1$H NMR (300 MHz, MeOD): δ 8.26 (s, 1H), 7.23-7.21 (d, J = 5.4 Hz, 1H), 6.60-6.58 (d, J = 5.4 Hz, 1H), 6.54 (s, 1H), 6.25 (s, 1H), 2.45 (s, 3H), 2.36 (s, 3H) |
| 225 | 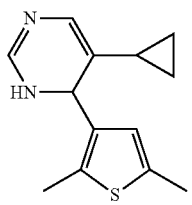 [SMILES: Cc1cc(C2NC=NC=C2C2CC2)c(C)s1] | 1 | MS (ESI+): m/z 233 (MH$^+$); $^1$H NMR (300 MHz, MeOD): δ 8.01 (s, 1H), 6.71 (s, 1H), 6.14 (s, 1H), 5.48 (s, 1H), 2.45 (s, 3H), 2.40 (s, 3H), 1.07-1.06 (m, 1H), 0.68-0.64 (m, 2H), 0.63-0.60 (m, 2H) |
| 226 | 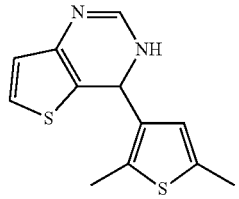 [SMILES: Cc1cc(C2NC=Nc3ccsc32)c(C)s1] | 28, 1 | MS (ESI+): m/z 249 (MH$^+$); $^1$H NMR (300 MHz, MeOD): δ 8.26 (s, 1H), 7.55-7.53 (d, J = 5.1 Hz, 1H), 6.94-6.92 (d, J = 5.4 Hz, 1H), 6.60 (s, 1H), 6.44 (s, 1H), 2.45 (s, 3H), 2.37 (s, 3H) |

-continued

| | Tabular Data | | |
|---|---|---|---|
| No. | Structure | Methods | Data |
| 227 | | 22, 1 | MS (ESI+): m/z 233 (MH+); ¹H NMR (300 MHz, MeOD): δ 6.70 (s, 1H), 6.33-6.30 (d, J = 8.83 Hz, 1H), 5.43 (s, 1H), 5.22-5.18 (dd, J = 8.00 Hz, J = 3.59 Hz, 1H), 2.40 (s, 6H), 1.96-1.87 (m, 1H), 1.30-1.14 (m, 4H) |
| 228 | | 32, 1 | MS (ESI+): m/z 221 (MH+); ¹H NMR (300 MHz, MeOD): δ 8.01 (s, 1H), 6.69 (s, 1H), 6.18 (s, 1H), 5.45 (s, 1H), 2.42 (s, 3H), 2.39 (s, 3H), 1.89-1.84 (q, 2H), 1.03-1.01 (t, J = 7.2 Hz, 3H) |
| 229 | | 31, 1 | MS (ESI+): m/z 261 (MH+); ¹H NMR (300 MHz, MeOD): δ 6.65 (s, 1H), 5.27 (s, 1H), 2.40 (s, 6H), 2.22 (s, 3H), 2.19-2.18 (m, 2H), 1.79-1.62 (m, 6H) |
| 230 | | 30, 1 | MS (ESI+): m/z 247 (MH+); ¹H NMR (300 MHz, MeOD): δ 8.00 (s, 1H), 6.67 (s, 1H), 5.30 (s, 1H), 2.40 (s, 6H), 2.20-2.19 (m, 2H), 1.80-1.62 (m, 6H) |
| 231 | | 33, 4 | MS (ESI+): m/z 261 (MH+); ¹H NMR (300 MHz, MeOD): δ 8.32 (s, 1H), 7.02-6.90 (m, 3H), 6.53 (s, 1H), 6.17 (s, 1H), 2.48 (s, 3H), 2.35 (s, 3H) |
| 232 | | 33, 4 | MS (ESI+): m/z 261 (MH+); ¹H NMR (300 MHz, MeOD): δ 8.27 (s, 1H), 7.20-7.14 (m, 2H), 6.72-6.68 (dd, J = 8.7 Hz, J = 2.7 Hz, 1H), 6.53 (s, 1H), 6.19 (s, 1H), 2.49 (s, 3H), 2.36 (s, 3H) |

-continued

| No. | Structure | Methods | Data |
|-----|-----------|---------|------|
| 233 | 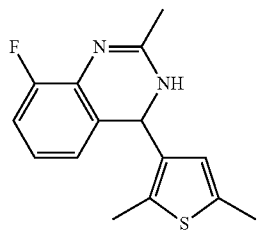 [SMILES: CC1=Nc2c(F)cccc2C(c2cc(C)sc2C)N1] | 33, 4 | MS (ESI+): m/z 275 (MH+); ¹H NMR (300 MHz, MeOD): δ 7.23-7.19 (m, 2H), 6.76-6.73 (m, 1H), 6.54 (s, 1H), 6.18 (s, 1H), 2.49 (s, 3H), 2.43 (s, 3H), 2.35 (s, 3H) |
| 234 | 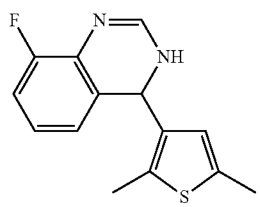 [SMILES: Cc1cc(C2NC=Nc3c(F)cccc32)c(C)s1] | 33, 4 | MS (ESI+): m/z 261 (MH+); ¹H NMR (300 MHz, MeOD): δ 8.29 (s, 1H), 7.27-7.21 (m, 2H), 6.79-6.76 (m, 1H), 6.55 (s, 1H), 6.22 (s, 1H), 2.49 (s, 3H), 2.35 (s, 3H) |
| 235 | 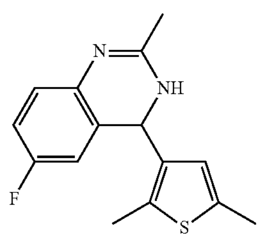 [SMILES: CC1=Nc2ccc(F)cc2C(c2cc(C)sc2C)N1] | 33, 4 | MS (ESI+): m/z 275 (MH+); ¹H NMR (300 MHz, MeOD): δ 7.15-7.12 (m, 2H), 6.68-6.65 (d, J = 8.4 Hz, 1H), 6.52 (s, 1H), 6.15 (s, 1H), 2.49 (s, 3H), 2.38 (s, 3H), 2.36 (s, 3H) |
| 236 | 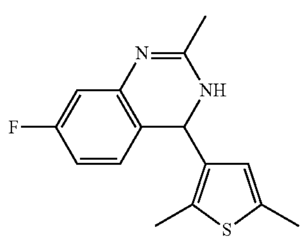 [SMILES: CC1=Nc2cc(F)ccc2C(c2cc(C)sc2C)N1] | 33, 4 | MS (ESI+): m/z 275 (MH+); ¹H NMR (300 MHz, MeOD): δ 6.99-6.94 (m, 2H), 6.89-6.85 (dd, J = 9.3 Hz, J = 2.4 Hz, 1H), 6.52 (s, 1H), 6.12 (s, 1H), 2.48 (s, 3H), 2.39 (s, 3H), 2.35 (s, 3H) |
| 237 | 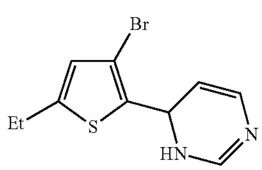 [SMILES: CCc1cc(Br)c(C2C=CN=CN2)s1] | 12, 1 | MS (ESI+): m/z 272 (MH+); ¹H NMR (300 MHz, MeOD): δ 8.14 (s, 1H), 6.84 (s, 1H), 6.49-6.47 (d, J = 8.4 Hz, 1H), 5.86-5.85 (dd, J = 3.6 Hz, J = 1.2 Hz, 1H), 5.40-5.37 (m, 1H), 2.91-2.83 (q, 2H), 1.33-1.28 (t, J = 7.5 Hz, 3H) |
| 238 | 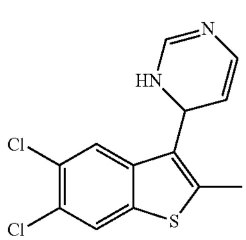 [SMILES: Cc1sc2cc(Cl)c(Cl)cc2c1C1C=CN=CN1] | 20, 1 | MS (ESI+): m/z 298 (MH+); ¹H NMR (300 MHz, MeOD): δ 8.23 (s, 1H), 8.10 (s, 1H), 8.04 (s, 1H), 6.51-6.48 (m, 1H), 6.11-6.10 (t, J = 2.4 Hz, 1H), 5.32-5.28 (m, 1H), 2.65 (s, 3H) |

-continued

Tabular Data

| No. | Structure | Methods | Data |
|---|---|---|---|
| 239 | 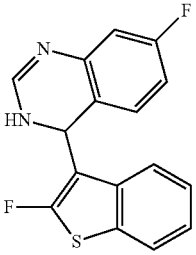 [SMILES: Fc1ccc2c(c1)N=CNC2c1c(F)sc2ccccc12] | 33, 13, 4 | MS (ESI+): m/z 301 (MH+); $^1$H NMR (300 MHz, MeOD): δ 8.50 (s, 1H), 7.88-7.85 (m, 1H), 7.63-7.60 (m, 1H), 7.45-7.41 (m, 2H), 7.09-6.98 (m, 3H), 6.7 (s, 1H) |

B. Animal Models

Anti-psychotic like activity of the compounds was evaluated in mice using the PCP hyperactivity (in rats) and Pre-Pulse Inhibition (PPI; in mice) models of schizophrenia.

1. Methods

Animals: PCP Hyperactivity: Male Sprague Dawley rats from Harlan (Indianapolis, Ind.) were used in these studies. Upon receipt, rats were assigned unique identification numbers and were group housed with 3 rats per cage in polycarbonate cages with micro-isolator filter tops. All rats were examined, handled, and weighed prior to initiation of the study to assure adequate health and suitability. The rats were maintained at 12/12 light/dark cycle with lights on at 7:00 am EST. The room temperature was maintained between 20 and 23° C. with a relative humidity maintained around 50%. Chow and water were provided ad libitum for the duration of the study. For each test, animals were randomly assigned across treatment groups.

Animals—PPI: Male C57Bl/6J mice from Jackson Laboratories (Bar Harbor, Me.) were used in these studies. Upon receipt, mice were assigned unique identification numbers (tail marked) and were group housed with 4 mice per cage in OptiMICE ventilated cages. All animals remained housed in groups of four during the remainder of the study. All mice were acclimated to the colony room for at least one week prior to testing. During the period of acclimation, mice were examined on a regular basis, handled, and weighed to assure adequate health and suitability. Animals were maintained on a 12/12 light/dark cycle. The room temperature was maintained between 20 and 23° C. with a relative humidity maintained between 30% and 70%. Chow and water were provided ad libitum for the duration of the study. In each test, animals were randomly assigned across treatment groups.

2. PCP Hyperactivity

The test chambers were Plexiglas rectangular chambers (24×45 cm) that fit inside two steel frames (9.5×18 inches) and were fitted with two-dimensional 4×8 beam grids to monitor horizontal and vertical locomotor activity (Hamilton Kinder, San Diego, Calif.). The analysis was configured to divide the open field of the chamber into a center and a periphery zone. Distance traveled was measured from horizontal beam breaks as the rat traveled whereas rearing activity was measured from vertical beam breaks.

Rats were administered with vehicle, test compound, or risperidone (0.5-1 mg/kg; i.p) and placed in the test chambers for 30 min measurement of baseline activity. Rats were then injected with either water or PCP (2.5 mg/kg; s.c) and placed back in the test chambers for a 60-minute session. At the end of each test session the chambers were thoroughly cleaned.

3. Prepulse Inhibition of Startle

The acoustic startle is an unconditioned reflex response to an external auditory stimulus. Prepulse inhibition of startle (PPI) refers to the reduction in the startle response caused by the presentation of a low-intensity auditory stimulus prior to the startle stimulus. The PPI paradigm is used for the study of schizophrenia and antipsychotic action due to the similarities between the results from human and rodent studies. PPI has been used as a tool for the assessment of deficiencies in sensory-motor gating observed in schizophrenia and to screen for potential antipsychotic drugs. Various psychotomimetic drugs such as PCP can disrupt PPI. In mice, antipsychotic drugs such as clozapine can reverse the disruption of PPI induced by PCP.

Mice were placed in the PPI chambers (Med Associates) for a 5 min session of white noise (70 dB) habituation. After the habituation period the test session was initiated. The session started with a habituation block of 6 presentations of the startle stimulus alone, followed by 10 PPI blocks, each of which consisted of 6 different types of trials. Trial types were: 'null' (no stimuli), 'startle' (120 dB), 'startle plus prepulse' (4, 8 and 12 dB over background noise, i.e., 74, 78 or 82 dB) and 'prepulse' (82 dB). Trial types were presented in a random order within each block. Each trial started with a 50 ms stimulus-free period during which baseline movements were recorded. This was followed by a subsequent 20 ms period during which the prepulse stimulus was presented and responses to the prepulse measured. After a further 100 ms period, the startle stimulus was presented for 40 ms and responses recorded for 100 ms from startle onset. Responses were sampled every ms. The inter-trial interval was variable with an average of 15 s (range from 10 to 20 s). In 'startle' trials the basic auditory startle response was measured. The basic startle response was calculated as the mean startle response of all 'startle' trials (i.e., excluding the first habituation block). In 'startle plus prepulse' trials the degree of inhibition of the normal startle was calculated and expressed as a percentage of the basic startle response.

Mice were treated with vehicle, haloperidol (1 mg/kg; i.p) or test compound 30 min prior to PPI test. The PPI enclosures were cleaned following each test.

4. Results

TABLE 1

Effects of Compounds on Pre-pulse Inhibition (PPI) in Mice

| Compound/Doses | Effect |
|---|---|
| 21 | |
| 3 mg/kg | − |
| 10 mg/kg | − |
| 30 mg/kg | − |
| 3 | |
| 3 mg/kg | + |
| 10 mg/kg | + |
| 30 mg/kg | +++ |
| 15 | |
| 3 mg/kg | − |
| 10 mg/kg | + |
| 30 mg/kg | ++ |
| 239 | |
| 3 mg/kg | − |
| 10 mg/kg | − |
| 30 mg/kg | +++ |
| 20 | |
| 3 mg/kg | − |
| 10 mg/kg | − |
| 30 mg/kg | − |

*$P < 0.05$ vs. vehicle
−: No change in PPI
+: Significant increase in PPI at one pre-pulse intensity (P value < 0.05)
++: Significant increase in PPI at two pre-pulse intensities (P value < 0.05)
+++: Significant increase in PPI at three pre-pulse intensities (P value < 0.05)

TABLE 2

Effects of Compounds on PCP-Induced Hyperactivity Responses in Rats

| Compound/Doses | Total Distance Traveled (cm) |
|---|---|
| 21 | |
| 10 mg/kg Compound + PCP | − |
| 30 mg/kg Compound + PCP | − |
| 100 mg/kg Compound + PCP | − |
| 3 | |
| 3 mg/kg Compound + PCP | − |
| 10 mg/kg Compound + PCP | + |
| 30 mg/kg Compound + PCP | + |
| 15 | |
| 3 mg/kg Compound + PCP | − |
| 10 mg/kg Compound + PCP | − |
| 30 mg/kg Compound + PCP | − |
| 239 | |
| 3 mg/kg Compound + PCP | + (increase) |
| 10 mg/kg Compound + PCP | + (increase) |
| 30 mg/kg Compound + PCP | + (increase) |
| 20 | |
| 3 mg/kg Compound + PCP | + |
| 10 mg/kg Compound + PCP | − |
| 30 mg/kg Compound + PCP | + |

*$P < 0.05$ vs. vehicle + PCP
−: No inhibition of PCP hyperactivity
+: Significant inhibition of PCP hyperactivity (P value < 0.05)

The embodiments described above are intended to be merely exemplary, and those skilled in the art will recognize, or will be able to ascertain using no more than routine experimentation, numerous equivalents of specific compounds, materials, and procedures. All such equivalents are considered to be within the scope of the disclosure and are encompassed by the appended claims.

All of the patents, patent applications and publications referred to herein are incorporated by reference herein in their entireties. Citation or identification of any reference in this application is not an admission that such reference is available as prior art to this application. The full scope of the disclosure is better understood with reference to the appended claims.

What is claimed:

1. A compound selected from:

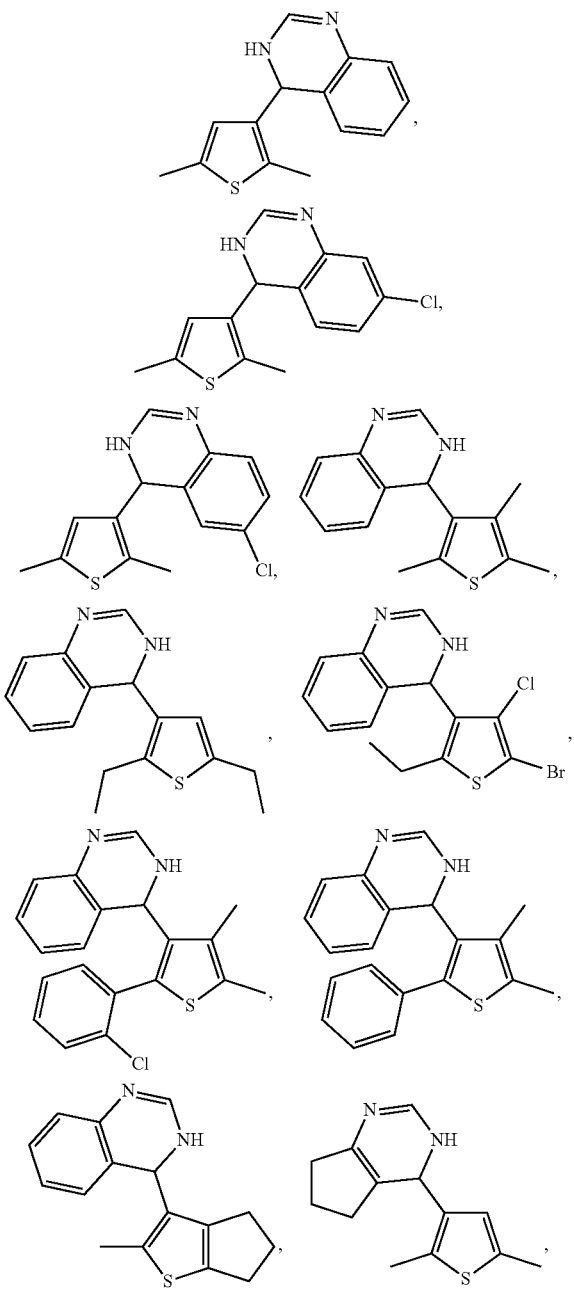

-continued
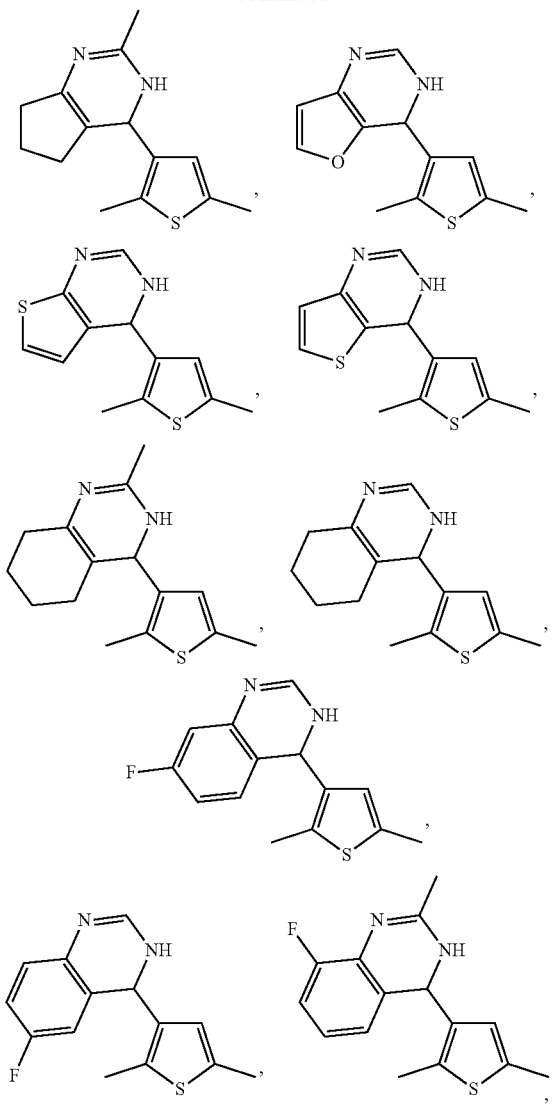
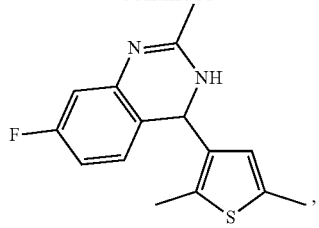
or a pharmaceutically acceptable salt thereof.
2. The compound of claim 1, or a pharmaceutically acceptable salt thereof, selected from:
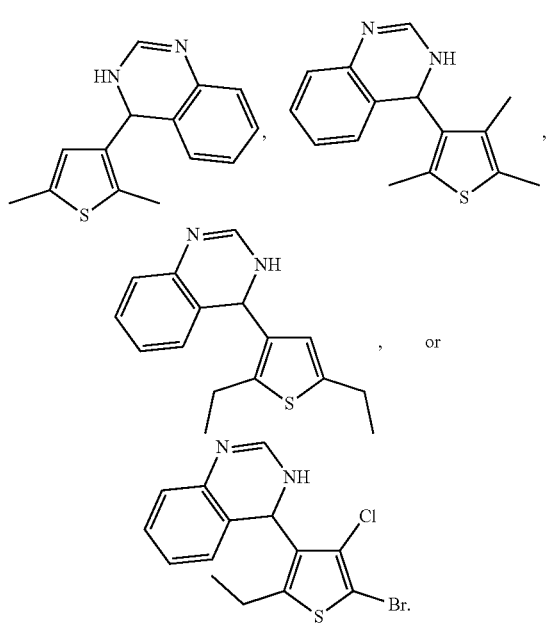
3. The compound of claim 1, or a pharmaceutically acceptable salt thereof, selected from:
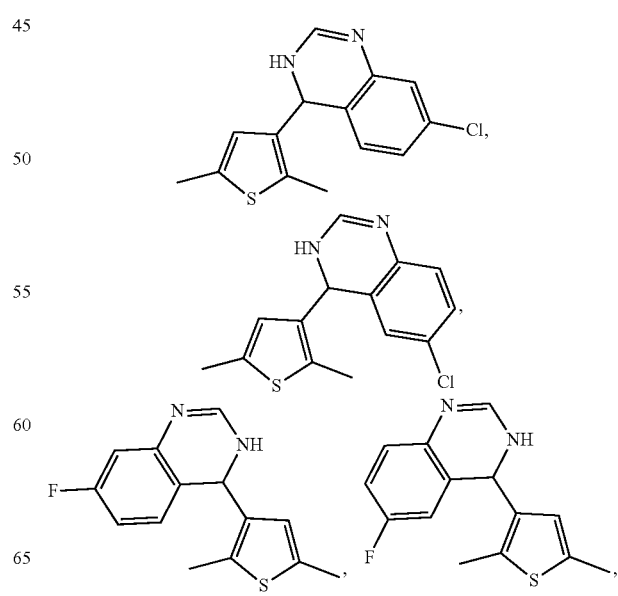

4. The compound of claim 1, or a pharmaceutically acceptable salt thereof, selected from:

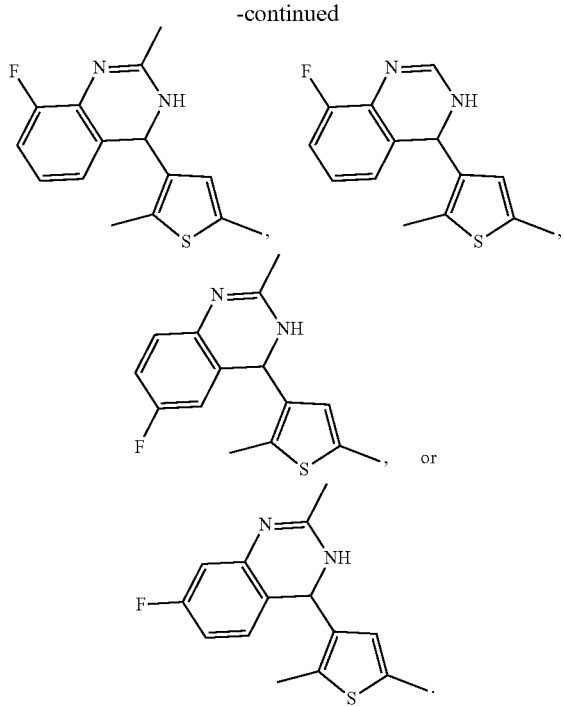

5. The compound of claim 1, or a pharmaceutically acceptable salt thereof, selected from:

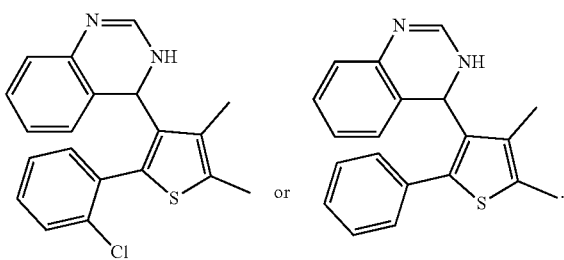 [SMILES: Cc1sc(-c2ccccc2Cl)c(C2NC=Nc3ccccc32)c1C ; Cc1sc(-c2ccccc2)c(C2NC=Nc3ccccc32)c1C]

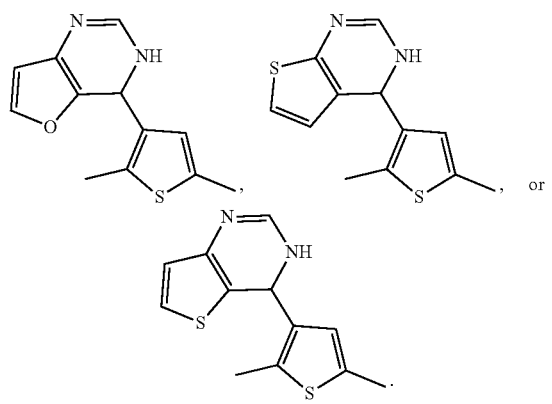

6. The compound of claim 1, or a pharmaceutically acceptable salt thereof, selected from:

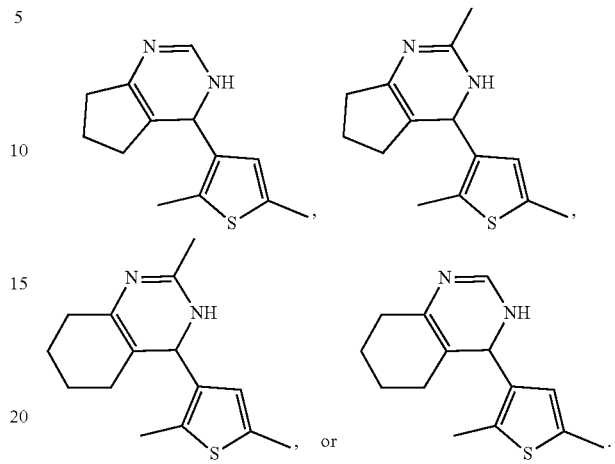

7. The compound of claim 1, wherein the compound is:

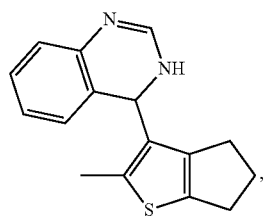 [SMILES: Cc1sc2c(c1C1NC=Nc3ccccc31)CCC2]

or a pharmaceutically acceptable salt thereof.

8. A pharmaceutical composition comprising a compound of claim 1, or a pharmaceutically acceptable salt thereof, and a pharmaceutically acceptable excipient or carrier.

9. A pharmaceutical composition comprising a compound of claim 2, or a pharmaceutically acceptable salt thereof, and a pharmaceutically acceptable excipient or carrier.

10. A pharmaceutical composition comprising a compound of claim 3, or a pharmaceutically acceptable salt thereof, and a pharmaceutically acceptable excipient or carrier.

11. A pharmaceutical composition comprising a compound of claim 4, or a pharmaceutically acceptable salt thereof, and a pharmaceutically acceptable excipient or carrier.

12. A pharmaceutical composition comprising a compound of claim 5, or a pharmaceutically acceptable salt thereof, and a pharmaceutically acceptable excipient or carrier.

13. A pharmaceutical composition comprising a compound of claim 6, or a pharmaceutically acceptable salt thereof, and a pharmaceutically acceptable excipient or carrier.

14. A pharmaceutical composition comprising a compound of claim 7, or a pharmaceutically acceptable salt thereof, and a pharmaceutically acceptable excipient or carrier.

* * * * *